(12) United States Patent
Aicher et al.

(10) Patent No.: US 9,783,511 B2
(45) Date of Patent: *Oct. 10, 2017

(54) CARBAMATE BENZOXAZINE PROPIONIC ACIDS AND ACID DERIVATIVES FOR MODULATION OF RORGAMMA ACTIVITY AND THE TREATMENT OF DISEASE

(71) Applicants: Merck Sharp & Dohme Corp., Rahway, NJ (US); Lycera Corporation, Ann Arbor, MI (US)

(72) Inventors: Thomas D. Aicher, Ann Arbor, MI (US); Chad A. VanHuis, Hartland, MI (US); John MacLean, Brookline, MA (US); Brian M. Andresen, Boston, MA (US); Kenneth J. Barr, Boston, MA (US); Corey Bienstock, Natick, MA (US); Matthew Daniels, Somerville, MA (US); Kun Liu, Boston, MA (US); Yuan Liu, Billerica, MA (US); Catherine White, Boston, MA (US); Nunzio Sciammetta, Boston, MA (US); Vladimir Simov, Boston, MA (US)

(73) Assignees: Lycera Corporation, Ann Arbor, MI (US); Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/103,409

(22) PCT Filed: Dec. 19, 2014

(86) PCT No.: PCT/US2014/071663
§ 371 (c)(1),
(2) Date: Jun. 10, 2016

(87) PCT Pub. No.: WO2015/095792
PCT Pub. Date: Jun. 25, 2015

(65) Prior Publication Data
US 2016/0311787 A1    Oct. 27, 2016

Related U.S. Application Data

(60) Provisional application No. 61/918,948, filed on Dec. 20, 2013.

(51) Int. Cl.
*C07D 265/36* (2006.01)
*A61K 31/538* (2006.01)
(Continued)

(52) U.S. Cl.
CPC .......... *C07D 265/36* (2013.01); *A61K 31/538* (2013.01); *C07D 413/12* (2013.01);
(Continued)

(58) Field of Classification Search
CPC .......................... C07D 265/36; A61K 31/538
(Continued)

(56) References Cited

U.S. PATENT DOCUMENTS 5,985,903 A   11/1999  Assmann et al.
6,020,354 A    2/2000  Assmann et al.
(Continued)

FOREIGN PATENT DOCUMENTS

EP   0882718 A1   12/1998
EP   1820515 A1    8/2007
(Continued)

OTHER PUBLICATIONS

International Search Report and Written Opinion for PCT/US2014/071663 dated Apr. 17, 2015 (6 pages).
International Search Report and Written Opinion for PCT/US2014/071671 dated Apr. 28, 2015 (10 pages).
Annunziato et al., "Type 17 T helper cells-origins, features and possible roles in rheumatic disease," 5 Nat. Rev. Rheumatol. 325-31 (2009).
Boaventura et al., "Human mucosal leishmaniasis: Neutrophils infiltrate areas of tissue damage that express high levels of Th17-related cytokines," 40 Eur. J. Immunol. 2830-36 (2010).
Buonocore et al., "Innate lymphoid cells drive interleukin-23-dependent innate intestinal pathology," 464 Nature 1371-75 (2010).
(Continued)

*Primary Examiner* — Niloofar Rahmani
(74) *Attorney, Agent, or Firm* — Goodwin Procter LLP

(57) ABSTRACT

The invention provides certain benzoxazine compounds of the Formula (I) or pharmaceutically acceptable salts thereof wherein $R^1$, $R^2$, $R^{a1}$, $R^{a2}$, $R^{b1}$, $R^{b2}$, $R^c$, $R^d$, and Cy are as defined herein. The invention also provides pharmaceutical compositions comprising such compounds of the Formula (I) or pharmaceutically acceptable salts thereof, and methods of using the compounds of the Formula (I) or pharmaceutically acceptable salts thereof or pharmaceutical compositions comprising the same for treating diseases or conditions mediated by RORgammaT.

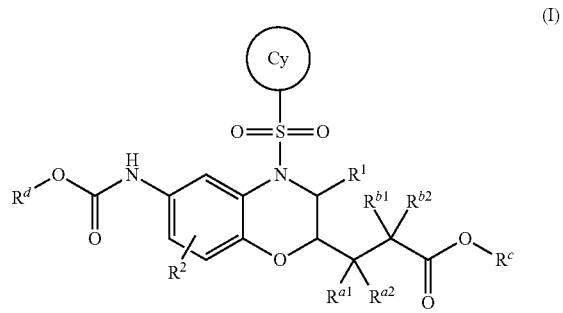

(I)

21 Claims, No Drawings

(51) Int. Cl.
*C07D 413/12* (2006.01)
*C07D 513/04* (2006.01)
*C07D 417/12* (2006.01)
*C07D 471/04* (2006.01)
*C07D 487/04* (2006.01)

(52) U.S. Cl.
CPC ......... *C07D 417/12* (2013.01); *C07D 471/04* (2013.01); *C07D 487/04* (2013.01); *C07D 513/04* (2013.01)

(58) Field of Classification Search
USPC .................................. 544/105; 514/230.5
See application file for complete search history.

(56) References Cited

U.S. PATENT DOCUMENTS

| | | | |
|---|---|---|---|
| 6,037,367 | A | 3/2000 | Christensen, IV et al. |
| 6,160,001 | A | 12/2000 | Assmann et al. |
| 6,172,092 | B1 | 1/2001 | Assmann et al. |
| 6,180,643 | B1 | 1/2001 | Zablocki et al. |
| 6,348,032 | B1 | 2/2002 | Sperl et al. |
| 6,352,985 | B1 | 3/2002 | Yamasaki et al. |
| 6,387,939 | B1 | 5/2002 | Assmann et al. |
| 6,440,973 | B1 | 8/2002 | Zablocki et al. |
| 6,534,535 | B1 | 3/2003 | Zhu et al. |
| 6,605,634 | B2 | 8/2003 | Zablocki et al. |
| 6,638,960 | B2 | 10/2003 | Assmann et al. |
| 6,683,091 | B2 | 1/2004 | Asberom et al. |
| 6,828,344 | B1 | 12/2004 | Seehra et al. |
| 7,084,176 | B2 | 8/2006 | Morie et al. |
| 7,115,750 | B1 | 10/2006 | Kato et al. |
| 7,138,401 | B2 | 11/2006 | Kasibhatla et al. |
| 7,329,675 | B2 | 2/2008 | Cox et al. |
| 7,420,059 | B2 | 9/2008 | O'Connor et al. |
| 7,482,342 | B2 | 1/2009 | D'Orchymont et al. |
| 7,569,571 | B2 | 8/2009 | Dong et al. |
| 7,696,200 | B2 | 4/2010 | Ackermann et al. |
| 7,713,996 | B2 | 5/2010 | Ackermann et al. |
| 7,741,495 | B2 | 6/2010 | Liou et al. |
| 7,799,933 | B2 | 9/2010 | Ceccarelli et al. |
| 9,266,827 | B2 | 2/2016 | Aicher et al. |
| 9,512,111 | B2 | 12/2016 | Glick et al. |
| 9,657,033 | B2 | 5/2017 | Aicher et al. |
| 9,663,502 | B2 | 5/2017 | Aicher et al. |
| 2006/0004000 | A1 | 1/2006 | D'Orchymont et al. |
| 2006/0100230 | A1 | 5/2006 | Bischoff et al. |
| 2007/0010537 | A1 | 1/2007 | Hamamura et al. |
| 2007/0010670 | A1 | 1/2007 | Hirata et al. |
| 2007/0049556 | A1 | 3/2007 | Zhang et al. |
| 2007/0060567 | A1 | 3/2007 | Ackermann et al. |
| 2007/0154487 | A1 | 7/2007 | Littman et al. |
| 2007/0191603 | A1 | 8/2007 | Ackermann et al. |
| 2007/0197782 | A1 | 8/2007 | Clough et al. |
| 2007/0281922 | A1 | 12/2007 | Liu et al. |
| 2008/0027100 | A1 | 1/2008 | McCormick et al. |
| 2008/0058386 | A1 | 3/2008 | Liou et al. |
| 2008/0153805 | A1 | 6/2008 | Ceccarelli et al. |
| 2008/0305169 | A1 | 12/2008 | Miki et al. |
| 2009/0005410 | A1 | 1/2009 | Charvat et al. |
| 2009/0075973 | A1 | 3/2009 | Newcom et al. |
| 2009/0247502 | A1 | 10/2009 | Newcom et al. |
| 2009/0275586 | A1 | 11/2009 | Govek et al. |
| 2010/0022515 | A1 | 1/2010 | Alper et al. |
| 2010/0130484 | A1 | 5/2010 | Ackermann et al. |
| 2010/0234340 | A1 | 9/2010 | Schunk et al. |
| 2011/0053915 | A1 | 3/2011 | Ivaschenko et al. |
| 2011/0112070 | A1 | 5/2011 | Baldwin et al. |
| 2011/0118246 | A1 | 5/2011 | Baldwin et al. |
| 2011/0130384 | A1 | 6/2011 | Setoh et al. |
| 2011/0178063 | A1 | 7/2011 | Baldwin et al. |
| 2014/0088094 | A1 | 3/2014 | Glick et al. |
| 2015/0111877 | A1 | 4/2015 | Aicher et al. |
| 2015/0126493 | A1 | 5/2015 | Aicher et al. |
| 2016/0304476 | A1* | 10/2016 | Aicher ............... C07D 265/36 |
| 2016/0304505 | A1 | 10/2016 | Aicher et al. |

FOREIGN PATENT DOCUMENTS

| | | |
|---|---|---|
| EP | 2181710 A1 | 5/2010 |
| JP | 6-250441 A | 9/1994 |
| JP | 2004307487 A | 11/2004 |
| WO | WO-92/13856 A1 | 8/1992 |
| WO | WO-97/01561 A1 | 1/1997 |
| WO | WO-97/48697 A1 | 12/1997 |
| WO | WO-98/22457 A1 | 5/1998 |
| WO | WO-00/17202 A1 | 3/2000 |
| WO | WO-01/12600 A1 | 2/2001 |
| WO | WO-02/100819 A1 | 12/2002 |
| WO | WO-03/014075 A2 | 2/2003 |
| WO | WO-2004/056830 A1 | 7/2004 |
| WO | WO-2005/028434 A2 | 3/2005 |
| WO | WO-2005/037834 A1 | 4/2005 |
| WO | WO-2006/007486 A2 | 1/2006 |
| WO | WO-2006/057460 A1 | 6/2006 |
| WO | WO-2007/024944 A1 | 3/2007 |
| WO | WO-2007/031429 A1 | 3/2007 |
| WO | WO-2007/093507 A1 | 8/2007 |
| WO | WO-2007/125405 A2 | 11/2007 |
| WO | WO-2007/138998 A1 | 12/2007 |
| WO | WO-2008/003703 A1 | 1/2008 |
| WO | WO-2008/045664 A2 | 4/2008 |
| WO | WO-2008/062740 A1 | 5/2008 |
| WO | WO-2008/074692 A1 | 6/2008 |
| WO | WO-2008/097428 A2 | 8/2008 |
| WO | WO-2008/150827 A1 | 12/2008 |
| WO | WO-2009/032667 A1 | 3/2009 |
| WO | WO-2009/035997 A2 | 3/2009 |
| WO | WO-2009/077956 A2 | 6/2009 |
| WO | WO-2009/147187 A1 | 12/2009 |
| WO | WO-2009/149819 A1 | 12/2009 |
| WO | WO-2009/149820 A1 | 12/2009 |
| WO | WO-2009/157196 A1 | 12/2009 |
| WO | WO-2010/017827 A1 | 2/2010 |
| WO | WO-2010/038901 A1 | 4/2010 |
| WO | WO-2010/057101 A2 | 5/2010 |
| WO | WO-2010/059602 A2 | 5/2010 |
| WO | WO-2010/071853 A1 | 6/2010 |
| WO | WO-2010/102958 A1 | 9/2010 |
| WO | WO-2010/117425 A1 | 10/2010 |
| WO | WO-2010/123139 A1 | 10/2010 |
| WO | WO-2010/125082 A1 | 11/2010 |
| WO | WO-2011/019634 A2 | 2/2011 |
| WO | WO-2011/059839 A1 | 5/2011 |
| WO | WO-2011/067364 A1 | 6/2011 |
| WO | WO-2011/067365 A1 | 6/2011 |
| WO | WO-2011/067366 A1 | 6/2011 |
| WO | WO-2011/109059 A1 | 9/2011 |
| WO | WO-2012/032065 A1 | 3/2012 |
| WO | WO-2012/032067 A1 | 3/2012 |
| WO | WO-2012/037108 A1 | 3/2012 |
| WO | WO-2012/064744 A2 | 5/2012 |
| WO | WO-2012/139775 A1 | 10/2012 |
| WO | WO-2013/169704 A2 | 11/2013 |

OTHER PUBLICATIONS

Eberl et al., "An essential function for the nuclear receptor RORγt in the generation of fetal lymphoid tissue inducer cells," 5(1) Nat. Immunol. 64-73 (2004).

Figueroa-Vega et al., "Increased Circulating Pro-Inflammatory Cytokines and Th17 Lymphocytes in Hashimoto's Thyroiditis," 95(2) J. Clin. Endocrinol. Metab. 953-62 (2010).

Gennaro (ed.), Remington: The Science and Practice of Pharmacy, 20th edition (2000).

He et al., "RORγt, a Novel Isoform of an Orphan Receptor, Negatively Regulates Fas Ligand Expression and IL-2 Production in T Cells," 9 Immunity 797-806 (1998).

Hirose et al., "RORγ: the third member of ROR/RZR orphan receptor subfamily that is highly expressed in skeletal muscle," 205 Biochem. Biophys. Res. Comm. 1976-83 (1994).

Hueber et al., "Cutting Edge: Mast Cells Express IL-17A in Rheumatoid Arthritis Synovium," 184 J. Immunol. 3336-40 (2010).

Ivanov et al., "The Orphan Nuclear Receptor RORγt Directs the Differentiation Program of Proinflammatory IL-17+ T Helper Cells," 126 Cell 1121-33 (2006).

(56) References Cited

OTHER PUBLICATIONS

Jia et al., "The T helper type 17/regulatory T cell imbalance in patients with acute Kawasaki disease," 162 Clin. Exp. Immunol. 131-37 (2010).
Jin et al., "Structural Basis for Hydroxycholesterols as Natural Ligands of Orphans Nuclear Receptor RORγ," 24(5) Mol. Endocrinol. 923-29 (2010).
Kastelein et al., "Discovery and Biology of IL-23 and IL-27: Related but Functionally Distinct Regulators of Inflammation," 25 Annu. Rev. Immunol. 221-42 (2007).
Kurebayashi et al., "Selective LXXLL peptides antagonize transcriptional activation by the retinoid-related orphan receptor RORγ," 315 Biochem. Biophys. Res. Comm. 919-27 (2004).
Louten et al., "Development and function of TH17 cells in health and disease," 123(5) J. Allergy Clin. Immunol. 1004-11 (2009).
Miossec et al., "Interleukin-17 and Type 17 Helper T Cells," 361(9) New Eng. J. Med. 888-98 (2009).
Sun et al., "Requirement for RORγ in Thymocyte Survival and Lymphoid Organ Development," 288 Science 2369-72 (2000).
Sutton et al., "Interleukin-1 and IL-23 Induce Innate IL-17 Production from γδ T Cells, Amplifying Th17 Responses and Autoimmunity," 31 Immunity 331-41 (2009).
Wang et al., "Identification of SR1078, a Synthetic Agonist for the Orphan Nuclear Receptors RORα and RORγ," 5(11) ACS Chem. Biol. 1029-34 (2010).
Wang et al., "Modulation of Retinoic Acid Receptor-related Orphan Receptor α and γ Activity by 7-Oxygenated Sterol Ligands," 285(7) J. Bio. Chem. 5013-25 (2010).
Xie et al., "RORγt Recruits Steroid Receptor Coactivators to Ensure Thymocyte Survival," 175(6) J. Immunol. 3800-09 (2005).
Yang et al., "T Helper 17 Lineage Differentiation is programmed by Orphan Nuclear Receptors RORα and RORγ," 28 Immunity 29-39 (2008).
André et al., "Disruption of retinoid-related orphan receptor β changes circadian behaviour, causes retinal degeneration and leads to vacillans phenotype in mice," 17(14) The EMBO J. 3867-77 (1998).
Becker-André et al., "Identification of nuclear receptor mRNAs by RT-PCR amplification of conserved zinc-finger motif sequences," 194(3) Biochem. Biophys. Res. Comm. 1371-79 (1993).
Burris et al., "Targeting Orphan Nuclear Receptors for Treatment of Metabolic Diseases and Autoimmunity," 19(1) Chem. Biol. 51-59 (2012).
Cai, et al., "Pivotal Role of Dermal IL-17-Producing γδ T Cells in Skin Inflammation", Immunity (2011) vol. 35, pp. 596-610.
Carlberg et al., "RZRs, a new family of retinoid-related orphan receptors that function as both monomers and homodimers," 8 Mol. Endocrinol. 757-70 (1994).
D. van der Heijde, et al., "Secukinumab Provides Significant and Sustained Inhibition of Joint Structural Damage in a Phase III Study of Active Psoriatic Arthritis" Arthritis & Rheumatology Brief Report, Accepted Article DOI: 10.1002/art.39685, American College of Rheumatology, (2016) pp. 1-27.
Baeten, et al., "Secukinumab, an Interleukin-17A Inhibitor, in Ankylosing Spondylitis", The New England Journal of Medicine, (2015) vol. 373, pp. 2534-2548.
Dussault et al., "Orphan nuclear receptor RORα-deficient mice display the cerebellar defects of staggerer," 70 Mech. Develop. 147-53 (1998).
Giguère et al., "Isoform-specific amino-terminal domains dictate DNA-binding properties of RORα, a novel family of orphan hormone nuclear receptors," 8 Genes & Develop. 538-53 (1994).
Huh et al., "Small molecule inhibitors of RORγt: Targeting Th17 cells and other applications," 42 Eur. J. Immunol. 2232-2237 (2012).
Krueger, "A welcome surprise in psoriasis", Nature Medicine, (2012) vol. 18, No. 12, pp. 1750-1751.
Leonardi, et al., "Anti-Interleukin-17 Monoclonal Antibody Ixekizumab in Chronic Plaque Psoriasis", The New England Journal of Medicine, (2012) vol. 366, Iss. 13, pp. 1-10.

Martinez, "Th17-biased RORγt transgenic mice become susceptible to a viral model for multiple sclerosis", Brain, Behavior, and Immunity, (2014) vol. 43, pp. 86-97.
Medvedev et al., "Cloning of a cDNA encoding the murine orphan receptor RZR/RORγ and characterization of its response element," 181 Gene 199-206 (1996).
Nakajima, et al., "IL-17A as an Inducer for Th2 Immune Responses in Murine Atopic Dermatitis Models", Journal of Investigative Dermatology, (2014) vol. 134, pp. 2122-2130.
Ortiz et al., "TOR: a new orphan receptor expressed in the thymus that can modulate retinoid and thyroid hormone signals," 9 Mol. Endocrinol. 1679-91 (1995).
Papp, et al. "Brodalumab, an Anti-Interleukin-17-Receptor Antibody for Psoriasis", The New England Journal of Medicine, (2012) vol. 366, Iss. 13, 9 pgs.
Skepner, et al., "Pharmacologic Inhibition of RORγt Regulates Th17 Signature Gene Expression and Suppresses Cutaneous Inflammation in Vivo", The Journal of Immunology, (2014) pp. 1-12.
Smith, "The Bench-to-Bedside Story of IL-17 and the Therapeutic Efficacy of its Targeting in Spondyloarthritis", Curr. Rheumatol. Rep. (2016) vol. 18, pp. 1-10.
Solt et al., "Action of RORs and their ligands in (patho)physiology," 23(12) Trends in Endocrinology and Metabolism. 619-627 (2012).
Tlustochowicz, et al. "Efficacy and Safety of Subcutaneous and Intravenous Loading Dose Regimens of Secukinumab in Patients with Active Rheumatoid Arthritis: Results from a Randomized Phase II Study" The Journal of Rheumatology, (2016) vol. 43, No. 3, pp. 495-503.
Villey et al., "RORγT, a thymus-specific isoform of the orphan nuclear receptor RORγ/TOR, is up-regulated by signaling through the pre-T cell receptor and binds to the TEA promoter," 29 Eur. J. Immunol. 4072-80 (1999).
Wiesenberg et al., "Transcriptional activation of the nuclear receptor RZRα by the pineal gland hormone melatonin and identification of CGP 52608 as a synthetic ligand," 23(3) Nucl. Acids Res. 327-33 (1995).
Xiao, et al., "Small-Molecule RORγt Antagonists Inhibit T Helper 17 Cell Transcriptional Network by Divergent Mechanisms", Immunity (2014) vol. 40, pp. 477-489.
Arisawa et al., "Development of Isomerization and Cycloisomerization with Use of a Ruthenium Hydride with N-Heterocyclic Carbene and Its Application to the Synthesis of Heterocycles," 71 J. Org. Chem. 4255-61 (2006).
Berge et al., "Pharmaceutical salts," 66(1) J. Pharm. Sci. 1-19 (1977).
Bhagawanth et al., "Room-Temperature Pd-Catalyzed Amidation of Aryl Bromides Using tert-Butyl Carbamate," 74 J. Org. Chem. 4634-37 (2009).
Boger et al., "Regiocontrolled Nucleophilic Addition to Selectively Activated p-Quinone Diimines: Alternative Preparation of a Key Intermediate Employed in the Preparation of the CC-1065 Lefthand Subunit," 55 J. Org. Chem. 1379-90 (1990).
Carroll et al., "Synthesis, Nicotinic Acetylcholine Receptor Binding, and Antinociceptive Properties of 2-exo-2-(2',3'-Disubstituted 5'-pyridinyl)-y-azabicyclo[2.2.1]heptanes: Epibatidine Analogues," 45 J. Med. Chem. 4755-61 (2002).
Chang et al., "7-Aroyl-aminoindoline-1-sulfonamides as a Novel Class of Potent Antitubulin Agents," 49 J. Med. Chem. 6656-59 (2006).
Colbon et al., "Double Arylation of Allyl Alcohol via a One-Pot Heck Arylation-Isomerization-Acylation Cascade," 13 Org. Lett. 5456-59 (2011).
De et al., Methods in Molecular Biology 1184, second edition, Human Press (2014).
Gould, "Salt selection for basic drugs," 33 Int'l J. Pharmaceutics 201-217 (1986).
Grasa et al., "Amination Reactions of Aryl Halides with Nitrogen-Containing Reagents Mediated by Palladium/Imidazolium Salt Systems," 66 J. Org. Chem. 7729-37 (2001).
Greene & Wuts, Protective Groups in Organic Synthesis, 2d Edition (1991).

(56) References Cited

OTHER PUBLICATIONS

Guimond et al., "Rhodium(III)-Catalyzed Isoquinolone Synthesis: The N—O Bond as a Handle for C—N Bond Formation and Catalyst Turnover," 132(20) J. Am. Chem. Soc. 6908-09 (2010).
Hanessian et al., "A versatile protocol for the stereocontrolled elaboration of vicinal secondary and tertiary centers of relevance to natural product synthesis," 52(6) J. Org. Chem. 1170-72 (1987).
Hauser et al., "Relative Ease of Cyclization of 2-, 3-, and 4-Aminopyridine Derivatives. Synthesis of Naphthyridines," 15 J. Org. Chem. 1224-32 (1950).
International Search Report and Written Opinion for PCT/US2011/059788 dated May 23, 2012 (23 pages).
International Search Report and Written Opinion for PCT/US2013/039422 dated Oct. 11, 2013 (9 pages).
International Search Report and Written Opinion for PCT/US2013/039839 dated Oct. 18, 2013 (8 pages).
International Search Report and Written Opinion for PCT/US2013/040085 dated Oct. 23, 2013 (9 pages).
Ishikura et al., "An Efficient Synthesis of 3-Heteroarylpyridines via Diethyl-(3-pyridyl)-borane," Synthesis 936-38 (1984).
Jayashree et al., "Design and synthesis of 2-quinolones as antioxidants and antimicrobials: a rational approach," 19 Med. Chem. Res. 193-209 (2010).
Jiang et al., "Synthesis and Cytotoxicity Evaluation of Novel Indolylpyrimidines and Indolylpyrazines as Potential Antitumor Agents," 9 Bioorg. Med. Chem. 1149-54 (2001).
Li et al., "Chemical Libraries via Sequential C—H Functionalization of Phenols," 10 J. Comb. Chem. 170-74 (2008).
Li et al., "Synthesis and Resolution of a Novel Chiral Diamine Ligand and Application to Asymmetric Lithiation-Substitution," 2 Org. Lett. 875-78 (2000).
Liu et al., "1-Sulfonylindazoles as potent and selective 5-HT6 ligands," 19 Bioorg. Med. Chem. Lett. 2413-15 (2009).
Murase et al., "A New Concise Synthesis of Arcyriacyanin A and Its Unique Inhibitory Activity against a Panel of Human Cancer Cell Line," 48(1) Chem. Pharm. Bull. 81-84 (2000).
Ninomiya et al., "Phosphorous in Organic Synthesis—VII: Diphenyl Phosphorazidate (DPPA). A New Convenient Reagent for a Modified Curtius Reaction," 30 Tetrahedron 2151-57 (1975).
Nyrkova et al., "Synthesis of a New Heterocyclic System—3,4-Diazaphenoxazine," 1(9) J. Org. Chem. USSR, 1711-14, translating 1(9) Zh. Org. Khimii, 1688-91 (1965).
Santilli et al., "Synthesis of 5,6,7,8-Tetrahydro-5-oxopyrido[2,3-d]pyrimidine-6-carbonitriles and -6-carboxylic Acid Esters," 12 J. Het. Chem. 311-16 (1975).
Skraup, "Eine Synthese des Chinolins," 13 Berichte 2086-87 (1880).
Stefko et al., "General and Modular Synthesis of Isomeric 5-Substituted Pyridin-2-yl and 6-Substituted Pyridin-3-yl C-Ribonucleosides Bearing Diverse Alkyl, Aryl, Hetaryl, Amino, Carbamoyl, and Hydroxy Groups," 76 J. Org. Chem. 6619-35 (2011).
STN Columbus, pp. 1-40 (2011).
Takano et al., "A new synthesis of a steroid side chain via stereocontrolled protonation: synthesis of (−)-desmosterol," 14 J. Chem. Soc., Chem. Commun. 760-61 (1983).
van Heerden et al., "Dibutylboron triflate promoted conjugate addition of benzylic and allylic organocopper reagents to chiral α,β-unsaturated N-acyl imidazolidinones" 38(10) Tet. Lett. 182-124 (1997).
Wang et al., "Synthesis of new carbon-11-labeled 7-aroyl-aminoindoline-1-sulfonamides as potential PET agents for imaging of tubulin polymerization in cancers," 51(1) J. Label. Compd. Radiopharm. 6-11 (2008).
Yeh et al., "Practical Cu-catalyzed amination of functionalized heteroaryl halides," 47(34) Tetrahedron Lett. 6011-16 (2006).
Zhu et al., "The Direct Formulation of Functionalized Alkyl(aryl)zinc halides by Oxidative Addition of Highly Reactive Zinc with Organic Halides and Their Reactions with Acid Chlorides, α,β-Unsaturated Ketones, and Allylic, Aryl, and Vinyl Halides," 56 J. Org. Chem. 1445-53 (1991).
International Search Report and Written Opinion for PCT/US2014/071656 dated Mar. 12, 2015 (8 pages).
U.S. Appl. No. 15/587,934, filed May 5, 2017, Tetrahydronaphthyridine and Related Bicyclic Compounds for Inhibition of RORgamma Activity and the Treatment of Disease.
U.S. Appl. No. 15/103,414, filed Jun. 10, 2016, Tetrahydronaphthyridine, Benzoxazine, Aza-Benzoxazine and Related Bicyclic Compounds for Inhibition of RORgamma Activity and the Treatment of Disease.

* cited by examiner

CARBAMATE BENZOXAZINE PROPIONIC ACIDS AND ACID DERIVATIVES FOR MODULATION OF RORGAMMA ACTIVITY AND THE TREATMENT OF DISEASE

CROSS-REFERENCE TO RELATED APPLICATIONS

This application is the national stage of International (PCT) Patent Application Serial No. PCT/US2014/071663, filed Dec. 19, 2014 which claims the benefit of and priority to U.S. Provisional Patent Application Ser. No. 61/918,948, filed Dec. 20, 2013, the contents of each of which are hereby incorporated by reference in their entirety.

FIELD OF THE INVENTION

The present invention relates to certain benzoxazine compounds of the Formula (I) (also referred to herein as the "compounds of the Formula (I)" or "compounds of Formula (I)") which are antagonists of a Thymocyte/T cell specific variant of Retinoic Acid Receptor-related Orphan Receptor (ROR), RORgammaT. The present invention also provides compositions comprising such compounds, and methods of using such compounds for treating conditions or disorders associated with inappropriate RORgammaT activity, in particular in the treatment and prevention of disease states mediated by RORgammaT. Such disease states may include immune and inflammatory disorders such as rheumatoid arthritis, psoriasis, multiple sclerosis, inflammatory bowel disease, and asthma.

BACKGROUND OF THE INVENTION

Upon activation by antigen-presenting cells, naïve T helper cells undergo clonal expansion and will ultimately differentiate into cytokine secreting effector T cells, such as Th1 and Th2 subtypes. A third and distinct effector subset has been identified, which plays a key role in providing immunity to bacteria and fungi at mucosal surfaces (Kastelein et al., *Annu. Rev. Immunol.* 25: 221-242, 2007). This effector T helper cell subset can be distinguished based on its ability to produce large quantities of IL-17/F, IL-21 and IL-22, and is named Th17 (Miossec et al., *New Eng. J. Med.* 361: 888-898, 2009).

Different T helper subsets are characterized by the expression of lineage specific master transcription factors. Th1 and Th2 effector cells express Tbet and GATA3, respectively. A Thymocyte/T cell specific variant of Retinoic Acid Receptor-related Orphan Receptor (ROR), RORgammaT, is highly expressed in Th17 cells (He et al., *Immunity* 9: 797-806, 1998). RORgammaT belongs to the nuclear hormone receptor superfamily (Hirose et al., *Biochem. Biophys. Res. Comm.* 205:1976-1983, 1994). RORgammaT is a truncated form of RORgamma, lacking the first N-terminal 21 amino acids and is, in contrast to RORgamma which is expressed in multiple tissues (heart, brain, kidney, lung, liver, and muscle), exclusively expressed in cells of the lymphoid lineage and embryonic lymphoid tissue inducers (Sun et al., *Science* 288: 2369-2372, 2000; Eberl et al., *Nat Immunol.* 5: 64-73, 2004).

Studies using heterozygous knock-in mice replacing the RORgammaT open reading frame with GFP (green fluorescent protein) revealed a constitutive expression of GFP in approximately 10% of the CD4+ T cells in the small intestinal lamina propria (LP), co-expressing the Th17 cytokines IL-17/F and IL-22 (Ivanov et al., *Cell* 126: 1121-1133, 2006). In mice deficient for RORgammaT, the number of Th17 cells was markedly decreased in the LP; and in vitro stimulation of CD4+ T cells under Th17 polarizing conditions resulted in a drastic decrease of IL-17 expression. These results were further substantiated via forced expression of RORgammaT in naïve CD4+ T cells, which resulted in an induction of IL-17/F and IL-22 (Ivanov et al., *Cell* 126: 1121-1133, 2006). The foregoing studies demonstrate the importance of RORgammaT in differentiation and stabilization of the Th17 lineage. In addition, a ROR family member, RORalpha, has been demonstrated to be involved in Th17 differentiation and stabilization (Yang et al., *Immunity* 28: 29-39, 2008).

Recently, RORgammaT was shown to play a crucial role in non-Th17 lymphoid cells. In these studies, RORgammaT was critically important in innate lymphoid cells expressing Thy1, SCA-1, and IL-23R proteins. Genetic disruption of RORgamma in a mouse colitis model dependent on these innate lymphoid cells prevented colitis development (Buonocore et al., *Nature* 464:1371-1375, 2010). In addition, RORgammaT was shown to play a crucial role in other non-Th17 cells, such as mast cells (Hueber et al., *J. Immunol.* 184: 3336-3340, 2010). Finally, RORgammaT expression and secretion of Th17-type of cytokines was reported for Lymphoid Tissue Inducer cells, NK T-cells, NK cells (Eberl et al., *Nat. Immunol.* 5: 64-73, 2004) and gamma-delta T-cells (Sutton et al., *Immunity* 31: 331-341, 2009; Louten et al., *J. Allergy Clin. Immunol.* 123:1004-1011, 2009), suggesting an important function for RORgammaT in these subtypes of cells.

Based on the role of IL-17 producing cells (either Th17 or non-Th17 cells) RORgammaT has been identified as a key mediator in the pathogenesis of several diseases (Louten et al., *J. Allergy Clin. Immunol.* 123:1004-1011, 2009; Annunziato et al., *Nat. Rev. Rheumatol.* 5: 325-331, 2009). This was confirmed using several disease models representative of autoimmune diseases. Genetic ablation of the RORgamma gene in mice prevented the development of experimental autoimmune diseases, such as experimental autoimmune encephalomyelitis (EAE) and colitis (Ivanov et al., *Cell* 126:1121-33, 2006; Buonocore et al., *Nature* 464:1371-1375, 2010).

With RORgammaT being a critical mediator in Th17-cells and non-Th17 cells, antagonism of the transcriptional activity of RORgammaT is expected to have a beneficial effect on autoimmune diseases, such as but not limited to rheumatoid arthritis, psoriasis, multiple sclerosis, inflammatory bowel disease (e.g., Crohn's disease, ulcerative colitis), and asthma (Annunziato et al., *Nat. Rev. Rheumatol.* 5: 325-331, 2009; Louten et al., *J. Allergy Clin. Immunol.* 123:1004-1011, 2009). Antagonism of RORgammaT may also be beneficial in other diseases that are characterized by increased levels of Th17 cells and/or elevated levels of Th17 hallmark cytokines such as IL-17, IL-22 and IL-23. Examples of such diseases are Kawasaki Disease (Jia et al., *Clin. Exp. Immunol.* 162:131-137, 2010) and Hashimoto's thyroiditis (Figueroa-Vega et al., *J. Clin. Endocrinol. Metab.* 95: 953-62, 2010). Another example includes infectious diseases, such as but not limited to mucosal leishmaniasis (Boaventura et al., *Eur. J. Immunol.* 40: 2830-2836, 2010). In each of the above examples the inhibition may be enhanced by simultaneous inhibition of RORalpha.

In another aspect, compounds of Formula (I) can be used in the treatment of cancer. Those skilled in the art will recognize the term "cancer" to be a name for diseases in which the body's cells become abnormal and divide without control. The term cancer includes, but is not limited to, colorectal, lung, and pancreatic cancer.

Compounds modulating RORgammaT have been reported. Examples of agonists include T0901317 and SR1078 (Wang et al., *ACS Chem. Biol.* 5:1029-1034, 2010). In addition, antagonists have been reported such as 7-oxygenated sterols (Wang et al., *J. Biol. Chem.* 285: 5013-5025, 2010) and the compounds described in EP 2181710 A1.

Numerous immune and inflammatory disorders continue to afflict millions of patients worldwide. Although significant advances have been made in treating these disorders, current therapies do not provide satisfactory results for all patients due to, for example, detrimental side effects or insufficient efficacy. One exemplary immune disorder in need of better therapy is psoriasis. Various therapeutics have been developed in an attempt to treat psoriasis. However, the traditional therapies for psoriasis often have toxic adverse effects. An exemplary inflammatory disorder in need of better treatment is rheumatoid arthritis. Numerous therapeutics have been developed in an attempt to treat this disorder. However, some patients develop resistance to current therapies.

Accordingly, a need exists for improved treatments for immune disorders and inflammatory disorders. The present invention addresses this need and provides other related advantages.

SUMMARY OF THE INVENTION

The present invention provides compounds that alter the interaction of coregulator proteins with RORgammaT and thereby antagonize RORgammaT-mediated transcriptional activity; pharmaceutical compositions comprising such compounds and pharmaceutically acceptable excipients; and the use of such compounds or such pharmaceutical compositions for the treatment of RORgammaT-mediated diseases or conditions, in particular autoimmune diseases and inflammatory diseases.

DETAILED DESCRIPTION OF THE INVENTION

Definitions

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. If a chemical compound is referred to using both a chemical structure and a chemical name, and an ambiguity exists between the structure and the name, the structure predominates. These definitions apply regardless of whether a term is used by itself or in combination with other terms, unless otherwise indicated. Hence, the definition of "alkyl" applies to "alkyl" as well as the "alkyl" portions of "hydroxyalkyl," "fluoroalkyl," "—O-alkyl," etc.

As used herein, and throughout this disclosure, the following terms, unless otherwise indicated, shall be understood to have the following meanings:

A "patient" is a human or non-human mammal. In one embodiment, a patient is a human. In another embodiment, a patient is a chimpanzee.

The term "therapeutically effective amount" as used herein refers to an amount of the compound of Formula (I) and/or an additional therapeutic agent, or a composition thereof that is effective in producing the desired therapeutic, ameliorative, inhibitory, or preventative effect when administered to a patient suffering from a disease or condition mediated by RORgammaT. In the combination therapies of the present invention, a therapeutically effective amount can refer to each individual agent or to the combination as a whole, wherein the amounts of all agents administered are together effective, but wherein the component agent of the combination may not be present individually in an effective amount.

The term "preventing," as used herein with respect to an inflammatory disease or disorder, refers to reducing the likelihood of an autoimmune or inflammatory disease or disorder.

The term "alkyl," as used herein, refers to an aliphatic hydrocarbon group having one of its hydrogen atoms replaced with a bond having the specified number of carbon atoms. In different embodiments, an alkyl group contains from 1 to 6 carbon atoms ($C_1$-$C_6$ alkyl) or from 1 to 3 carbon atoms ($C_1$-$C_3$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl, and neohexyl. In one embodiment, an alkyl group is linear. In another embodiment, an alkyl group is branched.

The term "fluoroalkyl," as used herein, refers to an alkyl group as defined above, wherein one or more of the alkyl group's hydrogen atoms has been replaced with a fluorine. In one embodiment, a fluoroalkyl group has from 1 to 6 carbon atoms. In another embodiment, a fluoroalkyl group has from 1 to 3 carbon atoms. In another embodiment, a fluoroalkyl group is substituted with from 1 to 3 fluorine atoms. Non-limiting examples of fluoroalkyl groups include —$CH_2F$, —$CHF_2$, and —$CF_3$. The term "$C_1$-$C_3$ fluoroalkyl" refers to a fluoroalkyl group having from 1 to 3 carbon atoms.

The term "alkylene," as used herein, refers to an alkyl group, as defined above, wherein one of the alkyl group's hydrogen atoms has been replaced with a bond. Non-limiting examples of alkylene groups include —$CH_2$—, —$CH_2CH_2$—, —$CH_2CH_2CH_2$—, —$CH_2CH_2CH_2CH_2$—, —$CH(CH_3)CH_2CH_2$—, —$CH(CH_3)$—, and —$CH_2CH(CH_3)CH_2$—. In one embodiment, an alkylene group has from 1 to about 6 carbon atoms ($C_1$-$C_6$ alkylene). In another embodiment, an alkylene group has from 1 to 3 carbon atoms ($C_1$-$C_3$ alkylene). In another embodiment, an alkylene group is branched. In another embodiment, an alkylene group is linear. In one embodiment, an alkylene group is —$CH_2$—. The term "$C_1$-$C_3$ alkylene" refers to an alkylene group having from 1 to 3 carbon atoms. Unless otherwise indicated, an alkylene group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to 4 carbon atoms. Non-limiting examples of alkenyl groups include ethenyl, propenyl, n-butenyl, 3-methylbut-2-enyl, n-pentenyl, octenyl, and decenyl. The term "$C_2$-$C_6$ alkenyl" refers to an alkenyl group having from 2 to 6 carbon atoms. The term "$C_2$-$C_4$ alkenyl" refers to an alkenyl group having from 2 to 4 carbon atoms. Unless otherwise indicated, an alkenyl group is unsubstituted.

The term "alkoxy," as used herein, refers to an —O-alkyl group, wherein an alkyl group is as defined above. Non-limiting examples of alkoxy groups include methoxy, ethoxy, n-propoxy, isopropoxy, n-butoxy, and tert-butoxy. An alkoxy group is bonded via its oxygen atom to the rest of the molecule.

The term "aryl," as used herein, refers to an aromatic monocyclic or multicyclic ring system comprising from about 6 to about 14 carbon atoms. In one embodiment, an aryl group contains from about 6 to 10 carbon atoms ($C_6$-$C_{10}$ aryl). In another embodiment an aryl group is phenyl. Non-limiting examples of aryl groups include phenyl and naphthyl.

The term "carbocycle," as used herein, refers to a fully saturated, partially unsaturated, or an aromatic monocyclic or multicyclic ring system comprising from about 6 to 14 carbon atoms. In one embodiment, an aryl group contains from 3 to 10 carbon atoms ($C_3$-$C_{10}$ carbocycle). Non-limiting examples of carbocyclic groups include cycloalkyl and aryl groups, as defined herein. In specific embodiments, the carbocyclic groups are selected from cyclopropyl, cyclobutyl, cyclopentyl, cyclohexyl, phenyl, indanyl, naphthyl, and tetrahydronaphthyl.

The term "cycloalkyl," as used herein, refers to a saturated ring containing the specified number of ring carbon atoms, and no heteroatom. In a like manner the term "$C_3$-$C_6$ cycloalkyl" refers to a saturated ring having from 3 to 6 ring carbon atoms. Non-limiting examples of monocyclic cycloalkyls include cyclopropyl, cyclobutyl, cyclopentyl, and cyclohexyl.

The term "halo," as used herein, means —F, —Cl, —Br or —I. In one embodiment, a halo group is —F or —Cl. In another embodiment, a halo group is —F.

"Heterocyclyl" refers to a 4-, 5-, 6-, or 7-membered monocyclic ring or 8-, 9-, or 10-membered bicyclic ring, or 13- or 14-membered tricyclic ring, saturated, unsaturated or aromatic, containing 1, 2, 3, or 4 heteroatoms selected from O, N, or S, and the heterocyclyl may optionally be substituted with one to four substituents. The nitrogen or sulfur atom of the heterocyclyl can be optionally oxidized to the corresponding N-oxide, S-oxide, or S,S-dioxide. A heterocyclyl group can be joined to the rest of the molecule via a ring carbon or ring nitrogen atom. Representative heterocyclyls are as follows: azetidinyl, pyrrolidinyl, pyrrolyl, tetrahydrofuran, imidazolyl, imidazolinyl, 1,3-oxazolidinyl, 1,2-oxazolidinyl, isoxazolyl, 1,2,4-oxadiazolyl, 1,3,4-oxadiazolyl, tetrahydropyranyl, piperidinyl, piperazinyl, morpholinyl, pyrimidinyl, pyrrolopyrazine, pyrrolopyridine, and indolyl.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation from a reaction mixture to a useful degree of purity, and formulation into an efficacious therapeutic agent.

When any substituent or variable occurs more than one time in any constituent or in the compound of Formula (I), its definition on each occurrence is independent of its definition at every other occurrence, unless otherwise indicated.

When an integer defining the presence of a certain number of atoms in a group is equal to zero, it means that the atoms adjacent thereto are connected directly by a bond; for example, in the structure

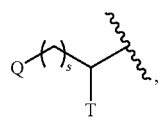

wherein s is an integer equal to zero, 1 or 2, the structure is

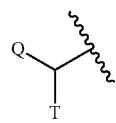

when s is zero; or it means that the indicated atom is absent; for example, —S(O)$_0$— means —S—.

The term "in purified form," as used herein, refers to the physical state of a compound after the compound has been isolated through a synthetic process (e.g., from a reaction mixture), from a natural source, or a combination thereof. The term "in purified form" also refers to the physical state of a compound after the compound has been obtained from a purification process or processes described herein or well-known to the skilled artisan (e.g., chromatography, recrystallization, and the like), in sufficient purity to be characterizable by standard analytical techniques described herein or well-known to the skilled artisan.

It should also be noted that any carbon as well as heteroatom with unsatisfied valences in the text, schemes, examples, and tables herein is assumed to have the sufficient number of hydrogen atom(s) to satisfy the valences.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves various degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula (I) may contain one or more stereogenic centers and can thus occur as racemates, racemic mixtures, single enantiomers, diastereomeric mixtures, and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Any formulas, structures, or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers, and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention.

All stereoisomers (for example, geometric isomers, optical isomers, and the like) of the present compounds (including stereoisomers of salts and solvates of the present compounds as well as stereoisomers of salts, solvates, and esters of prodrugs of the present compounds), such as those that may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

It is also noted that the compounds of Formula (I) can be chemically modified to yield prodrugs of the compounds of the compounds of Formula (I). For example, a carboxylic acid moiety present on $R^3$ of the compounds of Formula (I) can be reacted to prepare esters with certain moieties. Such prodrugs of the compounds of Formula (I) can transform in vivo to yield a compound of Formula (I). The transformation may occur by various mechanisms (e.g., by metabolic or chemical processes), such as, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The compounds of Formula (I) can form salts which are also within the scope of this invention. Reference to a compound of Formula (I) herein is understood to include reference to salts thereof, unless otherwise indicated. The term "salt(s)," as employed herein, denotes acidic salts formed with inorganic and/or organic acids, as well as basic salts formed with inorganic and/or organic bases. In addition, when a compound of Formula (I) contains both a basic moiety, such as but not limited to a pyridine or imidazole, and an acidic moiety, such as but not limited to a carboxylic acid, zwitterions ("inner salts") may be formed and are included within the term "salt(s)" as used herein. Such acidic and basic salts used within the scope of the invention are pharmaceutically acceptable (i.e., non-toxic, physiologically acceptable) salts. Salts of the compounds of Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids that are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine, and the like. Basic nitrogen-containing groups may be quaternized with agents such as lower alkyl halides (e.g., methyl, ethyl, and butyl chlorides, bromides, and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

The present invention further includes the compounds of Formula (I) in all their isolated forms. For example, the above-identified compounds are intended to encompass all forms of the compounds, such as any solvates, hydrates, stereoisomers, and tautomers thereof.

As used herein, the term "composition" is intended to encompass a product comprising the specified ingredients in the specified amounts, as well as any product that results, directly or indirectly, from combination of the specified ingredients in the specified amounts.

In the compounds of generic Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula (I). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. In light of the present disclosure, isotopically-enriched compounds within generic Formula (I) can be prepared without undue experimentation by conventional techniques well known to those skilled in the art or by processes analogous to those described in the examples herein using appropriate isotopically-enriched reagents and/or intermediates.

Compounds of the Invention

The present invention provides a compound of Formula (I) or a pharmaceutically acceptable salt thereof, wherein $R^1$, $R^2$, $R^{a1}$, $R^{a2}$, $R^{b1}$, $R^{b2}$, $R^c$, $R^d$, and Cy are as defined below. Described below are embodiments of the compound of Formula (I). The compounds of the Formulas (IA), (IB), and (IC), shown below, are embodiments of the compound of Formula (I).

In embodiment no. 1, the invention provides a compound of Formula (I), $$\text{(I)}$$

[chemical structure]

or a pharmaceutically acceptable salt thereof, wherein:
$R^1$ is H or $C_1$-$C_3$ alkyl,
$R^2$ is H, $C_1$-$C_3$ alkyl, or halo;
$R^{a1}$ and $R^{a2}$ are independently H, $C_1$-$C_3$ alkyl, trifluoromethyl, or cyclopropyl;
$R^{b1}$ and $R^{b2}$ are independently H, $C_1$-$C_3$ alkyl, trifluoromethyl, hydroxyl, hydroxymethyl, or cyclopropyl;
alternatively:
    (a.) $R^{a1}$ and $R^{b1}$ together with the carbon atoms to which they are attached form a $C_3$-$C_6$ cycloalkyl ring;
    (b.) $R^{a1}$ and $R^{b1}$ together form a second bond; or
    (c.) $R^{b1}$ and $R^{b2}$ together with the carbon atoms to which they are attached form a $C_3$-$C_6$ cycloalkyl ring;
$R^c$ is
    (a.) H or
    (b.) $C_1$-$C_6$ alkyl;
$R^d$ is
    (a.) $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl;
    (b.) $C_2$-$C_8$ alkenyl, wherein said $C_2$-$C_8$ alkenyl of $R^d$ is unsubstituted or independently substituted by 1 to 6 fluoro or cyano;
    (c.) a group of the formula -M-$R^{CH}$;
M is
    (i.) a bond; or
    (ii.) $C_1$-$C_6$ alkylene, wherein said $C_1$-$C_6$ alkylene of M is unsubstituted or substituted by 1 to 6 fluoro;
$R^{CH}$ is a ring selected from the group consisting of
    (i.) $C_3$-$C_9$ mono- or bicycloalkyl;
    (ii.) phenyl; and
    (iii.) a 3- to 6-membered heterocyclyl, wherein said heterocyclyl of $R^{CH}$ contains 1 to 2 heteroatoms independently selected from the group consisting of N, O, and S;
wherein $R^{CH}$ is unsubstituted or independently substituted by 1 to 4 halo, $C_1$-$C_3$ alkyl, $C_1$-$C_3$ trifluoroalkyl, cyano, $C_1$-$C_4$ alkylcarbonylamino, or oxo;
Cy is
    (a.) phenyl;
    (b.) a 5- to 7-membered, monocyclic heterocyclyl containing 1 to 3 heteroatoms independently selected from the group consisting of N, O, and S; or
    (c.) $C_3$-$C_6$ cycloalkyl;

wherein Cy is unsubstituted or independently substituted by 1 to 4 $R^k$ moieties selected from the group consisting of:
    (i.) $C_1$-$C_6$ alkyl, wherein said $C_1$-$C_6$ alkyl is unsubstituted or independently substituted by 1 to 3 hydroxy or fluoro;
    (ii.) $C_1$-$C_6$ alkoxy, wherein said $C_1$-$C_6$ alkoxy is unsubstituted or independently substituted by 1 to 3 fluoro, hydroxy, methoxy, or phenyl;
    (iii.) —N($R^e$)$_2$;
    (iv.) —O(CH$_2$)$_{n1}$C(O)N($R^e$)$_2$;
    (v.) —O(CH$_2$)$_{n2}$CO$_2$$R^f$;
    (vi.) hydroxyl;
    (vii.) oxo;
    (viii.) halo;
    (ix.) $C_1$-$C_3$ alkylsulfonyl;
    (x.) cyano;
    (xi.) oxetanyl;
    (xii.) cyclopropyl; and
    (xiii.) —SF$_5$;
or alternatively, two $R^k$ moieties, when substituted on adjacent ring atoms of Cy, form a second ring, wherein said second ring is a 5- to 7-membered saturated, partially saturated, or aromatic ring system that contains 0, 1, or 2 heteroatoms independently selected from the group consisting of N, O, and S; wherein said second ring is unsubstituted or substituted by 1 to 3 $R^k$ moieties independently selected from (i)-(xiii);
each $R^e$ is independently H or $C_1$-$C_3$ alkyl,
$R^f$ is H or $C_1$-$C_3$ alkyl;
the subscript n1 is 1, 2, or 3; and
the subscript n2 is 1, 2, or 3.

In embodiment no. 2, the invention provides a compound of Formula (I), wherein $R^{a1}$ and $R^{a2}$ are H, and the remaining variables are as set forth in embodiment no. 1.

In embodiment no. 3, the invention provides a compound of Formula (I), wherein wherein $R^{b1}$ is H, $R^{a1}$ and $R^{a2}$ are H, and the remaining variables are as set forth in embodiment no. 1.

In embodiment no. 4, the invention provides a compound of Formula (I), wherein $R^1$ is H, and the remaining variables are as set forth in embodiment no. 1.

In embodiment no. 5, the invention provides a compound of Formula (I), wherein $R^{a1}$ and $R^{b1}$ together with the carbon atoms to which they are attached form a $C_3$-$C_6$ cycloalkyl ring, such that the group

[chemical structure]

forms a group

[chemical structure]

wherein the subscript t1 is 1, 2, 3, or 4; and the remaining variables are as set forth in embodiment no. 1.

In embodiment no. 6, the invention provides a compound of Formula (I), wherein $R^{a1}$ and $R^{b1}$ form a second bond, such that the group

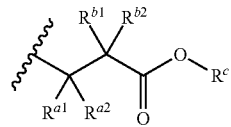

forms a group

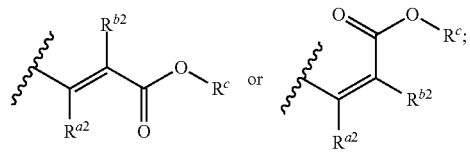

and the remaining variables are as set forth in embodiment no. 1.

In embodiment no. 7, the invention provides a compound of Formula (I), wherein $R^{b1}$ and $R^{b2}$ together with the carbon atoms to which they are attached form a $C_3$-$C_6$ cycloalkyl ring, such that the group

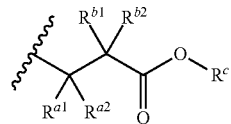

forms a group

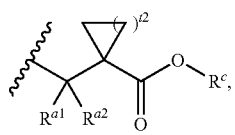

wherein the subscript t2 is 1, 2, 3, or 4; and the remaining variables are as set forth in embodiment no. 1.

In embodiment no. 8, the invention provides a compound of Formula (I), wherein $R^1$ is methyl, and the remaining variables are as set forth in embodiment no. 1.

In embodiment no. 9, the invention provides a compound of Formula (I), wherein $R^d$ is $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl.

In embodiment no. 10, the invention provides a compound of Formula (I), wherein $R^d$ is

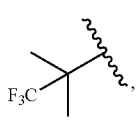

and the remaining variables are as set forth in embodiment no. 1.

In embodiment no. 11, the invention provides a compound of Formula (I) wherein Cy is a group of the formula

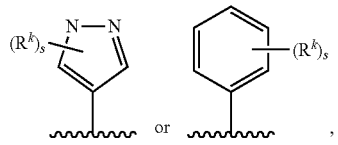

wherein the subscript s is 0, 1, 2, or 3, and the remaining variables are as set forth in embodiment no. 1.

In embodiment no. 12, the invention provides a compound of Formula (I), wherein $R^1$ is H or methyl;

$R^2$ is H or halo;

$R^{a1}$ and $R^{a2}$ are independently H or $C_1$-$C_3$ alkyl;

$R^{b1}$ and $R^{b2}$ are independently H or $C_1$-$C_3$ alkyl;

$R^c$ is H;

$R^d$ is $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl;

Cy is a group of the formula

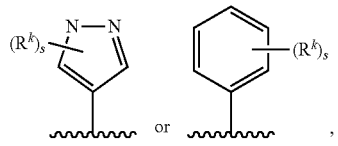

wherein the subscript s is 0, 1, 2, or 3; and $R^k$ is as set forth in embodiment no. 1.

In embodiment no. 13, the invention provides a compound of Formula (I) as set forth in any one of embodiments nos. 1-12, wherein the compound of Formula (I) has the Formula (IA)

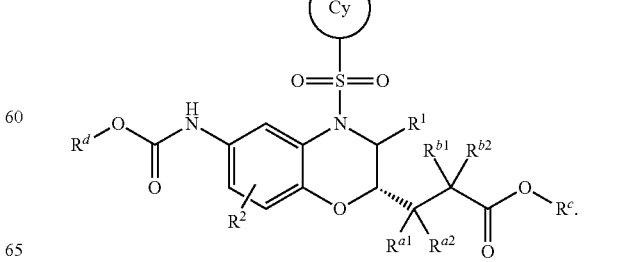

(IA)

In embodiment no. 14, the invention provides a compound of Formula (IB),

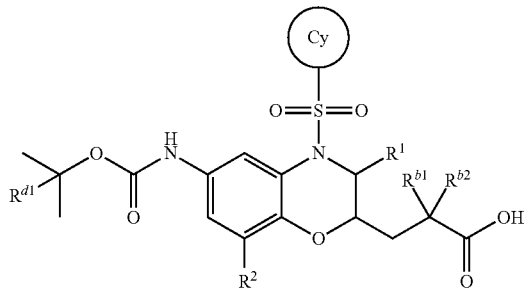
(IB)

wherein
Cy is

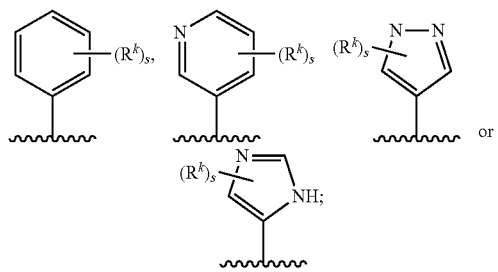
or $R^2$ is H or F;
the subscript s is 0, 1, 2, or 3;
$R^{b1}$ and $R^{b2}$ are independently H or $CH_3$;
$R^{d1}$ is $CH_3$, $CHF_2$, $CH_2F$, or $CF_3$; and
$R^k$ is as set forth in embodiment no. 1.

In embodiment no. 15, the invention provides a compound of Formula (IB), wherein each $R^k$ is independently:
(i.) $C_1$-$C_6$ alkyl, wherein said $C_1$-$C_6$ alkyl is unsubstituted or independently substituted by 1 to 3 hydroxy or fluoro;
(ii.) $C_1$-$C_6$ alkoxy, wherein said $C_1$-$C_6$ alkoxy is unsubstituted or independently substituted by 1 to 3 fluoro, hydroxy, methoxy, or phenyl;
(iii). a halo selected from fluoro or chloro; or
(iv.) cyano; or
alternatively, two $R^k$ moieties, when substituted on adjacent ring atoms of Cy, form said second ring, wherein said second ring is a 5- to 6-membered partially saturated or aromatic ring system that contains 0 or 1 N atom; wherein said second ring is unsubstituted or substituted by 1 to 2 $R^k$ moieties independently selected from (i)-(iv); and
the remaining variables are as set forth as in embodiment no. 14.

In embodiment no. 16, the invention provides a compound of Formula (IB), wherein Cy is:

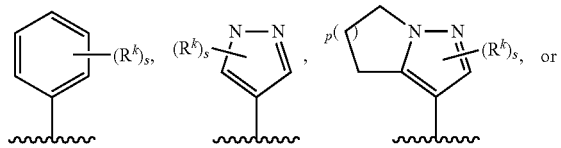
,

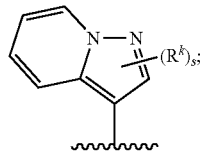

wherein
the subscript p is 1 or 2;
the subscript s is 0, 1, or 2;
$R^k$ is as set forth in embodiment no. 15; and
$R^2$ $R^{b1}$, $R^{b2}$, and $R^{d1}$ are as set forth in embodiment no. 14.

In embodiment no. 17, the invention provides a compound of Formula (IB) wherein Cy is

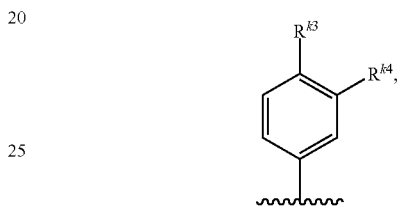

wherein $R^{k3}$ and $R^{k4}$ are independently F, Cl, $CF_3$, methyl, methoxy, cyclopropyl, or cyano; and
$R^2$ $R^{b1}$, $R^{b2}$, and $R^{d1}$ are as set forth in embodiment no. 14.

In embodiment no. 18, the invention provides a compound of Formula (IB) wherein Cy is

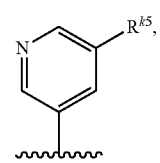

wherein $R^{k5}$ is F, Cl, $CF_3$, methyl, methoxy, cyclopropyl, or cyano; and
$R^2$ $R^{b1}$, $R^{b2}$, and $R^{d1}$ are as set forth in embodiment no. 14.

In embodiment no. 19, the invention provides a compound of Formula (IB) wherein Cy is

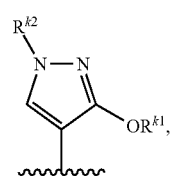

wherein
$R^{k1}$ is $C_1$-$C_6$ alkyl or $CH_2CH_2OH$;
$R^{k2}$ is $C_1$-$C_3$ alkyl or $CHF_2$; and
$R^2$ $R^{b1}$, $R^{b2}$, and $R^{d1}$ are as set forth in embodiment no. 14.

In embodiment no. 20, the invention provides a compound of Formula (IB) wherein Cy is

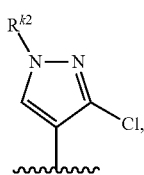

wherein $R^{k2}$ is $C_1$-$C_3$ alkyl or $CHF_2$; and
$R^2$ $R^{b1}$, $R^{b2}$, and $R^{d1}$ are as set forth in embodiment no. 14.

In embodiment no. 21, the invention provides a compound of Formula (IB) wherein Cy is

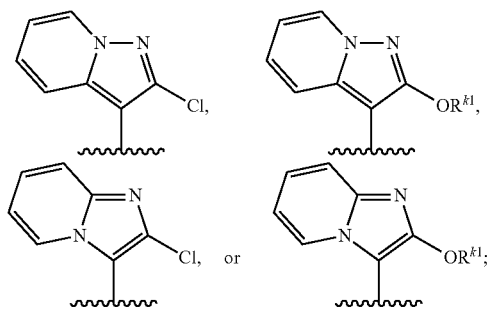

wherein
$R^{k1}$ is $C_1$-$C_6$ alkyl or $CH_2CH_2OH$; and
$R^2$ $R^{b1}$, $R^{b2}$, and $R^{d1}$ are as set forth in embodiment no. 14.

In embodiment no. 22, the invention provides a compound of Formula (IB) wherein $R^{d1}$ is $CF_3$; and
Cy, $R^2$ $R^{b1}$, $R^{b2}$, and $R^{d1}$ are as set forth in embodiment no. 14.

In embodiment no. 23, the invention provides a compound of Formula (IB) wherein $R^{d1}$ is $CF_3$; and
Cy is as set forth in any one of embodiment nos. 16, 17, 18, 19, 20, or 21; and
$R^2$ $R^{b1}$, $R^{b2}$, and $R^{d1}$ are as set forth in embodiment no. 14.

In embodiment no. 24, the invention provides a compound as set forth in any one of embodiment nos. 14-23, wherein the compound of Formula (IB) has the Formula (IC):

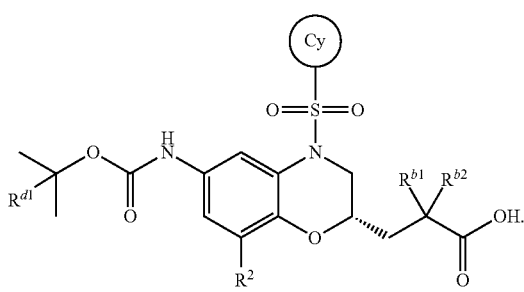

In embodiment no. 25, the invention provides a compound as set forth in embodiment no. 1, wherein
$R^{a1}$ and $R^{a2}$ are independently H, $C_1$-$C_3$ alkyl, or trifluoromethyl;
$R^{b1}$ and $R^{b2}$ are independently H, $C_1$-$C_3$ alkyl, trifluoromethyl, or hydroxyl;

alternatively:
(a.) $R^{a1}$ and $R^{b1}$ together with the carbon atoms to which they are attached form a $C_3$-$C_6$ cycloalkyl ring;
(b.) $R^{a1}$ and $R^{b1}$ together form a second bond; or
(c.) $R^{b1}$ and $R^{b2}$ together with the carbon atoms to which they are attached form a $C_3$-$C_6$ cycloalkyl ring; and
$R^k$ is selected from the group of moieties (i.)-(xii.) as set forth in embodiment no. 1,
or alternatively, two $R^k$ moieties, when substituted on adjacent ring atoms of Cy, form a second ring, wherein said second ring is a 5- to 7-membered saturated, partially saturated, or aromatic ring system that contains 0, 1, or 2 heteroatoms independently selected from the group consisting of N, O, and S; wherein said second ring is unsubstituted or substituted by 1 to 3 $R^k$ moieties independently selected from (i)-(xii).

In embodiment no. 26, the compound is selected from any one of the compounds described in Examples 1-30 (or a pharmaceutically acceptable salt thereof).

In embodiment no. 27, the compound is selected from any one of the following compounds (or a pharmaceutically acceptable salt thereof):

(S)-ethyl 3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate;

(S)-ethyl 3-(6-((tert-butoxycarbonyl)amino)-4-((4-fluoro-3-(trifluoromethyl)phenyl)sulfonyl)-3,4-dihydro-2H-benzo[b][1,4]oxazin-2-yl)propanoate;

(S)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-ethyl 3-(6-((tert-butoxycarbonyl)amino)-4-((4-fluoro-3-(trifluoromethyl)phenyl)sulfonyl)-3,4-dihydro-2H-benzo[b][1,4]oxazin-2-yl)propanoate;

(R)-ethyl 3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate;

(S)-ethyl 3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate;

(S)-ethyl 3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate;

(R)-ethyl 3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate;

(S)-ethyl 3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate;

(R)-ethyl 3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate;

(S)-ethyl 3-(4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate;

(S)-ethyl 3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate;

(S)-ethyl 3-(4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoate;

(S)-ethyl 3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoate (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-3-(4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(S)-3-(4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(R)-3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-3-(4-((3-cyanophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3,4-difluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-methoxy-5,6-dihydro-4H-pyrrolo[1,2-b]pyrazol-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(6-((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid;

(S)-3-(4-((3-(difluoromethoxy)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-(methylsulfonyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

(S)-3-(4-((2-methoxy-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-bromophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((1-(difluoromethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-chlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2,3-dihydrobenzofuran-5-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-5-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-6-chloroimidazo[2,1-b]thiazole;

(S)-3-(4-((2-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3,4-dichlorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-chloro-2-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chloro-4-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chloro-5-fluoro-2-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-2-((2-(2-carboxyethyl)-6-(((((1,1,1-trifluoro-2-methylpropan-2-yl)oxy)carbonyl)amino)-2H-benzo[b][1,4]oxazin-4(3H)-yl)sulfonyl)-5-chloropyridine;

(S)-3-(4-((4-chloro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((5-chloro-2-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-chloro-5-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-methoxy-5-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-methoxy-4-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-4-((2-(2-carboxyethyl)-6-(((((1,1,1-trifluoro-2-methylpropan-2-yl)oxy)carbonyl)amino)-2H-benzo[b][1,4]oxazin-4(3H)-yl)sulfonyl)-1-(2,2-difluoroethyl)-3-ethoxy-1H-pyrazole;

(S)-4-((2-(2-carboxyethyl)-6-(((((1,1,1-trifluoro-2-methylpropan-2-yl)oxy)carbonyl)amino)-2H-benzo[b][1,4]oxazin-4(3H)-yl)sulfonyl)-3-(2,2-difluoroethoxy)-1-ethyl-1H-pyrazole;

(S)-3-(4-((3-fluoro-5-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3,5-bis(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-4-((2-(2-carboxyethyl)-6-(((((1,1,1-trifluoro-2-methylpropan-2-yl)oxy)carbonyl)amino)-2H-benzo[b][1,4]oxazin-4(3H)-yl)sulfonyl)-2-methoxypyridine;

(S)-3-(4-((2,4-difluoro-5-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-4-((2-(2-carboxyethyl)-6-(((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-methyl-1H-pyrazole;

(S)-3-(4-((2-chloro-4,5,6,7-tetrahydropyrazolo[1,5-a]pyridin-3-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluoro-3,5-dimethylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-chloro-4-fluoro-5-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-(difluoromethoxy)-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

3-[(2S)-4-{[3-(pentafluoro-lambda~6~-sulfanyl)phenyl]sulfonyl}-6-{[(2,2,2-trifluoro-1,1-dimethylethoxy)carbonyl]amino}-3,4-dihydro-2H-1,4-benzoxazin-2-yl]propanoic acid;

(R or S)-3-((S)-4-((3-chloro-1-isopropyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-chloro-1-cyclopropyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((1-(difluoromethyl)-3-methyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((1-(difluoromethyl)-3-ethoxy-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-(difluoromethoxy)-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((1-(2,2-difluoroethyl)-3-ethoxy-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-(2,2-difluoroethoxy)-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-methoxy-5,6-dihydro-4H-pyrrolo[1,2-b]pyrazol-3-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-methoxy-4,5,6,7-tetrahydropyrazolo[1,5-a]pyridin-3-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-chloro-4,5,6,7-tetrahydropyrazolo[1,5-a]pyridin-3-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((5-ethoxy-2-ethylthiazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-cyclopropyl-5-ethoxythiazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-ethyl-5-isopropoxythiazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-ethyl-5-(2,2,2-trifluoroethoxy)thiazol-4-yl)sulfonyl)-6-(((((1,1,1-trifluoro-2-methylpropan-2-yl)

oxy)carbonyl)amino)-3,4-dihydro-2H-benzo[b][1,4]ox-
azin-2-yl)-2-methylpropanoic acid;
(S)-3-(4-((3-chloro-1-isopropyl-1H-pyrazol-4-yl)sulfonyl)-
   6-((((1,1,1-trifluoro-2-methylpropan-2-yl)oxy)carbonyl)
   amino)-3,4-dihydro-2H-benzo[b][1,4]oxazin-2-yl)pro-
   panoic acid;
(S)-3-(4-((3-chloro-1-cyclopropyl-1H-pyrazol-4-yl)sulfo-
   nyl)-6-((((1,1,1-trifluoro-2-methylpropan-2-yl)oxy)car-
   bonyl)amino)-3,4-dihydro-2H-benzo[b][1,4]oxazin-2-yl)
   propanoic acid;
3-[(2S)-4-[(5-bromopyridin-3-yl)sulfonyl]-6-{[(2,2,2-trif-
   luoro-1,1-dimethylethoxy)carbonyl]amino}-3,4-dihydro-
   2H-1,4-benzoxazin-2-yl]propanoic acid;
3-[(2S)-4-[(5-cyclopropylpyridin-3-yl)sulfonyl]-6-{[(2,2,2-
   trifluoro-1,1-dimethylethoxy)carbonyl]amino}-3,4-di-
   hydro-2H-1,4-benzoxazin-2-yl]propanoic acid;
3-[(2S)-6-{[(2,2,2-trifluoro-1,1-dimethylethoxy)carbonyl]
   amino}-4-{[6-(trifluoromethyl)pyridin-2-yl]sulfonyl}-3,
   4-dihydro-2H-1,4-benzoxazin-2-yl]propanoic acid;
3-[(2S)-4-[(5-methylpyridin-3-yl)sulfonyl]-6-{[(2,2,2-trif-
   luoro-1,1-dimethylethoxy)carbonyl]amino}-3,4-dihydro-
   2H-1,4-benzoxazin-2-yl]propanoic acid;
3-[(2S)-4-[(5-methoxypyridin-3-yl)sulfonyl]-6-{[(2,2,2-tri-
   fluoro-1,1-dimethylethoxy)carbonyl]amino}-3,4-di-
   hydro-2H-1,4-benzoxazin-2-yl]propanoic acid;
3-[(2S)-4-[(3-cyclopropyl-4-fluorophenyl)sulfonyl]-6-{[(2,
   2,2-trifluoro-1,1-dimethylethoxy)carbonyl]amino}-3,4-
   dihydro-2H-1,4-benzoxazin-2-yl]propanoic acid;
3-(4-{[1-ethyl-3-(2-hydroxyethoxy)-1H-pyrazol-4-yl]sulfo-
   nyl}-6-{[(2,2,2-trifluoro-1,1-dimethylethoxy)carbonyl]
   amino}-3,4-dihydro-2H-1,4-benzoxazin-2-yl)propanoic
   acid;
3-(4-[(3-ethoxy-1-ethyl-1H-pyrazol-4-yl)sulfonyl]-6-{[(2,2,
   2-trifluoro-1,1-dimethylethoxy)carbonyl]amino}-3,4-di-
   hydro-2H-1,4-benzoxazin-2-yl)propanoic acid;
3-[(2S)-4-[(5-ethoxy-2-ethyl-1,3-thiazol-4-yl)sulfonyl]-6-
   {[(2,2,2-trifluoro-1,1-dimethylethoxy)carbonyl]amino}-
   3,4-dihydro-2H-1,4-benzoxazin-2-yl]propanoic acid;
3-[(2S)-4-[(2-cyclopropyl-5-ethoxy-1,3-thiazol-4-yl)sulfo-
   nyl]-6-{[(2,2,2-trifluoro-1,1-dimethylethoxy)carbonyl]
   amino}-3,4-dihydro-2H-1,4-benzoxazin-2-yl]propanoic
   acid;
3-[(2S)-4-{[5-ethoxy-2-(trifluoromethyl)-1,3-thiazol-4-yl]
   sulfonyl}-6-{[(2,2,2-trifluoro-1,1-dimethylethoxy)carbo-
   nyl]amino}-3,4-dihydro-2H-1,4-benzoxazin-2-yl]pro-
   panoic acid;
3-[(2S)-4-{[2-ethyl-5-(1-methylethoxy)-1,3-thiazol-4-yl]
   sulfonyl}-6-{[(2,2,2-trifluoro-1,1-dimethylethoxy)carbo-
   nyl]amino}-3,4-dihydro-2H-1,4-benzoxazin-2-yl]pro-
   panoic acid;
3-[(2S)-4-{[2-ethyl-5-(2,2,2-trifluoroethoxy)-1,3-thiazol-4-
   yl]sulfonyl}-6-{[(2,2,2-trifluoro-1,1-dimethylethoxy)car-
   bonyl]amino}-3,4-dihydro-2H-1,4-benzoxazin-2-yl]pro-
   panoic acid;
3-[(2S)-4-[(5-cyclopropyl-2-fluorophenyl)sulfonyl]-6-{[(2,
   2,2-trifluoro-1,1-dimethylethoxy)carbonyl]amino}-3,4-
   dihydro-2H-1,4-benzoxazin-2-yl]propanoic acid;
(S or R)-2-methyl-3-((S)-6-((((1,1,1-trifluoro-2-methylpro-
   pan-2-yl)oxy)carbonyl)amino)-4-((3-(trifluoromethyl)
   phenyl)sulfonyl)-3,4-dihydro-2H-benzo[b][1,4]oxazin-2-
   yl)propanoic acid;
(S or R)-2-methyl-3-((S)-6-((((1,1,1-trifluoro-2-methylpro-
   pan-2-yl)oxy)carbonyl)amino)-4-((3-(trifluoromethyl)
   phenyl)sulfonyl)-3,4-dihydro-2H-benzo[b][1,4]oxazin-2-
   yl)propanoic acid;
(S or R)-2-methyl-3-((S)-4-(m-tolylsulfonyl)-6-((((1,1,1-tri-
   fluoro-2-methylpropan-2-yl)oxy)carbonyl)amino)-3,4-di-
   hydro-2H-benzo[b][1,4]oxazin-2-yl)propanoic acid;
(S or R)-3-((S)-4-((4-fluoro-3-methoxyphenyl)sulfonyl)-6-
   ((((1,1,1-trifluoro-2-methylpropan-2-yl)oxy)carbonyl)
   amino)-3,4-dihydro-2H-benzo[b][1,4]oxazin-2-yl)-2-
   methylpropanoic acid;
(S or R)-3-((S)-4-((3-(difluoromethoxy)phenyl)sulfonyl)-6-
   ((((1,1,1-trifluoro-2-methylpropan-2-yl)oxy)carbonyl)
   amino)-3,4-dihydro-2H-benzo[b][1,4]oxazin-2-yl)-2-
   methylpropanoic acid;
(S or R)-3-((S)-4-((4-fluoro-3-methoxyphenyl)sulfonyl)-6-
   ((((1,1,1-trifluoro-2-methylpropan-2-yl)oxy)carbonyl)
   amino)-3,4-dihydro-2H-benzo[b][1,4]oxazin-2-yl)-2-
   methylpropanoic acid;
(S or R)-3-((S)-4-((3-(difluoromethoxy)phenyl)sulfonyl)-6-
   ((((1,1,1-trifluoro-2-methylpropan-2-yl)oxy)carbonyl)
   amino)-3,4-dihydro-2H-benzo[b][1,4]oxazin-2-yl)-2-
   methylpropanoic acid;
(S or R)-2-methyl-3-((S)-4-(m-tolylsulfonyl)-6-((((1,1,1-tri-
   fluoro-2-methylpropan-2-yl)oxy)carbonyl)amino)-3,4-di-
   hydro-2H-benzo[b][1,4]oxazin-2-yl)propanoic acid;
(R or S)-2-methyl-3-((S)-6-((((1,1,1-trifluoro-2-methylpro-
   pan-2-yl)oxy)carbonyl)amino)-4-((3-(trifluoromethoxy)
   phenyl)sulfonyl)-3,4-dihydro-2H-benzo[b][1,4]oxazin-2-
   yl)propanoic acid;
(S or R)-2-methyl-3-((S)-6-((((1,1,1-trifluoro-2-methylpro-
   pan-2-yl)oxy)carbonyl)amino)-4-((3-(trifluoromethoxy)
   phenyl)sulfonyl)-3,4-dihydro-2H-benzo[b][1,4]oxazin-2-
   yl)propanoic acid;
(R or S)-3-((S)-4-((4-fluoro-3-methylphenyl)sulfonyl)-6-
   ((((1,1,1-trifluoro-2-methylpropan-2-yl)oxy)carbonyl)
   amino)-3,4-dihydro-2H-benzo[b][1,4]oxazin-2-yl)-2-
   methylpropanoic acid;
(S or R)-3-((S)-4-((4-fluoro-3-methylphenyl)sulfonyl)-6-
   ((((1,1,1-trifluoro-2-methylpropan-2-yl)oxy)carbonyl)
   amino)-3,4-dihydro-2H-benzo[b][1,4]oxazin-2-yl)-2-
   methylpropanoic acid;
(S or R)-3-((S)-4-((3-cyclopropylphenyl)sulfonyl)-6-((((1,1,
   1-trifluoro-2-methylpropan-2-yl)oxy)carbonyl)amino)-3,
   4-dihydro-2H-benzo[b][1,4]oxazin-2-yl)-2-methylpro-
   panoic acid;
(R or S)-2-methyl-3-((S)-6-((((1,1,1-trifluoro-2-methylpro-
   pan-2-yl)oxy)carbonyl)amino)-4-((3-(trifluoromethyl)
   phenyl)sulfonyl)-3,4-dihydro-2H-benzo[b][1,4]oxazin-2-
   yl)propanoic acid;
(R or S)-3-((S)-4-((3-cyclopropylphenyl)sulfonyl)-6-((((1,1,
   1-trifluoro-2-methylpropan-2-yl)oxy)carbonyl)amino)-3,
   4-dihydro-2H-benzo[b][1,4]oxazin-2-yl)-2-methylpro-
   panoic acid;
(5 or R)-2-methyl-3-((S)-6-((((1,1,1-trifluoro-2-methylpro-
   pan-2-yl)oxy)carbonyl)amino)-4-((5-(trifluoromethyl)
   pyridin-3-yl)sulfonyl)-3,4-dihydro-2H-benzo[b][1,4]ox-
   azin-2-yl)propanoic acid;
(S or R)-2-methyl-3-((S)-6-((((1,1,1-trifluoro-2-methylpro-
   pan-2-yl)oxy)carbonyl)amino)-4-((5-(trifluoromethyl)
   pyridin-3-yl)sulfonyl)-3,4-dihydro-2H-benzo[b][1,4]ox-
   azin-2-yl)propanoic acid;
(R or S)-2-methyl-3-((S)-6-((((1,1,1-trifluoro-2-methylpro-
   pan-2-yl)oxy)carbonyl)amino)-4-((2-(trifluoromethyl)
   pyridin-4-yl)sulfonyl)-3,4-dihydro-2H-benzo[b][1,4]ox-
   azin-2-yl)propanoic acid;
(R or S)-2-methyl-3-((S)-6-((((1,1,1-trifluoro-2-methylpro-
   pan-2-yl)oxy)carbonyl)amino)-4-((2-(trifluoromethyl)
   pyridin-4-yl)sulfonyl)-3,4-dihydro-2H-benzo[b][1,4]ox-
   azin-2-yl)propanoic acid;

(R or S)-3-((S)-4-((2-cyclopropylpyridin-4-yl)sulfonyl)-6-(((((1,1,1-trifluoro-2-methylpropan-2-yl)oxy)carbonyl) amino)-3,4-dihydro-2H-benzo[b][1,4]oxazin-2-yl)-2-methylpropanoic acid;
(R or S)-3-((S)-4-((2-cyclopropylpyridin-4-yl)sulfonyl)-6-(((((1,1,1-trifluoro-2-methylpropan-2-yl)oxy)carbonyl) amino)-3,4-dihydro-2H-benzo[b][1,4]oxazin-2-yl)-2-methylpropanoic acid;
(R or S)-3-((S)-4-((3-chloro-1-(difluoromethyl)-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;
(R or S)-3-((S)-4-((3-chloro-1-(difluoromethyl)-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;
(R)-2-(((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid;
(S)-2-(((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid;
(S)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-cyclopropylpropanoic acid;
(R)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-cyclopropylpropanoic acid;
(R or S)-2-(((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl) methyl)butanoic acid;
(R or S)-2-(((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl) methyl)butanoic acid;
(R or S)-2-(((S)-4-((4-fluoro-3-methylphenyl)sulfonyl)-6-(((((1,1,1-trifluoro-2-methylpropan-2-yl)oxy)carbonyl) amino)-3,4-dihydro-2H-benzo[b][1,4]oxazin-2-yl) methyl)butanoic acid;
(R or S)-2-(((S)-4-((3-cyclopropylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)butanoic acid;
(R or S)-2-(((S)-4-((4-fluoro-3-methylphenyl)sulfonyl)-6-(((((1,1,1-trifluoro-2-methylpropan-2-yl)oxy)carbonyl) amino)-3,4-dihydro-2H-benzo[b][1,4]oxazin-2-yl) methyl)butanoic acid;
(R or S)-2-(((S)-4-((3-cyclopropylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)butanoic acid;
(R or S)-2-(((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl) methyl)butanoic acid;
(R or S)-2-(((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl) methyl)butanoic acid;
(R or S)-2-(((S)-4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl) methyl)butanoic acid;
(R or S)-2-(((S)-4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl) methyl)butanoic acid;
(R or S)-2-(((S)-4-((4-fluoro-3-methoxyphenyl)sulfonyl)-6-(((((1,1,1-trifluoro-2-methylpropan-2-yl)oxy)carbonyl) amino)-3,4-dihydro-2H-benzo[b][1,4]oxazin-2-yl) methyl)butanoic acid;
(R or S)-2-(((S)-4-((1-ethyl-3-(2-hydroxyethoxy)-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)butanoic acid;
(R or S)-2-(((S)-4-((4-fluoro-3-methoxyphenyl)sulfonyl)-6-(((((1,1,1-trifluoro-2-methylpropan-2-yl)oxy)carbonyl) amino)-3,4-dihydro-2H-benzo[b][1,4]oxazin-2-yl) methyl)butanoic acid;
(R or S)-2-(((S)-4-((1-ethyl-3-(2-hydroxyethoxy)-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)butanoic acid;
(R or S)-2-(((S)-6-(((((1,1,1-trifluoro-2-methylpropan-2-yl) oxy)carbonyl)amino)-4-((2-(trifluoromethyl)pyridin-4-yl)sulfonyl)-3,4-dihydro-2H-benzo[b][1,4]oxazin-2-yl) methyl)butanoic acid;
(R or S)-2-(((S)-6-(((((1,1,1-trifluoro-2-methylpropan-2-yl) oxy)carbonyl)amino)-4-((2-(trifluoromethyl)pyridin-4-yl)sulfonyl)-3,4-dihydro-2H-benzo[b][1,4]oxazin-2-yl) methyl)butanoic acid;
(S or R)-2-cyclopropyl-3-((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;
(R or S)-2-cyclopropyl-3-((S)-4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;
(R or S)-2-cyclopropyl-3-((S)-4-((4-fluoro-3-methoxyphenyl)sulfonyl)-6-(((((1,1,1-trifluoro-2-methylpropan-2-yl) oxy)carbonyl)amino)-3,4-dihydro-2H-benzo[b][1,4]oxazin-2-yl)propanoic acid;
(R or S)-2-cyclopropyl-3-((S)-4-((4-fluoro-3-methylphenyl) sulfonyl)-6-(((((1,1,1-trifluoro-2-methylpropan-2-yl)oxy) carbonyl)amino)-3,4-dihydro-2H-benzo[b][1,4]oxazin-2-yl)propanoic acid;
(S or R)-2-cyclopropyl-3-((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;
(R or S)-2-cyclopropyl-3-((S)-4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;
(R or S)-2-cyclopropyl-3-((S)-4-((4-fluoro-3-methoxyphenyl)sulfonyl)-6-(((((1,1,1-trifluoro-2-methylpropan-2-yl) oxy)carbonyl)amino)-3,4-dihydro-2H-benzo[b][1,4]oxazin-2-yl)propanoic acid;
(R or S)-2-cyclopropyl-3-((S)-4-((4-fluoro-3-methylphenyl) sulfonyl)-6-(((((1,1,1-trifluoro-2-methylpropan-2-yl)oxy) carbonyl)amino)-3,4-dihydro-2H-benzo[b][1,4]oxazin-2-yl)propanoic acid;
(S or R)-2-cyclopropyl-3-((S)-4-((1-ethyl-3-(2-hydroxyethoxy)-1H-pyrazol-4-yl)sulfonyl)-6-(((((1,1,1-trifluoro- 2-methylpropan-2-yl)oxy)carbonyl)amino)-3,4-dihydro-2H-benzo[b][1,4]oxazin-2-yl)propanoic acid;

(S or R)-2-cyclopropyl-3-((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-2,2-dimethyl-3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-2,2-dimethyl-3-(6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

(S)-2,2-dimethyl-3-(6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

3-[(2S)-4-[(5-cyanopyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(3-chloro-1-cyclopropyl-1H-pyrazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[1-(difluoromethyl)-3-methyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(5-ethoxy-2-ethyl-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(2-cyclopropyl-5-ethoxy-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[2-ethyl-5-(2,2,2-trifluoroethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[2-ethyl-5-(1-methylethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[3-chloro-1-(1-methylethyl)-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[1-(difluoromethyl)-3-ethoxy-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[3-(difluoromethoxy)-1-ethyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[1-(2,2-difluoroethyl)-3-ethoxy-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[3-(2,2-difluoroethoxy)-1-ethyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(2-chloro-4,5,6,7-tetrahydropyrazolo[1,5-a]pyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(2-methoxy-4,5,6,7-tetrahydropyrazolo[1,5-a]pyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(2-methoxy-5,6-dihydro-4H-pyrrolo[1,2-b]pyrazol-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

(S)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid;

(R)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid;

(S)-1-((4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(S)-1-((4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(R)-1-((4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(R)-1-((4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(S)-1-((4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(R)-1-((4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(S)-1-((4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(R)-1-((4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;

(S and R)-2-hydroxy-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;

(R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;

(S)-3-hydroxy-2-methyl-2-(S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;

(R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;

(R or S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;

(R or S)-2-hydroxy-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R or S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid;

(R and S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid;

(R or S)-2-hydroxy-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R and S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid;

(S or R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;

(S or R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;

(S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;

(S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;

(S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;

(S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;

(R)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)butanoic acid;

(S)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)butanoic acid;

(R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-3-cyclopropylpropanoic acid;

(S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-3-cyclopropylpropanoic acid;

(S or R)-3-cyclopropyl-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S or R)-3-cyclopropyl-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S or R)-3-cyclopropyl-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S or R)-3-cyclopropyl-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(1R,2S)-2-(((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl) cyclopropanecarboxylic acid;
(1S,2R)-2-(((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl) cyclopropanecarboxylic acid;
(1R,2R)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl) cyclopropanecarboxylic acid;
(1S,2S)-2-(((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl) cyclopropanecarboxylic acid;
(1S,2S)-2-(((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1R,2R)-2-(((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1S,2R)-2-(((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1R,2S)-2-(((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1R,2S)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1R,2R)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1R,2S)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1R,2R)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1S,2S)-2-(((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1S,2R)-2-(((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1S,2S)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
(1S,2R)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;
3-((S)-4-((4-fluoro-3-methoxyphenyl)sulfonyl)-6-(((((S)-1,1,1-trifluoro-3,3-dimethylbutan-2-yl)oxy)carbonyl)amino)-3,4-dihydro-2H-benzo[b][1,4]oxazin-2-yl)propanoic acid;
3-((S)-4-((4-fluoro-3-methoxyphenyl)sulfonyl)-6-(((((R)-1,1,1-trifluoro-3,3-dimethylbutan-2-yl)oxy)carbonyl)amino)-3,4-dihydro-2H-benzo[b][1,4]oxazin-2-yl)propanoic acid;
3-{(2S)-4-[(4-fluoro-3-methoxyphenyl)sulfonyl]-6-[({[1-(trifluoromethyl)cyclopropyl]methoxy}carbonyl)amino]-3,4-dihydro-2H-1,4-benzoxazin-2-yl}propanoic acid;
3-{(2S)-4-[(4-fluoro-3-methoxyphenyl)sulfonyl]-6-[({[1-(trifluoromethyl)cyclobutyl]oxy}carbonyl)amino]-3,4-dihydro-2H-1,4-benzoxazin-2-yl}propanoic acid;
3-{(2S)-4-[(4-fluoro-3-methoxyphenyl)sulfonyl]-6-[({[(1S or 1R)-1,2,2-trimethylpropyl]oxy}carbonyl)amino]-3,4-dihydro-2H-1,4-benzoxazin-2-yl}propanoic acid;
3-{(2S)-4-[(4-fluoro-3-methoxyphenyl)sulfonyl]-6-[({[(1S or 1R)-1,2,2-trimethylpropyl]oxy}carbonyl)amino]-3,4-dihydro-2H-1,4-benzoxazin-2-yl}propanoic acid;
3-{(2S)-4-[(4-fluoro-3-methoxyphenyl)sulfonyl]-6-[({[1-(trifluoromethyl)cyclohexyl]oxy}carbonyl)amino]-3,4-dihydro-2H-1,4-benzoxazin-2-yl}propanoic acid;
3-((S)-4-((4-fluoro-3-methoxyphenyl)sulfonyl)-6-(((((R and S)-1,1,1-trifluoro-2-methylbutan-2-yl)oxy)carbonyl)amino)-3,4-dihydro-2H-benzo[b][1,4]oxazin-2-yl)propanoic acid;
3-((2S,3R)-3-methyl-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;
3-((2S,3S)-4-((3-chloro-1-ethyl-1H-pyrazol-4-yl)sulfonyl)-3-methyl-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;
3-((2S,3R)-4-((3-chloro-1-ethyl-1H-pyrazol-4-yl)sulfonyl)-3-methyl-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;
3-((2R,3R)-4-((3-chloro-1-ethyl-1H-pyrazol-4-yl)sulfonyl)-3-methyl-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;
3-((2R,3S)-4-((3-chloro-1-ethyl-1H-pyrazol-4-yl)sulfonyl)-3-methyl-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;
3-[(2R,3S)-4-[(4-fluoro-3-methoxyphenyl)sulfonyl]-3-methyl-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S,3R)-4-[(4-fluoro-3-methoxyphenyl)sulfonyl]-3-methyl-6-{[(2,2,2-trifluoro-1,1-dimethylethoxy)carbonyl]amino}-3,4-dihydro-2H-1,4-benzoxazin-2-yl]-2,2-dimethylpropanoic acid;
(S)-3-(8-fluoro-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;
3-[(2S)-8-fluoro-4-[(4-fluoro-3-methylphenyl)sulfonyl]-6-{[(2,2,2-trifluoro-1,1-dimethylethoxy)carbonyl]amino}-3,4-dihydro-2H-1,4-benzoxazin-2-yl]propanoic acid;
3-[(2S)-8-fluoro-4-[(4-fluoro-3-methoxyphenyl)sulfonyl]-6-{[(2,2,2-trifluoro-1,1-dimethylethoxy)carbonyl]amino}-3,4-dihydro-2H-1,4-benzoxazin-2-yl]propanoic acid;
3-[(2S)-4-[(3-chloro-1-ethyl-1H-pyrazol-4-yl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-4-[(3-ethoxy-1-ethyl-1H-pyrazol-4-yl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;

3-[(2S)-8-fluoro-6-{[(2,2,2-trifluoro-1,1-dimethylethoxy) carbonyl]amino}-4-{[3-(trifluoromethyl)phenyl]sulfonyl}-3,4-dihydro-2H-1,4-benzoxazin-2-yl]propanoic acid;
3-[(2S)-4-[(3-chloro-4-fluorophenyl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-4-[(3-cyclopropylphenyl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-8-fluoro-6-{[(2,2,2-trifluoro-1,1-dimethylethoxy) carbonyl]amino}-4-{[2-(trifluoromethyl)pyridin-4-yl] sulfonyl}-3,4-dihydro-2H-1,4-benzoxazin-2-yl]propanoic acid;
3-[(2S)-8-fluoro-6-{[(2,2,2-trifluoro-1,1-dimethylethoxy) carbonyl]amino}-4-{[5-(trifluoromethyl)pyridin-3-yl] sulfonyl}-3,4-dihydro-2H-1,4-benzoxazin-2-yl]propanoic acid;
(R)-3-(4-((3-chloro-1-ethyl-1H-pyrazol-4-yl)sulfonyl)-5-methyl-6-((((1,1,1-trifluoro-2-methylpropan-2-yl)oxy) carbonyl)amino)-3,4-dihydro-2H-benzo[b][1,4]oxazin-2-yl)-2,2-dimethylpropanoic acid; and
(S)-3-(4-((3-chloro-1-ethyl-1H-pyrazol-4-yl)sulfonyl)-5-methyl-6-((((1,1,1-trifluoro-2-methylpropan-2-yl)oxy) carbonyl)amino)-3,4-dihydro-2H-benzo[b][1,4]oxazin-2-yl)-2,2-dimethylpropanoic acid.

The invention also provides a compound of Formula (I) or a pharmaceutically acceptable salt thereof in purified form.

Uses of the Compounds

Compounds of Formula (I) alter the interaction of coregulator proteins with Retinoic Acid Receptor-related Orphan Receptor gamma t (RORgammaT) and thereby antagonize RORgammaT-mediated transcriptional activity, and as such are useful in the treatment of diseases and conditions in which inhibition of RORgammaT is desirable, such as autoimmune and inflammatory diseases and disorders.

Accordingly, another embodiment of the present invention provides a method for treating a disease or condition mediated by RORgammaT in a subject comprising administering to the subject an amount of a compound of Formula (I) that is effective for treating the disease or condition mediated by RORgammaT in the subject.

The compounds according to the invention can be used in therapy.

A further aspect of the invention resides in the use of compounds of Formula (I) for the treatment of RORgammaT-mediated diseases or RORgammaT-mediated conditions.

Another aspect of the invention resides in the use of a compound of Formula (I) in the manufacture of a medicament for the treatment of a disease or condition mediated by RORgammaT.

Another aspect of the invention resides in the use of compounds of Formula (I) for the treatment of autoimmune diseases, in particular those diseases in which Th17 cells and non-Th17 cells, which express Th17 hallmark cytokines, play a prominent role. These include, but are not limited to, the treatment of rheumatoid arthritis, psoriasis, inflammatory bowel disease (e.g., Crohn's disease, ulcerative colitis), ankylosing spondylitis, and multiple sclerosis.

In another aspect, compounds of Formula (I) can be used for treatment of inflammatory diseases in which Th17 cells and/or non-Th17 cells, which express Th17 hallmark cytokines, play a prominent role, such as but not limited to respiratory diseases, osteoarthritis, and asthma. Also, compounds of Formula (I) can be used for treatment of infectious diseases in which Th17 cells and/or non-Th17 cells, which express Th17 hallmark cytokines, play a prominent role, such as but not limited to mucosal leishmaniasis.

Compounds of Formula (I) can also be used for treatment of other diseases in which Th17 cells and/or non-Th17 cells, which express Th17 hallmark cytokines, play a prominent role, such as but not limited to Kawasaki disease and Hashimoto's thyroiditis.

In one aspect, the disease or condition is an autoimmune disease or inflammatory disease. The disease or condition includes, but is not limited to, multiple sclerosis, inflammatory bowel disease (e.g., Crohn's disease, ulcerative colitis), psoriasis, rheumatoid arthritis, asthma, osteoarthritis, Kawasaki disease, Hashimoto's thyroiditis, and mucosal leishmaniasis.

In another aspect, the compounds of Formula (I) can be used in therapies to treat or prevent multiple sclerosis, inflammatory bowel disease (e.g., Crohn's disease ulcerative colitis), psoriasis, rheumatoid arthritis, asthma, osteoarthritis, Kawasaki disease, Hashimoto's thyroiditis, and mucosal leishmaniasis.

In another aspect, the compounds of Formula (I) can be used to treat or prevent psoriasis.

In yet another aspect, the compounds of Formula (I) can be used to treat inflammatory bowel disease (e.g., Crohn's disease, ulcerative colitis).

In another aspect, the compound of Formula (I) can be used to treat colorectal cancer.

In another aspect, the compound of Formula (I) can be used to treat lung cancer.

In another aspect, the compound of Formula (I) can be used to treat pancreatic cancer.

Route of Administration/Dosage

The compounds of this invention can be administered for the treatment or prevention of afflictions, diseases, and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal, and parenteral. The term "parenteral" as used herein refers to modes of administration that include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health, and weight of the recipient; the extent of disease; kind of concurrent treatment, if any; frequency of treatment; and the nature of the effect desired. Usually, a daily dosage of active ingredient compound will be from about 1.0-2000 milligrams per day. Ordinarily, from 10 to 500 milligrams per day in one or more applications is effective to obtain desired results. These dosages are the effective amounts for the treatment and prevention of afflictions, diseases, and illnesses described above, e.g., autoimmune and inflammatory diseases and disorders.

Compositions include those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g., injection liquids in predetermined amounts, for example in sealed vials and ampoules, and may also be stored in a freeze dried (lyophilized) condition requiring only the addition of sterile liquid carrier, e.g., water, prior to use.

Mixed with such pharmaceutically acceptable auxiliaries, e.g., as described in the standard reference, Gennaro, A. R. et al., Remington: The Science and Practice of Pharmacy (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g., as an injection preparation, in the form of a solution, suspension, emulsion, or as a spray, e.g., a nasal spray.

For making solid dosage units, the use of conventional additives such as fillers, colorants, polymeric binders, and the like is contemplated. In general any pharmaceutically acceptable additive that does not interfere with the function of the active compounds can be used. Suitable carriers with which the active agent of the invention can be administered as solid compositions include lactose, starch, cellulose derivatives, and the like, or mixtures thereof, used in suitable amounts. For parenteral administration, aqueous suspensions, isotonic saline solutions, and sterile injectable solutions may be used, containing pharmaceutically acceptable dispersing agents and/or wetting agents, such as propylene glycol or butylene glycol.

Pharmaceutical Compositions

Another aspect of the present invention provides pharmaceutical compositions comprising a compound of Formula (I) or a pharmaceutically acceptable salt thereof and one or more pharmaceutically acceptable excipients. The term "excipient" and "carrier" may be used interchangeably. The term "composition," as in pharmaceutical composition, is intended to encompass a product comprising the active ingredient(s), and the inert ingredient(s) (pharmaceutically acceptable excipients) that make up the carrier, as well as any product that results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I), additional active ingredient(s), and pharmaceutically acceptable excipients.

The pharmaceutical compositions of the present invention comprise a compound represented by Formula (I) (or pharmaceutically acceptable salts thereof) as an active ingredient, a pharmaceutically acceptable carrier, and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy in light of the present disclosure.

The active ingredient can be administered orally in solid dosage forms, such as capsules, tablets, troches, dragées, granules, and powders, or in liquid dosage forms, such as elixirs, syrups, emulsions, dispersions, and suspensions. The active ingredient can also be administered parenterally, in sterile liquid dosage forms, such as dispersions, suspensions, or solutions. Other dosages forms that can also be used to administer the active ingredient as an ointment, cream, drops, transdermal patch, or powder for topical administration, as an ophthalmic solution or suspension formation, i.e., eye drops, for ocular administration, as an aerosol spray or powder composition for inhalation or intranasal administration, or as a cream, ointment, spray, or suppository for rectal or vaginal administration.

Gelatin capsules can contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours, for example. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, A. Osol, a standard reference text in this field.

For administration by inhalation, the compounds of Formula (I) may be conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula (I) in suitable propellants, such as fluorocarbons or hydrocarbons.

For ocular administration, an ophthalmic preparation may be formulated with an appropriate weight percent solution or suspension of the compounds of Formula (I) in an appropriate ophthalmic vehicle, such that the compound is maintained in contact with the ocular surface for a sufficient time period to allow the compound to penetrate the corneal and internal regions of the eye.

Useful pharmaceutical dosage forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil, or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contains 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term "coadministration" is understood to include the administration of the two agents concomitantly or sequentially, or alternatively as a fixed dose combination of the two active components.

The present invention also relates to a pharmaceutical composition comprising compounds of Formula (I) or pharmaceutically acceptable salts thereof in admixture with pharmaceutically acceptable auxiliaries and optionally other therapeutic agents. The auxiliaries must be "acceptable" in the sense of being compatible with the other ingredients of the composition and not deleterious to the recipients thereof.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general, parenteral administration requires lower dosages than other methods of administration which are more dependent upon absorption. However, a dosage for humans preferably contains 0.0001-100 mg per kg body weight. The desired dose may be presented as one dose or as multiple subdoses administered at appropriate intervals throughout the day. The dosage as well as the regimen of administration may differ between a female and a male recipient.

Combination Therapy

Compounds of Formula (I), and pharmaceutically acceptable salts and physiologically functional derivatives (e.g., prodrugs) thereof, may be employed alone or in combination with other therapeutic agents for the treatment of diseases and conditions associated with inappropriate IL-17 pathway activity. Combination therapies according to the present invention thus comprise the administration of at least one compound of Formula (I) or a pharmaceutically acceptable salt thereof, or a physiologically functional derivative thereof, and the use of at least one other pharmaceutically active agent. The compound(s) of Formula (I) and the other pharmaceutically active agent(s) may be administered together or separately and, when administered separately, this may occur simultaneously or sequentially in any order. The amounts of the compound(s) of Formula (I) and the other pharmaceutically active agent(s) and the relative timings of administration will be selected in order to achieve the desired combined therapeutic effect.

For the treatment of the inflammatory and autoimmune diseases, rheumatoid arthritis, psoriasis, inflammatory bowel disease, ankylosing spondylitis, SLE (systemic lupus erythematosus), uveitis, atopic dermatitis, COPD, asthma, and allergic rhinitis, a compound of Formula (I) may be combined with one or more other active agents such as: (1) TNF-α inhibitors; (2) non-selective COX-1/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine HI receptor antagonists; (9) a1- and a2-adrenoceptor agonist; (10) anticholinergic agents; (11) β-adrenoceptor agonists; (12) insulin-like growth factor type I (IGF-1) mimetic; (13) glucocorticosteroids; (14) kinase inhibitors such as inhibitors of the Janus Kinases (JAK1 and/or JAK2 and/or JAK3 and/or TYK2), p38 MAPK and IKK2; (15) B-cell targeting biologics such as rituximab; (16) selective costimulation modulators such as abatacept; (17) interleukin inhibitors, such as IL-1 inhibitor anakinra, IL-6 inhibitor tocilizumab, and IL12/IL-23 inhibitor ustekinumab. The compound of Formula (I) may also be combined with anti-IL17 antibodies to obtain additive/synergistic responses for the treatment of inflammatory and autoimmune diseases.

For the treatment of cancer, the compounds of Formula (I) can be combined with other therapeutic, chemotherapeutic, and anti-cancer agents. Combinations of the compounds of Formula (I) with other therapeutic, chemotherapeutic, and anti-cancer agents are within the scope of the invention. Examples of such agents can be found in *Cancer Principles and Practice of Oncology* by V. T. Devita and S. Hellman (editors), $6^{th}$ edition (Feb. 15, 2001), Lippincott Williams & Wilkins Publishers. In light of the present disclosure, a person of ordinary skill in the art would be able to discern which combinations of the compounds of Formula (I) with the other therapeutic, chemotherapeutic, and anti-cancer agents would be useful based on the particular characteristics of the drugs and the cancer involved. The compounds of Formula (I) may also be useful when co-administered with radiation therapy. The compounds of Formula (I) can be present in the same dosage unit as the other therapeutic, chemotherapeutic, and anti-cancer agents. The compounds of Formula (I) and the other therapeutic, chemotherapeutic, and anti-cancer agents can also be present in separate dosage units.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimize the activity and/or stability and/or physical characteristics, such as solubility, of the therapeutic ingredient. It will be clear also that, where appropriate, the other therapeutic ingredients may be used in optically pure form.

The combinations referred to above may conveniently be presented for use in the form of a pharmaceutical composition and thus, pharmaceutical compositions comprising a combination as defined above together with a pharmaceutically acceptable diluent or carrier represent a further aspect of the invention. These combinations are of particular interest in respiratory diseases and are conveniently adapted for inhaled or intranasal delivery.

The individual compounds of such combinations may be administered either sequentially or simultaneously in separate or combined pharmaceutical compositions. Preferably, the individual compounds will be administered simultaneously in a combined pharmaceutical composition. Appropriate doses of known therapeutic agents will be readily appreciated by those skilled in the art.

Accordingly, the pharmaceutical compositions of the present invention include those that also comprise at least one additional therapeutically active agent, in addition to the compound of Formula (I).

The invention further includes a compound of Formula (I) in combination with one or more other drug(s).

Methods of Preparing the Compounds of Formula (I)

The compounds of this invention may be made by a variety of methods, including standard chemistry in light of the present disclosure. Illustrative general synthetic methods are set out below and then specific compounds of the Formula (I) are prepared in the Examples.

Compounds of Formula (I) may be prepared in light of the present disclosure via techniques known in the art of organic synthesis, examples of which are set forth in the following synthesis schemes. It would be well understood by those skilled in the art in light of the present disclosure that in all of the schemes described below, protecting groups for sensitive or reactive groups should be employed where necessary in accordance with general principles of chemistry. Protecting groups can be manipulated according to standard methods of organic synthesis (T. W. Green and P. G. M. Wuts (1991) Protecting Groups in Organic Synthesis, John Wiley & Sons). These groups can be removed at a convenient stage of the compound synthesis using methods that are readily apparent to those skilled in the art. In certain other embodiments, a functional group presented in these schemes below can be converted to another functional group using standard functional group manipulation procedures known in the art. See, for example, "Comprehensive Organic Synthesis" (B. M. Trost & I. Fleming, eds., 1991-1992).

The selection of protecting groups as well as the reaction conditions and order of reaction steps shall be consistent with the preparation of compounds of Formula (I). Those skilled in the art will recognize in light of the present disclosure whether a stereocenter exists in compounds of Formula (I). When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994).

The following solvents, reagents, protecting groups, moieties, and other designations may be referred to by their abbreviations:

Me=methyl; Et=ethyl; Pr=propyl; iPr=isopropyl, Bu=butyl; t-Bu=tert-butyl; Ph=phenyl, and Ac=acetyl
μL=microliters
AcOH or HOAc=acetic acid
APCI=atmospheric-pressure chemical ionization
aq=aqueous
Bn=benzyl
Boc or BOC=tert-butoxycarbonyl
Bz=benzoyl
Cbz=benzyloxycarbonyl
DBU=1,8-diazabicyclo[5.4.0]undec-7-ene
DCM=dichloromethane:
DEA=diethylamine
DMAP=4-dimethylaminopyridine
DIBAL=diisobutylaluminum hydride
DIAD=diisopropyl azodicarboxylate
DIEA or Hünig's Base=N,N-diisopropylethylamine
DMF=dimethylformamide
DMSO=dimethyl sulfoxide
EA=ethyl acetate
EDC=1-ethyl-3-(3-dimethylaminopropyl)carbodiimide
EDTA=ethylenediamine tetraacetic acid
ESI=electrospray ionization
EtOAc=ethyl acetate
g=grams
h=hour
HMDS=1,1,1,3,3,3-hexamethyldisilazane
Hex=hexanes
HPLC=high-performance liquid chromatography
LDA=lithium diisopropylamide
LCMS=liquid chromatography mass spectrometry
LRMS=low resolution mass spectroscopy
min=minute
mg=milligrams
mL=milliliters
mmol=millimoles
MeOH=methanol
MPLC=medium pressure liquid chromatography
MTBE=methyl tert-butyl ether
MS=mass spectrometry
NBS=N-bromosuccinimide
NMO=4-methylmorpholine N-oxide
NMR=nuclear magnetic resonance spectroscopy
rac=racemic mixture
rt=room temperature (ambient, about 25° C.)
sat=saturated
SFC=supercritical fluid chromatography
TBSCl=t-butyldimethylsilyl chloride TBS=t-butyldimethyl silyl
TEA=triethylamine (Et₃N)
TFA=trifluoroacetic acid
THF=tetrahydrofuran
TLC=thin layer chromatography
TMS=trimethylsilyl
TPAP=tetrapropylammonium perruthenate
TsOH=p-toluenesulfonic acid General Methods Methods for preparing compounds described herein are illustrated in the following synthetic schemes. The schemes are given for the purpose of illustrating the invention, but not for limiting the scope or spirit of the invention. Starting materials shown in the schemes can be obtained from commercial sources or be prepared based on procedures described in the literature.

The synthetic route illustrated in Scheme 1 is a general method for preparing various carbamates. Reaction of a starting amine A with a carbamoylating agent of structure B where X is a leaving group which includes halides, electron deficient phenols, imidazole, triazoles, or other moieties well-known to those trained in the art affords the target carbamate C.

The reaction procedures in Scheme 1 are contemplated to be amenable to preparing a wide variety of carbamoyl-substituted benzoxazines compounds having different substituents at the $R^1$, $R^2$, $R^{a1}$, $R^{a2}$, $R^{b1}$, $R^{b2}$, $R^c$, $R^d$, and Cy positions. A wide variety of alcohol starting materials necessary to prepare the carbamoylating reagent B (wherein X is a suitable leaving group, e.g., chloro) are commercially available or readily prepared via known methods.

SCHEME 1

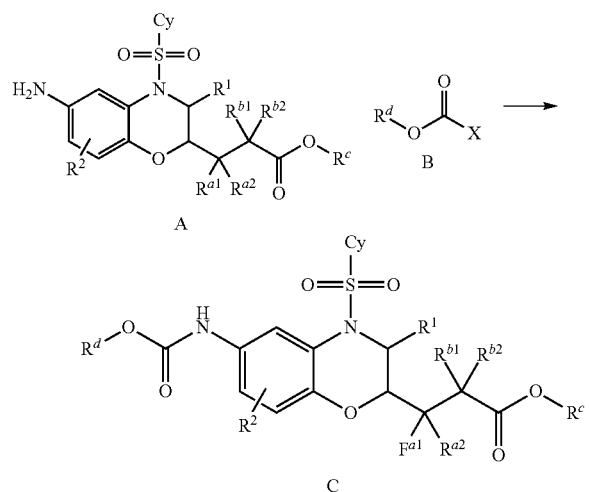

Scheme 2 illustrates a different general method for preparing carbamates. Treatment of the amine A with phosgene, triphosgene, or other reagents known to convert aromatic or heteroaromatic amines to isocyanates, affords the isocyanate B which when treated with an alcohol C, either without or with a catalyst (a base which includes but is not limited to triethyl amine, DBU, Hunig's base, or a metal catalyst such as a dibutyl tin dilaurate and numerous others known to those trained in the art), affords the carbamate D.

SCHEME 2

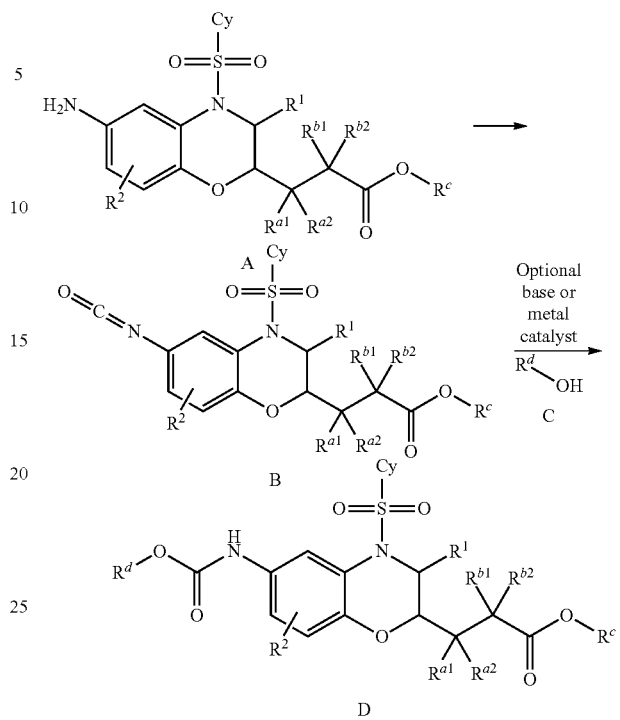

Scheme 3 illustrates a different general method for preparing carbamates. Treatment of the carboxylic acid A under conditions suitable to prepare an acyl azide (diphenyl phosphoryl azide, or isobutyl chloroformate and sodium azide, or other similar conditions known to those trained in the art) affords the acyl azide, which upon heating rearranges to form the isocyanate B. Treatment of the isocyanate with an alcohol C affords the carbamate D.

SCHEME 3

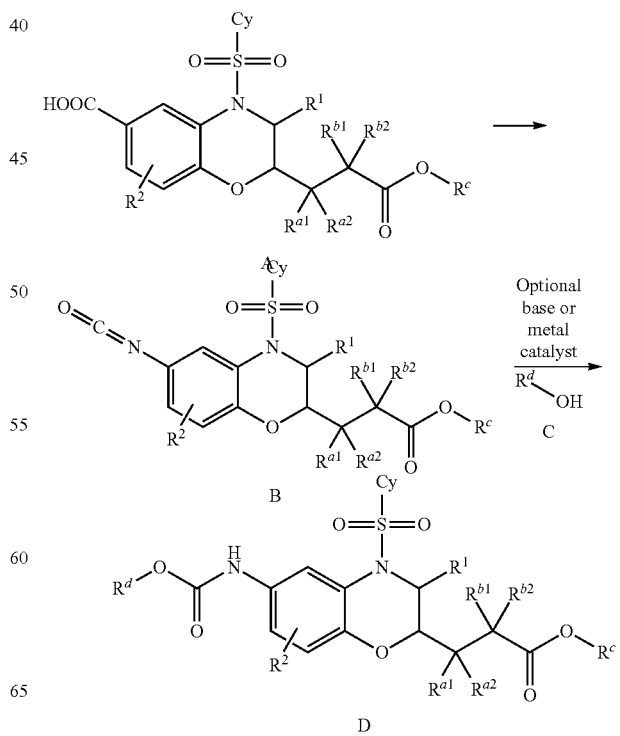

Scheme 4 illustrates another general method for preparing carbamates of the invention. Treatment of a halide or triflate (X=OTf) A under Pd-mediated coupling conditions with a unsubstituted carbamate C affords the carbamate D. The unsubstituted carbamate C can be prepared from alcohols B via treatment with either potassium isocyanate and acid or with sulfurisocyanatidic chloride.

The synthetic route in Scheme 6 is a general method for preparing various carbamoyl-substituted benzoxazine compounds having a propionic acid or acid derivative sidechain. Reaction of nitro-aryl aniline A with an epoxide provides benzoxazine B. The nitro group in benzoxazine B can be reduced in the presence of $Boc_2O$ to a Boc carbamate group to provide Boc benzoxazine C. Reaction of benzox-

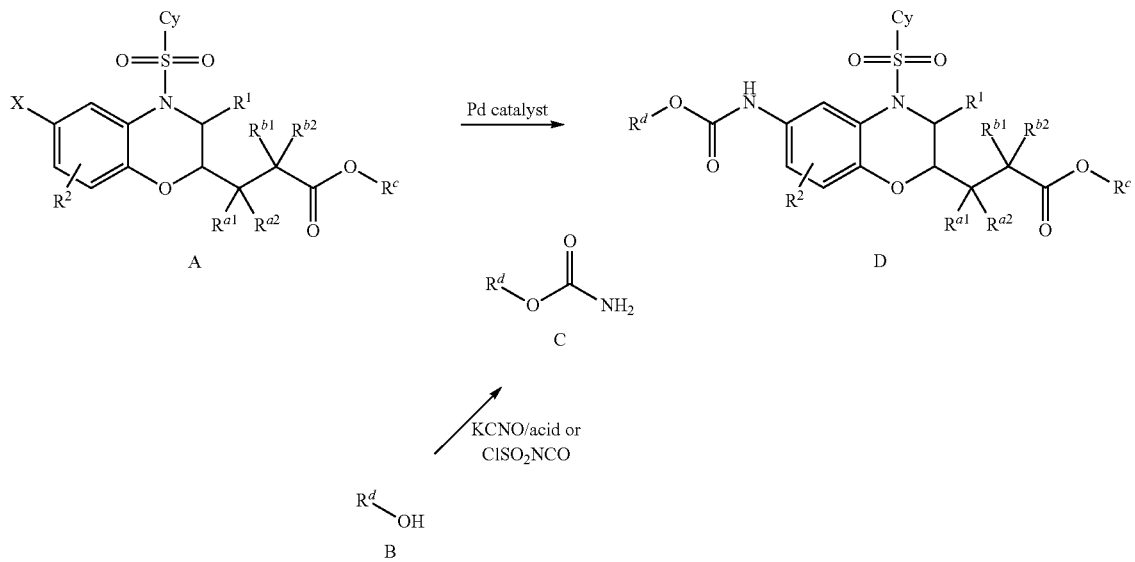

SCHEME 4 azine C with a sulfonylating reagent provides sulfonamide-substituted benzoxazine D. To install the acid or acid derivative side-chain, the alcohol is activated with MsCl and displaced in a $S_N2$ fashion to afford tri-ester F. Decarboxylation with LiCl, followed by removal of the Boc carbamate group under acidic conditions, and subsequent installation of the desired carbamate affords ethyl ester H. Hydrolysis of the ester under basic conditions (aq. LiOH) furnishes the carboxylic acid benzoxazine I.

Scheme 5 illustrates a general method for preparing alcohols and carbamoylating reagents suitable for use in Scheme 1 and in the other general schemes below. Treatment of a ketone or aldehyde A with a Grignard reagent, $R^{fs}Li$, a $R^{fs}$ metal, or a trialkylsilyl reagent (i.e., trimethyl silyl trifluoromethane) affords the alcohol B, which can be reacted with p-nitrochloroformate, carbonyldiimide, or phosgene to afford the carbamoylating reagents.

SCHEME 5

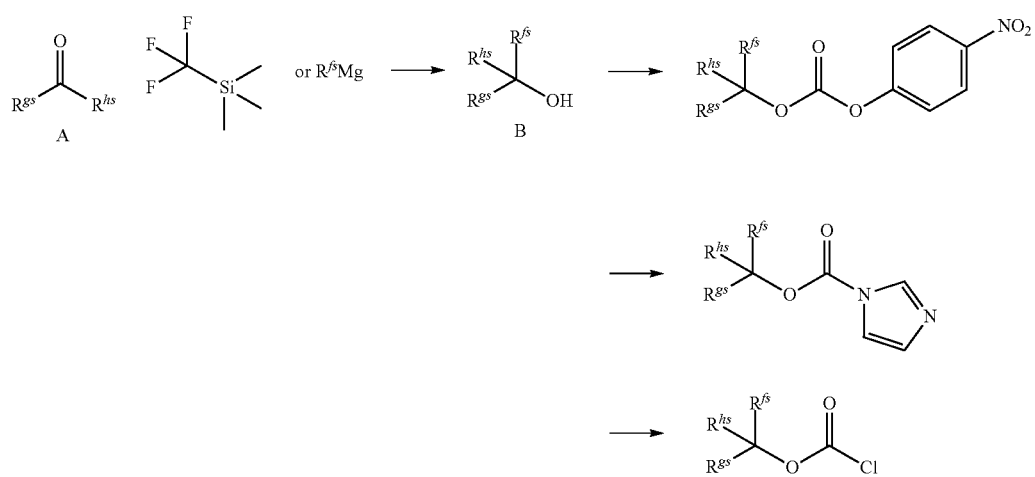

SCHEME 6

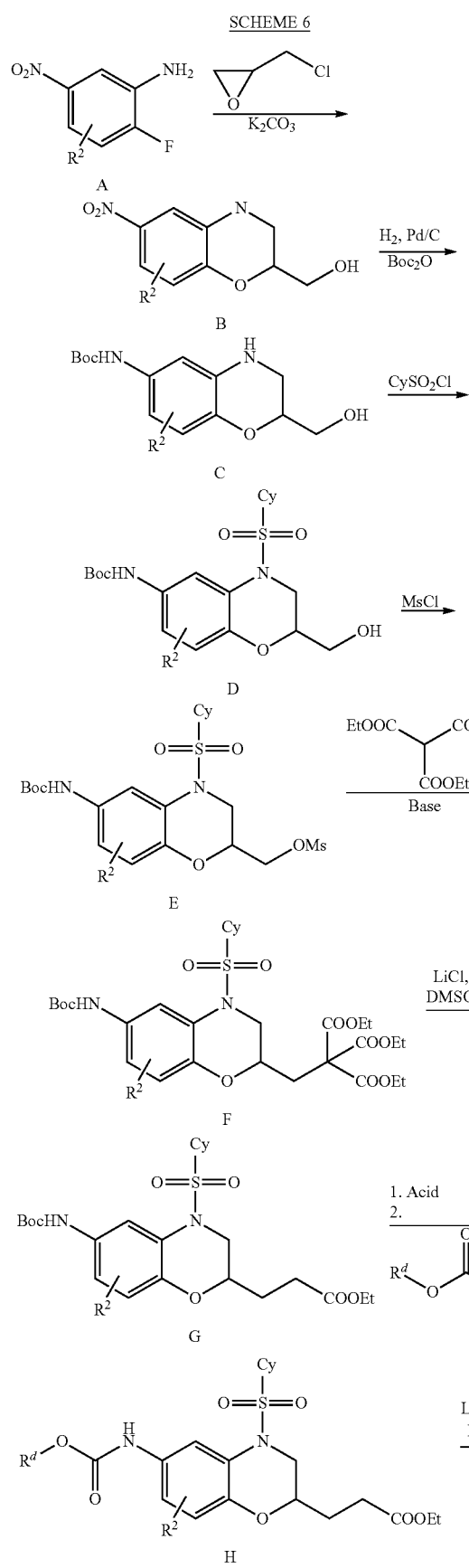

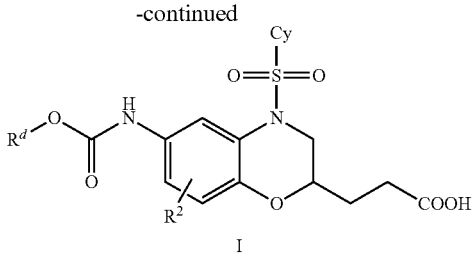

Scheme 7 shows the general synthetic route to alpha-substituted ($R^{b1}$) carboxylic acids and acid derivatives. Treatment of mesylate A (see Scheme 6 for synthesis) with a di-ester reagent affords compound B, which is next treated with base and $R^{b1}$—X to afford alpha-substituted ester D. Decarboxylation, acidic removal of the Boc carbamate, and subsequent installation of the desired carbamate affords ester E. Hydrolysis of the ester under basic conditions gives carboxylic acid F.

SCHEME 7

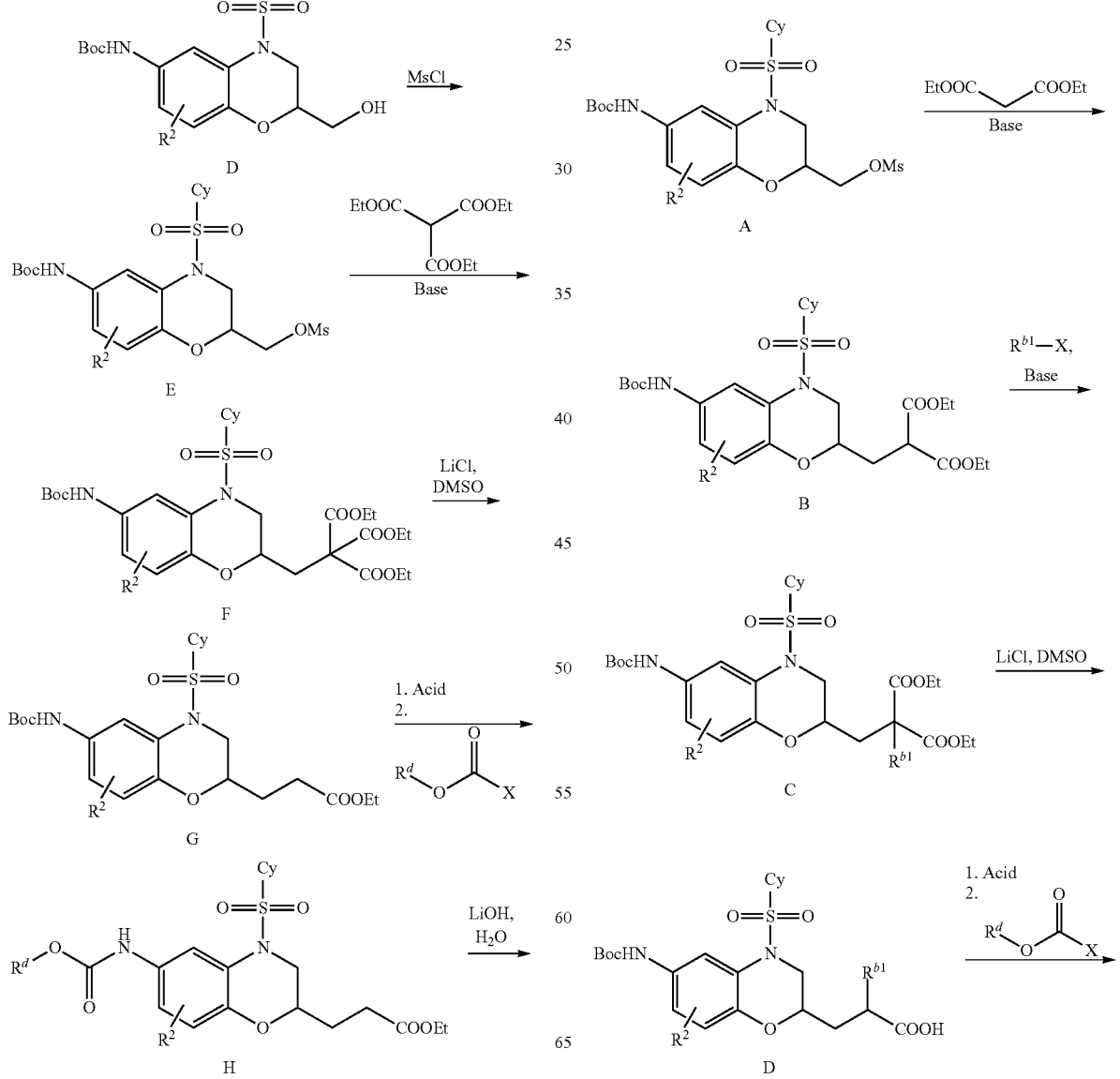

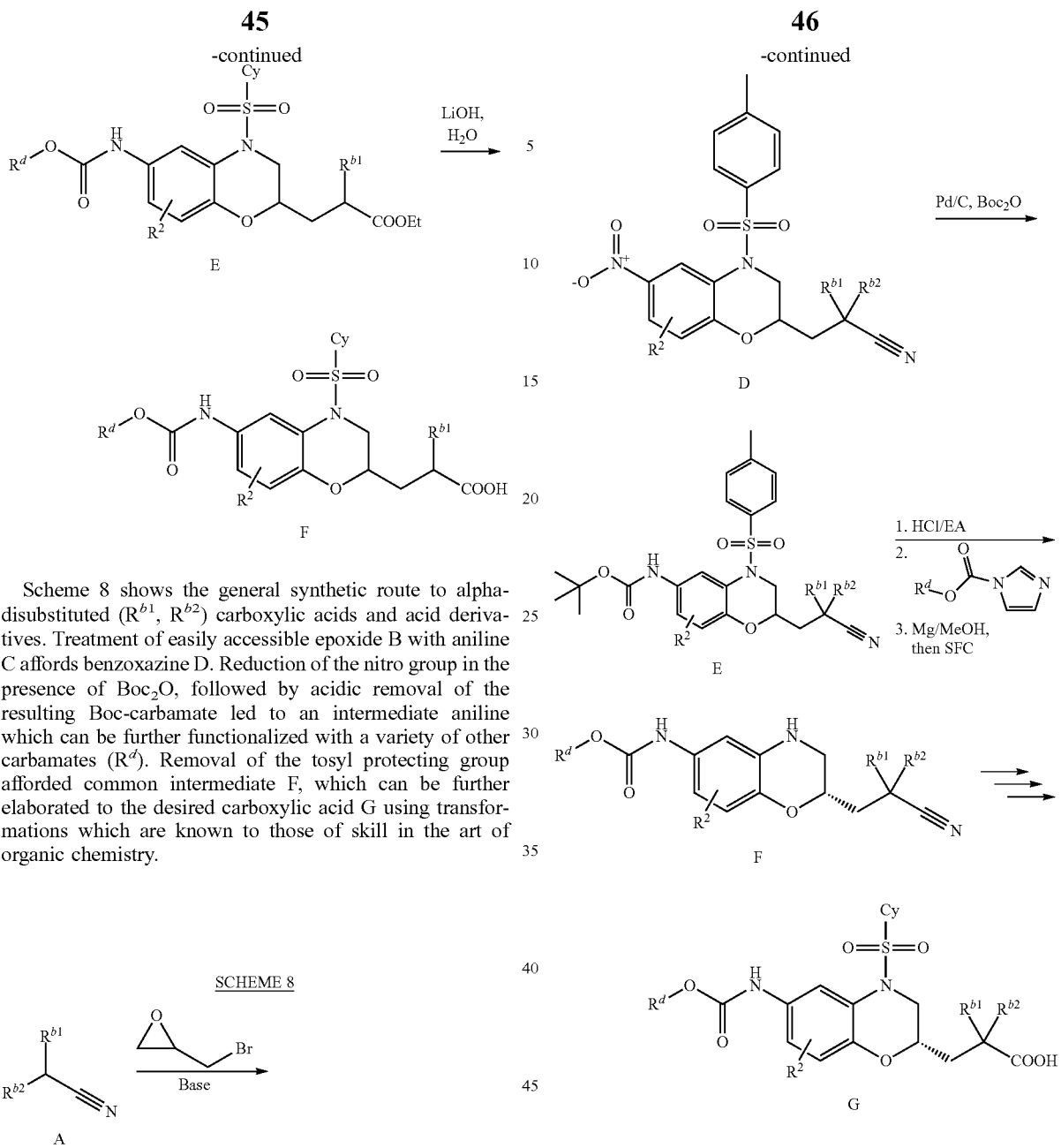

Scheme 8 shows the general synthetic route to alpha-disubstituted ($R^{b1}$, $R^{b2}$) carboxylic acids and acid derivatives. Treatment of easily accessible epoxide B with aniline C affords benzoxazine D. Reduction of the nitro group in the presence of Boc$_2$O, followed by acidic removal of the resulting Boc-carbamate led to an intermediate aniline which can be further functionalized with a variety of other carbamates ($R^d$). Removal of the tosyl protecting group afforded common intermediate F, which can be further elaborated to the desired carboxylic acid G using transformations which are known to those of skill in the art of organic chemistry.

SCHEME 8

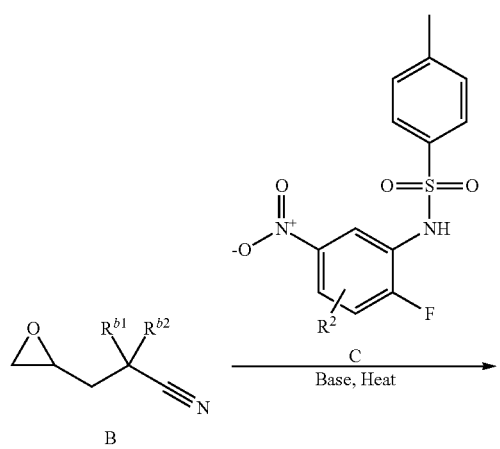

Scheme 9 shows the general synthetic route to beta-disubstituted ($R^{b1}$, $R^{b2}$) carboxylic acids and acid derivatives. Treatment of readily accessible Weinreb amide B with a Grignard reagent $R^{a1}$MgBr affords ketone C. Olefination of the carbonyl group and reduction of the resulting double bond leads to common ester intermediate E. Hydrolysis of the ester moiety and sulfonylation provides the desired beta-substituted benzoxazine carboxylic acid.

SCHEME 9

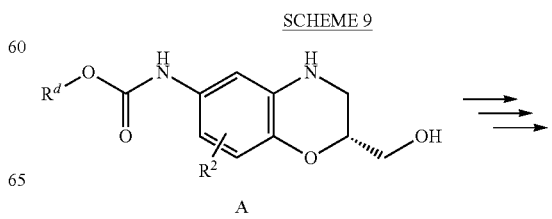

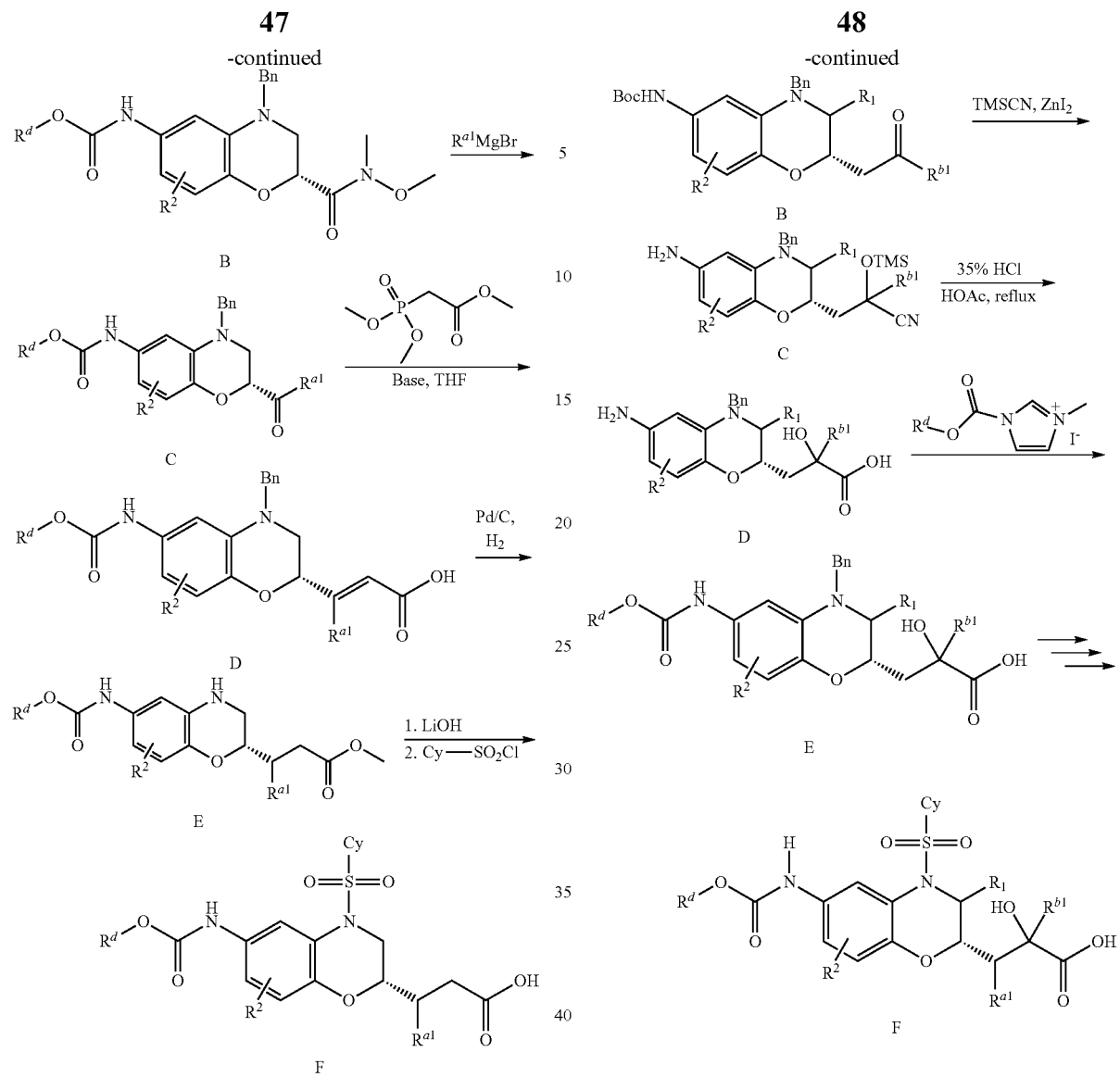

Scheme 10 shows the general synthetic route to alpha-hydroxy carboxylic acids and acid derivatives as analogues of the benzoxazine core. Treatment of previously described ketone B with TMSCN affords trimethylsioxy nitrile C. Removal of the silyl group and hydrolysis of the nitrile can be accomplished under strong acidic conditions (HCl and AcOH, reflux) to give hydroxy acid D. Introduction of the desired carbamate ($R^d$) leads to alpha-hydroxy acid E, which can subsequently be elaborated to the desired benzoxazine carboxylic acid derivative F using similar chemistry as described above.

INTERMEDIATES

The following experimental procedures detail the preparation of chemical materials used in the synthesis of Examples of the instant invention. The exemplified procedures are for illustrative purposes only, and are not intended to limit the scope of the instant invention in any way.

Intermediate 1: Preparation of methyl 2-((4-(chlorosulfonyl)-1-ethyl-1H-pyrazol-3-yl)oxy)acetate

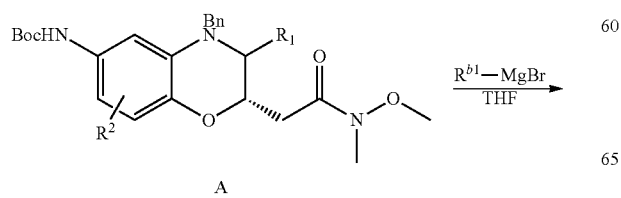

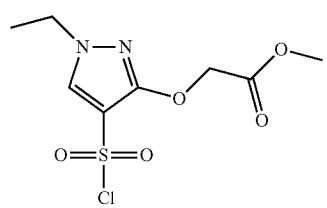

Step 1—Preparation of methyl 2-((1-ethyl-1H-pyrazol-3-yl)oxy)acetate

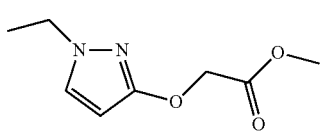

To a solution of 1-ethyl-1,2-dihydro-3H-pyrazol-3-one (13.8 g, 124 mmol) in N,N-dimethylformamide (75 mL) was added potassium carbonate (25.5 g, 185 mmol) followed by methyl bromoacetate (16.3 mL, 172 mmol). The reaction was stirred at ambient temperature overnight. The solution was partitioned between ethyl acetate and water, washed with brine, dried with sodium sulfate, filtered and concentrated in vacuo. The residue was purified by column chromatography eluting with a gradient of ethyl acetate in hexanes. The pure fractions were combined and concentrated in vacuo to yield the title compound.

Step 2—Preparation of methyl 2-((4-(chlorosulfonyl)-1-ethyl-1H-pyrazol-3-yl)oxy)acetate

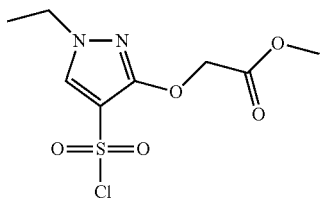 [SMILES: CCn1cc(S(=O)(=O)Cl)c(OCC(=O)OC)n1]

To a suspension of sulfur trioxide dimethylformamide complex (0.42 g, 2.7 mmol) in dichloromethane (10 mL) under nitrogen at 0° C. was added a solution of methyl 2-((1-ethyl-1H-pyrazol-3-yl)oxy)acetate (0.5 g, 2.7 mmol) in dichloromethane (1 mL). The reaction was allowed to warm to ambient temperature and stirred for 1 hour. The solution was recooled to 0° C., and anhydrous pyridine was added (0.65 mL, 8.1 mmol), followed by phosphorus pentachloride (0.62 g, 3 mmol) in portions. After 30 minutes the cooling bath was removed, and the mixture was stirred at ambient temperature overnight. The reaction was concentrated in the presence of silica. The residue was purified by column chromatography eluting with a gradient of 10-60% ethyl acetate in hexanes. The pure fractions were combined and concentrated in vacuo to yield the title compound.

Intermediate 2: Preparation of 3-Ethoxy-1-ethyl-1H-pyrazole-4-sulfonyl chloride

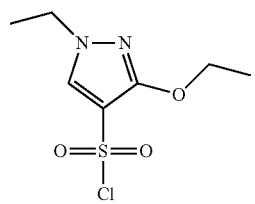

Step 1—Preparation of 1-ethyl-1,2-dihydro-3H-pyrazol-3-one

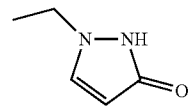

To methyl 2-chloroprop-2-enoate (5 mL, 49.8 mmol) in anhydrous tetrahydrofuran (75 mL) was added ethylhydrazine oxalate (11.2 g, 74.7 mmol) followed by triethylamine (13.9 mL, 99.6 mmol). The reaction was stirred at ambient temperature overnight. The solids were filtered off, then the filtrates were concentrated. The residue was purified by column chromatography eluting with a gradient of methanol in dichloromethane. The pure fractions were combined and concentrated in vacuo to yield the title compound.

Step 2—Preparation of 3-ethoxy-1-ethyl-1H-pyrazole

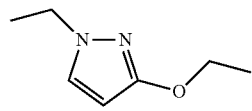

To a solution of 1-ethyl-1,2-dihydro-3H-pyrazol-3-one (1.55 g, 13.8 mmol) in N,N-dimethylformamide (15 mL) was added potassium carbonate (3.8 g, 27.6 mmol) followed by ethyl bromide (2.1 mL, 27.6 mmol). The reaction was stirred at ambient temperature for 3 hours. The solution was diluted with ethyl acetate, washed with water, brine, dried with sodium sulfate, filtered and concentrated in vacuo to yield the title compound.

Step 3—Preparation of 3-Ethoxy-1-ethyl-1H-pyrazole-4-sulfonyl chloride

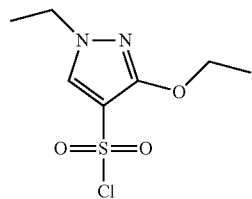

To 3-ethoxy-1-ethyl-1H-pyrazole (3.14 g, 22.4 mmol) in chloroform (25 mL) at 0° C. was added chlorosulfonic acid (15 mL, 224 mmol) dropwise. The resulting solution was stirred for 3 hours at 70° C. The solution was cooled in an ice bath and then quenched by pouring into ice water. The resulting suspension was extracted with dichloromethane and the combined organic layers were dried over anhydrous sodium sulfate and concentrated under vacuum to yield the title compound as an oil.

Intermediate 3: Preparation of 5-ethoxy-2-ethylthiazole-4-sulfonyl chloride

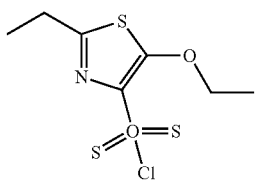

Step 1—Preparation of ethyl 2-propionamidoacetate

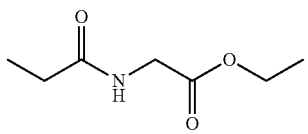

Into a 500-mL 3-necked round-bottom flask, was placed a solution of ethyl 2-aminoacetate hydrochloride (21 g, 150.45 mmol, 1.00 equiv) in saturated sodium bicarbonate/tetrahydrofuran (75/150 mL), followed by the addition of propanoyl chloride (20 g, 216.16 mmol, 1.50 equiv) dropwise with stirring at 0° C. The resulting solution was stirred for 2 h at room temperature. The resulting solution was extracted with 3×200 mL of ethyl acetate and the organic layers combined. The resulting mixture was washed with 2×500 mL of water. The mixture was dried over anhydrous sodium sulfate and concentrated under vacuum to afford ethyl 2-propanamidoacetate as yellow oil.

Step 2—Preparation of 5-ethoxy-2-ethylthiazole

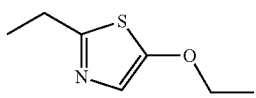

Into a 250-mL round-bottom flask, was placed a solution of ethyl 2-propanamidoacetate (6 g, 37.69 mmol, 1.00 equiv) in dioxane (150 mL) and P$_2$S$_5$ (17 g, 76.48 mmol, 2.00 equiv). The resulting solution was stirred overnight at 60° C. The reaction was then quenched by the addition of 50 mL of sodium hydroxide. The resulting solution was extracted with 3×100 mL of dichloromethane and the organic layers combined and dried over anhydrous sodium sulfate and concentrated under vacuum. The crude product was applied onto a silica gel column eluting with petroleum ether/ether (3:2) to afford 5-ethoxy-2-ethyl-1,3-thiazole as yellow oil.

Step 3—Preparation of 5-ethoxy-2-ethylthiazole-4-sulfonic acid

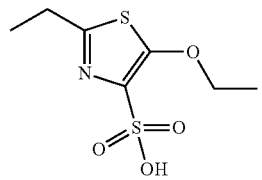

Into a 25-mL round-bottom flask, was placed a solution of 5-ethoxy-2-ethyl-1,3-thiazole (300 mg, 1.91 mmol, 1.00 equiv) in chloroform (5 mL), followed by the addition of sulfonoperoxoyl chloride (1.1 g, 9.44 mmol, 5.00 equiv) dropwise with stirring at room temperature. The resulting solution was stirred for 2 h at 60° C. The resulting mixture was concentrated under vacuum to afford 5-ethoxy-2-ethyl-1,3-thiazole-4-sulfonic acid as a yellow oil.

Step 4—Preparation of 5-ethoxy-2-ethylthiazole-4-sulfonyl chloride

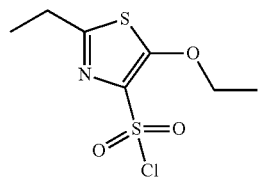

Into a 250-mL round-bottom flask, was placed 5-ethoxy-2-ethyl-1,3-thiazole-4-sulfonic acid (2.7 g, 11.38 mmol, 1.00 equiv) and thionyl chloride (20 mL, 5.00 equiv). The resulting solution was stirred for 2 h at 78° C. in an oil bath. The reaction was then quenched by the addition of 100 mL of water/ice. The resulting solution was extracted with 2×100 mL of dichloromethane and the organic layers combined and dried over anhydrous sodium sulfate and concentrated under vacuum. The crude product was applied onto a silica gel column eluting with ether/petroleum ether (3:1) to afford 5-ethoxy-2-ethyl-1,3-thiazole-4-sulfonyl chloride as a brown solid. MS ESI calculated for C$_7$H$_{11}$ClNO$_3$S$_2$ (M+H)$^+$ 256, found 256 (M+H)$^+$; $^1$H-NMR (300 MHz, CDCl$_3$): δ 4.38-4.28 (q, 2H), 2.99-2.92 (q, 2H), 1.61-1.53 (t, 3H), 1.45-1.34 (t, 3H).

Intermediate 4: Preparation of 2-cyclopropyl-5-ethoxythiazole-4-sulfonyl chloride

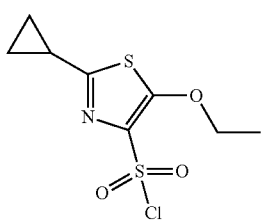

Step 1—Preparation of ethyl 2-(cyclopropanecarboxamido)acetate

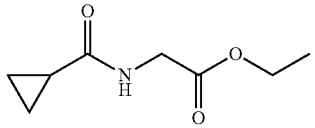

Into a 250-mL round-bottom flask, was placed a solution of ethyl 2-aminoacetate hydrochloride (10 g, 71.64 mmol, 1.00 equiv) in saturated sodium bicarbonate/tetrahydrofuran (50/50 mL). This was followed by the addition of a solution of cyclopropanecarbonyl chloride (9.0 g, 86.10 mmol, 1.20 equiv) in tetrahydrofuran (50 mL) dropwise with stirring at room temperature. The resulting solution was stirred overnight at room temperature. The resulting solution was extracted with 2×100 mL of ethyl acetate and the organic layers concentrated under vacuum. The crude product was applied onto a silica gel column eluting with ethyl acetate/petroleum ether (1:20 to 1:5) to afford ethyl 2-(cyclopropylformamido)acetate as a white solid.

Step 2—Preparation of 2-cyclopropyl-5-ethoxythiazole

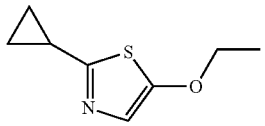

Into a 50-mL round-bottom flask, was placed ethyl 2-(cyclopropylformamido)acetate (171 mg, 1.00 mmol, 1.00 equiv) and $P_2S_5$ (333 mg, 1.50 mmol, 1.50 equiv) in 1,4-dioxane (5 mL). The resulting solution was stirred overnight at 70° C. The reaction was quenched with 10 mL of water and the resulting solution extracted with 2×10 mL of ethyl acetate. The organic layers were combined and concentrated under vacuum. The crude product was applied onto a silica gel column eluting with petroleum ether:ethyl acetate (30:1 to 10:1) to afford 2-cyclopropyl-5-ethoxy-1,3-thiazole as a yellow oil.

Step 3—Preparation of 2-cyclopropyl-5-ethoxythiazole-4-sulfonyl chloride

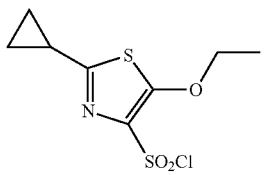

Into a 25-mL round-bottom flask, was placed 2-cyclopropyl-5-ethoxy-1,3-thiazole (600 mg, 3.55 mmol, 1.00 equiv) and $HSO_3Cl$ (1.65 g, 14.22 mmol, 4.00 equiv) in chloroform (10 mL). The resulting solution was heated to reflux for 2 h. The reaction was concentrated under vacuum and the crude residue was dissolved in thionyl chloride (10 mL). The resulting solution was heated to 80° C. for 3 h. The reaction was then quenched by the addition of 30 mL of water. The resulting solution was extracted with 2×30 mL of ethyl acetate and the organic layers combined and concentrated under vacuum. The crude product was applied onto a silica gel column eluting with ethyl acetate/petroleum ether (1:20 to 1:5) to afford 2-cyclopropyl-5-ethoxy-1,3-thiazole-4-sulfonyl chloride as a brown solid. MS ESI calculated for $C_8H_{ii}ClNO_3S_2$ $(M+H)^+$ 268, found 268 $(M+H)^+$; $^1$H-NMR (400 MHz, $CDCl_3$): δ 4.27-4.33 (m, 2H), 2.17-2.23 (m, 1H), 1.52-1.56 (t, 3H), 1.11-1.17 (m, 4H).

Intermediate 5: Preparation of 5-ethoxy-2-(trifluoromethyl)thiazole-4-sulfonyl chloride

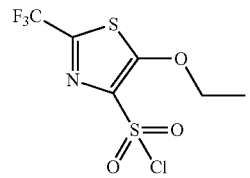 [SMILES: CCOc1sc(C(F)(F)F)nc1S(=O)(=O)Cl]

Step 1—Preparation of ethyl 2-(2,2,2-trifluoroacetamido)acetate

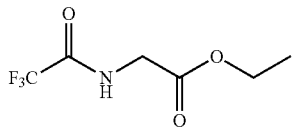

Into a 250-mL round-bottom flask, was placed a solution of trifluoroacetamide (20.3 g, 179.58 mmol, 2.00 equiv) in acetonitrile (150 mL), TEBA (1.5 g, 6.60 mmol, 0.07 equiv), potassium carbonate (24.8 g, 179.44 mmol, 2.00 equiv) and ethyl 2-bromoacetate (15 g, 89.82 mmol, 1.00 equiv). The resulting solution was heated to reflux for 1 h. The solids were filtered out and the filtrate was concentrated under vacuum. The crude product was applied onto a silica gel column eluting with ethyl acetate/petroleum ether (1:20 to 1:1) to afford ethyl 2-(trifluoroacetamido)acetate as a colorless solid.

Step 2—Preparation of 5-ethoxy-2-(trifluoromethyl)thiazole

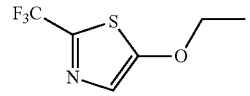

Into a 25-mL round-bottom flask, was placed ethyl 2-(trifluoroacetamido)acetate (10 g, 50.22 mmol, 1.00 equiv), $P_2S_5$ (16.7 g, 75.13 mmol, 1.50 equiv) and toluene (150 mL). The resulting solution was heated to reflux overnight, then diluted with 100 mL of water. The resulting mixture was extracted with 3×100 mL of ethyl acetate and the organic layers combined and concentrated under vacuum.

The residue was applied onto a silica gel column eluting with ethyl acetate/petroleum ether (1:30 to 1:5) to afford 5-ethoxy-2-(trifluoromethyl)-1,3-thiazole as a yellow liquid.

Step 3—Preparation of 4-bromo-5-ethoxy-2-(trifluoromethyl)thiazole

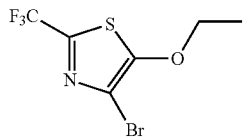

Into a 50-mL round-bottom flask, was placed a solution of 5-ethoxy-2-(trifluoromethyl)-1,3-thiazole (1 g, 5.07 mmol, 1.00 equiv) in chloroform (20 mL), followed by the addition of NBS (1.17 g, 1.30 equiv). The resulting solution was heated to reflux overnight, then concentrated under vacuum. The crude product was applied onto a silica gel column eluting with ethyl acetate/petroleum ether (1:30 to 1:10) to afford 4-bromo-5-ethoxy-2-(trifluoromethyl)-1,3-thiazole as a yellow liquid.

Step 4—Preparation of 5-ethoxy-2-(trifluoromethyl)thiazole-4-sulfonyl chloride

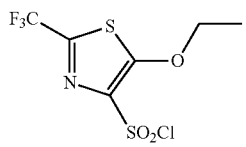 [SMILES: CCOc1sc(C(F)(F)F)nc1S(=O)(=O)Cl]

Into a 50-mL 3-necked round-bottom flask purged and maintained under an inert atmosphere of nitrogen, was placed 4-bromo-5-ethoxy-2-(trifluoromethyl)-1,3-thiazole (1 g, 3.62 mmol, 1.00 equiv) in tetrahydrofuran (20 mL), followed by the addition of n-BuLi (2.9 mL, 2.00 equiv) dropwise with stirring at −78° C. The resulting solution was stirred for 30 min at −78° C. and followed by the addition of $SO_2$ (460 mg, 7.19 mmol, 2.00 equiv) at −78° C. The resulting solution was stirred for 30 more minutes at room temperature and then concentrated under vacuum. The crude intermediate was dissolved in dichloromethane (20 mL) and treated with NCS (1.44 g, 10.78 mmol, 3.00 equiv). The resulting solution was stirred for 30 min at room temperature, then concentrated under vacuum. The crude product was applied onto a silica gel column eluting with ethyl acetate/petroleum ether (1:20 to 1:2) to afford 5-ethoxy-2-(trifluoromethyl)-1,3-thiazole-4-sulfonyl chloride as a yellow solid. MS ESI calculated for $C_6H_5F_3NO_3S_2$ (M−Cl)$^+$ 260, found 260 (M−Cl)$^+$; $^1$H-NMR (400 MHz, CDCl$_3$): δ 4.38-4.49 (m, 2H), 1.60-1.69 (m, 3H).

Intermediate 6: Preparation of 2-methoxy-5,6-dihydro-4H-pyrrolo[1,2-b]pyrazole-3-sulfonyl chloride

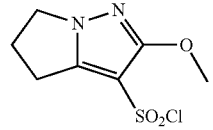

Step 1—Preparation of ethyl 6-chloro-3-oxohexanoate

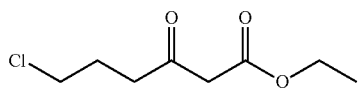

Into a 1000-mL 3-necked round-bottom flask purged and maintained under an inert atmosphere of nitrogen, was placed tetrahydrofuran (160 mL), followed by the addition of lithium diisopropylamide (86 mL, 2.00 equiv) at −78° C. A solution of ethyl 3-oxobutanoate (11.2 g, 86.06 mmol, 1.00 equiv) in tetrahydrofuran (6 mL) was next added dropwise with stirring at −78° C., followed by the addition of a solution of 1-bromo-2-chloroethane (12.2 g, 85.07 mmol, 1.00 equiv) in tetrahydrofuran (6 mL) dropwise with stirring at 0° C. After stirring for 1 h at 0° C., the pH value of the solution was adjusted to 7 with hydrogen chloride (2 N). The resulting mixture was extracted with of ethyl acetate (3×) and the organic layers combined and dried over anhydrous sodium sulfate and concentrated under vacuum to afford ethyl 6-chloro-3-oxohexanoate as a colorless liquid.

Step 2—Preparation of 5,6-dihydro-4H-pyrrolo[1,2-b]pyrazol-2-ol

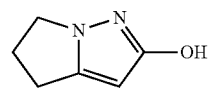

Into a 20 mL sealed tube was placed ethyl 6-chloro-3-oxohexanoate (9.0 g, 46.72 mmol, 1.00 equiv), ethanol (20 mL) and hydrazine hydrate (3.0 mL). The reaction mixture was heated in a microwave for 2 h at 120° C., cooled to room temperature and concentrated under vacuum. The resulting solution was extracted with ethyl acetate and the organic layers combined, dried over anhydrous sodium sulfate, filtered and concentrated under vacuum. The crude product was applied onto a silica gel column eluting with dichloromethane/methanol (10:1) to afford the title compound as a light yellow solid.

Step 3—Preparation of 2-methoxy-5,6-dihydro-4H-pyrrolo[1,2-b]pyrazole

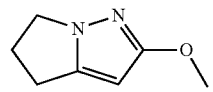

Into a 50 mL round-bottom flask was placed 5,6-dihydro-4H-pyrrolo[1,2-b]pyrazol-2-ol (1.0 g, 8.06 mmol, 1.00 equiv), acetone (20 mL) and potassium carbonate (2.2 g, 15.92 mmol, 2.00 equiv). The mixture was stirred for 5 min, followed by the addition of iodomethane (2.3 g, 16.20 mmol, 2.00 equiv) dropwise with stirring. The resulting solution was stirred overnight at room temperature. The solids were filtered out and the resulting filtrate was concentrated under vacuum. The crude product was applied onto a silica gel column eluting with dichloromethane/methanol (10:1) to afford 2-methoxy-5,6-dihydro-4H-pyrrolo[1,2-b]pyrazole as a yellow liquid.

Step 4—Preparation of 2-methoxy-5,6-dihydro-4H-pyrrolo[1,2-b]pyrazole-3-sulfonyl chloride

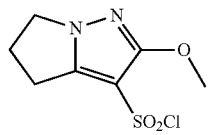

To a 25-mL round-bottom flask was added 2-methoxy-5,6-dihydro-4H-pyrrolo[1,2-b]pyrazole (300 mg, 2.17 mmol, 1.00 equiv) and chloroform (3.0 mL), followed by the addition of chlorosulfonic acid (1.5 mL) dropwise with stirring at −78° C. The resulting solution was stirred for 3 h at 60° C. and then cooled to 0° C. with a water/ice bath. The reaction was quenched by the addition of water/ice and the resulting solution was extracted with of dichloromethane. The organic layers were combined, dried over anhydrous sodium sulfate and concentrated under vacuum to afford 2-methoxy-5,6-dihydro-4H-pyrrolo[1,2-b]pyrazole-3-sulfonyl chloride as a yellow liquid.

Intermediate 7: Preparation of 2-chloro-5,6-dihydro-4H-pyrrolo[1,2-b]pyrazole-3-sulfonyl chloride

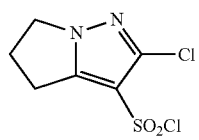 [SMILES: O=S(=O)(Cl)c1c(Cl)nn2c1CCC2]

Step 1—Preparation of 2-chloro-5,6-dihydro-4H-pyrrolo[1,2-b]pyrazole

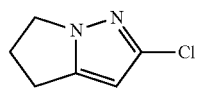

To a 30 mL sealed tube was added 5,6-dihydro-4H-pyrrolo[1,2-b]pyrazol-2-ol (1.8 g, 14.50 mmol, 1.00 equiv) and POCl$_3$ (10 mL). The resulting solution was stirred for 8 h at 200° C., cooled to room temperature with a water/ice bath and then quenched by the addition of water/ice. The resulting solution was extracted with dichloromethane (3×) and the organic layers combined, dried over anhydrous sodium sulfate and concentrated under vacuum. The crude product was applied onto a silica gel column eluting with dichloromethane/methanol (100:0 to 10:1) to afford the title compound as a brown oil.

Step 2—Preparation of 2-chloro-5,6-dihydro-4H-pyrrolo[1,2-b]pyrazole-3-sulfonyl chloride

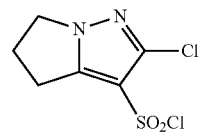

To a 25 mL round-bottom flask was added 2-chloro-5,6-dihydro-4H-pyrrolo[1,2-b]pyrazole (100 mg, 0.70 mmol, 1.00 equiv) and chloroform (2.0 mL), followed by the addition of chlorosulfonic acid (1.0 mL) at −78° C. The resulting solution was stirred for 12 h at 60° C., then cooled to 25° C. The reaction was quenched by the addition of water/ice and the resulting mixture was extracted with dichloromethane (3×). The organic layers were combined, dried over anhydrous sodium sulfate and concentrated under vacuum. The crude product was applied onto a silica gel column eluting with ethyl acetate/petroleum ether (1:10 to 1:1) to afford 2-chloro-5,6-dihydro-4H-pyrrolo[1,2-b]pyrazole-3-sulfonyl chloride as a white solid.

Intermediate 8: Preparation of 2-methoxy-4,5,6,7-tetrahydropyrazolo[1,5-a]pyridine-3-sulfonyl chloride

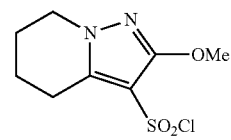

Step 1—Preparation of ethyl 7-chloro-3-oxoheptanoate

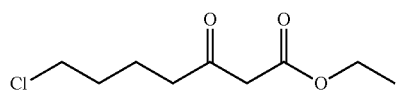

To a 1000-mL 3-necked round-bottom flask purged and maintained under an inert atmosphere of nitrogen was added tetrahydrofuran (160 mL), followed by the addition of lithium diisopropylamide (100 mL) at −78° C. A solution of ethyl 3-oxobutanoate (13 g, 99.89 mmol, 1.00 equiv) in tetrahydrofuran (6 mL) was next added dropwise with stirring at −78° C., followed by a solution of 1-bromo-3-chloropropane (15.7 g, 99.72 mmol, 1.00 equiv) in tetrahydrofuran (6 mL) dropwise with stirring at 0° C. The resulting solution was stirred for 1 h at 0° C. The pH value of the reaction was adjusted to 7 with 2 N hydrogen chloride and the resulting solution was extracted with ethyl acetate (3×).

The organic layers were combined and concentrated under vacuum to afford ethyl 7-chloro-3-oxoheptanoate as a colorless liquid.

Step 2—Preparation of 4,5,6,7-tetrahydropyrazolo[1,5-a]pyridin-2-ol

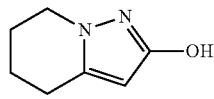

To a 10 mL sealed tube was added ethyl 7-chloro-3-oxoheptanoate (900 mg, 4.35 mmol, 1.00 equiv), ethanol (5.0 mL) and hydrazine hydrate (0.5 mL). The reaction mixture was irradiated with microwave radiation for 2 h at 120° C., cooled to room temperature and concentrated under vacuum. The crude product was applied onto a silica gel column eluting with dichloromethane/methanol (10:1) to afford 4,5,6,7-tetrahydropyrazolo[1,5-a]pyridin-2-ol.

Step 3—Preparation of 2-methoxy-4,5,6,7-tetrahydropyrazolo[1,5-a]pyridine

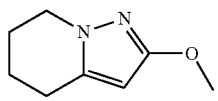

To a 50 mL round-bottom flask was added 4,5,6,7-tetrahydropyrazolo[1,5-c]pyridin-2-ol (250 mg, 1.81 mmol, 1.00 equiv), acetone (5.0 mL) and potassium carbonate (500 mg, 3.62 mmol, 2.00 equiv). The reaction mixture was stirred for 5 min at room temperature, followed by the addition of CH$_3$I (511 mg, 3.60 mmol, 2.00 equiv) dropwise with stirring. The resulting solution was stirred overnight at room temperature and quenched with 20 mL of water. The resulting mixture was extracted with ethyl acetate (3×), the combined organic layers dried over anhydrous sodium sulfate and concentrated under vacuum. The crude product was applied onto a silica gel column eluting with dichloromethane/methanol (10:1) to afford the title compound as a yellow liquid.

Step 4—Preparation of 2-methoxy-4,5,6,7-tetrahydropyrazolo[1,5-a]pyridine-3-sulfonyl chloride

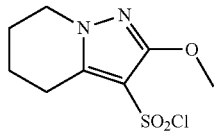

To a 50 mL round-bottom flask was added 2-methoxy-4,5,6,7-tetrahydropyrazolo[1,5-a]pyridine (150 mg, 0.99 mmol, 1.00 equiv) and chloroform (1.5 mL), followed by the addition of chlorosulfonic acid (0.5 mL) dropwise with stirring at −78° C. The resulting solution was stirred for 3 h at 60° C., then cooled to room temperature with a water/ice bath. The reaction was quenched by the addition of water/ice and the resulting mixture was extracted with dichloromethane (3×). The organic layers were combined, dried over anhydrous sodium sulfate and concentrated under vacuum to afford the title compound as a yellow liquid. $^1$H-NMR (400 MHz, CDCl$_3$): δ 4.03 (s, 3H), 4.02 (m, 2H), 3.06 (m, 2H), 2.05 (m, 2H), 1.95 (m, 2H).

Intermediate 9: Preparation of 2-chloro-4,5,6,7-tetrahydropyrazolo[1,5-a]pyridine-3-sulfonyl chloride

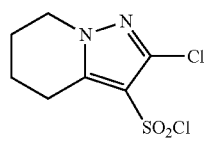 [SMILES: O=S(=O)(Cl)c1c(Cl)nn2c1CCCC2]

Step 1. Preparation of 2-chloro-4,5,6,7-tetrahydropyrazolo[1,5-a]pyridine

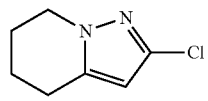

To a 30 mL sealed tube was added 4,5,6,7-tetrahydropyrazolo[1,5-a]pyridin-2-ol (3.0 g, 21.71 mmol, 1.00 equiv) and POCl$_3$ (12.0 mL). The resulting solution was stirred for 8 h at 200° C., then cooled to room temperature. The reaction was quenched by the addition of water/ice and the resulting solution was extracted with dichloromethane (3×). The combined organic layers were dried over anhydrous sodium sulfate and concentrated under vacuum. The residue was applied onto a silica gel column eluting with dichloromethane/methanol (100:0 to 10:1) to afford the title compound as a colorless liquid.

Step 2—Synthesis of 2-chloro-4,5,6,7-tetrahydropyrazolo[1,5-a]pyridine-3-sulfonyl chloride

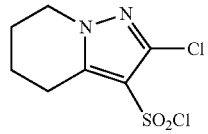 [SMILES: O=S(=O)(Cl)c1c(Cl)nn2c1CCCC2]

To a 25-mL round-bottom flask was added 2-chloro-4,5,6,7-tetrahydropyrazolo[1,5-a]pyridine (350 mg, 2.23 mmol, 1.00 equiv) and chloroform (3.5 mL), followed by the addition of sulfonoperoxoyl chloride (1.5 mL) at −78° C. The resulting solution was stirred for 12 h at 60° C., then cooled to room temperature. The reaction was quenched by the addition of water/ice and the resulting solution was extracted with dichloromethane (3×). The combined organic layers dried over anhydrous sodium sulfate and concentrated under vacuum. The crude product was applied onto a silica gel column eluting with ethyl acetate/petroleum ether (0:100 to 1:1) to afford the title compound as a brown solid. $^1$H-NMR (400 MHz, CDCl$_3$): δ 4.19 (m, 2H), 3.11 (m, 2H), 2.12 (m, 2H), 2.05 (m, 2H), 1.92 (m, 2H).

Intermediate 10: Synthesis of 3-(difluoromethoxy)-1-ethyl-1H-pyrazole-4-sulfonyl chloride

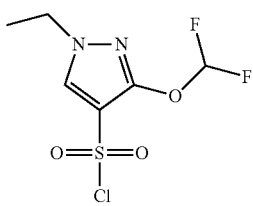

Step 1—Synthesis of 1H-pyrazol-3-ol

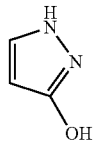

To a 100 mL round-bottom flask was added methyl (2E)-3-methoxyprop-2-enoate (11.6 g, 99.90 mmol, 1.00 equiv) and methanol (10.0 mL), followed by the addition of hydrazine hydrate (7.8 mL) dropwise with stirring. The resulting solution was stirred for 90 min at 85° C., then concentrated under vacuum to afford crude 1H-pyrazol-3-ol as a white solid.

Step 2—Synthesis of 1-(3-hydroxy-1H-pyrazol-1-yl)ethanone

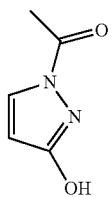

To a 250 mL round-bottom flask was added 1H-pyrazol-3-ol (8.5 g, 101.10 mmol, 1.00 equiv), and pyridine (50 mL), followed by the addition of a solution of acetic anhydride (47.5 mL) in pyridine (10.0 mL) dropwise with stirring over 15 min at 95° C. The resulting solution was stirred for 1 h at 95° C. and then concentrated under vacuum. The crude product was applied onto a silica gel column eluting with ethyl acetate/petroleum ether (1:100 to 1:1) to afford the title compound as a white solid.

Step 3—Synthesis of 1-(3-(difluoromethoxy)-1H-pyrazol-1-yl)ethanone

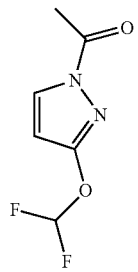

To a 250 mL round-bottom flask was added 1-(3-hydroxy-1H-pyrazol-1-yl)ethanone (5.0 g, 39.65 mmol, 1.00 equiv), N,N-dimethylformamide (50.0 mL), potassium carbonate (11.0 g, 79.02 mmol, 2.00 equiv) and ethyl 2-chloro-2,2-difluoroacetate (7.5 g, 47.31 mmol, 1.20 equiv). The resulting solution was stirred for 12 h at 60° C., then diluted with water. The resulting mixture was extracted with ethyl ether (3×) and the combined organic layers washed with water, dried over anhydrous sodium sulfate and concentrated under vacuum. The crude product was applied onto a silica gel column eluting with ethyl ether/hexanes (0:100 to 1:1) to afford the title compound as colorless oil. $^1$H-NMR (400 MHz, CDCl$_3$): δ 8.15 (d, 1H), 7.02 (t, 1H), 6.14 (d, 1H), 2.62 (s, 3H).

Step 4—Synthesis of 3-(difluoromethoxy)-1H-pyrazole

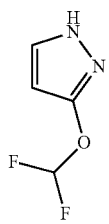

To a 25 mL round-bottom flask was added 1-[3-(difluoromethoxy)-1H-pyrazol-1-yl]ethan-1-one (110 mg, 0.62 mmol, 1.00 equiv), methanol (2.0 mL), tetrahydrofuran (2.0 mL) and sodium hydroxide (2.0 mL, 1 M). The resulting solution was stirred for 1 h at 25° C., then diluted with water. The resulting mixture was extracted with dichloromethane (3×) and the combined organic layers dried over anhydrous sodium sulfate and concentrated under vacuum to afford the title compound as a colorless liquid. $^1$H-NMR (400 MHz, CDCl$_3$): δ 7.48 (d, 1H), 6.74 (t, 1H), 5.99 (d, 1H).

Step 5—Synthesis of 3-(difluoromethoxy)-1-ethyl-1H-pyrazole

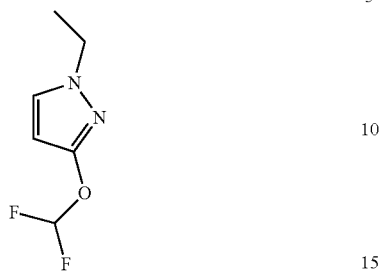

To a 100 mL round-bottom flask was added 3-(difluoromethoxy)-1H-pyrazole (500 mg, 3.73 mmol, 1.00 equiv) and N,N-dimethylformamide (15 mL), followed by the addition of sodium hydride (360 mg, 15.00 mmol, 4.00 equiv). The mixture was stirred for 10 min before the addition of bromoethane (1620 mg, 15.00 mmol, 4.00 equiv). The resulting solution was stirred for 12 h at 25° C., then quenched by the addition of water. The resulting mixture was extracted with ethyl ether and the combined organic layers washed with water, dried over anhydrous sodium sulfate and concentrated under vacuum. The crude product was applied onto a silica gel column eluting with ethyl ether/hexane (0:100 to 1:1) to afford 3-(difluoromethoxy)-1-ethyl-1H-pyrazole as a colorless liquid.

Step 6—Synthesis of 3-(difluoromethoxy)-1-ethyl-1H-pyrazole-4-sulfonyl chloride

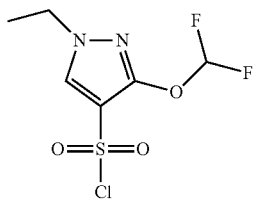

To a 250 mL round-bottom flask was added 3-(difluoromethoxy)-1-ethyl-1H-pyrazole (3.0 g, 18.50 mmol, 1.00 equiv) and chloroform (20.0 mL), followed by the addition of sulfonoperoxoyl chloride (8.0 mL) at −78° C. The mixture was stirred for 2 h at 60° C., then concentrated under vacuum. To the resulting residue was added sulfuroyl dichloride (20.0 mL) and the solution was stirred for 2 h at 85° C. The reaction mixture was cooled to room temperature and then quenched by the addition of water/ice. The resulting mixture was extracted with ethyl acetate (3×) and the combined organic layers dried over anhydrous sodium sulfate and concentrated under vacuum. The crude product was applied onto a silica gel column eluting with ethyl acetate/petroleum ether (0:100 to 100:0) to afford 3-(difluoromethoxy)-1-ethyl-1H-pyrazole-4-sulfonyl chloride as a brown liquid. MS ESI calculated for $C_6H_8ClF_2N_2O_3S$ $(M+H)^+$ 260.6, found 260.8 $(M+H)^+$; $^1$H-NMR (300 MHz, CDCl$_3$): δ 7.91 (s, 1H), 7.05 (t, J=71.7 Hz, 1H), 4.12 (q, J=7.5 Hz, 2H), 1.53 (t, J=7.2 Hz, 3H); F-NMR (300 MHz, CDCl$_3$): δ −85.82.

Intermediate 11: Synthesis of 1-(difluoromethyl)-3-ethoxy-1H-pyrazole-4-sulfonyl chloride

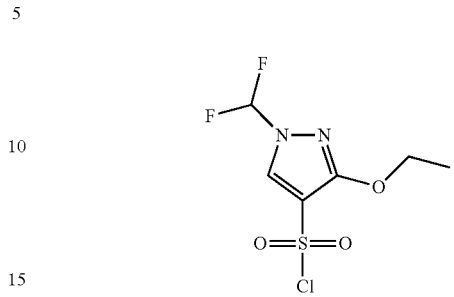

Step 1—Synthesis of 1-(3-ethoxy-1H-pyrazol-1-yl)ethanone

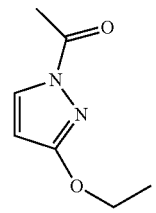

To a 100 mL round-bottom flask was added 1-(3-hydroxy-1H-pyrazol-1-yl)ethan-1-one (2.0 g, 15.86 mmol, 1.00 equiv), N,N-dimethylformamide (20.0 mL) and potassium carbonate (4.4 g, 31.61 mmol, 2.00 equiv), followed by the addition of bromoethane (2.4 mL, 2.00 equiv) dropwise with stirring. The resulting solution was stirred for 12 h at 25° C., then diluted with ethyl acetate. The resulting solution was washed with water and the organic layer dried over anhydrous sodium sulfate and concentrated under vacuum. The crude product was applied onto a silica gel column eluting with ethyl acetate/petroleum ether (0:100 to 1:1) to afford 1-(3-ethoxy-1H-pyrazol-1-yl)ethanone as a white solid. $^1$H-NMR (300 MHz, CDCl$_3$): δ 8.05 (d, 1H), 5.95 (d, 1H), 4.32 (q, 2H), 2.58 (s, 3H), 1.43 (t, 3H).

Step 2—Synthesis of 3-ethoxy-1H-pyrazole

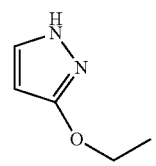

To a 100 mL round-bottom flask was added 1-(3-ethoxy-1H-pyrazol-1-yl)ethan-1-one (1.26 g, 8.17 mmol, 1.00 equiv), methanol (15 mL), tetrahydrofuran (10 mL) and sodium hydroxide aqueous (12 mL, 1 M). The resulting solution was stirred for 1 h at 25° C., then diluted with H$_2$O. The resulting mixture was extracted with dichloromethane (3×) and the combined organic layers dried over anhydrous

Step 3—Synthesis of 1-(difluoromethyl)-3-ethoxy-1H-pyrazole

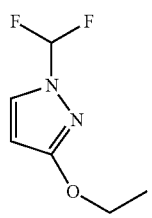

To a 100 mL round-bottom flask was added 3-ethoxy-1H-pyrazole (2.0 g, 17.84 mmol, 1.00 equiv), N,N-dimethylformamide (30 mL) and potassium carbonate (4.9 g, 35.45 mmol, 2.00 equiv), followed by the addition of ethyl 2-chloro-2,2-difluoroacetate (3.4 g, 21.45 mmol, 1.20 equiv) dropwise with stirring. The resulting solution was stirred for 12 h at 60° C., then diluted with H$_2$O. The resulting mixture was extracted with dichloromethane (3×) and the combined organic layers washed with water, dried over anhydrous sodium sulfate and concentrated under vacuum. The crude product was applied onto a silica gel column with ethyl ether/hexane (0:100 to 1:1) to afford 1-(difluoromethyl)-3-ethoxy-1H-pyrazole as a colorless liquid. $^1$H-NMR (300 MHz, CDCl$_3$): δ 7.56 (d, 1H), 7.17 (t, 1H), 5.86 (d, 1H), 4.29 (q, 2H), 1.39 (t, 3H).

Step 4—Synthesis of 1-(difluoromethyl)-3-ethoxy-1H-pyrazole-4-sulfonic acid

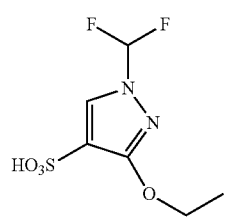

To a 25 mL round-bottom flask was added 1-(difluoromethyl)-3-ethoxy-1H-pyrazole (600 mg, 3.70 mmol, 1.00 equiv) and trichloromethane (2.0 mL), followed by the addition of chlorosulfonic acid (1.0 mL) at −78° C. The resulting solution was stirred for 2 h at 60° C. and then concentrated under vacuum to afford 1-(difluoromethyl)-3-ethoxy-1H-pyrazole-4-sulfonic acid as colorless oil, which was used in the next step without further purification.

Step 5—Synthesis of 1-(difluoromethyl)-3-ethoxy-1H-pyrazole-4-sulfonyl chloride

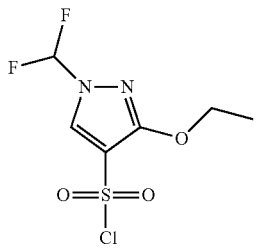

To a 25 mL round-bottom flask was added 1-(difluoromethyl)-3-ethoxy-1H-pyrazole-4-sulfonic acid (800 mg, 3.30 mmol, 1.00 equiv) and sulfuroyl dichloride (3.0 mL). The resulting solution was stirred for 2 h at 85° C. and then quenched by the addition of water/ice. The resulting mixture was extracted with dichloromethane (3×) and the combined organic layers dried over anhydrous sodium sulfate and concentrated under vacuum. The crude product was applied onto a silica gel column eluting with ethyl acetate/petroleum ether (0:100 to 100:0) to afford 1-(difluoromethyl)-3-ethoxy-1H-pyrazole-4-sulfonyl chloride as brown liquid. $^1$H-NMR (300 MHz, CDCl$_3$): δ 8.23 (s, 1H), 7.01 (t, J=60.6 Hz, 1H), 4.44 (q, J=7.2 Hz, 2H), 1.48 (t, J=7.2 Hz, 1H); F-NMR (300 MHz, CDCl$_3$): δ −96.34.

Intermediate 12: Synthesis of (R)-tert-butyl (2-(hydroxymethyl)-3,4-dihydro-2H-benzo[b][1,4]oxazin-6-yl)carbamate

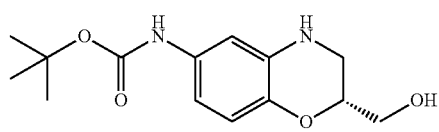 [SMILES: CC(C)(C)OC(=O)Nc1ccc2c(c1)NC[C@H](CO)O2]

Step 1—Synthesis of 2-[[(2S)-3-chloro-2-hydroxypropyl]amino]-4-nitrophenol

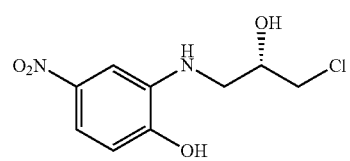 [SMILES: O=[N+]([O-])c1ccc(O)c(NC[C@H](O)CCl)c1]

A solution of 2-amino-4-nitrophenol (250.0 g, 1.62 mol) and (2S)-2-(chloromethyl)oxirane (330.0 g, 3.57 mol) in ethanol:water (2500 mL: 25 mL) was stirred for twelve hours at 60° C. in an oil bath. The resulting mixture was cooled and concentrated to afford 2-[[(2S)-3-chloro-2-hydroxypropyl]amino]-4-nitrophenol as a brown oil.

Step 2—Synthesis of [(2R)-6-nitro-3,4-dihydro-2H-1,4-benzoxazin-2-yl]methanol

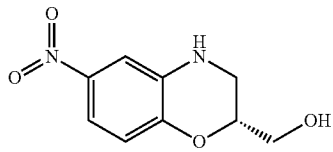 [SMILES: O=[N+]([O-])c1ccc2c(c1)NC[C@H](CO)O2]

A solution of 2-[[(2S)-3-chloro-2-hydroxypropyl]amino]-4-nitrophenol (400 g, 1.62 mol) in ethanol (2.5 L) and potassium carbonate (134.5 g, 973 mmol) was stirred for twelve hours at 90° C. in an oil bath. The mixture was filtered and the filtrate was concentrated. The residue was diluted with water (1.5 L) and extracted three times with ethyl acetate (1 L). The combined organic layers were washed with brine, dried (Na$_2$SO$_4$), and concentrated. The residue was purified via MPLC over silica gel eluting with ethyl acetate/petroleum ether (1:1) to afford [(2R)-6-nitro-3,4-dihydro-2H-1,4-benzoxazin-2-yl]methanol as a red solid.

Part 3—Synthesis of ((R)-2-hydroxymethyl-3,4-dihydro-2H-benzo[1,4]oxazin-6-yl)-carbamic acid tert-butyl ester

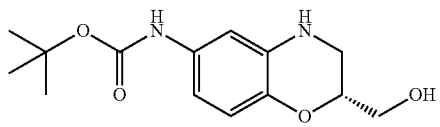 [SMILES: CC(C)(C)OC(=O)Nc1ccc2c(c1)NC[C@H](CO)O2]

The atmosphere above a solution of [(2R)-6-nitro-3,4-dihydro-2H-1,4-benzoxazin-2-yl]methanol (137 g, 652 mmol), palladium on carbon (13.7 g) and di-tert-butyl dicarbonate (157 g, 717 mmol) in methanol (1400 mL) was exchanged with hydrogen. The resulting solution was stirred for twelve hours at room temperature. The mixture was filtered, and the filtrate was concentrated. The crude product was purified by re-crystallization from ether to afford ((R)-2-hydroxymethyl-3,4-dihydro-2H-benzo[1,4]oxazin-6-yl)-carbamic acid tert-butyl ester as an off-white solid. LRMS (ESI) calculated for C$_{14}$H$_{21}$N$_2$O$_4$ 280. Found: 281 (M+H)$^+$.
$^1$H NMR (300 MHz, CDCl$_3$): δ 6.92 (s, 1H), 6.71 (d, J=8.7 Hz, 1H), 6.41 (dd, J=8.7, 2.4 Hz, 1H), 6.26 (s, 1H), 4.20-4.21 (m, 1H), 3.76-3.86 (m, 2H), 3.26-3.35 (m, 2H), 1.53 (s, 9H).

Intermediate 13: Synthesis of (S)-methyl 2-(6-((tert-butoxycarbonyl)amino)-3,4-dihydro-2H-benzo[b][1,4]oxazin-2-yl)acetate

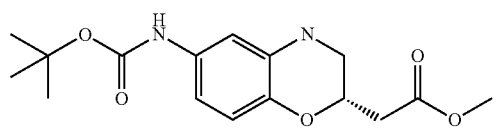 [SMILES: COC(=O)C[C@H]1CNc2cc(NC(=O)OC(C)(C)C)ccc2O1]

Step 1—Synthesis of (R and S)-methyl 2-(6-nitro-3,4-dihydro-2H-benzo[b][1,4]oxazin-2-yl)acetate To a stirred mixture of 2-amino-4-nitrophenol (5 g, 32.4 mmol), sodium bicarbonate (3.27 g, 38.9 mmol), and methanol (100 mL) was added a solution of methyl 4-bromocrotonate (3.82 mL, 32.4 mmol) in methanol (50 mL) dropwise during a 30 minute period. The reaction mixture was stirred an additional 18 hours at room temperature. The reaction mixture was concentrated under reduced pressure and partitioned between ethyl acetate and water. The organic layer was dried (MgSO$_4$) and concentrated. The residual oil was dissolved in ethanol (100 mL) and potassium carbonate (1.614 g, 11.68 mmol) was added. The reaction was stirred for 2.5 hours at room temperature and concentrated. The residue was partitioned between dichloromethane and water. The organic layer was extracted with 1 N HCl. The aqueous solution was neutralized with 1N NaOH and extracted with ethyl acetate. This organic layer was dried (Na$_2$SO$_4$) and concentrated to afford the title compound. LRMS ESI calculated for C$_{11}$H$_{13}$N$_2$O$_5$ (M+H)$^+$: 253. Found: 253.

Step 2—Synthesis of (R)-methyl 2-(6-((tert-butoxycarbonyl)amino)-3,4-dihydro-2H-benzo[b][1,4]oxazin-2-yl)acetate and (S)-methyl 2-(6-((tert-butoxycarbonyl)amino)-3,4-dihydro-2H-benzo[b][1,4]oxazin-2-yl)acetate

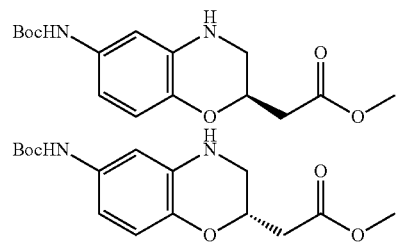

To a stirred solution of methyl 2-(6-nitro-3,4-dihydro-2H-benzo[b][1,4]oxazin-2-yl)acetate (6.09 g, 24.15 mmol) and methanol (48 mL) purged with nitrogen was added 10% Pd/C (7.71 g, 7.24 mmol) followed by di-tert-butyl dicarbonate (6.73 mL, 29.0 mmol). The atmosphere above the reaction was purged and replaced with an atmosphere of hydrogen and was stirred at room temperature for 24 h. The crude mixture was filtered through CELITE, rinsing with methanol. The combined filtrates were concentrated. The residue was purified via MPLC eluting with a gradient of 0-100% ethyl acetate in hexanes. The racemic product was submitted for chiral SFC separation (SFC Column: Chiral Technology AZ-H 2.1×25 cm, 5 uM; MP: 30%/70% Ethanol/CO$_2$ (no other modifiers); Flow rate: 70 mL/Min, 6 min run time; WL: 220 nm; Injections of 0.30 mL were performed on the Berger Multigram II SFC). Mixture of Enantiomers LRMS ESI calculated for C$_{16}$H$_{23}$N$_2$O$_5$ (M+H)$^+$: 323. Found: 323; (R)-Enantiomer: LRMS ESI calculated for $C_{16}H_{23}N_2O_5$ (M+H)$^+$: 323. Found: 323; (S)-Enantiomer: LRMS ESI calculated for $C_{16}H_{23}N_2O_5$ (M+H)$^+$: 323. Found: 323.

EXAMPLES

The invention now being generally described will be more readily understood by reference to the following examples, which are included for purposes of illustration of certain aspects and embodiments of the present invention, and are not intended to limit the invention. Starting materials useful for preparing the compounds of Formula (I) can be obtained from commercial sources or are readily prepared from commercially available materials using transformations which are known to those of skill in the art of organic chemistry.

Example 1

Preparation of (S)-ethyl 3-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoate (Example No. 1A)

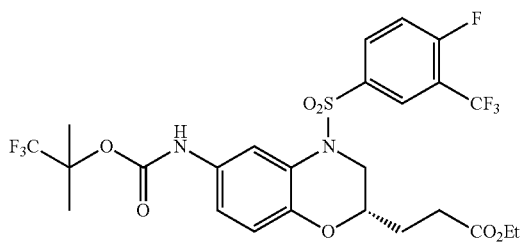 [SMILES: CCOC(=O)CC[C@H]1CN(S(=O)(=O)c2ccc(F)c(C(F)(F)F)c2)c2cc(NC(=O)OC(C)(C)C(F)(F)F)ccc2O1]

Part I—Preparation of (R)-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)methyl methanesulfonate

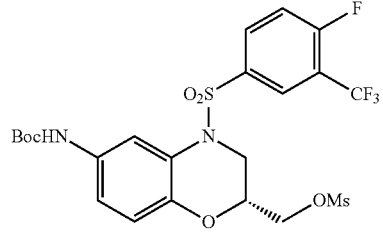 [SMILES: CC(C)(C)OC(=O)Nc1ccc2c(c1)N(S(=O)(=O)c1ccc(F)c(C(F)(F)F)c1)C[C@H](COS(C)(=O)=O)O2]

To a solution of (R)-tert-butyl (4-((4-fluoro-3-(trifluoromethyl)phenyl)sulfonyl)-2-(hydroxymethyl)-3,4-dihydro-2H-benzo[b][1,4]oxazin-6-yl)carbamate (2.0 g, 3.95 mmol) in dichloromethane (20 mL) at room temperature under N$_2$ was added methanesulfonyl chloride (0.462 mL, 5.92 mmol) followed by triethylamine (1.101 mL, 7.90 mmol). The mixture was stirred at 45° C. for an hour, cooled down to room temperature, diluted with EtOAc, washed with saturated NaHCO$_3$, brine, dried (MgSO$_4$), and concentrated. The crude product was obtained as orange solid, which was used in the next step without further purification. MS ESI calculated for $C_{22}H_{24}F_4N_2O_8S_2$ (M+H)$^+$ 585, found 442 (M-tBu+H)$^+$ and 607 (M+Na)$^+$.

Part II—Preparation of (S)-triethyl 2-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)ethane-1,1,1-tricarboxylate

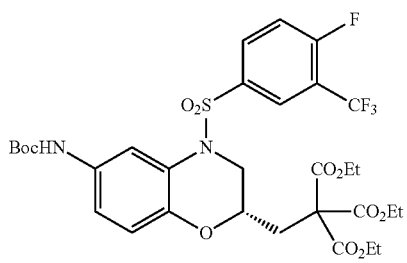 [SMILES: CCOC(=O)C(C[C@H]1CN(S(=O)(=O)c2ccc(F)c(C(F)(F)F)c2)c2cc(NC(=O)OC(C)(C)C)ccc2O1)(C(=O)OCC)C(=O)OCC]

To a solution of (R)-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)methyl methanesulfonate (500 mg, 0.855 mmol) and tetrabutyl ammonium iodide (348 mg, 0.941 mmol) in acetonitrile (10 mL) at room temperature was added triethyl methanetricarboxylate (0.983 mL, 4.28 mmol) followed by potassium carbonate (591 mg, 4.28 mmol). The mixture was stirred at 80° C. for sixty hours. The mixture was cooled, diluted with EtOAc, washed with water and brine, dried (MgSO$_4$), and concentrated. The residue was purified by normal phase flash chromatography eluting with EtOAc/hexane (0~50%) to give the desired product as a white solid after lyophilization. MS ESI calculated for $C_{32}H_{36}F_4N_2O_{ii}$ S (M+H)$^+$ 721, found 665 (M-tBu+H)$^+$.

Step III—Preparation of (S)-ethyl 3-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)propanoate (Example No. 1B)

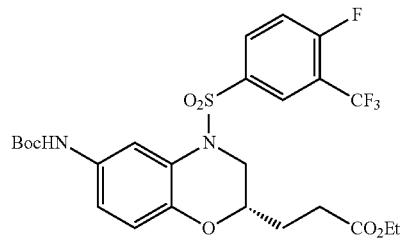 [SMILES: CCOC(=O)CC[C@H]1CN(S(=O)(=O)c2ccc(F)c(C(F)(F)F)c2)c2cc(NC(=O)OC(C)(C)C)ccc2O1]

To a solution of (S)-triethyl 2-(6-(((tert-butoxycarbonyl)amino)-4-((4-fluoro-3-(trifluoromethyl)phenyl)sulfonyl)-3,4-dihydro-2H-benzo[b][1,4]oxazin-2-yl)ethane-1,1,1-tricarboxylate (300 mg, 0.42 mmol) in DMSO (2.5 mL) was added water (0.015 mL, 0.833 mmol) and lithium chloride (52.9 mg, 1.25 mmol). The mixture was stirred at 170° C. for two hours, cooled to room temperature, and then stirred an additional 18 hours. The reaction mixture was diluted with EtOAc, washed with water and brine, dried (MgSO$_4$), and concentrated. The brown oil residue was used in the next step without further purification. MS ESI calculated for $C_{25}H_{28}F_4N_2O_7S$ (M+H)$^+$ 577, found 599 (M+Na)$^+$.

Step IV—Preparation of (S)-ethyl 3-(6-amino-4-((4-fluoro-3-(trifluoromethyl)phenyl)sulfonyl)-3,4-dihydro-2H-benzo[b][1,4]oxazin-2-yl)propanoate

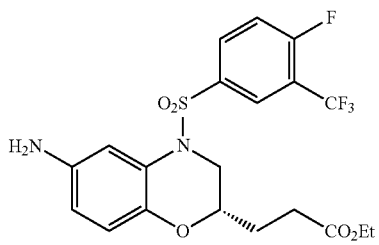 [SMILES: CCOC(=O)CC[C@H]1CN(S(=O)(=O)c2ccc(F)c(C(F)(F)F)c2)c2cc(N)ccc2O1]

To a room temperature solution of (S)-ethyl 3-(6-((tert-butoxycarbonyl)amino)-4-((4-fluoro-3-(trifluoromethyl)phenyl)sulfonyl)-3,4-dihydro-2H-benzo[b][1,4]oxazin-2-yl)propanoate (250 mg, 0.434 mmol) in dichloromethane (5 mL) was added trifluoroacetic acid (1 mL, 13.0 mmol) and the mixture was stirred for ninety minutes. The solvent was removed in vacuo followed by lyophilization. MS ESI calculated for $C_{20}H_{20}F_4N_2O_5S$ $(M+H)^+$ 477, found 477 and 499 $(M+Na)^+$.

Step V—Preparation of (S)-ethyl 3-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoate (Example No. 1-A))

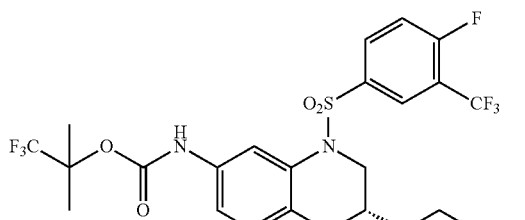

To a room temperature solution of (S)-ethyl 3-(6-amino-4-((4-fluoro-3-(trifluoromethyl)phenyl)sulfonyl)-3,4-dihydro-2H-benzo[b][1,4]oxazin-2-yl)propanoate (300 mg, 0.630 mmol) in DMF (12 mL) was added 1,1,1-trifluoro-2-methylpropan-2-yl 1H-imidazole-1-carboxylate (210 mg, 0.945 mmol) and the mixture was stirred at 100° C. for two hours. The reaction mixture was allowed to cool down to room temperature, diluted with EtOAc, washed with saturated $NaHCO_3$, brine, dried ($MgSO_4$), filtered and concentrated. The residue was purified by normal phase chromatography eluting with EtOAc/hexane (0~25%), to give the desired product as a white solid after lyophization. MS ESI calculated for $C_{25}H_{25}F_7N_2O_7S$ $(M+H)^+$ 631, found 648 $(M+NH_4)^+$. $^1$H-NMR (600 MHz, DMSO-$d_6$) 1.13 (3H, t, J=7.12 Hz), 1.67 (6H, s), 1.68-1.80 (1H, m), 1.88-1.82 (1H, m), 2.40 (2H, d, J=7.31 Hz), 3.3.36-3.40 (1H, m), 3.65 (1H, s), 4.01 (2H, q, J=7.12 Hz), 4.29 (1H, d, J=13.89 Hz), 6.73 (1H, d, J=8.85 Hz), 7.02 (1H, d, J=8.93 Hz), 7.75 (1H, t, J=9.50 Hz), 7.92 (1H, s), 8.16-8.12 (2H, m), 9.71 (1H, s).

Example 2

Preparation of (S or R)-3-((S)-4-((3-chloro-4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid and (R or S)-3-((S)-4-((3-chloro-4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid (Example Nos. 2A and 2B)

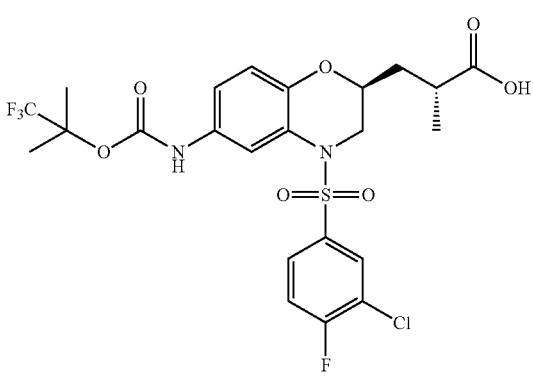

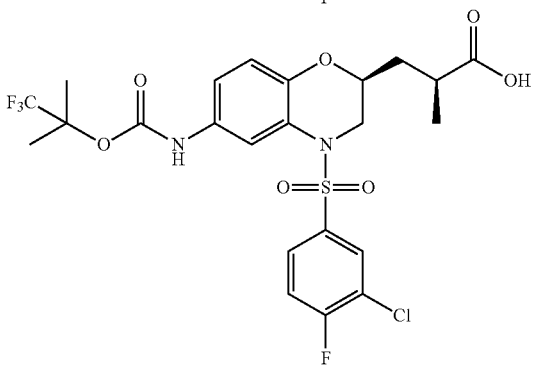

Step 1—Preparation of (R)-4-benzyl-2-(bromomethyl)-6-nitro-3,4-dihydro-2H-benzo[b][1,4]oxazine

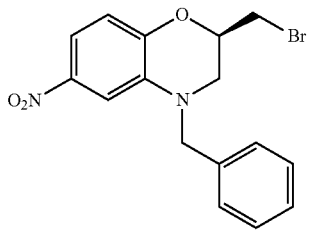 [SMILES: O=[N+]([O-])c1ccc2c(c1)N(Cc1ccccc1)C[C@H](CBr)O2]

To a room temperature solution of (R)-(4-benzyl-6-nitro-3,4-dihydro-2H-benzo[b][1,4]oxazin-2-yl)methanol (5.0 g, 16.7 mmol) and $CBr_4$ (12.0 g, 36.2 mmol) in THF (50 mL) was added $PPh_3$ (10.0 g, 38.1 mmol) portionwise. The reaction mixture was stirred at 60° C. overnight, cooled, and concentrated in vacuo. The residue was purified by column chromatography (petroleum ether:ethyl acetate=10:1) to give the title compound as a yellow solid. LCMS (ESI) calculated for $C_{16}H_{15}BrN_2O_3$ (M+H)$^+$: 363. found: 363.

Step 2—Preparation of (S)-diethyl 2-((4-benzyl-6-nitro-3,4-dihydro-2H-benzo[b][1,4]oxazin-2-yl)methyl)malonate

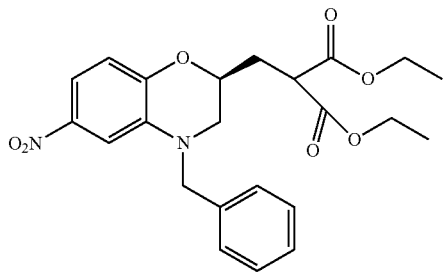 [SMILES: CCOC(=O)C(C[C@H]1CN(Cc2ccccc2)c2cc([N+](=O)[O-])ccc2O1)C(=O)OCC]

To a room temperature solution of (R)-4-benzyl-2-(bromomethyl)-6-nitro-3,4-dihydro-2H-benzo[b][1,4]oxazine (6.0 g, 16.5 mmol) and diethyl malonate (3.5 g, 21.9 mmol) in DMF (15 mL) was added $K_2CO_3$ (4.8 g, 34.73 mmol). The mixture was stirred at 100° C. overnight. The mixture was cooled, and diluted with water and 1N HCl. The mixture was extracted with three times with EtOAc. The combined organic layers were washed with brine, dried ($Na_2SO_4$) and concentrated. The residue was purified by column chromatography (petroleum ether:ethyl acetate=10:1) to give the title compound as a yellow oil. LCMS (ESI) calculated for $C_{23}H_{26}N_2O_7$ (M+H)$^+$: 443. found: 443.

Step 3—Preparation of (S)-diethyl 2-((4-benzyl-6-nitro-3,4-dihydro-2H-benzo[b][1,4]oxazin-2-yl)methyl)-2-methylmalonate

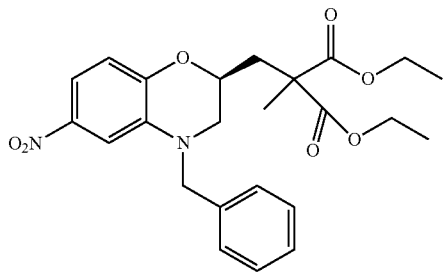 [SMILES: CCOC(=O)C(C)(C[C@H]1CN(Cc2ccccc2)c2cc([N+](=O)[O-])ccc2O1)C(=O)OCC]

To a room temperature solution of (S)-diethyl 2-((4-benzyl-6-nitro-3,4-dihydro-2H-benzo[b][1,4]oxazin-2-yl)methyl)malonate (5.0 g, 11.3 mmol) and $Cs_2CO_3$ (8.0 g, 24.55 mmol) in DMF (50 mL) was added MeI (3.5 g, 16.5 mmol). The reaction mixture was stirred at 80° C. for two hours. The mixture was cooled, diluted with water and 1N HCl, and extracted with three times with EtOAc. The combined organic layers were washed with water, brine, ($Na_2SO_4$), and concentrated to give the title compound as a yellow oil. LCMS (ESI) calculated for $C_{24}H_{28}N_2O_7$(M+H)$^+$: 457. found: 457.

Step 4—Preparation of ethyl 3-((S)-4-benzyl-6-nitro-3,4-dihydro-2H-benzo[b][1,4]oxazin-2-yl)-2-methylpropanoate

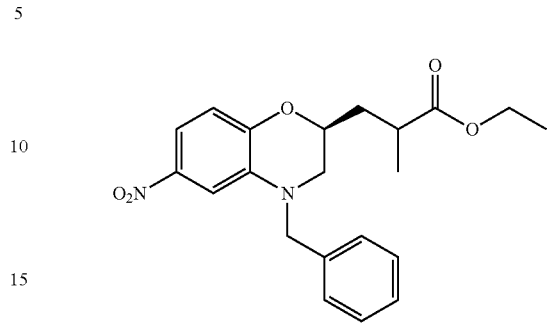

To a mixture of (S)-diethyl 2-((4-benzyl-6-nitro-3,4-dihydro-2H-benzo[b][1,4]oxazin-2-yl)methyl)-2-methylmalonate (2.0 g, 4.38 mmol) in DMSO (20 mL) was added LiCl (1.0 g, 23.6 mmol) and several drops of water. The reaction mixture was stirred at 170° C. for 10 hours. The reaction mixture was cooled, diluted with water, and extracted with EtOAc. The organic layer was washed with brine, dried ($Na_2SO_4$) and concentrated. The residue was purified by column chromatography (petroleum ether:ethyl acetate=20:1) to give the title compound as a yellow oil. LCMS (ESI): calculated for $C_{21}H_{24}N_2O_5$(M+H)$^+$: 385. found: 385.

Step 5—Preparation of ethyl 3-((S)-6-amino-3,4-dihydro-2H-benzo[b][1,4]oxazin-2-yl)-2-methylpropanoate

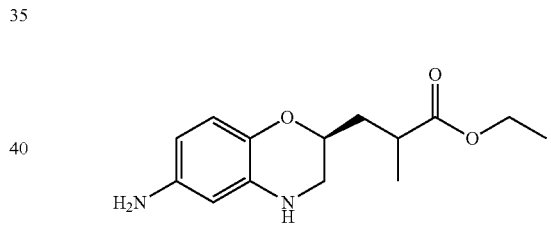

To a room temperature solution of ethyl 3-((S)-4-benzyl-6-nitro-3,4-dihydro-2H-benzo[b][1,4]oxazin-2-yl)-2-methylpropanoate (800 mg, 2.08 mmol) in MeOH (20 mL) was added Pd/C (500 mg). The mixture was stirred overnight under a hydrogen atmosphere (50 psi). The reaction mixture was filtered through a CELITE pad. The filtrate was concentrated to give the title compound as a black oil. LCMS (ESI): calculated for $C_{14}H_{20}N_2O_3$(M+H)$^+$: 265. found: 265.

Step 6—Preparation of ethyl 2-methyl-3-((S)-6-((((1,1,1-trifluoro-2-methylpropan-2-yl)oxy)carbonyl)amino)-3,4-dihydro-2H-benzo[b][1,4]oxazin-2-yl)propanoate

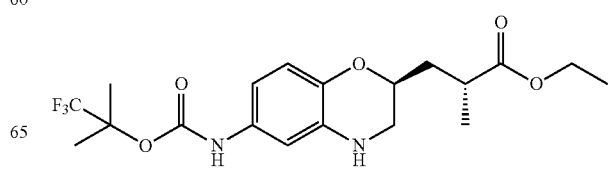

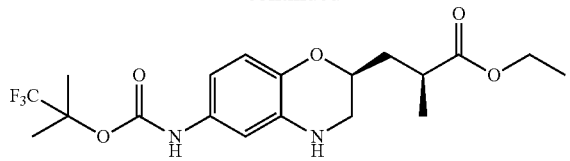

To a mixture of ethyl 3-((S)-6-amino-3,4-dihydro-2H-benzo[b][1,4]oxazin-2-yl)-2-methylpropanoate (950 mg, 3.59 mmol) and 1,1,1-trifluoro-2-methylpropan-2-yl 1H-imidazole-1-carboxylate (900 mg, 4.05 mmol) in DMSO (10 mL) was added concentrated HCl (150 mg) and the mixture was stirred at 80° C. for 5 hours. The reaction mixture was cooled, diluted with water, and extracted with EtOAc. The organic layer was washed with water, brine, dried ($Na_2SO_4$), and concentrated. The residue was purified by column chromatography (petroleum ether:ethyl acetate=3:1) to give the title compound as a colorless oil, which was further separated by SFC (Column: Chiralcel OJ-H 250×4.6 mm I.D., 5 um Mobile phase:ethanol (0.05% DEA) in $CO_2$ from 5% to 40% Flow rate: 2.35 mL/min wavelength: 220 nm) to give two isomers (peak 1 & peak 2). LCMS (ESI) calculated for $C_{19}H_{25}F_3N_2O_5$ (M+H)$^+$: 419. found: 419.

Step 7—Preparation of (S or R)-ethyl 3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate and (R or S)-ethyl 3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate

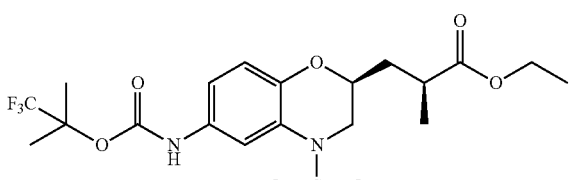

To a solution of ethyl 2-methyl-3-((S)-6-((((1,1,1-trifluoro-2-methylpropan-2-yl)oxy)carbonyl)amino)-3,4-dihydro-2H-benzo[b][1,4]oxazin-2-yl)propanoate (peak 1) (400 mg, 0.96 mmol) in pyridine (2 mL) and THF (4 mL) was added 3-chloro-4-fluorobenzene-1-sulfonyl chloride (500 mg, 2.18 mmol). The mixture was stirred at 60° C. for 1.5 h. The mixture was cooled, diluted with water and 1N HCl, and extracted with EtOAc. The organic layer was washed with water, brine, dried ($Na_2SO_4$), and concentrated. The residue was purified by column chromatography (petroleum ether:ethyl acetate=5:1) to give the title compound as a colorless solid, which was further separated by SFC (Column: Chiralcel OJ-3 150×4.6 mm I.D., 3 um Mobile phase: ethanol (0.05% DEA) in $CO_2$ from 5% to 40% Flow rate: 2.5 mL/min Wavelength: 220 nm) to give two isomers.

(S or R)-ethyl 3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate LCMS (ESI): calculated for $C_{25}H_{27}ClF_4N_2O_7S$ (M+H)$^+$: 611. found: 611; $^1$H NMR (400 MHz, $CDCl_3$) δ 7.85 (dd, J=6.5, 1.8 Hz, 1H), 7.81 (br s, 1H), 7.54~7.62 (m, 1H), 7.21 (t, J=8.5 Hz, 1H), 7.10 (dd, J=8.8, 2.3 Hz, 1H), 6.77 (d, J=9.0 Hz, 1H), 6.62 (br s, 1H), 4.21 (dd, J=14.1, 2.3 Hz, 1H), 4.02~4.18 (m, 2H), 3.49 (t, J=9.0 Hz, 1H), 3.17 (dd, J=14.1, 9.8 Hz, 1H), 2.71 (ddd, J=10.4, 6.9, 4.0 Hz, 1H), 1.90 (ddd, J=14.1, 10.4, 3.4 Hz, 1H), 1.77 (s, 6H), 1.50~1.58 (m, 1H), 1.16~1.27 (m, 6H).

(R or S)-ethyl 3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate LCMS (ESI): calculated for $C_{25}H_{27}ClF_4N_2O_7S$ (M+H)$^+$: 611. found: 611; $^1$H NMR (400 MHz, $CDCl_3$) δ7.89 (dd, J=6.3, 1.8 Hz, 1H), 7.82 (br s, 1H), 7.61 (dd, J=4.5, 2.5 Hz, 1H), 7.22 (t, J=8.5 Hz, 1H), 7.06 (dd, J=8.8, 2.3 Hz, 1H), 6.75 (d, J=8.8 Hz, 1H), 6.63 (br s, 1H), 4.23 (dd, J=13.9, 2.1 Hz, 1H), 4.14 (q, J=7.0 Hz, 2H), 3.63 (br s, 1H), 3.18 (dd, J=13.9, 9.7 Hz, 1H), 2.67 (sxt, J=7.0 Hz, 1H), 1.94-2.04 (m, 1H), 1.77 (s, 6H), 1.55~1.59 (m, 1H), 1.25 (t, J=7.0 Hz, 3H), 1.14 (d, J=7.0 Hz, 3H).

Example 3

Preparation of Additional Ethyl Propanoate Derivatives

The compounds in Table 1 were prepared based on the experimental procedures described in Examples 1 and 2, and can be achieved by one of skill in the art in light of the present disclosure.

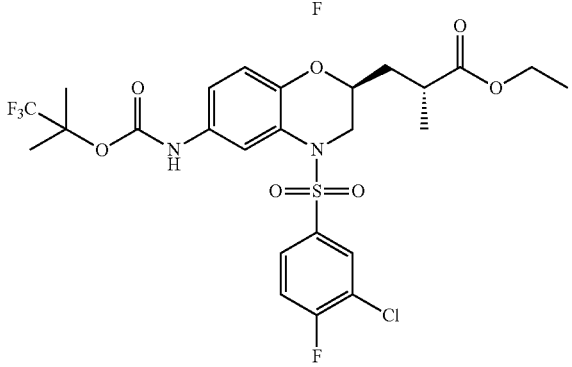

TABLE 1

| Ex. No. | Structure | Name | Observed m/z |
|---|---|---|---|
| 3A | 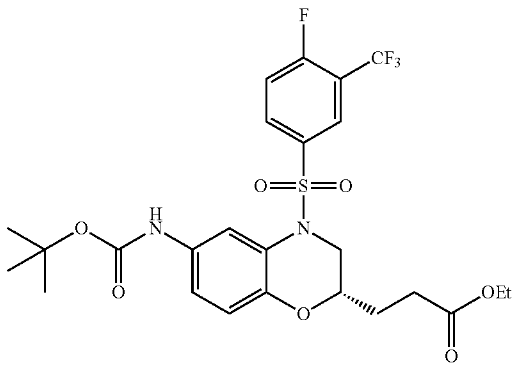 [SMILES: CCOC(=O)CC[C@H]1CN(S(=O)(=O)c2ccc(F)c(C(F)(F)F)c2)c2cc(NC(=O)OC(C)(C)C)ccc2O1] | (S)-ethyl 3-(6-((tert-butoxycarbonyl)amino)-4-((4-fluoro-3-(trifluoromethyl)phenyl)sulfonyl)-3,4-dihydro-2H-benzo[b][1,4]oxazin-2-yl)propanoate | 594.2 [M + NH$_4$]$^+$ |
| 3B | 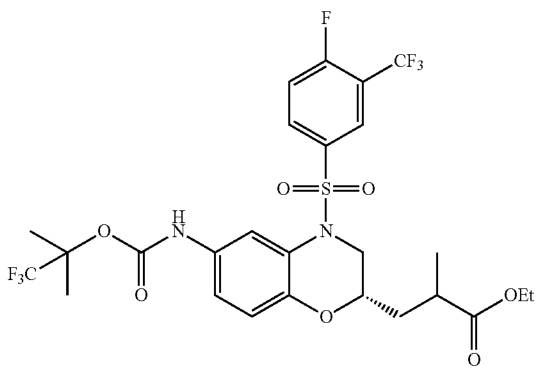 [SMILES: CCOC(=O)C(C)C[C@H]1CN(S(=O)(=O)c2ccc(F)c(C(F)(F)F)c2)c2cc(NC(=O)OC(C)(C)C(F)(F)F)ccc2O1] | (R and S)-ethyl 3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 645 (M + H)$^+$ |
| 3C | 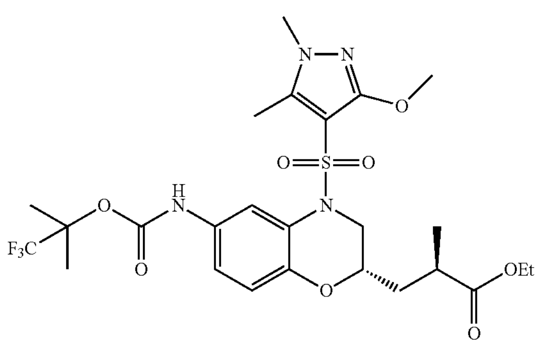 [SMILES: CCOC(=O)[C@H](C)C[C@H]1CN(S(=O)(=O)c2c(OC)nn(C)c2C)c2cc(NC(=O)OC(C)(C)C(F)(F)F)ccc2O1] | (R or S)-ethyl 3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 607 (M + H)$^+$ |
| 3D | 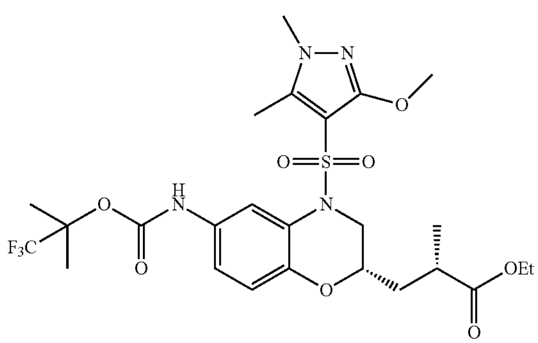 [SMILES: CCOC(=O)[C@@H](C)C[C@H]1CN(S(=O)(=O)c2c(OC)nn(C)c2C)c2cc(NC(=O)OC(C)(C)C(F)(F)F)ccc2O1] | (S or R)-ethyl 3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 607 (M + H)$^+$ |

TABLE 1-continued

| Ex. No. | Structure | Name | Observed m/z |
|---|---|---|---|
| 3E | 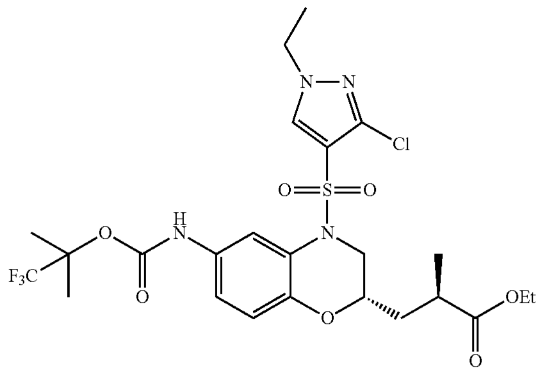 [SMILES: CCOC(=O)[C@H](C)C[C@H]1CN(S(=O)(=O)c2cn(CC)nc2Cl)c2cc(NC(=O)OC(C)(C)C(F)(F)F)ccc2O1] | (S or R)-ethyl 3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 611 (M + H)+ |
| 3F | 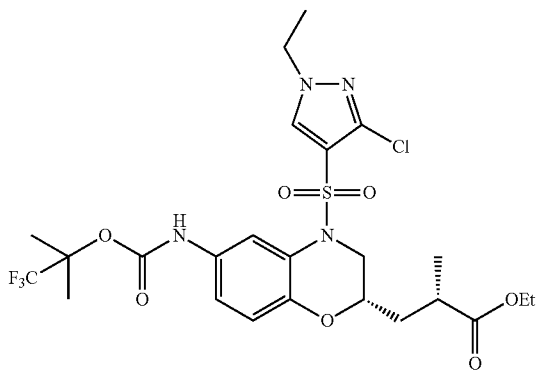 [SMILES: CCOC(=O)[C@@H](C)C[C@H]1CN(S(=O)(=O)c2cn(CC)nc2Cl)c2cc(NC(=O)OC(C)(C)C(F)(F)F)ccc2O1] | (R or S)-ethyl 3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 611 (M + H)+ |
| 3G | 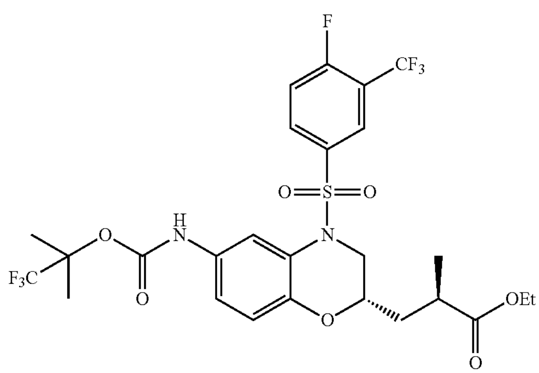 [SMILES: CCOC(=O)[C@H](C)C[C@H]1CN(S(=O)(=O)c2ccc(F)c(C(F)(F)F)c2)c2cc(NC(=O)OC(C)(C)C(F)(F)F)ccc2O1] | (S or R)-ethyl 3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 645 (M + H)+ |
| 3H | 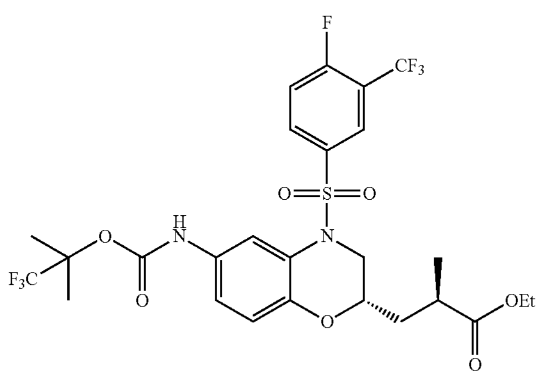 [SMILES: CCOC(=O)[C@H](C)C[C@H]1CN(S(=O)(=O)c2ccc(F)c(C(F)(F)F)c2)c2cc(NC(=O)OC(C)(C)C(F)(F)F)ccc2O1] | (R or S)-ethyl 3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate | 645 (M + H)+ |

TABLE 1-continued

| Ex. No. | Structure | Name | Observed m/z |
|---|---|---|---|
| 3i | 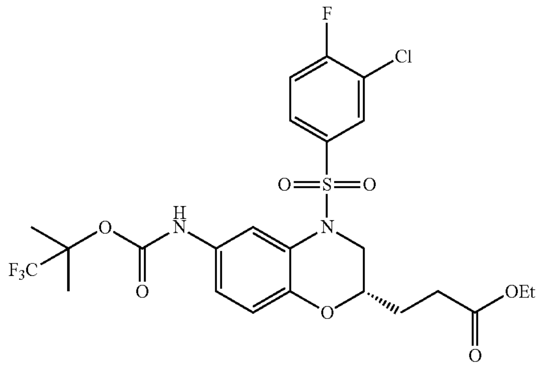 [SMILES: CCOC(=O)CC[C@H]1CN(S(=O)(=O)c2ccc(F)c(Cl)c2)c2cc(NC(=O)OC(C)(C)C(F)(F)F)ccc2O1] | (S)-ethyl 3-(4-((3-chloro-4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoate | 597 (M + H)+ |
| 3J | 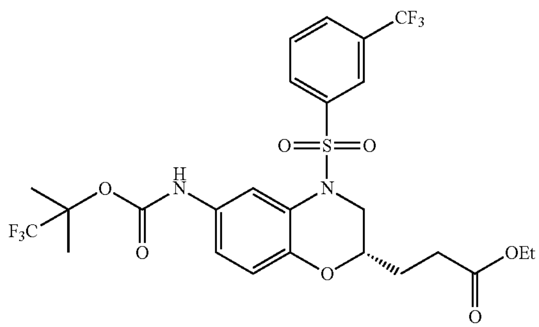 [SMILES: CCOC(=O)CC[C@H]1CN(S(=O)(=O)c2cccc(C(F)(F)F)c2)c2cc(NC(=O)OC(C)(C)C(F)(F)F)ccc2O1] | (S)-ethyl 3-(6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate | 613 (M + H)+ |
| 3K | 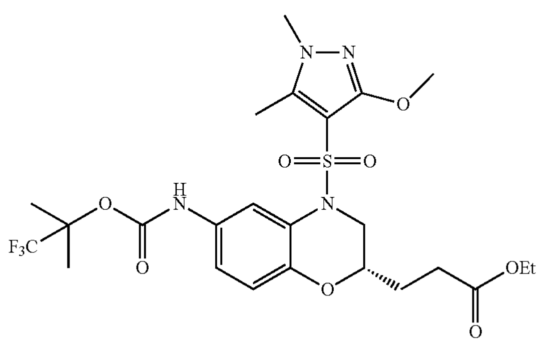 [SMILES: CCOC(=O)CC[C@H]1CN(S(=O)(=O)c2c(OC)nn(C)c2C)c2cc(NC(=O)OC(C)(C)C(F)(F)F)ccc2O1] | (S)-ethyl 3-(4-((3-methoxy-1,5-dimethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoate | 593 (M + H)+ |
| 3L | 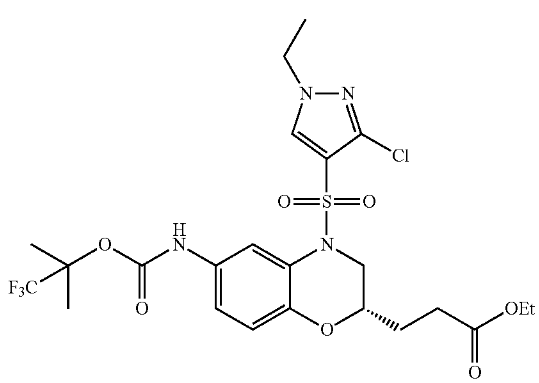 [SMILES: CCOC(=O)CC[C@H]1CN(S(=O)(=O)c2cn(CC)nc2Cl)c2cc(NC(=O)OC(C)(C)C(F)(F)F)ccc2O1] | (S)-ethyl 3-(4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoate | 598 (M + H)+ |

Example 4

Preparation of (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid (4)

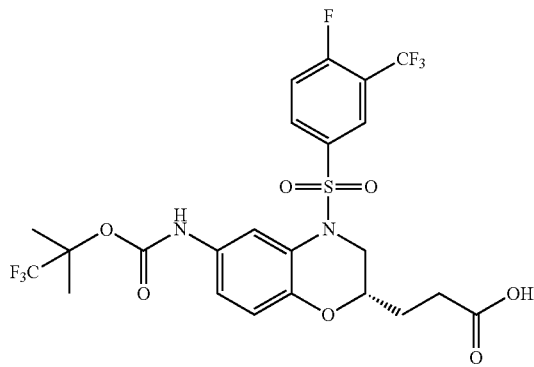 [SMILES: CC(C)(OC(=O)Nc1ccc2c(c1)N(S(=O)(=O)c1ccc(F)c(C(F)(F)F)c1)C[C@H](CCC(=O)O)O2)C(F)(F)F]

To a room temperature solution of (S)-ethyl 3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate (50 mg, 0.079 mmol) in THF (1 mL) was added aqueous 1 M lithium hydroxide (0.2 mL, 0.200 mmol). The mixture was stirred for an hour, and then additional aqueous 1M LiOH solution (0.5 mL) was added and the stirring continued for another four hours. The reaction mixture was neutralized with 1N HCl (0.7 mL) and concentrated. The residue was purified by reverse phase chromatograrphy. After drying down, the desired product was obtained as a white solid. MS ESI calculated for $C_{23}H_{21}F_7N_2O_7S$ (M+H)$^+$ 603, found 625 (M+Na)$^+$. $^1$H NMR (600 MHz, DMSO-$d_6$) δ 12.25 (s, 1H), 9.71 (s, 1H), 8.17 (1H, d, J=8.50 Hz), 8.12 (1H, d, J=5.97 Hz), 7.91 (1H, s), 7.74 (1H, t, J=9.51 Hz), 7.01 (1H, dd, J=8.87, 2.44 Hz), 6.74 (1H, d, J=8.84 Hz), 4.29 (1H, dd, J=13.92, 2.31 Hz), 3.66 (1H, s), 2.38-2.28 (2H, m), 1.84-1.77 (1H, m), 1.75-1.70 (1H, m), 1.67 (6H, s).

Example 5

Preparation of (S or R)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid and (R or S)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid (Example Nos. 5A and 5B)

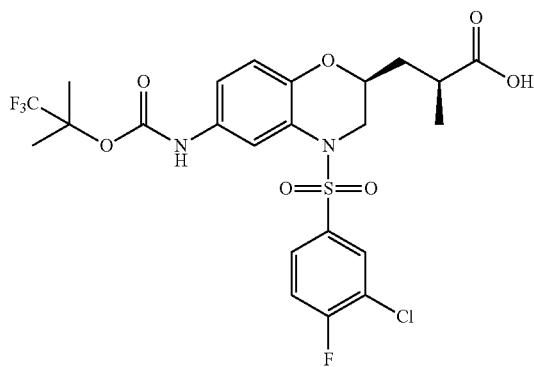

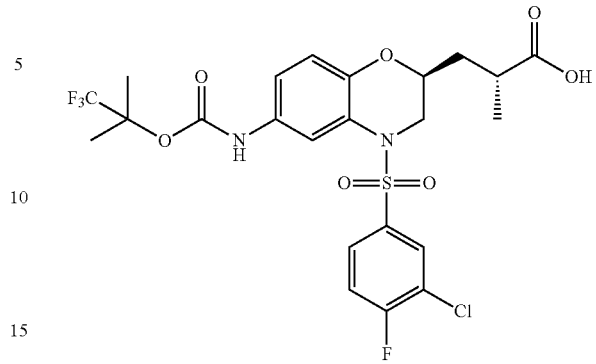

To a solution of (S or R)-ethyl 3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate (100 mg, 0.15 mmol) in dioxane (3 mL) and $H_2O$ (3 mL) was added LiOH $H_2O$ (100 mg, 2.38 mmol), and the mixture was stirred at 10° C. for 2 hours. The mixture was diluted with water and 1N HCl, and extracted with EtOAc. The organic layer was washed with water, brine, dried ($Na_2SO_4$) and concentrated. The residue was purified by prep-TLC (DCM: MeOH=30:1) to give the title compound as a white solid. LCMS (ESI): calculated for $C_{23}H_{23}ClF_4N_2O_7S$ (M+H)$^+$: 583. found: 583; $^1$H NMR (400 MHz, CDCl$_3$) δ 7.75~7.93 (m, 2H), 7.54~7.65 (m, 1H), 7.20 (t, J=8.5 Hz, 1H), 7.06 (dd, J=8.8, 2.3 Hz, 1H), 6.76 (d, J=9.0 Hz, 1H), 6.68 (br s, 1H), 4.24 (dd, J=14.1, 2.0 Hz, 1H), 3.57~3.69 (m, 1H), 3.19 (dd, J=14.1, 10.0 Hz, 1H), 2.75-2.89 (m, 1H), 1.88~1.97 (m, 1H), 1.77 (s, 6H), 1.54~1.65 (m, 1H), 1.26 (d, J=7.5 Hz, 3H).

The other diastereomer was prepared utilizing the above route from (R or S)-3-((S)-4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoate: LCMS (ESI): calculated for $C_{23}H_{23}ClF_4N_2O_7S$ (M+H)$^+$: 583. found: 583; $^1$H NMR (400 MHz, CDCl$_3$) δ 7.75~7.95 (m, 2H), 7.56-7.65 (m, 1H), 7.22 (t, J=8.5 Hz, 1H), 7.04 (dd, J=8.8, 2.3 Hz, 1H), 6.75 (d, J=8.5 Hz, 1H), 6.67 (br s, 1H), 4.25 (dd, J=14.1, 2.0 Hz, 1H), 3.59~3.72 (m, 1H), 3.21 (dd, J=14.1, 9.5 Hz, 1H), 2.73 (sxt, J=6.9 Hz, 1H), 1.97~2.10 (m, 1H), 1.77 (s, 6H), 1.61 (ddd, J=14.2, 7.2, 4.8 Hz, 1H), 1.20 (d, J=7.0 Hz, 3H).

Example 6

Preparation of Additional Propionic Acid-Substituted Benzoxazines

The compounds in Table 2 were prepared based on the experimental procedures described in Examples 4 and 5, and can be achieved by one of skill in the art in light of the present disclosure.

TABLE 2

| Ex. No. | Structure | Name | Observed m/z |
|---|---|---|---|
| 6A | 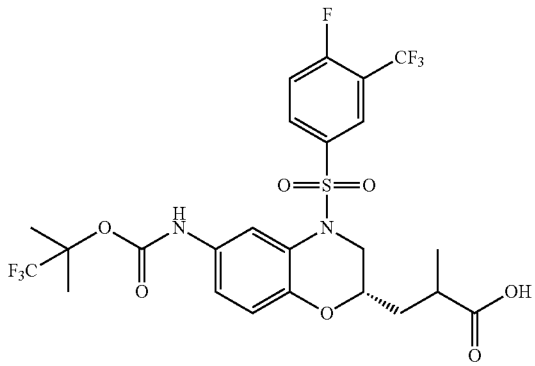 [SMILES: CC(C[C@H]1CN(S(=O)(=O)c2ccc(F)c(C(F)(F)F)c2)c2cc(NC(=O)OC(C)(C)C(F)(F)F)ccc2O1)C(=O)O] | (S and R)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 617 (M + H)+ |
| 6B | 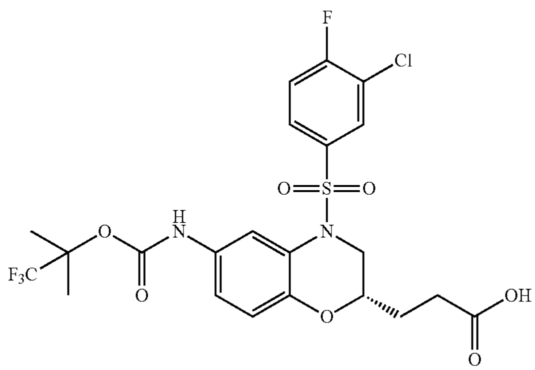 | (S)-3-(4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 569 (M + H)+ |
| 6C | 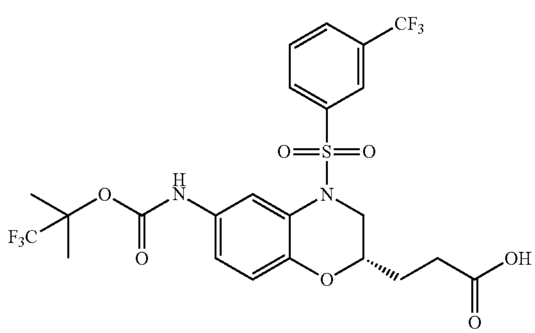 [SMILES: CC(C)(OC(=O)Nc1ccc2c(c1)N(S(=O)(=O)c1cccc(C(F)(F)F)c1)C[C@H](CCC(=O)O)O2)C(F)(F)F] | (S)-3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 585 (M + H)+ |
| 6D | 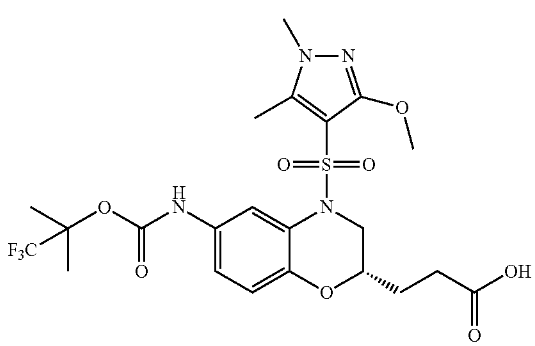 [SMILES: COc1nn(C)c(C)c1S(=O)(=O)N1C[C@H](CCC(=O)O)Oc2ccc(NC(=O)OC(C)(C)C(F)(F)F)cc21] | (S)-3-(4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 565 (M + H)+ |

TABLE 2-continued

| Ex. No. | Structure | Name | Observed m/z |
|---|---|---|---|
| 6E | 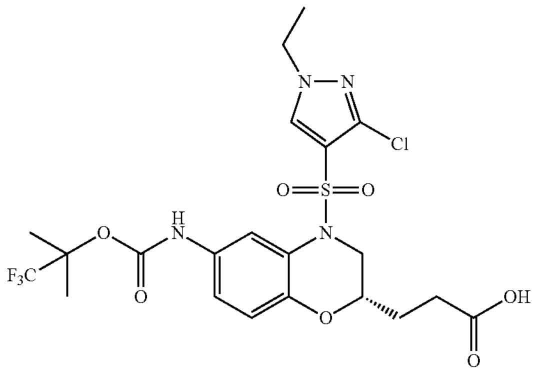 [SMILES: CCn1cc(S(=O)(=O)N2C[C@H](CCC(=O)O)Oc3ccc(NC(=O)OC(C)(C)C(F)(F)F)cc32)c(Cl)n1] | (S)-3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 591 [M + Na]$^+$ |
| 6F | 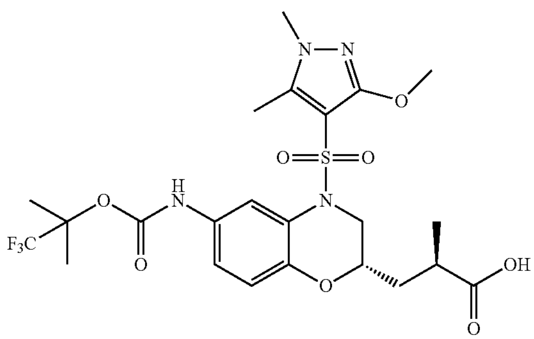 [SMILES: COc1nn(C)c(C)c1S(=O)(=O)N1C[C@H](C[C@@H](C)C(=O)O)Oc2ccc(NC(=O)OC(C)(C)C(F)(F)F)cc21] | (R or S)-3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 579 (M + H)$^+$ |
| 6G | 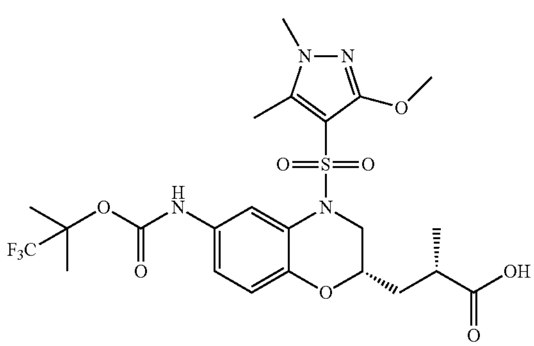 [SMILES: COc1nn(C)c(C)c1S(=O)(=O)N1C[C@H](C[C@H](C)C(=O)O)Oc2ccc(NC(=O)OC(C)(C)C(F)(F)F)cc21] | (S or R)-3-((S)-4-((3-methoxy-1,5-dimethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 579 (M + H)$^+$ |
| 6H | 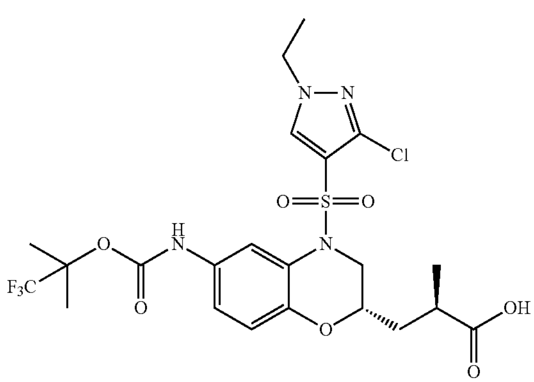 [SMILES: CCn1cc(S(=O)(=O)N2C[C@H](C[C@@H](C)C(=O)O)Oc3ccc(NC(=O)OC(C)(C)C(F)(F)F)cc32)c(Cl)n1] | (R or S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 583 (M + H)$^+$ |

TABLE 2-continued

| Ex. No. | Structure | Name | Observed m/z |
|---|---|---|---|
| 6i | 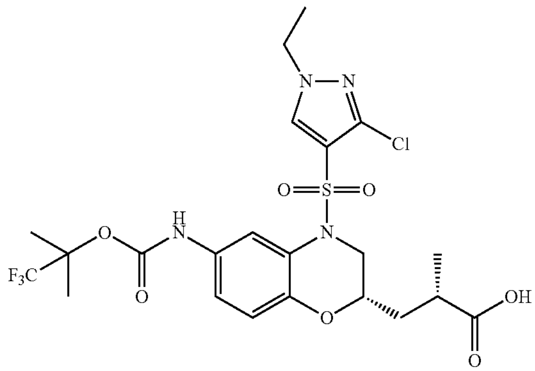 [SMILES: CCn1cc(S(=O)(=O)N2C[C@H](C[C@H](C)C(=O)O)Oc3ccc(NC(=O)OC(C)(C)C(F)(F)F)cc32)c(Cl)n1] | (S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 583 (M + H)+ |
| 6J | 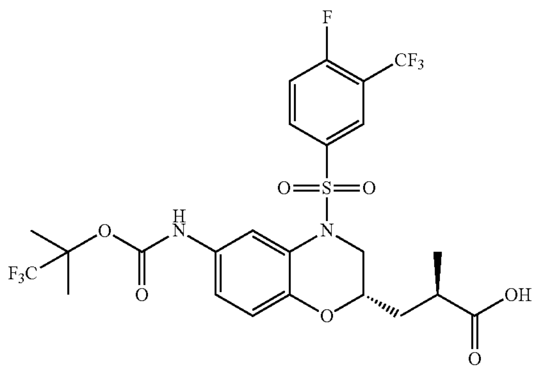 [SMILES: C[C@H](C[C@H]1CN(S(=O)(=O)c2ccc(F)c(C(F)(F)F)c2)c2cc(NC(=O)OC(C)(C)C(F)(F)F)ccc2O1)C(=O)O] | (R or S)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 617 (M + H)+ |
| 6K | 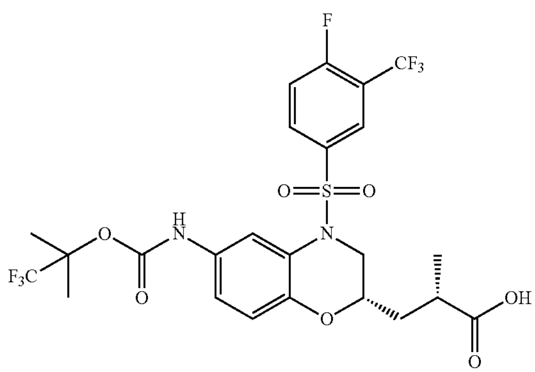 [SMILES: C[C@@H](C[C@H]1CN(S(=O)(=O)c2ccc(F)c(C(F)(F)F)c2)c2cc(NC(=O)OC(C)(C)C(F)(F)F)ccc2O1)C(=O)O] | (S or R)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 617 (M + H)+ |
| 6L | 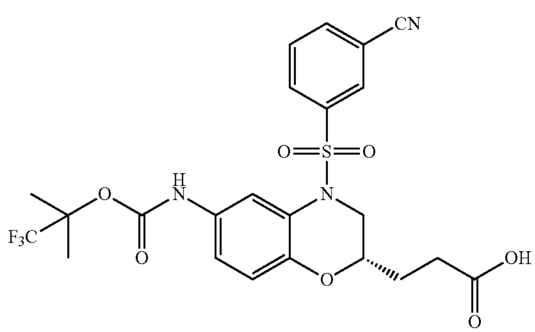 [SMILES: CC(C)(OC(=O)Nc1ccc2c(c1)N(S(=O)(=O)c1cccc(C#N)c1)C[C@H](CCC(=O)O)O2)C(F)(F)F] | (S)-3-(4-((3-cyanophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 542 (M + H)+ |

TABLE 2-continued

| Ex. No. | Structure | Name | Observed m/z |
|---|---|---|---|
| 6M | 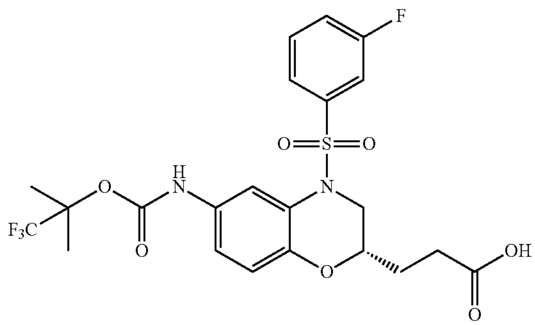 | (S)-3-(4-((3-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 535 (M + H)+ |
| 6N | 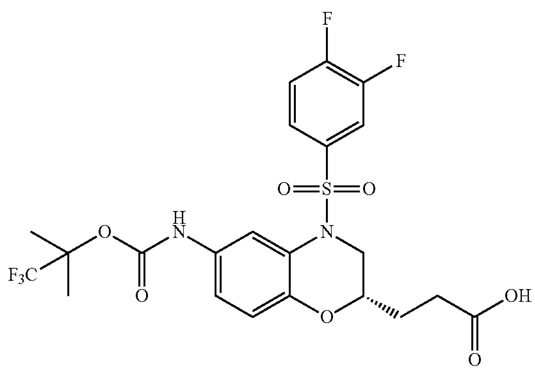 | (S)-3-(4-((3,4-difluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 553 (M + H)+ |
| 6o | 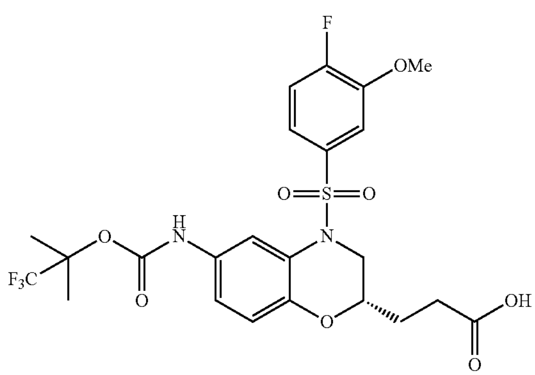 [SMILES: COc1cc(S(=O)(=O)N2C[C@H](CCC(=O)O)Oc3ccc(NC(=O)OC(C)(C)C(F)(F)F)cc32)ccc1F] | (S)-3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 565 (M + H)+ |
| 6P | 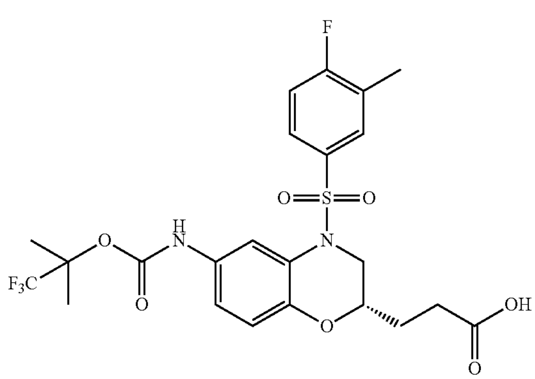 [SMILES: Cc1cc(S(=O)(=O)N2C[C@H](CCC(=O)O)Oc3ccc(NC(=O)OC(C)(C)C(F)(F)F)cc32)ccc1F] | (S)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 549 (M + H)+ |

TABLE 2-continued

| Ex. No. | Structure | Name | Observed m/z |
|---|---|---|---|
| 6Q | 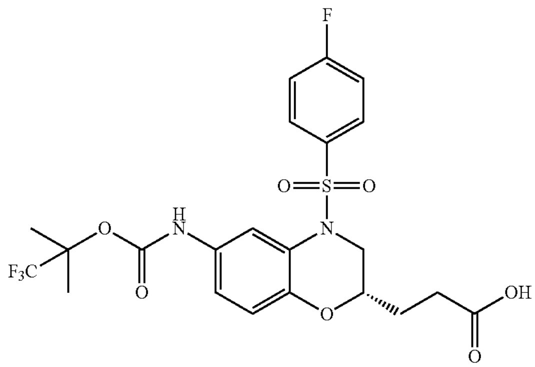 | (S)-3-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 535 (M + H)+ |
| 6R | 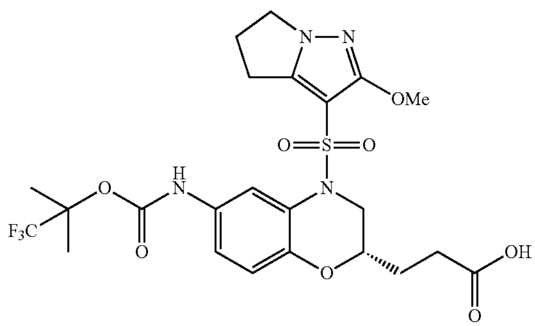 [SMILES: COc1nn2c(c1S(=O)(=O)N1C[C@H](CCC(=O)O)Oc3ccc(NC(=O)OC(C)(C)C(F)(F)F)cc31)CCC2] | (S)-3-(4-((2-methoxy-5,6-dihydro-4H-pyrrolo[1,2-b]pyrazol-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 577 (M + H)+ |
| 6S | 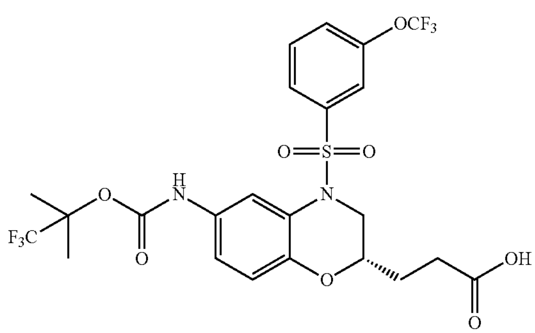 [SMILES: CC(C)(OC(=O)Nc1ccc2c(c1)N(S(=O)(=O)c1cccc(OC(F)(F)F)c1)C[C@H](CCC(=O)O)O2)C(F)(F)F] | (S)-3-(6-((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid | 601 (M + H)+ |
| 6T | 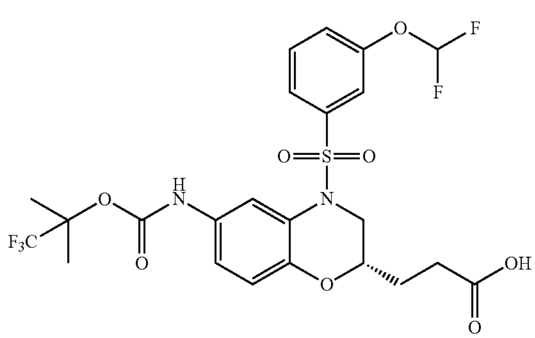 [SMILES: CC(C)(OC(=O)Nc1ccc2c(c1)N(S(=O)(=O)c1cccc(OC(F)F)c1)C[C@H](CCC(=O)O)O2)C(F)(F)F] | (S)-3-(4-((3-(difluoromethoxy)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 583 (M + H)+ |

TABLE 2-continued

| Ex. No. | Structure | Name | Observed m/z |
|---|---|---|---|
| 6U | 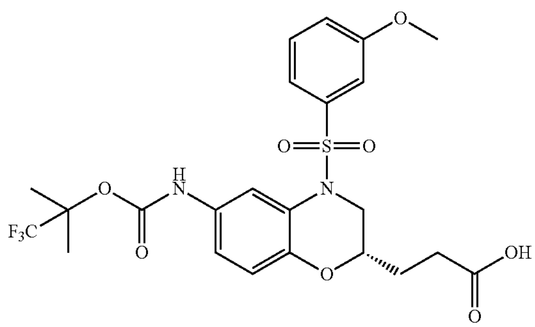 | (S)-3-(4-((3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 547 (M + H)+ |
| 6V | 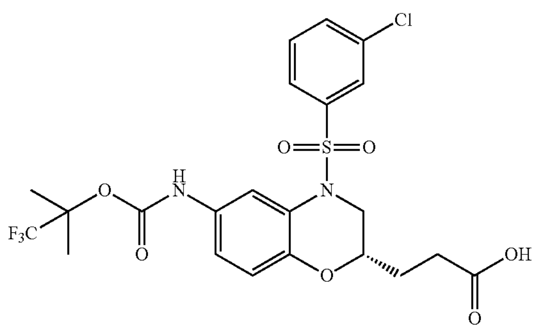 [SMILES: CC(C)(OC(=O)Nc1ccc2c(c1)N(S(=O)(=O)c1cccc(Cl)c1)C[C@H](CCC(=O)O)O2)C(F)(F)F] | (S)-3-(4-((3-chlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 551.5 (M + H)+ |
| 6W | 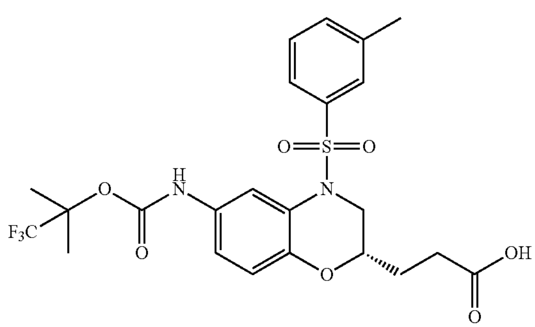 [SMILES: Cc1cccc(S(=O)(=O)N2C[C@H](CCC(=O)O)Oc3ccc(NC(=O)OC(C)(C)C(F)(F)F)cc32)c1] | (S)-3-(4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 531 (M + H)+ |
| 6X | 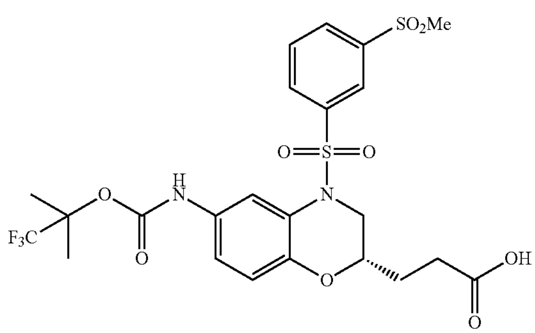 [SMILES: CC(C)(OC(=O)Nc1ccc2c(c1)N(S(=O)(=O)c1cccc(S(C)(=O)=O)c1)C[C@H](CCC(=O)O)O2)C(F)(F)F] | (S)-3-(4-((3-(methylsulfonyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 595 (M + H)+ |

TABLE 2-continued

| Ex. No. | Structure | Name | Observed m/z |
|---|---|---|---|
| 6Y | 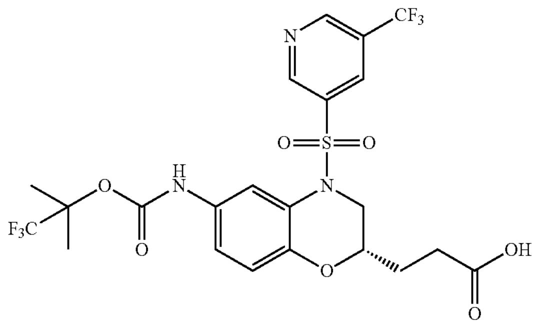 | (S)-3-(6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid | 586 (M + H)+ |
| 6Z | 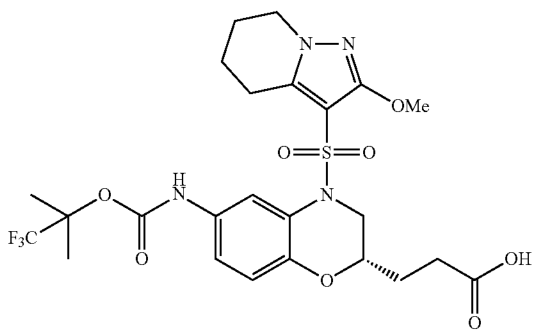 [SMILES: COc1nn2c(c1S(=O)(=O)N1C[C@H](CCC(=O)O)Oc3ccc(NC(=O)OC(C)(C)C(F)(F)F)cc31)CCCC2] | (S)-3-(4-((2-methoxy-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 591 (M + H)+ |
| 6AA | 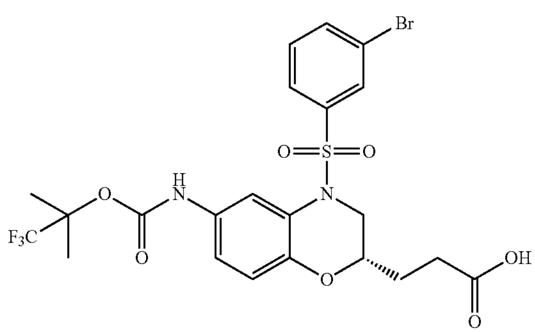 | (S)-3-(4-((3-bromophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 595 (M + H)+ |
| 6AB | 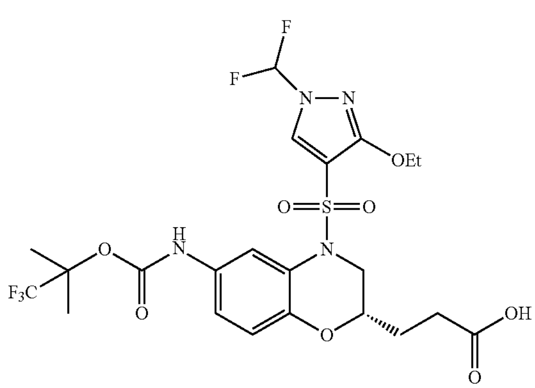 [SMILES: CCOc1nn(C(F)F)cc1S(=O)(=O)N1C[C@H](CCC(=O)O)Oc2ccc(NC(=O)OC(C)(C)C(F)(F)F)cc21] | (S)-3-(4-((1-(difluoromethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 601 (M + H)+ |

TABLE 2-continued

| Ex. No. | Structure | Name | Observed m/z |
|---|---|---|---|
| 6AC | 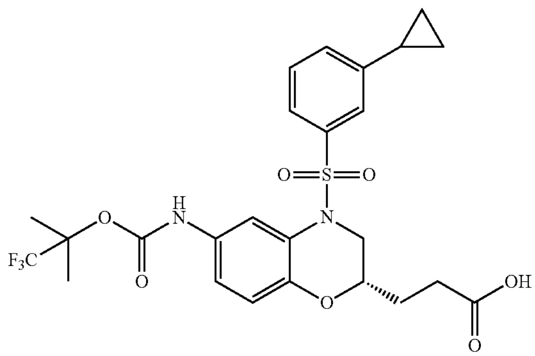 [SMILES: CC(C)(OC(=O)Nc1ccc2c(c1)N(S(=O)(=O)c1cccc(C3CC3)c1)C[C@H](CCC(=O)O)O2)C(F)(F)F] | (S)-3-(4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 557 (M + H)+ |
| 6AD | 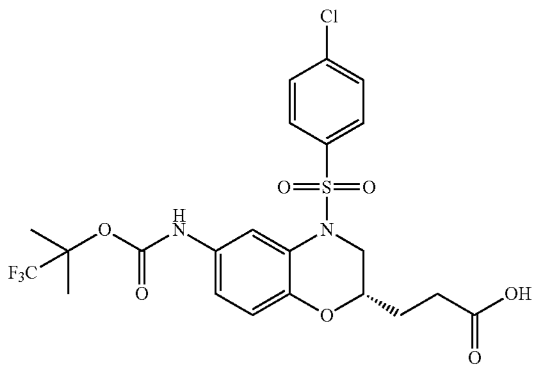 [SMILES: CC(C)(OC(=O)Nc1ccc2c(c1)N(S(=O)(=O)c1ccc(Cl)cc1)C[C@H](CCC(=O)O)O2)C(F)(F)F] | (S)-3-(4-((4-chlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 551 (M + H)+ |
| 6AE | 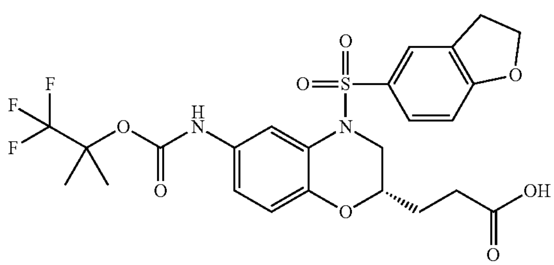 [SMILES: CC(C)(OC(=O)Nc1ccc2c(c1)N(S(=O)(=O)c1ccc3c(c1)CCO3)C[C@H](CCC(=O)O)O2)C(F)(F)F] | (S)-3-(4-((2,3-dihydrobenzofuran-5-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 559 [M + H]+ |
| 6AF | 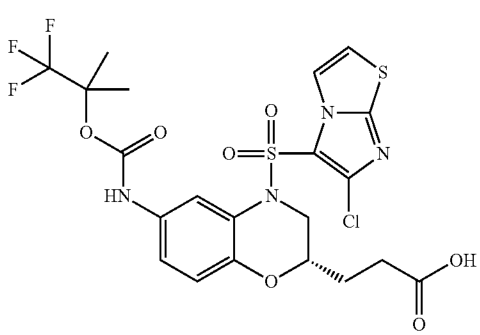 [SMILES: CC(C)(OC(=O)Nc1ccc2c(c1)N(S(=O)(=O)c1c(Cl)nc3sccn13)C[C@H](CCC(=O)O)O2)C(F)(F)F] | (S)-5-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-6-chloroimidazo[2,1-b]thiazole | 597 [M + H]+ |
| 6AG | 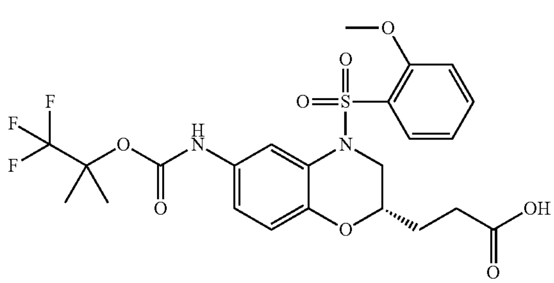 [SMILES: COc1ccccc1S(=O)(=O)N1C[C@H](CCC(=O)O)Oc2ccc(NC(=O)OC(C)(C)C(F)(F)F)cc21] | (S)-3-(4-((2-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 547 [M + H]+ |

TABLE 2-continued

| Ex. No. | Structure | Name | Observed m/z |
|---|---|---|---|
| 6AH | 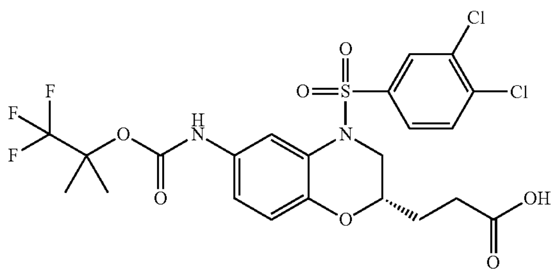 [SMILES: CC(C)(OC(=O)Nc1ccc2c(c1)N(S(=O)(=O)c1ccc(Cl)c(Cl)c1)C[C@H](CCC(=O)O)O2)C(F)(F)F] | (S)-3-(4-((3,4-dichlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 587 [M + H]+ |
| 6Ai | 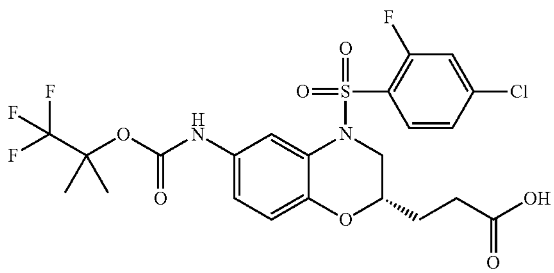 [SMILES: CC(C)(OC(=O)Nc1ccc2c(c1)N(S(=O)(=O)c1ccc(Cl)cc1F)C[C@H](CCC(=O)O)O2)C(F)(F)F] | (S)-3-(4-((4-chloro-2-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 586 [M + NH4]+ |
| 6AJ | 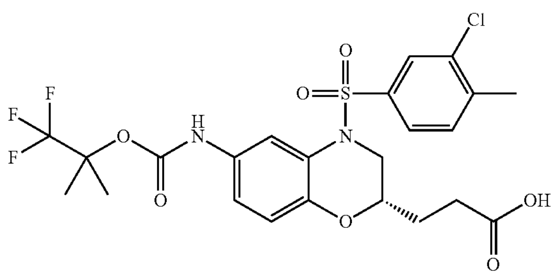 [SMILES: Cc1ccc(S(=O)(=O)N2C[C@H](CCC(=O)O)Oc3ccc(NC(=O)OC(C)(C)C(F)(F)F)cc32)cc1Cl] | (S)-3-(4-((3-chloro-4-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 582 [M + NH4]+ |
| 6AK | 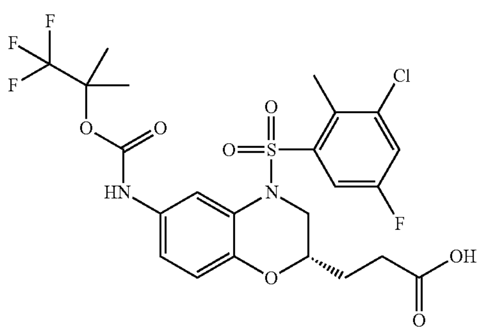 [SMILES: Cc1c(Cl)cc(F)cc1S(=O)(=O)N1C[C@H](CCC(=O)O)Oc2ccc(NC(=O)OC(C)(C)C(F)(F)F)cc21] | (S)-3-(4-((3-chloro-5-fluoro-2-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 600 [M + NH4]+ |
| 6AL | 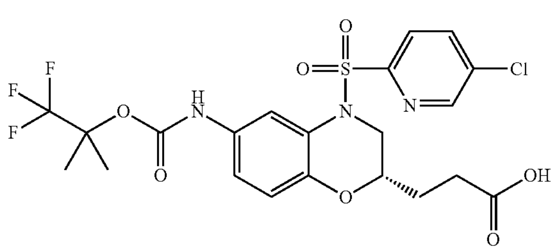 [SMILES: CC(C)(OC(=O)Nc1ccc2c(c1)N(S(=O)(=O)c1ccc(Cl)cn1)C[C@H](CCC(=O)O)O2)C(F)(F)F] | (S)-2-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-5-chloropyridine | 552 [M + H]+ |

TABLE 2-continued

| Ex. No. | Structure | Name | Observed m/z |
|---|---|---|---|
| 6AM | 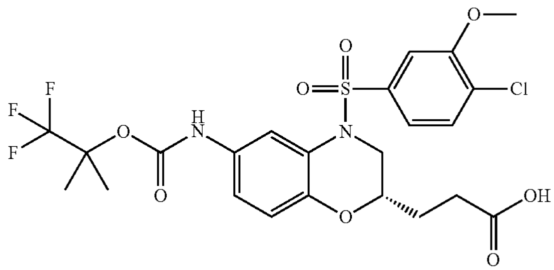 [SMILES: COc1cc(S(=O)(=O)N2C[C@H](CCC(=O)O)Oc3ccc(NC(=O)OC(C)(C)C(F)(F)F)cc32)ccc1Cl] | (S)-3-(4-((4-chloro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 581 [M + H]+ |
| 6AN | 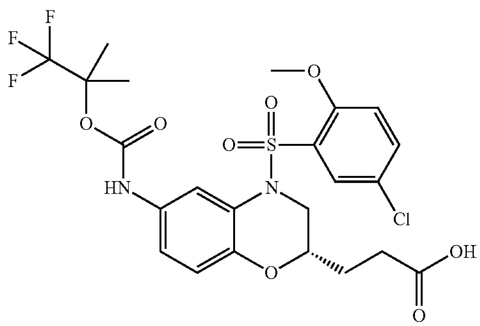 | (S)-3-(4-((5-chloro-2-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 581 [M + H]+ |
| 6Ao | 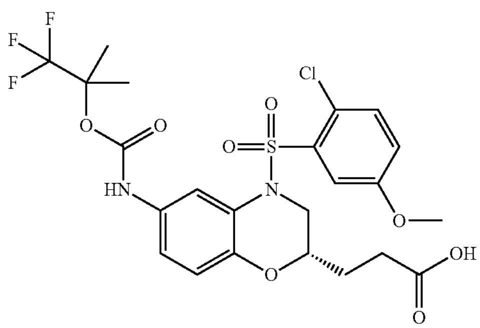 [SMILES: COc1ccc(Cl)c(S(=O)(=O)N2C[C@H](CCC(=O)O)Oc3ccc(NC(=O)OC(C)(C)C(F)(F)F)cc32)c1] | (S)-3-(4-((2-chloro-5-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 581 [M + H]+ |
| 6AP | 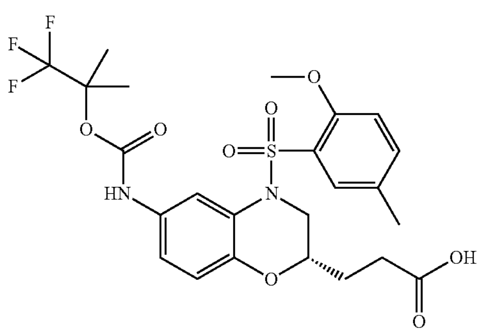 [SMILES: COc1ccc(C)cc1S(=O)(=O)N1C[C@H](CCC(=O)O)Oc2ccc(NC(=O)OC(C)(C)C(F)(F)F)cc21] | (S)-3-(4-((2-methoxy-5-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 561 [M + H]+ |
| 6AQ | 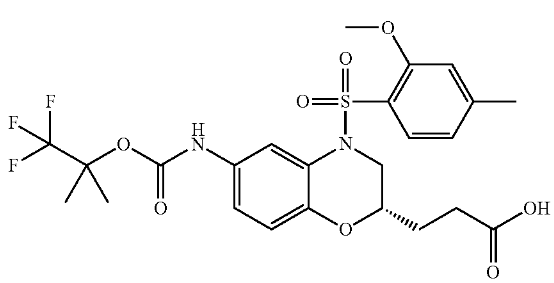 [SMILES: COc1cc(C)ccc1S(=O)(=O)N1C[C@H](CCC(=O)O)Oc2ccc(NC(=O)OC(C)(C)C(F)(F)F)cc21] | (S)-3-(4-((2-methoxy-4-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 561 [M + H]+ |

TABLE 2-continued

| Ex. No. | Structure | Name | Observed m/z |
|---|---|---|---|
| 6AR | 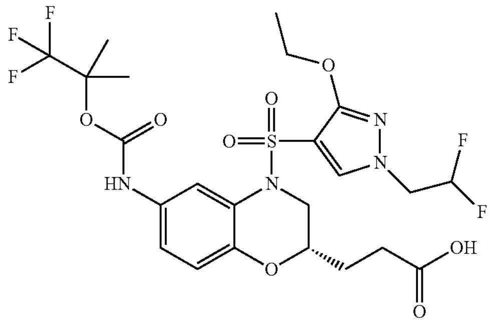 [SMILES: CCOc1nn(CC(F)F)cc1S(=O)(=O)N1C[C@H](CCC(=O)O)Oc2ccc(NC(=O)OC(C)(C)C(F)(F)F)cc21] | (S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-1-(2,2-difluoroethyl)-3-ethoxy-1H-pyrazole | 615 [M + H]+ |
| 6AS | 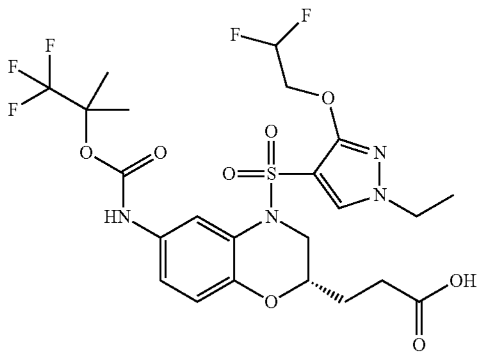 [SMILES: CCn1cc(S(=O)(=O)N2C[C@H](CCC(=O)O)Oc3ccc(NC(=O)OC(C)(C)C(F)(F)F)cc32)c(OCC(F)F)n1] | (S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-3-(2,2-difluoroethoxy)-1-ethyl-1H-pyrazole | 615 [M + H]+ |
| 6AT | 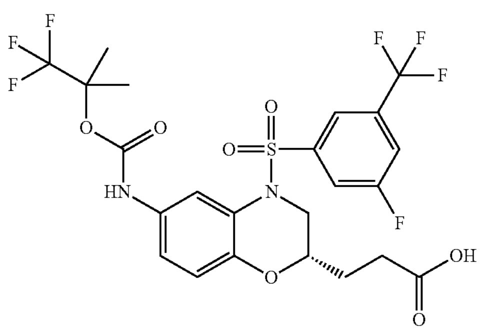 [SMILES: CC(C)(OC(=O)Nc1ccc2c(c1)N(S(=O)(=O)c1cc(F)cc(C(F)(F)F)c1)C[C@H](CCC(=O)O)O2)C(F)(F)F] | (S)-3-(4-((3-fluoro-5-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 620 [M + NH4]+ |
| 6AU | 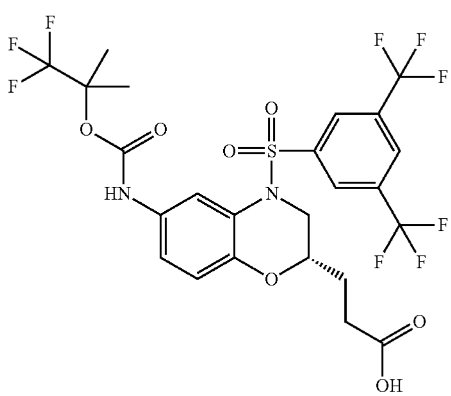 [SMILES: CC(C)(OC(=O)Nc1ccc2c(c1)N(S(=O)(=O)c1cc(C(F)(F)F)cc(C(F)(F)F)c1)C[C@H](CCC(=O)O)O2)C(F)(F)F] | (S)-3-(4-((3,5-bis(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 675 [M + Na]+ |

| Ex. No. | Structure | Name | Observed m/z |
|---|---|---|---|
| 6AV | 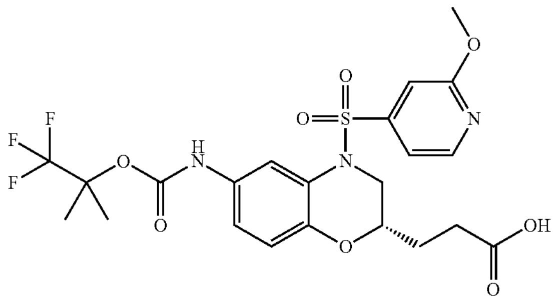 [SMILES: COc1cc(S(=O)(=O)N2C[C@H](CCC(=O)O)Oc3ccc(NC(=O)OC(C)(C)C(F)(F)F)cc32)ccn1] | (S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-2-methoxypyridine | 548 [M + H]+ |
| 6AW | 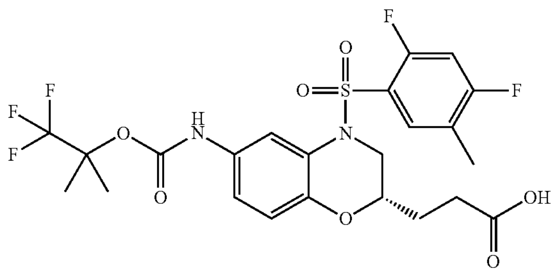 | (S)-3-(4-((2,4-difluoro-5-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 584 [M + NH4]+ |
| 6AX | 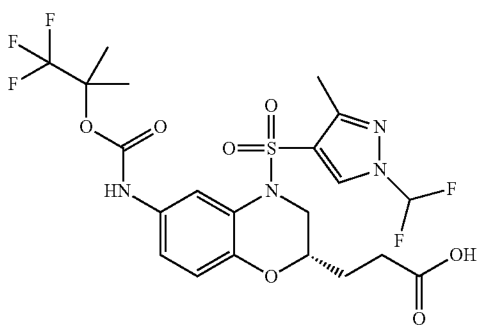 [SMILES: Cc1nn(C(F)F)cc1S(=O)(=O)N1C[C@H](CCC(=O)O)Oc2ccc(NC(=O)OC(C)(C)C(F)(F)F)cc21] | (S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-methyl-1H-pyrazole | 571 [M + H]+ |
| 6AY | 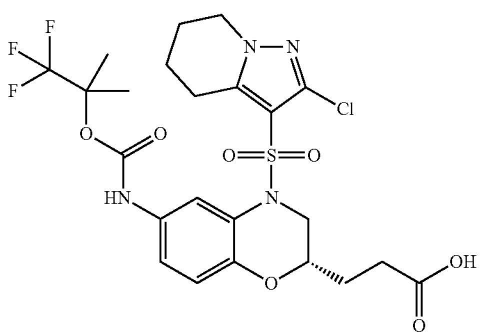 [SMILES: CC(C)(OC(=O)Nc1ccc2c(c1)N(S(=O)(=O)c1c(Cl)nn3c1CCCC3)C[C@H](CCC(=O)O)O2)C(F)(F)F] | (S)-3-(4-((2-chloro-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 595 [M + H]+ |
| 6AZ | 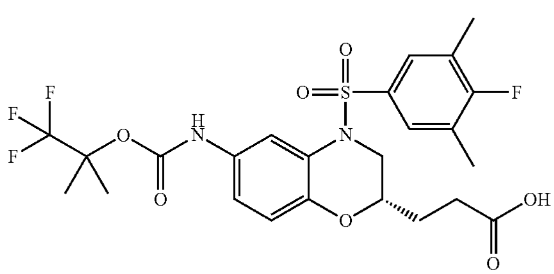 [SMILES: Cc1cc(S(=O)(=O)N2C[C@H](CCC(=O)O)Oc3ccc(NC(=O)OC(C)(C)C(F)(F)F)cc32)cc(C)c1F] | (S)-3-(4-((4-fluoro-3,5-dimethylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 563 [M + H]+ |

TABLE 2-continued

| Ex. No. | Structure | Name | Observed m/z |
|---|---|---|---|
| 6BA | 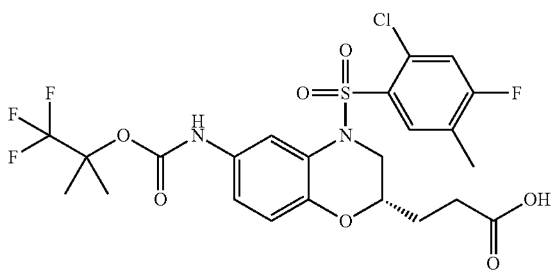 | (S)-3-(4-((2-chloro-4-fluoro-5-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 600 [M + NH$_4$]+ |
| 6BC | 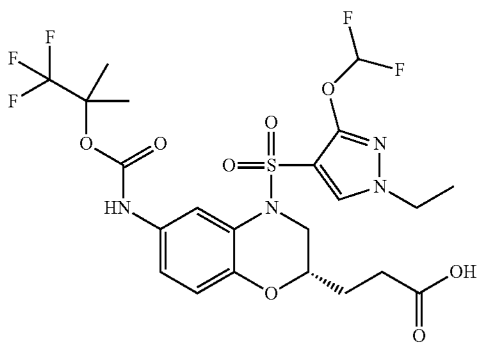 [SMILES: CCn1cc(S(=O)(=O)N2C[C@H](CCC(=O)O)Oc3ccc(NC(=O)OC(C)(C)C(F)(F)F)cc32)c(OC(F)F)n1] | (S)-3-(4-((3-(difluoromethoxy)-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 601 [M + H]+ |
| 6BD | 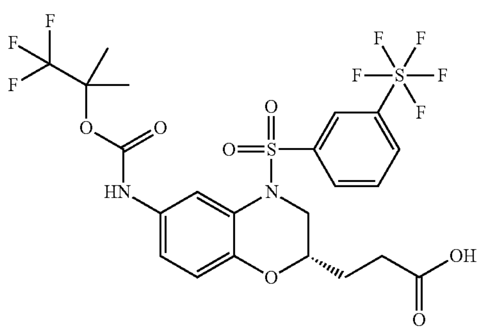 [SMILES: CC(C)(OC(=O)Nc1ccc2c(c1)N(S(=O)(=O)c1cccc(S(F)(F)(F)(F)F)c1)C[C@H](CCC(=O)O)O2)C(F)(F)F] | 3-[(2S)-4-{[3-(pentafluoro-lambda~6~-sulfanyl)phenyl]sulfonyl}-6-{[(2,2,2-trifluoro-1,1-dimethylethoxy)carbonyl]amino}-3,4-dihydro-2H-1,4-benzoxazin-2-yl]propanoic acid | 665 [M + Na]+ |
| 6BE | 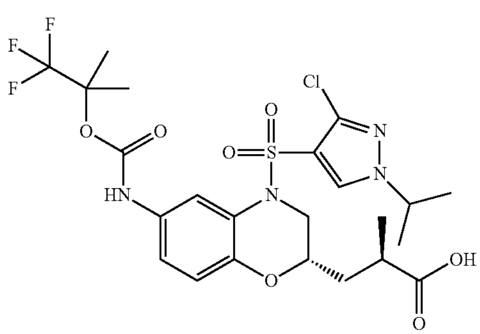 [SMILES: CC(C)n1cc(S(=O)(=O)N2C[C@H](C[C@@H](C)C(=O)O)Oc3ccc(NC(=O)OC(C)(C)C(F)(F)F)cc32)c(Cl)n1] | (R or S)-3-((S)-4-((3-chloro-1-isopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 597 [M + H]+ |

TABLE 2-continued

| Ex. No. | Structure | Name | Observed m/z |
|---|---|---|---|
| 6BF | 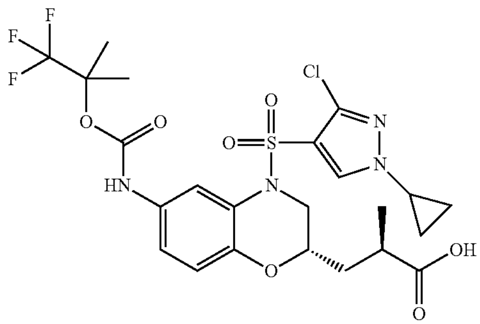 [SMILES: C[C@H](C[C@H]1CN(S(=O)(=O)c2cn(C3CC3)nc2Cl)c2cc(NC(=O)OC(C)(C)C(F)(F)F)ccc2O1)C(=O)O] | (R or S)-3-((S)-4-((3-chloro-1-cyclopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 595 [M + H]+ |
| 6BG | 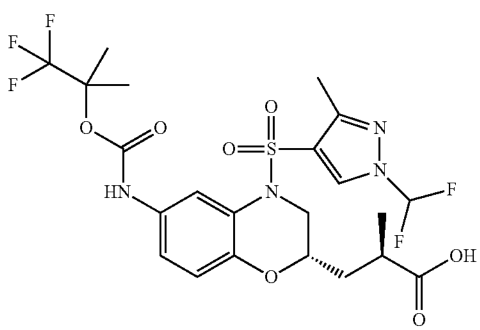 [SMILES: Cc1nn(C(F)F)cc1S(=O)(=O)N1C[C@H](C[C@@H](C)C(=O)O)Oc2ccc(NC(=O)OC(C)(C)C(F)(F)F)cc21] | (R or S)-3-((S)-4-((1-(difluoromethyl)-3-methyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 585 [M + H]+ |
| 6BH | 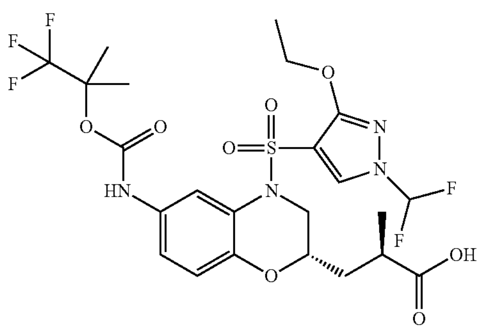 [SMILES: CCOc1nn(C(F)F)cc1S(=O)(=O)N1C[C@H](C[C@@H](C)C(=O)O)Oc2ccc(NC(=O)OC(C)(C)C(F)(F)F)cc21] | (R or S)-3-((S)-4-((1-(difluoromethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 615 [M + H]+ |
| 6Bi | 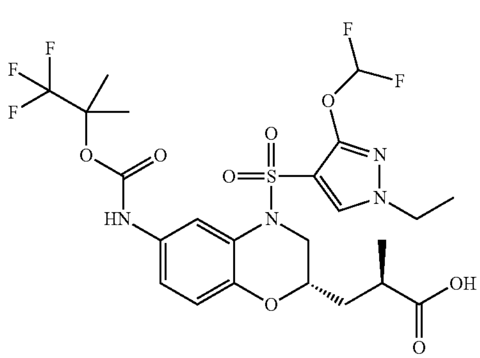 [SMILES: CCn1cc(S(=O)(=O)N2C[C@H](C[C@@H](C)C(=O)O)Oc3ccc(NC(=O)OC(C)(C)C(F)(F)F)cc32)c(OC(F)F)n1] | (R or S)-3-((S)-4-((3-(difluoromethoxy)-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 615 [M + H]+ |

TABLE 2-continued

| Ex. No. | Structure | Name | Observed m/z |
|---|---|---|---|
| 6BJ | 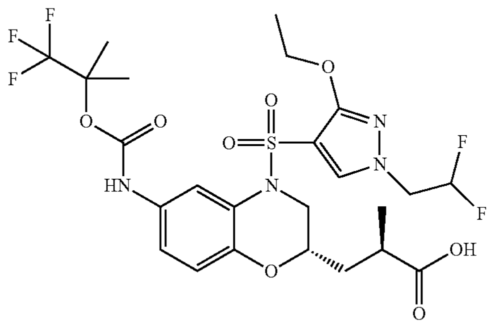 [SMILES: CCOc1nn(CC(F)F)cc1S(=O)(=O)N1C[C@H](C[C@@H](C)C(=O)O)Oc2ccc(NC(=O)OC(C)(C)C(F)(F)F)cc21] | (R or S)-3-((S)-4-((1-(2,2-difluoroethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 629 [M + H]+ |
| 6BK | 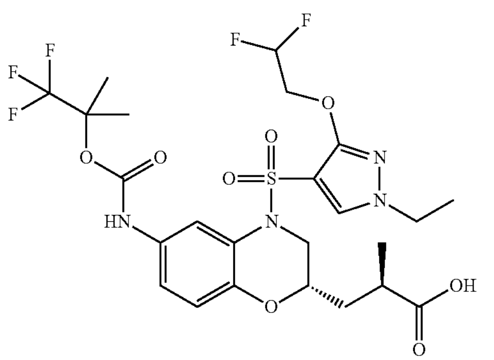 [SMILES: CCn1cc(S(=O)(=O)N2C[C@H](C[C@@H](C)C(=O)O)Oc3ccc(NC(=O)OC(C)(C)C(F)(F)F)cc32)c(OCC(F)F)n1] | (R or S)-3-((S)-4-((3-(2,2-difluoroethoxy)-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 651 [M + Na]+ |
| 6BL | 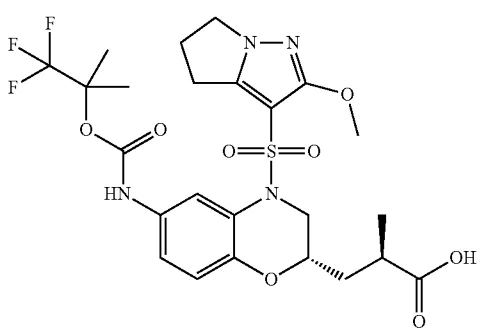 [SMILES: COc1nn2c(c1S(=O)(=O)N1C[C@H](C[C@@H](C)C(=O)O)Oc3ccc(NC(=O)OC(C)(C)C(F)(F)F)cc31)CCC2] | (R or S)-3-((S)-4-((2-methoxy-5,6-dihydro-4H-pyrrolo[1,2-b]pyrazol-3-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 591 [M + H]+ |
| 6BM | 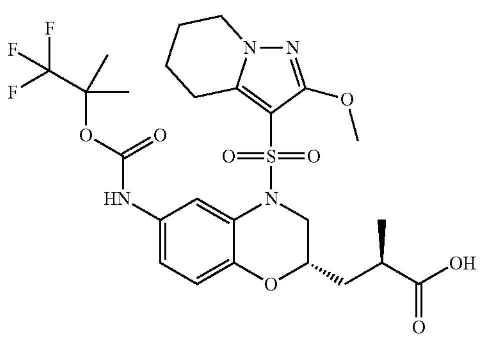 [SMILES: COc1nn2c(c1S(=O)(=O)N1C[C@H](C[C@@H](C)C(=O)O)Oc3ccc(NC(=O)OC(C)(C)C(F)(F)F)cc31)CCCC2] | (R or S)-3-((S)-4-((2-methoxy-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 605 [M + H]+ |

TABLE 2-continued

| Ex. No. | Structure | Name | Observed m/z |
|---|---|---|---|
| 6BN | 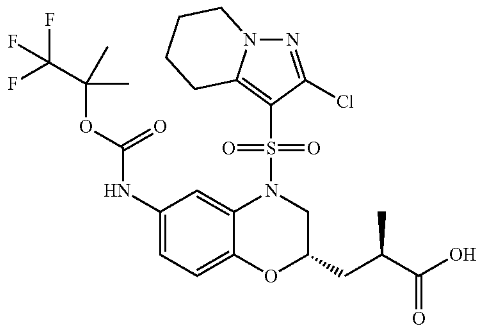 [SMILES: C[C@H](C[C@H]1CN(S(=O)(=O)c2c(Cl)nn3c2CCCC3)c2cc(NC(=O)OC(C)(C)C(F)(F)F)ccc2O1)C(=O)O] | (R or S)-3-((S)-4-((2-chloro-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 609 [M + H]+ |
| 6Bo | 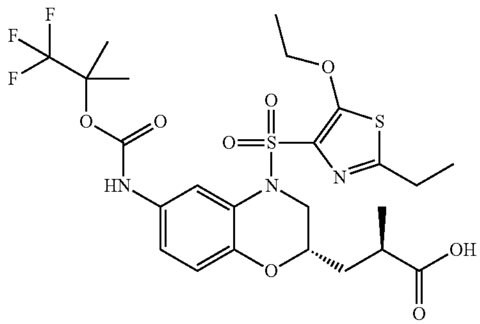 [SMILES: CCOc1sc(CC)nc1S(=O)(=O)N1C[C@H](C[C@@H](C)C(=O)O)Oc2ccc(NC(=O)OC(C)(C)C(F)(F)F)cc21] | (R or S)-3-((S)-4-((5-ethoxy-2-ethylthiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 610 [M + H]+ |
| 6BP | 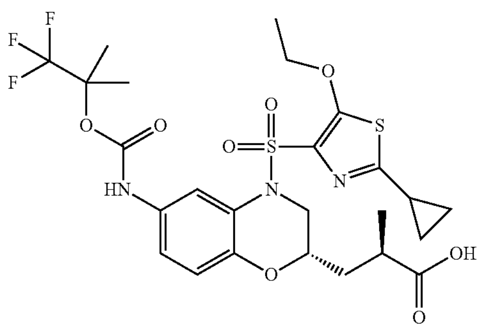 [SMILES: CCOc1sc(C2CC2)nc1S(=O)(=O)N1C[C@H](C[C@@H](C)C(=O)O)Oc2ccc(NC(=O)OC(C)(C)C(F)(F)F)cc21] | (R or S)-3-((S)-4-((2-cyclopropyl-5-ethoxythiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 622 [M + H]+ |
| 6BQ | 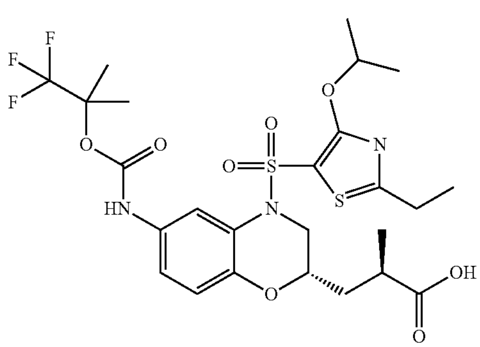 | (R or S)-3-((S)-4-((2-ethyl-5-isopropoxythiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 624 [M + H]+ |

TABLE 2-continued

| Ex. No. | Structure | Name | Observed m/z |
|---|---|---|---|
| 6BR | 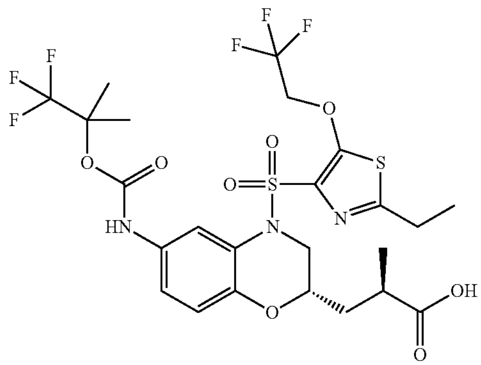 [SMILES: CCc1nc(S(=O)(=O)N2C[C@H](C[C@@H](C)C(=O)O)Oc3ccc(NC(=O)OC(C)(C)C(F)(F)F)cc32)c(OCC(F)(F)F)s1] | (R or S)-3-((S)-4-((2-ethyl-5-(2,2,2-trifluoroethoxy)thiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 664 [M + H]+ |
| 6BS | 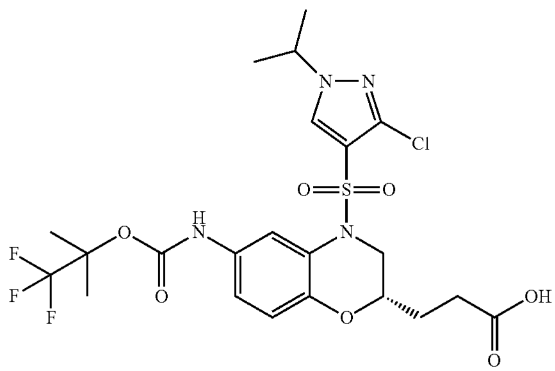 [SMILES: CC(C)n1cc(S(=O)(=O)N2C[C@H](CCC(=O)O)Oc3ccc(NC(=O)OC(C)(C)C(F)(F)F)cc32)c(Cl)n1] | (S)-3-(4-((3-chloro-1-isopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 605 [M + Na]+ |
| 6BT | 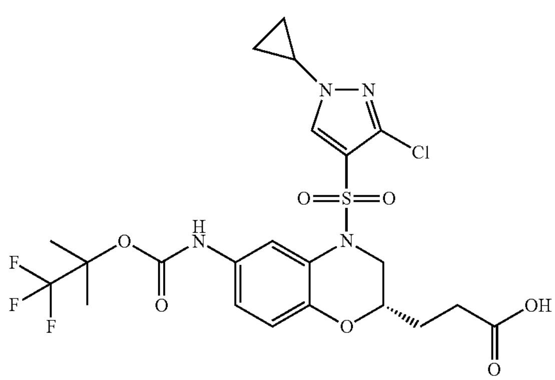 [SMILES: CC(C)(OC(=O)Nc1ccc2c(c1)N(S(=O)(=O)c1cn(C3CC3)nc1Cl)C[C@H](CCC(=O)O)O2)C(F)(F)F] | (S)-3-(4-((3-chloro-1-cyclopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 603 [M + Na]+ |
| 6BU | 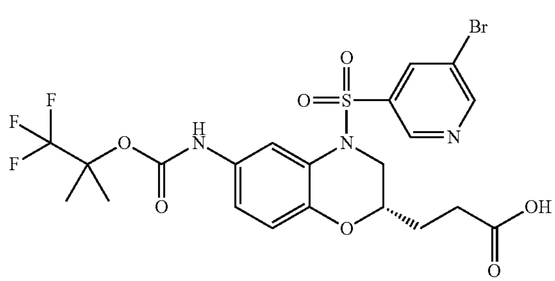 [SMILES: CC(C)(OC(=O)Nc1ccc2c(c1)N(S(=O)(=O)c1cncc(Br)c1)C[C@H](CCC(=O)O)O2)C(F)(F)F] | 3-[(2S)-4-[(5-bromopyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid | 596 [M + H]+ |

TABLE 2-continued

| Ex. No. | Structure | Name | Observed m/z |
|---|---|---|---|
| 6BV | 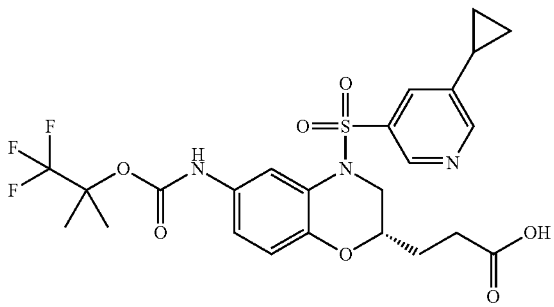 [SMILES: CC(C)(OC(=O)Nc1ccc2c(c1)N(S(=O)(=O)c1cncc(C3CC3)c1)C[C@H](CCC(=O)O)O2)C(F)(F)F] | 3-[(2S)-4-[(5-cyclopropylpyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid | 558 [M + H]+ |
| 6BW | 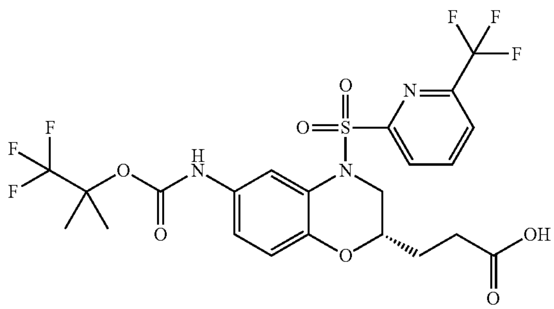 [SMILES: CC(C)(OC(=O)Nc1ccc2c(c1)N(S(=O)(=O)c1cccc(C(F)(F)F)n1)C[C@H](CCC(=O)O)O2)C(F)(F)F] | 3-[(2S)-6-{[(2,2,2-trifluoro-1,1-dimethylethoxy)carbonyl]amino}-4-{[6-(trifluoromethyl)pyridin-2-yl]sulfonyl}-3,4-dihydro-2H-1,4-benzoxazin-2-yl]propanoic acid | 586 [M + H]+ |
| 6BX | 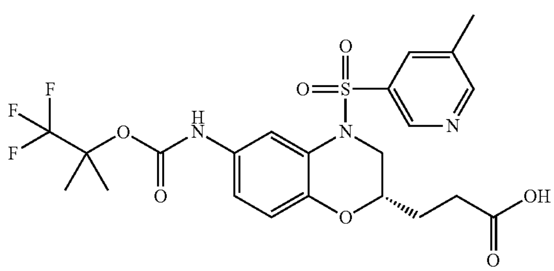 [SMILES: Cc1cncc(S(=O)(=O)N2C[C@H](CCC(=O)O)Oc3ccc(NC(=O)OC(C)(C)C(F)(F)F)cc32)c1] | 3-[(2S)-4-[(5-methylpyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid | 532 [M + H]+ |
| 6BY | 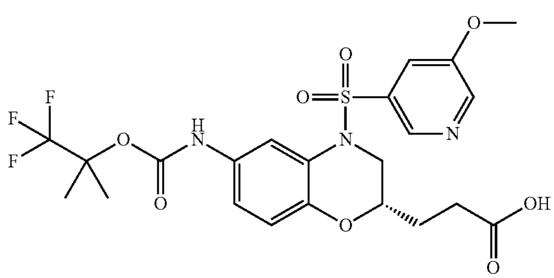 [SMILES: COc1cncc(S(=O)(=O)N2C[C@H](CCC(=O)O)Oc3ccc(NC(=O)OC(C)(C)C(F)(F)F)cc32)c1] | 3-[(2S)-4-[(5-methoxypyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid | 548 [M + H]+ |
| 6BZ | 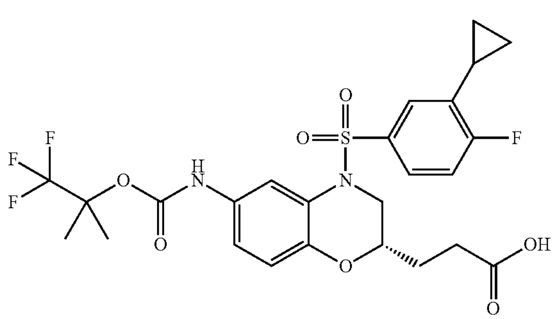 [SMILES: CC(C)(OC(=O)Nc1ccc2c(c1)N(S(=O)(=O)c1ccc(F)c(C3CC3)c1)C[C@H](CCC(=O)O)O2)C(F)(F)F] | 3-[(2S)-4-[(3-cyclopropyl-4-fluorophenyl)sulfonyl]-6-{[(2,2,2-trifluoro-1,1-dimethylethoxy)carbonyl]amino}-3,4-dihydro-2H-1,4-benzoxazin-2-yl]propanoic acid | 575 [M + H]+ |

TABLE 2-continued

| Ex. No. | Structure | Name | Observed m/z |
|---|---|---|---|
| 6CA | 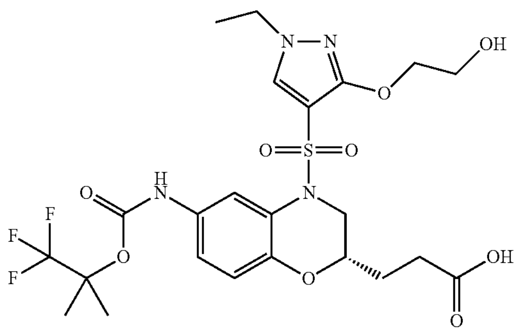 [SMILES: CCn1cc(S(=O)(=O)N2C[C@H](CCC(=O)O)Oc3ccc(NC(=O)OC(C)(C)C(F)(F)F)cc32)c(OCCO)n1] | 3-(4-{[1-ethyl-3-(2-hydroxyethoxy)-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl)propanoic acid | 595 [M + H]+ |
| 6CB | 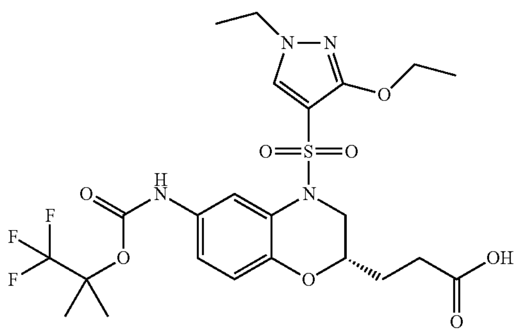 [SMILES: CCOc1nn(CC)cc1S(=O)(=O)N1C[C@H](CCC(=O)O)Oc2ccc(NC(=O)OC(C)(C)C(F)(F)F)cc21] | 3-(4-[(3-ethoxy-1-ethyl-1H-pyrazol-4-yl)sulfonyl]-6-{[(2,2,2-trifluoro-1,1-dimethylethoxy)carbonyl]amino}-3,4-dihydro-2H-1,4-benzoxazin-2-yl)propanoic acid | 579 [M + H]+ |
| 6CC | 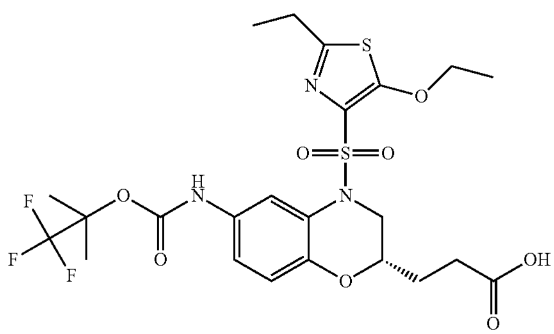 [SMILES: CCOc1sc(CC)nc1S(=O)(=O)N1C[C@H](CCC(=O)O)Oc2ccc(NC(=O)OC(C)(C)C(F)(F)F)cc21] | 3-[(2S)-4-[(5-ethoxy-2-ethyl-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]propanoic acid | 596 [M + H]+ |
| 6CD | 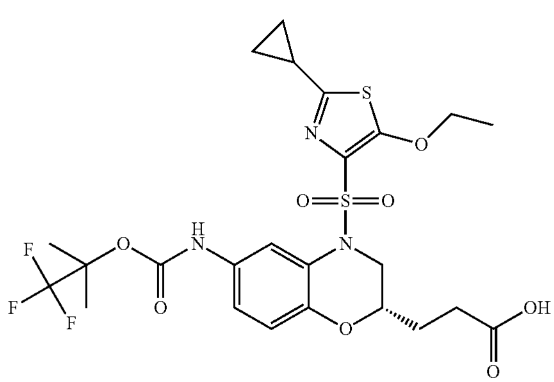 [SMILES: CCOc1sc(C2CC2)nc1S(=O)(=O)N1C[C@H](CCC(=O)O)Oc2ccc(NC(=O)OC(C)(C)C(F)(F)F)cc21] | 3-[(2S)-4-[(2-cyclopropyl-5-ethoxy-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]propanoic acid | 608 [M + H]+ |

TABLE 2-continued

| Ex. No. | Structure | Name | Observed m/z |
|---|---|---|---|
| 6CE | 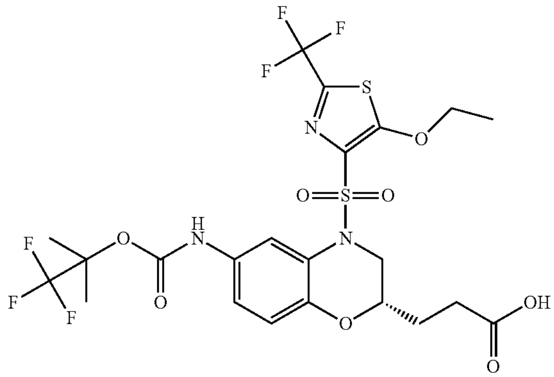 [SMILES: CCOc1sc(C(F)(F)F)nc1S(=O)(=O)N1C[C@H](CCC(=O)O)Oc2ccc(NC(=O)OC(C)(C)C(F)(F)F)cc21] | 3-[(2S)-4-{[5-ethoxy-2-(trifluoromethyl)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]propanoic acid | 636 [M + H]+ |
| 6CF | 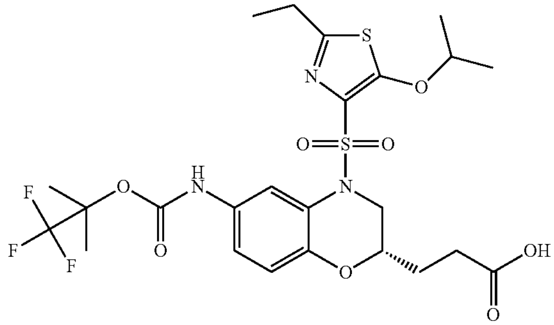 [SMILES: CCc1nc(S(=O)(=O)N2C[C@H](CCC(=O)O)Oc3ccc(NC(=O)OC(C)(C)C(F)(F)F)cc32)c(OC(C)C)s1] | 3-[(2S)-4-{[2-ethyl-5-(1-methylethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]propanoic acid | 610 [M + H]+ |
| 6CG | 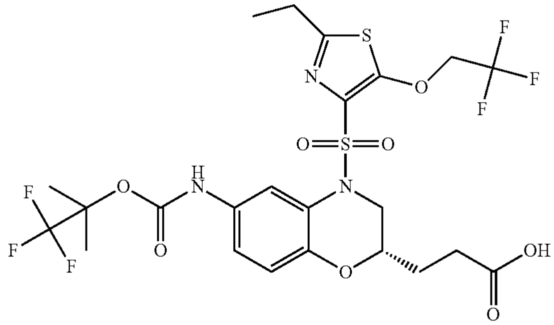 [SMILES: CCc1nc(S(=O)(=O)N2C[C@H](CCC(=O)O)Oc3ccc(NC(=O)OC(C)(C)C(F)(F)F)cc32)c(OCC(F)(F)F)s1] | 3-[(2S)-4-{[2-ethyl-5-(2,2,2-trifluoroethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]propanoic acid | 650 [M + H]+ |
| 6CH | 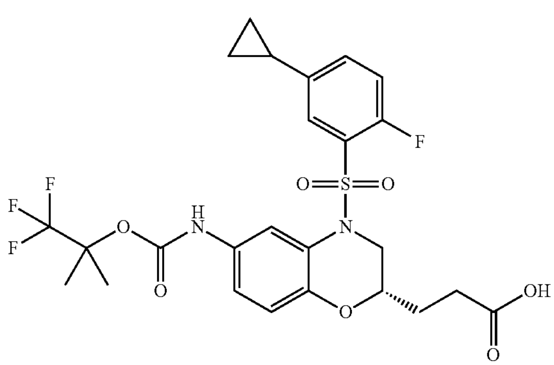 [SMILES: CC(C)(OC(=O)Nc1ccc2c(c1)N(S(=O)(=O)c1cc(C3CC3)ccc1F)C[C@H](CCC(=O)O)O2)C(F)(F)F] | 3-[(2S)-4-[(5-cyclopropyl-2-fluorophenyl)sulfonyl]-6-{[(2,2,2-trifluoro-1,1-dimethylethoxy)carbonyl]amino}-3,4-dihydro-2H-1,4-benzoxazin-2-yl]propanoic acid | 575 [M + H]+ |

TABLE 2-continued

| Ex. No. | Structure | Name | Observed m/z |
|---|---|---|---|
| 6Ci | 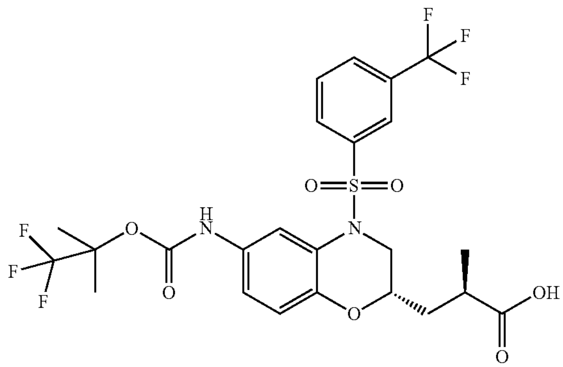 [SMILES: C[C@H](C[C@H]1CN(S(=O)(=O)c2cccc(C(F)(F)F)c2)c2cc(NC(=O)OC(C)(C)C(F)(F)F)ccc2O1)C(=O)O] | (S or R)-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 599 [M + H]+ |
| 6CJ | 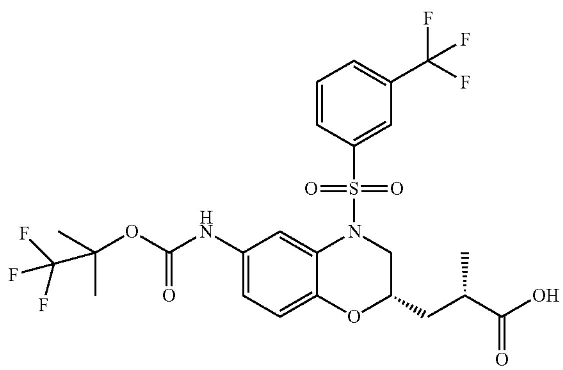 [SMILES: C[C@@H](C[C@H]1CN(S(=O)(=O)c2cccc(C(F)(F)F)c2)c2cc(NC(=O)OC(C)(C)C(F)(F)F)ccc2O1)C(=O)O] | (S or R)-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 599 [M + H]+ |
| 6CK | 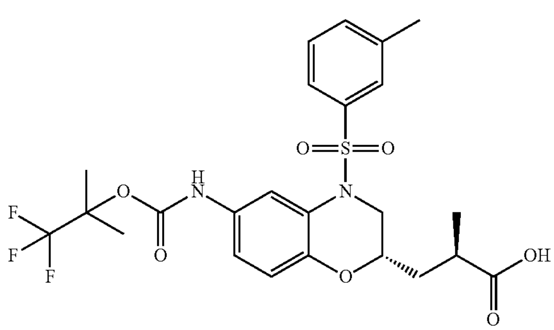 [SMILES: Cc1cccc(S(=O)(=O)N2C[C@H](C[C@@H](C)C(=O)O)Oc3ccc(NC(=O)OC(C)(C)C(F)(F)F)cc32)c1] | (S or R)-2-methyl-3-((S)-4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 545 [M + H]+ |
| 6CL | 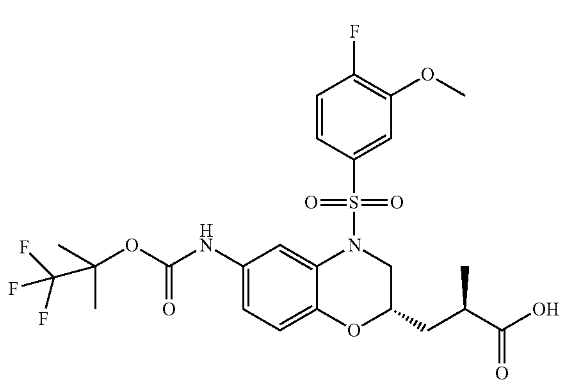 [SMILES: COc1cc(S(=O)(=O)N2C[C@H](C[C@@H](C)C(=O)O)Oc3ccc(NC(=O)OC(C)(C)C(F)(F)F)cc32)ccc1F] | (S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 579 [M + H]+ |

TABLE 2-continued

| Ex. No. | Structure | Name | Observed m/z |
|---|---|---|---|
| 6CM | 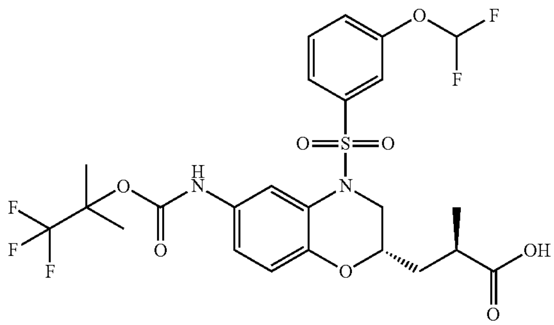 [SMILES: C[C@H](C[C@H]1CN(S(=O)(=O)c2cccc(OC(F)F)c2)c2cc(NC(=O)OC(C)(C)C(F)(F)F)ccc2O1)C(=O)O] | (S or R)-3-((S)-4-((3-(difluoromethoxy)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 597 [M + H]+ |
| 6CN | 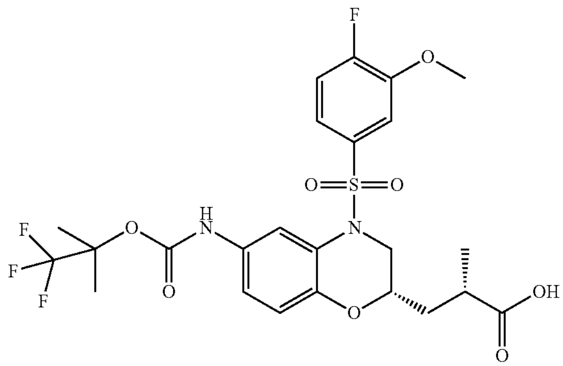 [SMILES: COc1cc(S(=O)(=O)N2C[C@H](C[C@H](C)C(=O)O)Oc3ccc(NC(=O)OC(C)(C)C(F)(F)F)cc32)ccc1F] | (S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 579 [M + H]+ |
| 6Co | 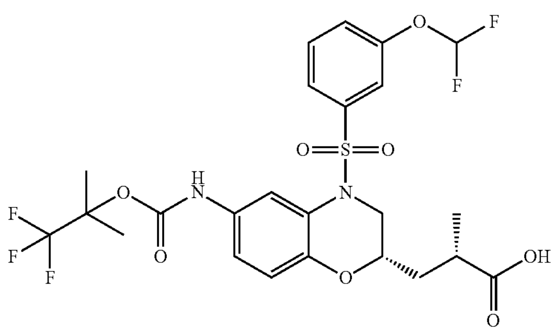 [SMILES: C[C@@H](C[C@H]1CN(S(=O)(=O)c2cccc(OC(F)F)c2)c2cc(NC(=O)OC(C)(C)C(F)(F)F)ccc2O1)C(=O)O] | (S or R)-3-((S)-4-((3-(difluoromethoxy)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 597 [M + H]+ |
| 6CP | 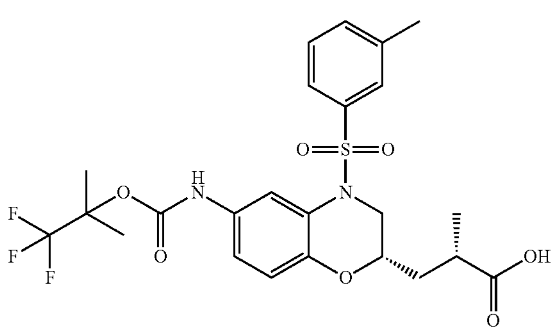 [SMILES: Cc1cccc(S(=O)(=O)N2C[C@H](C[C@H](C)C(=O)O)Oc3ccc(NC(=O)OC(C)(C)C(F)(F)F)cc32)c1] | (S or R)-2-methyl-3-((S)-4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 545 [M + H]+ |

TABLE 2-continued

| Ex. No. | Structure | Name | Observed m/z |
|---|---|---|---|
| 6CQ | 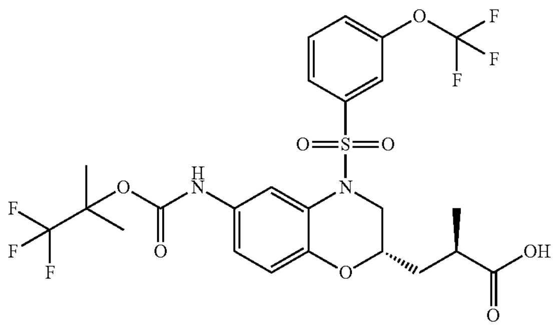 [SMILES: C[C@H](C[C@H]1CN(S(=O)(=O)c2cccc(OC(F)(F)F)c2)c2cc(NC(=O)OC(C)(C)C(F)(F)F)ccc2O1)C(=O)O] | (R or S)-2-methyl-3-((S)-6-((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid | 615 [M + H]+ |
| 6CR | 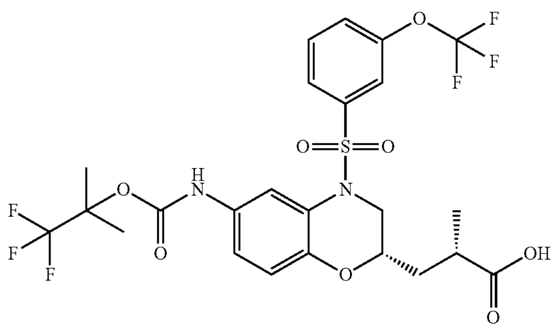 [SMILES: C[C@@H](C[C@H]1CN(S(=O)(=O)c2cccc(OC(F)(F)F)c2)c2cc(NC(=O)OC(C)(C)C(F)(F)F)ccc2O1)C(=O)O] | (S or R)-2-methyl-3-((S)-6-((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid | 615 [M + H]+ |
| 6CS | 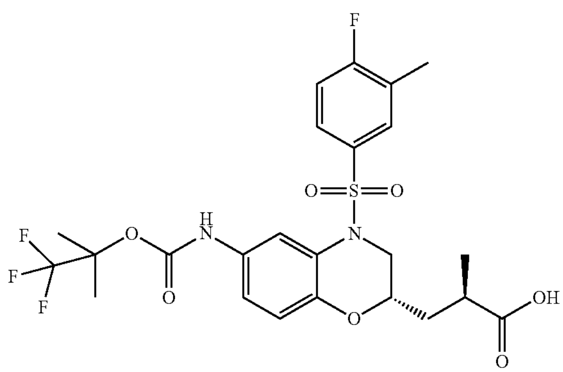 [SMILES: Cc1cc(S(=O)(=O)N2C[C@H](C[C@@H](C)C(=O)O)Oc3ccc(NC(=O)OC(C)(C)C(F)(F)F)cc32)ccc1F] | (R or S)-3-((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 563 [M + H]+ |
| 6CT | 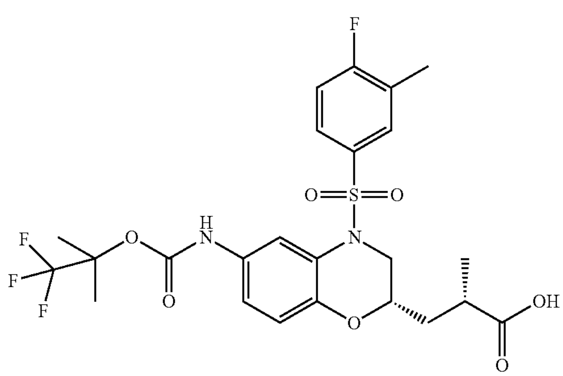 [SMILES: Cc1cc(S(=O)(=O)N2C[C@H](C[C@H](C)C(=O)O)Oc3ccc(NC(=O)OC(C)(C)C(F)(F)F)cc32)ccc1F] | (S or R)-3-((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 563 [M + H]+ |

TABLE 2-continued

| Ex. No. | Structure | Name | Observed m/z |
|---|---|---|---|
| 6CU | 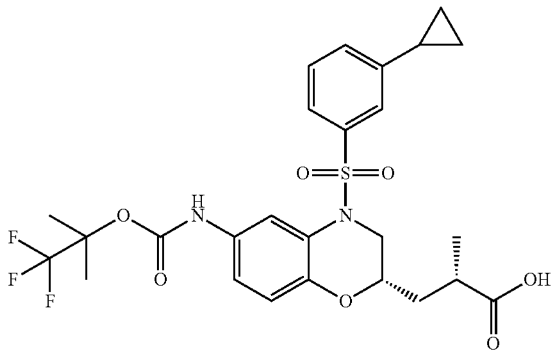 [SMILES: C[C@@H](C[C@H]1CN(S(=O)(=O)c2cccc(C3CC3)c2)c2cc(NC(=O)OC(C)(C)C(F)(F)F)ccc2O1)C(=O)O] | (S or R)-3-((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 571 [M + H]+ |
| 6CV | 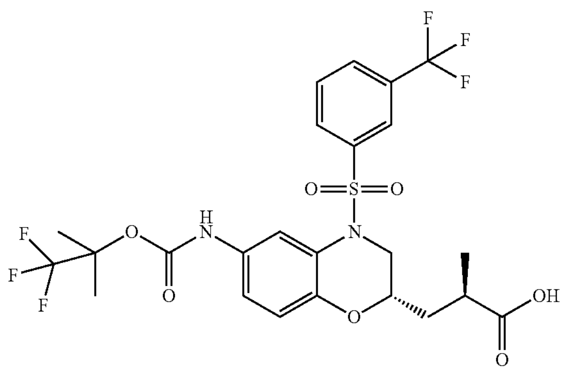 [SMILES: C[C@H](C[C@H]1CN(S(=O)(=O)c2cccc(C(F)(F)F)c2)c2cc(NC(=O)OC(C)(C)C(F)(F)F)ccc2O1)C(=O)O] | (R or S)-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 599 [M + H]+ |
| 6CW | 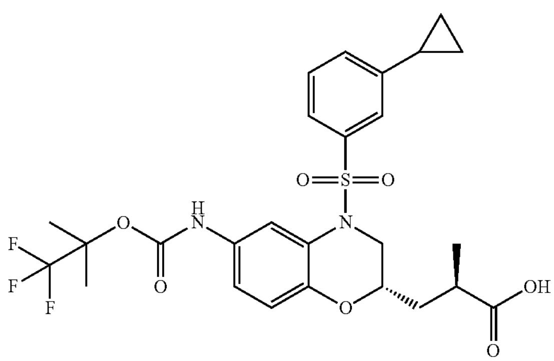 [SMILES: C[C@H](C[C@H]1CN(S(=O)(=O)c2cccc(C3CC3)c2)c2cc(NC(=O)OC(C)(C)C(F)(F)F)ccc2O1)C(=O)O] | (R or S)-3-((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 571 [M + H]+ |
| 6CX | 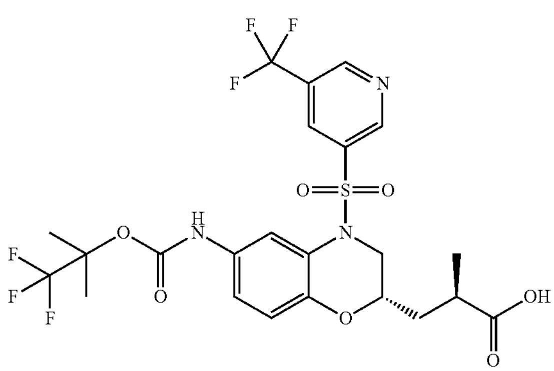 [SMILES: C[C@H](C[C@H]1CN(S(=O)(=O)c2cncc(C(F)(F)F)c2)c2cc(NC(=O)OC(C)(C)C(F)(F)F)ccc2O1)C(=O)O] | (S or R)-2-methyl-3-((S)-6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid | 600 [M + H]+ |

TABLE 2-continued

| Ex. No. | Structure | Name | Observed m/z |
|---|---|---|---|
| 6CY | 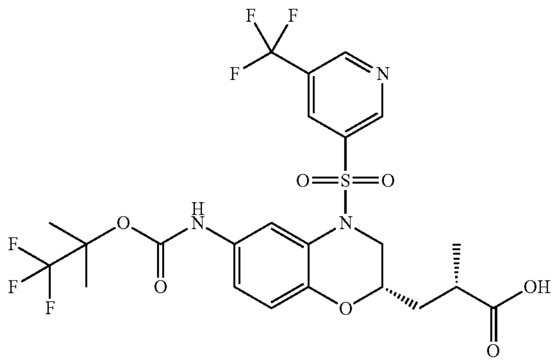 [SMILES: C[C@@H](C[C@H]1CN(S(=O)(=O)c2cncc(C(F)(F)F)c2)c2cc(NC(=O)OC(C)(C)C(F)(F)F)ccc2O1)C(=O)O] | (S or R)-2-methyl-3-((S)-6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid | 600 [M + H]+ |
| 6CZ | 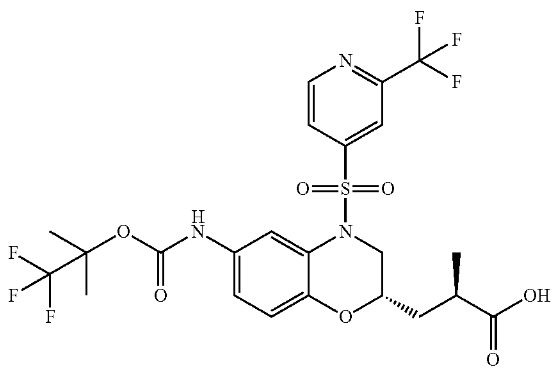 [SMILES: C[C@H](C[C@H]1CN(S(=O)(=O)c2ccnc(C(F)(F)F)c2)c2cc(NC(=O)OC(C)(C)C(F)(F)F)ccc2O1)C(=O)O] | (R or S)-2-methyl-3-((S)-6-((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)propanoic acid | 600 [M + H]+ |
| 6DA | 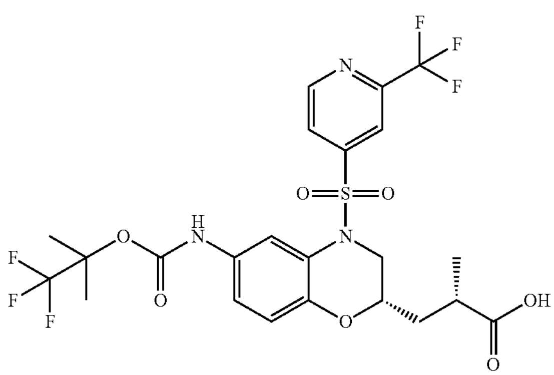 [SMILES: C[C@@H](C[C@H]1CN(S(=O)(=O)c2ccnc(C(F)(F)F)c2)c2cc(NC(=O)OC(C)(C)C(F)(F)F)ccc2O1)C(=O)O] | (R or S)-2-methyl-3-((S)-6-((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)propanoic acid | 600 [M + H]+ |
| 6DB | 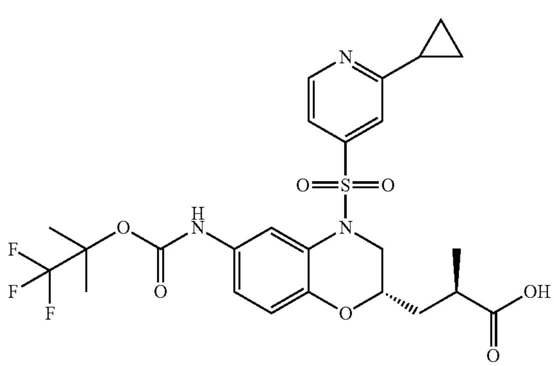 [SMILES: C[C@H](C[C@H]1CN(S(=O)(=O)c2ccnc(C3CC3)c2)c2cc(NC(=O)OC(C)(C)C(F)(F)F)ccc2O1)C(=O)O] | (R or S)-3-((S)-4-((2-cyclopropylpyridin-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 572 [M + H]+ |

TABLE 2-continued

| Ex. No. | Structure | Name | Observed m/z |
|---|---|---|---|
| 6DC | 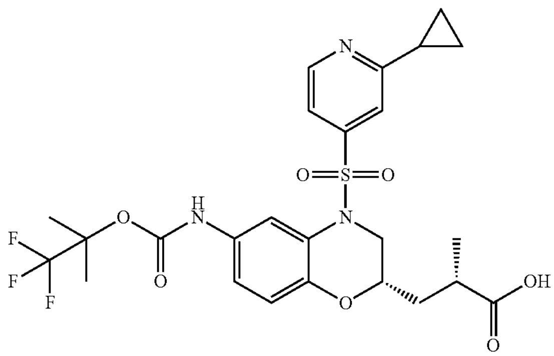 [SMILES: C[C@@H](C[C@H]1CN(S(=O)(=O)c2ccnc(C3CC3)c2)c2cc(NC(=O)OC(C)(C)C(F)(F)F)ccc2O1)C(=O)O] | (R or S)-3-((S)-4-((2-cyclopropylpyridin-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 572 [M + H]+ |
| 6DD | 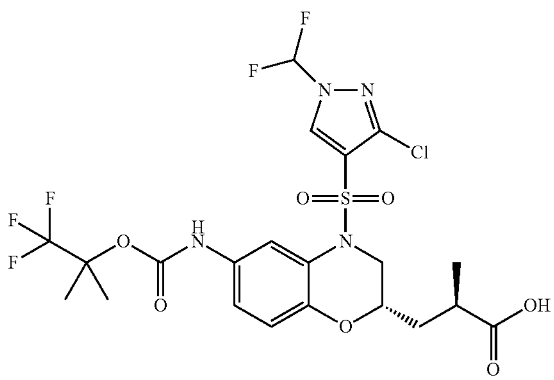 [SMILES: C[C@H](C[C@H]1CN(S(=O)(=O)c2cn(C(F)F)nc2Cl)c2cc(NC(=O)OC(C)(C)C(F)(F)F)ccc2O1)C(=O)O] | (R or S)-3-((S)-4-((3-chloro-1-(difluoromethyl)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 605 [M + H]+ |
| 6DE | 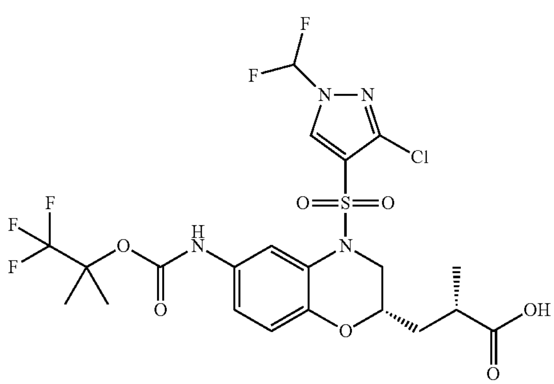 [SMILES: C[C@@H](C[C@H]1CN(S(=O)(=O)c2cn(C(F)F)nc2Cl)c2cc(NC(=O)OC(C)(C)C(F)(F)F)ccc2O1)C(=O)O] | (R or S)-3-((S)-4-((3-chloro-1-(difluoromethyl)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid | 605 [M + H]+ |

Example 7

Alternative Synthesis of (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid (4)

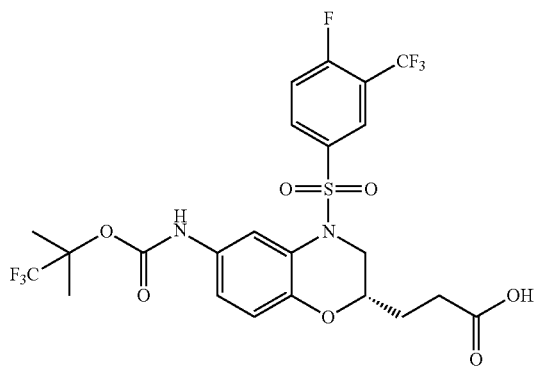 [SMILES: CC(C)(OC(=O)Nc1ccc2c(c1)N(S(=O)(=O)c1ccc(F)c(C(F)(F)F)c1)C[C@H](CCC(=O)O)O2)C(F)(F)F]

Step 1—Synthesis of 2-(benzylamino)-4-nitrophenol

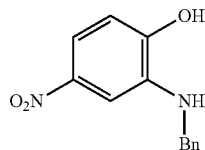 [SMILES: O=[N+]([O-])c1ccc(O)c(NCc2ccccc2)c1]

To a solution of compound 2-amino-4-nitrophenol (100 g, 0.648 mol) and benzaldehyde (82.6 g, 0.778 mol) in 2 L of MeOH was added $NaBH_4$ (24.6 g, 0.648 mol) at 0° C. under $N_2$. The mixture was stirred for 0.5 h, then poured into a mixture of ice and $H_2O$. After extraction with EtOAc (100 mL×2), the combined organic phase was washed with brine and dried over $Na_2SO_4$. The crude product was purified by column chromatography (petroleum ether:EtOAc=20:1 to 3:1) to give the title compound as a red solid. $^1$H NMR (400 MHz, Methanol-$d_4$) δ 7.44 (d, J=2.8 Hz, 1H), 7.20-7.39 (m, 6H), 6.71 (d, J=8.6 Hz, 1H), 4.39 (s, 2H).

Step 2—Synthesis of (R)-(4-benzyl-6-nitro-3,4-dihydro-2H-benzo[b][1,4]oxazin-2-yl)methanol

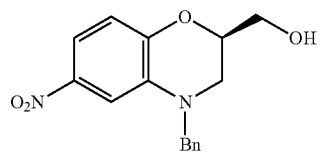 [SMILES: O=[N+]([O-])c1ccc2c(c1)N(Cc1ccccc1)C[C@H](CO)O2]

To a solution of 2-(benzylamino)-4-nitrophenol (75 g, 0.307 mol) and $LiClO_4$ (65.3 g, 0.614 mol) in 1 L of toluene was added (S)-2-(chloromethyl)oxirane (102 g, 1.11 mol) at 50° C. The solution was stirred at 50° C. for 16 hours. Then NaOMe (33 g, 0.614 mol) in 125 mL MeOH was added slowly. The resulting solution was stirred at 50° C. for 16 hours. The reaction was quenched with $H_2O$ and extracted with EtOAc. The organic layer was dried and concentrated. The crude product was purified by column chromatography (petroleum ether:DCM=3:1 to 1:3) to afford the title compound as red oil. $^1$H NMR (400 MHz, Methanol-$d_4$) δ 7.51-7.53 (m, 2H), 7.26-7.35 (m, 5H), 6.88 (d, J=9.6 Hz, 1H), 4.56-4.87 (m, 2H), 4.30-4.32 (m, 1H), 3.50-3.77 (m, 2H), 3.47-3.51 (m, 1H), 3.31-3.37 (m, 1H).

Step 3—Synthesis of (R)-4-benzyl-2-(bromomethyl)-6-nitro-3,4-dihydro-2H benzo[b][1,4]oxazine

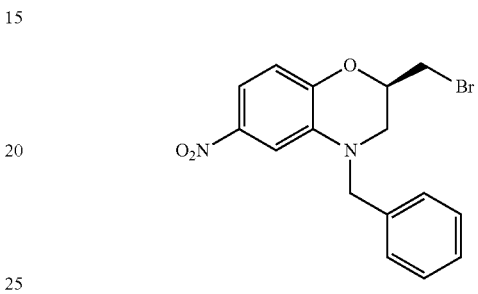

To a solution of (R)-(4-benzyl-6-nitro-3,4-dihydro-2H-benzo[b][1,4]oxazin-2-yl)methanol (5.0 g, 16.65 mmol) and $CBr_4$ (12.0 g, 36.19 mmol) in THF (50 mL) was added $PPh_3$ (10.0 g, 38.13 mmol) portionwise at room temperature. The reaction mixture was stirred at 60° C. overnight, then concentrated in vacuo. The crude product was purified by column chromatography (petroleum ether:EA=10:1) to give the title compound as a yellow solid. LCMS (ESI) calculated for $C_{16}H_{16}BrN_2O_3$ [M+H]$^+$: 363. found: 363.

Step 4—Synthesis of (S)-diethyl 2-((4-benzyl-6-nitro-3,4-dihydro-2H-benzo[b][1,4]oxazin-2-yl)methyl)malonate

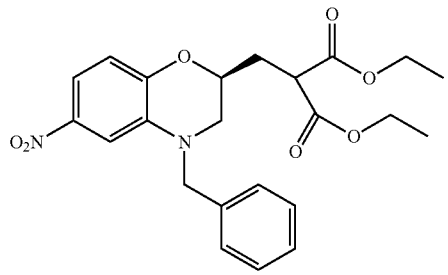 [SMILES: CCOC(=O)C(C[C@H]1CN(Cc2ccccc2)c2cc([N+](=O)[O-])ccc2O1)C(=O)OCC]

To a solution of (R)-4-benzyl-2-(bromomethyl)-6-nitro-3,4-dihydro-2H-benzo[b][1,4]oxazine (6.0 g, 16.52 mmol) and diethyl malonate (3.5 g, 21.85 mmol) in DMF (15 mL) was added $K_2CO_3$ (4.8 g, 34.73 mmol) at room temperature. The reaction mixture was stirred at 100° C. overnight, then quenched with water and 1N HCl. The mixture was extracted with 3×EtOAc. The combined organic phase was washed with brine, dried over $Na_2SO_4$, and concentrated in vacuo. The residue was purified by column chromatography (petroleum ether:EtOAc=10:1) to give the title compound as a yellow oil. LCMS (ESI) calculated for $C_{23}H_{27}N_2O_7$ [M+H]$^+$: 443. found: 443.

Step 5—Synthesis of (S)-ethyl 3-(4-benzyl-6-nitro-3,4-dihydro-2H-benzo[b][1,4]oxazin-2-yl)propanoate

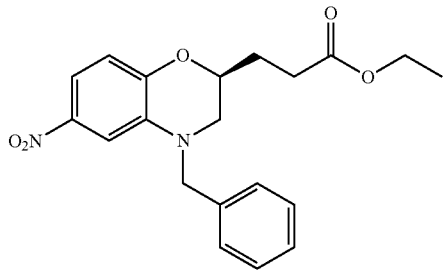 [SMILES: CCOC(=O)CC[C@H]1CN(Cc2ccccc2)c2cc([N+](=O)[O-])ccc2O1]

To a mixture of (S)-diethyl 2-((4-benzyl-6-nitro-3,4-dihydro-2H-benzo[b][1,4]oxazin-2-yl)methyl)malonate (700 mg, 1.58 mmol) in DMSO (10 mL) was added LiCl (350 mg, 8.26 mmol) and several drops of water. The reaction mixture was stirred at 170° C. for 3 h, then quenched with water and extracted with EtOAc. The organic layer was washed with brine, dried over $Na_2SO_4$ and concentrated in vacuo. The crude product was purified by column chromatography (petroleum ether:EtOAc=10:1) to give the title compound. LCMS (ESI) calculated for $C_{20}H_{23}N_2O_5$ $[M+H]^+$: 371. found: 371.

Step 6—Synthesis of (S)-ethyl 3-(6-amino-3,4-dihydro-2H-benzo[b][1,4]oxazin-2-yl)propanoate

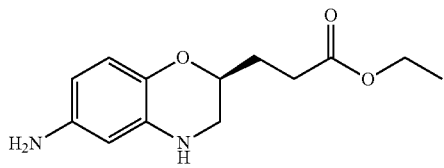 [SMILES: CCOC(=O)CC[C@H]1CNc2cc(N)ccc2O1]

To a solution of (S)-ethyl 3-(4-benzyl-6-nitro-3,4-dihydro-2H-benzo[b][1,4]oxazin-2-yl)propanoate (1.0 g, 2.70 mmol) in MeOH (20 mL) was added Pd/C (500 mg) at room temperature. The reaction mixture was stirred under $H_2$ atmosphere (50 psi) until completion, then filtered through a CELITE pad. The filtrate was concentrated to give the title compound. LCMS (ESI) calculated for $C_{13}H_{19}N_2O_3$ $[M+H]^+$: 251. found: 251.

Step 7—Synthesis of (S)-ethyl 3-(6-((((1,1,1-trifluoro-2-methylpropan-2-yl)oxy)carbonyl)amino)-3,4-dihydro-2H-benzo[b][1,4]oxazin-2-yl)propanoate

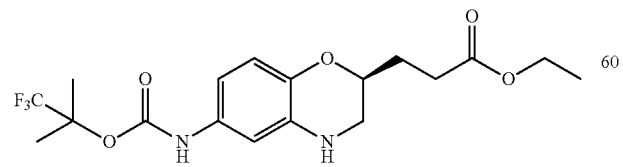

To a mixture of (S)-ethyl 3-(6-amino-3,4-dihydro-2H-benzo[b][1,4]oxazin-2-yl)propanoate (1.5 g, 5.99 mmol) and 1,1,1-trifluoro-2-methylpropan-2-yl 1H-imidazole-1-carboxylate (1.5 g, 6.75 mmol) in 15 mL of DMSO was added concentrated HCl (0.6 mL) and stirred at 80° C. for 4 hours. The reaction mixture was diluted with water and extracted 3× with EtOAc. The organic layer was washed with water, brine, dried over $Na_2SO_4$ and concentrated in vacuo. The residue was purified by column chromatography (petroleum ether:EA=5:1) to give the title compound as an off-white solid. LCMS (ESI) calculated for $C_{18}H_{24}F_3N_2O_5$ $[M+H]^+$: 405. found: 405. $^1$H-NMR (400 MHz, $CDCl_3$) δ 6.82 (br s, 1H), 6.69 (d, J=8.5 Hz, 1H), 6.43 (d, J=6.0 Hz, 2H), 4.15 (q, J=7.1 Hz, 2H), 4.08 (d, J=7.5 Hz, 1H), 3.36 (dd, J=11.5, 2.3 Hz, 1H), 3.13 (dd, J=11.5, 7.5 Hz, 1H), 2.46~2.64 (m, 2H), 1.91-2.01 (m, 2H), 1.73 (s, 6H), 1.26 (t, J=7.2 Hz, 3H).

Step 8—Synthesis of (S)-ethyl 3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate

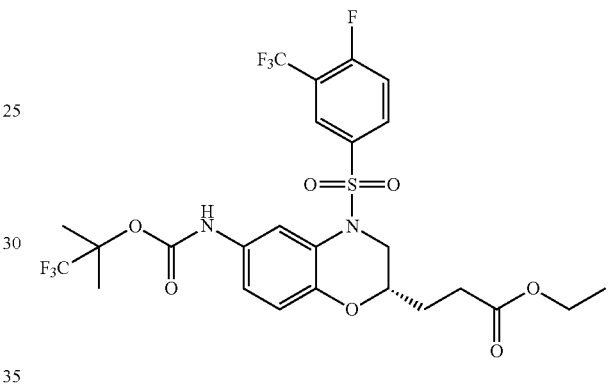

To a vial equipped with a stir bar was added (S)-ethyl 3-(6-((((1,1,1-trifluoro-2-methylpropan-2-yl)oxy)carbonyl)amino)-3,4-dihydro-2H-benzo[b][1,4]oxazin-2-yl)propanoate (20 mg, 0.049 mmol), pyridine (500 μl), and 4-fluoro-3-(trifluoromethyl)benzene-1-sulfonyl chloride (3 equiv., 0.148 mmol). The reaction mixture was heated at 40° C. for 2 h, then extracted with ethyl acetate and saturated $NaHCO_3$. The combined organic layer was dried over sodium sulfate, filtered, and concentrated under reduced pressure. The crude product was taken forward without further purification. LCMS (ESI) calculated for $C_{25}H_{26}F_7N_2O_7S$ $[M+H]^+$: 631. found: 631.

Step 9—Synthesis of (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid

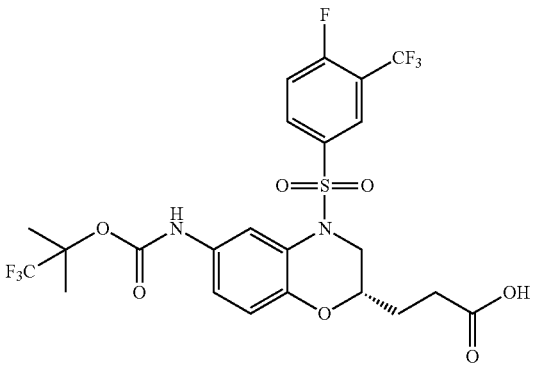 [SMILES: CC(C)(OC(=O)Nc1ccc2c(c1)N(S(=O)(=O)c1ccc(F)c(C(F)(F)F)c1)C[C@H](CCC(=O)O)O2)C(F)(F)F]

To a room temperature solution of (S)-ethyl 3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate (50 mg, 0.079 mmol) in dioxane (1 mL) was added aqueous 1 M lithium hydroxide (0.79 mL, 0.790 mmol). After 0.5 h, the reaction mixture was acidified with 1N HCl to pH 1-2, extracted with EtOAc and concentrated. The crude product was purified by reverse phase chromatograrphy using MeCN/water and TFA buffer to afford the title compound as a white solid. MS ESI calculated for $C_{23}H_{22}F_7N_2O_7S$ $(M+H)^+$ 603, found 625 $(M+Na).^+$ $^1$H NMR (600 MHz, DMSO-$d_6$) δ 12.25 (s, 1H), 9.71 (s, 1H), 8.17 (1H, d, J=8.50 Hz), 8.12 (1H, d, J=5.97 Hz), 7.91 (1H, s), 7.74 (1H, t, J=9.51 Hz), 7.01 (1H, dd, J=8.87, 2.44 Hz), 6.74 (1H, d, J=8.84 Hz), 4.29 (1H, dd, J=13.92, 2.31 Hz), 3.66 (1H, s), 2.38-2.28 (2H, m), 1.84-1.77 (1H, m), 1.75-1.70 (1H, m), 1.67 (6H, s).

Example 8

Synthesis of (R)-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid and (S)-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid (Example Nos. 8A and 8B)

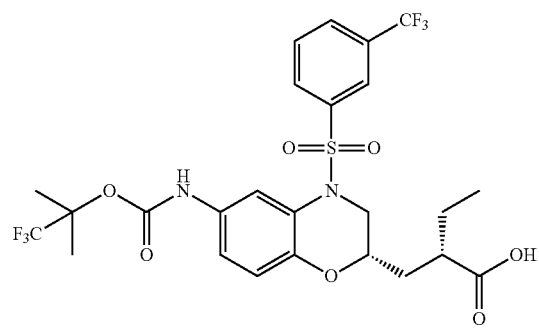

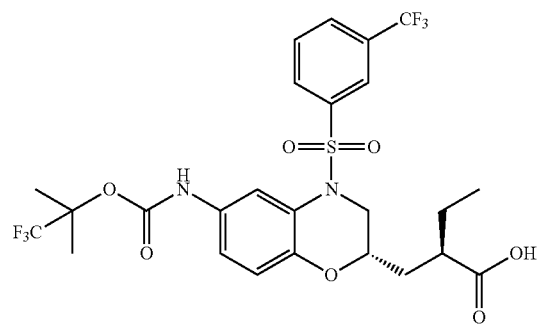

Step 1—Synthesis of (S)-diethyl 2-((4-benzyl-6-nitro-3,4-dihydro-2H-benzo[b][1,4]oxazin-2-yl)methyl)-2-ethylmalonate

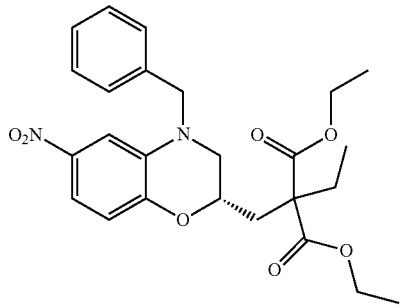 [SMILES: CCOC(=O)C(CC)(C[C@H]1CN(Cc2ccccc2)c2cc([N+](=O)[O-])ccc2O1)C(=O)OCC]

To a mixture of (S)-diethyl 2-((4-benzyl-6-nitro-3,4-dihydro-2H-benzo[b][1,4]oxazin-2-yl)methyl)malonate (4.00 g, 9.04 mmol; see Example 2) and $K_2CO_3$ (1.90 g, 13.8 mmol) in 120 mL of acetonitrile was added iodoethane (28.20 g, 181 mmol) and the resulting mixture was stirred at 80° C. for 30 h. The reaction mixture was quenched with $H_2O$, extracted with EtOAc (3×100 mL), washed with brine, dried over $Na_2SO_4$, filtered and concentrated. The crude product was purified by flash column chromatography (0-30% ethyl acetate in petroleum ether) to afford the title compound as a yellow oil. LCMS (ESI) calculated for $C_{25}H_{31}N_2O_7$ $[M+H]^+$: 471. found: 471, $^1$H NMR (400 MHz, CDCl$_3$) 7.49-7.65 (2H, m), 7.20-7.39 (5H, m), 6.73 (1H, d, J=8.6 Hz), 4.60-4.41 (2H, m), 4.32 (1H, t, J=7.6 Hz), 4.07-4.25 (4H, m), 3.13-3.36 (2H, m), 2.16-2.32 (2H, m), 2.04-2.11 (2H, m), 1.18-1.29 (6H, m), 0.80-0.89 (3H, m).

Step 2—Synthesis of (S and R)-2-(((S)-4-benzyl-6-nitro-3,4-dihydro-2H-benzo[b][1,4]oxazin-2-yl)methyl)butanoic acid

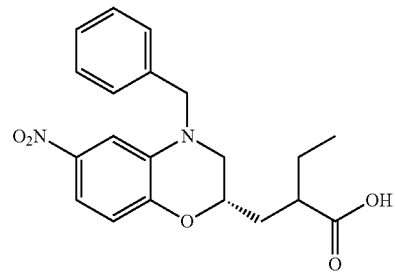 [SMILES: CCC(C[C@H]1CN(Cc2ccccc2)c2cc([N+](=O)[O-])ccc2O1)C(=O)O]

To a solution of (S)-diethyl 2-((4-benzyl-6-nitro-3,4-dihydro-2H-benzo[b][1,4]oxazin-2-yl)methyl)-2-ethylmalonate (2.50 g, 5.31 mmol)) in 30 mL of THF and 30 mL of water was added KOH (1.50 g, 26.7 mmol). The resulting mixture was stirred at 60° C. for 16 h, then adjusted the pH to ~1 with 5 mL of 6 M aq. HCl. The organic layer was concentrated in vacuo, then 40 mL of concentrated HCl was added and the resulting mixture was stirred at 100° C. for 16 h. The solution was concentrated in vacuo, purified by flash chromatography (50-100% EtOAc in petroleum ether) to afford the title compound as a yellow solid. LCMS (ESI) calculated for $C_{20}H_{23}N_2O_5$ $[M+H]^+$: 371. found: 371, $^1$H NMR (400 MHz, CDCl$_3$) δ 7.49 (1H, dd, J=8.8 Hz, 2.3 Hz), 7.41 (1H, brs), 6.66-6.78 (1H, m), 4.12-4.25 (1H, m), 3.32-3.41 (1H, m), 3.11 (1H, ddd, J=11.7 Hz, 7.0 Hz, 4.7 Hz), 2.68-2.79 (1H, m), 2.49-2.60 (1H, m), 2.10 (1H, dd, J=14.2 Hz, 8.8 Hz), 1.87-1.97 (1H, m), 1.57-1.78 (4H, m), 0.87-1.00 (3H, m).

Step 3—Synthesis of (S and R)-2-(((S)-6-amino-3,4-dihydro-2H-benzo[b][1,4]oxazin-2-yl)methyl)butanoic acid

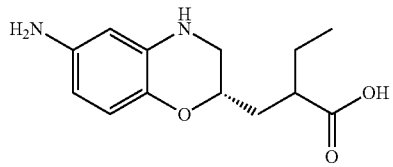 [SMILES: CCC(C[C@H]1CNc2cc(N)ccc2O1)C(=O)O]

To a solution of (S and R)-2-(((S)-4-benzyl-6-nitro-3,4-dihydro-2H-benzo[b][1,4]oxazin-2-yl)methyl)butanoic acid (800 mg, 2.85 mmol) in 15 mL of MeOH was added 200 mg of Raney Ni. The resulting mixture was stirred at 25° C. under $H_2$ (15 psi) for 3 h, then filtered and concentrated in vacuo to afford the title compound as a brown oil. LCMS (ESI) calculated for $C_{13}H_{19}N_2O_3$ [M+H]$^+$: 251. found: 251.

Step 4—Synthesis of (S)-2-(((S)-6-((((1,1,1-trifluoro-2-methylpropan-2-yl)oxy)carbonyl)amino)-3,4-dihydro-2H-benzo[b][1,4]oxazin-2-yl)methyl)butanoic acid and (R)-2-(((S)-6-((((1,1,1-trifluoro-2-methylpropan-2-yl)oxy)carbonyl)amino)-3,4-dihydro-2H-benzo[b][1,4]oxazin-2-yl)methyl)butanoic acid

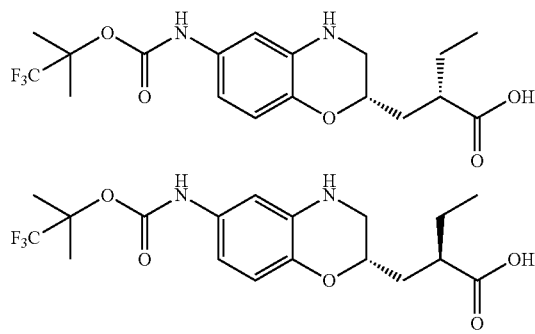

To a solution of (S and R)-2-(((S)-6-amino-3,4-dihydro-2H-benzo[b][1,4]oxazin-2-yl)methyl)butanoic acid (650 mg, 2.60 mmol) in DMSO (5 mL) was added 3-methyl-1-((((1,1,1-trifluoro-2-methylpropan-2-yl)oxy)carbonyl)-1H-imidazol-3-ium iodide (946 mg, 2.60 mmol) and the resulting mixture was stirred at room temperature for 0.5 h. Upon completion, the reaction mixture was poured into $H_2O$ (50 mL), extracted with EtOAc (30 mL×3) and the combined organic layers washed with brine, dried over $Na_2SO_4$, filtered and concentrated. The crude product was by purified by flash chromatography (0-60% EtOAc in petroleum ether) to afford the product of the title mixture as a yellow solid.

The two isomers were separated by chiral SFC purification (Column: Chiralpak AD-3 150×4.6 mm I.D., 3 um; Mobile phase: iso-propanol (0.05% DEA) in $CO_2$ from 5% to 40%; Flow rate: 2.5 mL/min; Wavelength: 220 nm).

Isomer 1 (faster-eluting peak): LCMS (ESI) calculated for $C_{18}H_{24}F_3N_2O_5$ [M+H]$^+$: 405. found: 405, $^1$H NMR (400 MHz, CDCl$_3$) 6.86 (1H, brs), 6.63-6.75 (1H, m), 6.58 (1H, brs), 6.39-6.51 (1H, m,), 3.38 (1H, t, J=11.0 Hz), 3.08-3.16 (1H, m), 2.79 (1H, d, J=6.3 Hz), 2.55-2.66 (1H, m), 2.10-2.17 (1H, m), 1.88-1.99 (1H, m), 1.60-1.74 (4H, m), 0.99 (3H, t, J=7.4 Hz). Isomer 2 (slower-eluting peak): LCMS (ESI) calculated for $C_{18}H_{24}F_3N_2O_5$ [M+H]$^+$: 405. found: 405.

Step 5—Preparation of (S)-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid and (R)-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid

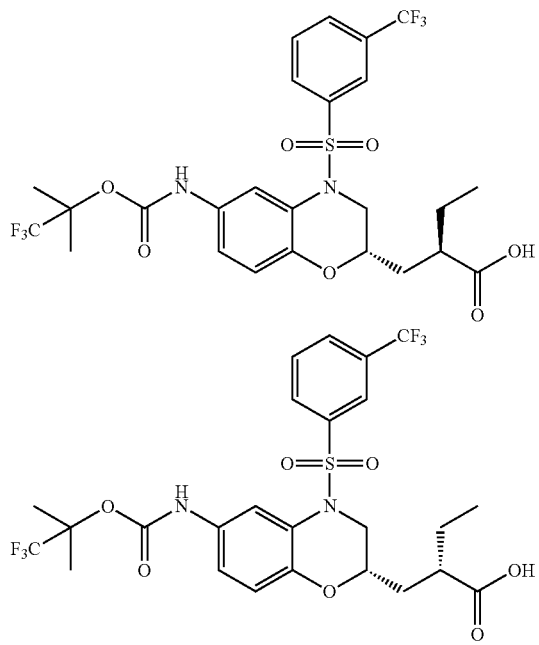

To a solution of (S or R)-2-(((S)-6-((((1,1,1-trifluoro-2-methylpropan-2-yl)oxy)carbonyl)amino)-3,4-dihydro-2H-benzo[b][1,4]oxazin-2-yl)methyl)butanoic acid (Isomer 1 from Step 4; 20 mg, 0.049 mmol) in THF (2 mL) and pyridine (1 mL) was added 3-(trifluoromethyl)benzene-1-sulfonyl chloride (40 mg, 0.16 mmol) and the resulting mixture was stirred at room temperature for 36 h. The reaction mixture was poured inter 5 mL of water, extracted with EtOAc (5 mL×3), washed with brine and dried over $Na_2SO_4$. After concentration, the crude product was purified by prep-HPLC to afford Example No. 8A as a white solid. LCMS (ESI) calculated for $C_{25}H_{27}F_6N_2O_7S$ [M+H]$^+$: 613. found: 613, $^1$H NMR (400 MHz, MeOD) 7.88-8.13 (4H, m), 7.75 (1H, t, J=7.8 Hz), 7.00 (1H, dd, J=8.8 Hz, 2.2 Hz), 6.70 (1H, d, J=9.0 Hz), 4.39 (1H, d, J=12.5 Hz), 3.49 (1H, br s), 3.20-3.28 (1H, m), 2.36-2.46 (1H, m), 1.84-1.93 (1H, m), 1.76 (6H, s), 1.64-1.72 (1H, m), 1.46-1.59 (2H, m), 0.90 (3H, t, J=7.4 Hz).

The other isomer (Example No. 8B) was prepared from Isomer 2 from Step 4 using the above procedure. LCMS (ESI) calculated for $C_{25}H_{27}F_6N_2O_7S$ [M+H]$^+$: 613. found: 613, $^1$H NMR (400 MHz, MeOD) 7.93 (1H, d, J=6.3 Hz), 7.88-8.11 (4H, m), 7.75 (1H, t, J=7.6 Hz), 7.01 (1H, d, J=9.0 Hz), 6.67-6.75 (1H, m), 4.32-4.41 (1H, m), 3.43 (1H, br s), 3.20-3.28 (1H, m), 2.50 (1H, brs), 1.73-1.91 (7H, m), 1.48-1.63 (3H, m), 0.91 (3H, t, J=7.2 Hz).

Example 9

Preparation of (S)-3-((S)-4-((3-chloro-1-ethyl-1H-pyrazol-4-yl)sulfonyl)-6-((((1,1,1-trifluoro-2-methyl-propan-2-yl)oxy)carbonyl)amino)-3,4-dihydro-2H-benzo[b][1,4]oxazin-2-yl)-2-cyclopropylpropanoic acid and (R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-cyclopropylpropanoic acid (Example Nos. 9A and 9B)

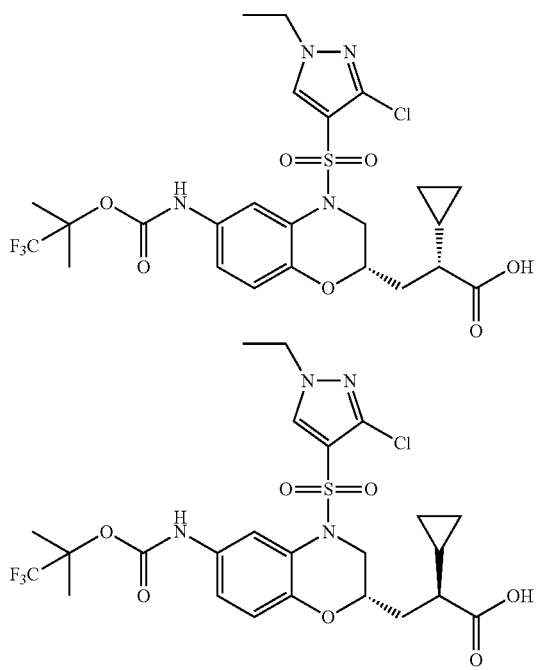

Step 1—Preparation of (S)-methyl 2-(4-benzyl-6-((tert-butoxycarbonyl)amino)-3,4-dihydro-2H-benzo[b][1,4]oxazin-2-yl)acetate

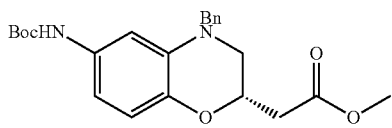 [SMILES: COC(=O)C[C@H]1CN(Cc2ccccc2)c2cc(NC(=O)OC(C)(C)C)ccc2O1]

To a solution of (S)-methyl 2-(6-((tert-butoxycarbonyl)amino)-3,4-dihydro-2H-benzo[b][1,4]oxazin-2-yl)acetate (1.3 g, 4.03 mmol) in dimethyl formamide (7 mL) were added potassium carbonate (0.836 g, 6.05 mmol) and (bromomethyl)benzene (1.035 g, 6.05 mmol). The resulting mixture was stirred at 20° C. for 18 h, then diluted with water (150 mL) and extracted with ethyl acetate (3×100 mL). The separated organic layers were washed with brine, dried with Na$_2$SO$_4$ and concentrated under reduced pressure to give the crude product which was purified by flash column chromatography (petroleum ether:ethyl acetate=10:1 to 5:1) to give the title compound as a white solid. LCMS (ESI) calculated for $C_{23}H_{29}N_2O_5$ [M+H]$^+$: 413. found: 413. $^1$H NMR (400 MHz, CDCl3) 7.28-7.38 (5H, m), 6.78 (1H, br s), 6.72 (1H, d, J=8.61 Hz), 6.59 (1H, d, J=7.43 Hz), 6.24 (1H, brs), 4.54-4.60 (1H, m), 4.37-4.49 (2H, m), 3.69 (3H, s), 3.33 (1H, dd, J=1.96, 11.74 Hz), 3.12 (1H, dd, J=6.85, 11.54 Hz), 2.76 (1H, dd, J=6.85, 15.85 Hz), 2.57 (1H, dd, J=6.26, 16.04 Hz), 1.46 (9H, s).

Step 2—Preparation of (S)-2-(4-benzyl-6-((tert-butoxycarbonyl)amino)-3,4-dihydro-2H-benzo[b][1,4]oxazin-2-yl)acetic acid

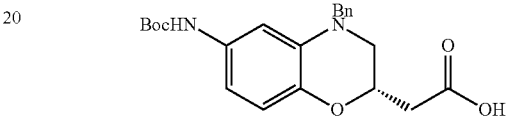

To a solution of (S)-methyl 2-(4-benzyl-6-((tert-butoxycarbonyl)amino)-3,4-dihydro-2H-benzo[b][1,4]oxazin-2-yl)acetate (2.6 g, 6.30 mmol) in dioxane (26 mL) and water (26 mL) was added lithium hydroxide (0.226 g, 9.46 mmol), and the resulting mixture was stirred at 20° C. for 18 h. The reaction was diluted with water (100 mL), extracted with ethyl acetate (50 mL×3) and the aqueous layer was acidified with hydrochloric acid (1M, 10 mL) to pH=3. The mixture was extracted with ethyl acetate (100 mL) and the combined organic layers were dried (Na$_2$SO$_4$), filtered and concentrated under reduced pressure to give the crude title compound as a yellow solid, which was used in next step without further purification. LCMS (ESI) calculated for $C_{22}H_{27}N_2O_5$ [M+H]$^+$: 399. found: 399. $^1$H NMR (400 MHz, Methanol-d4) 7.31-7.35 (5H, m), 7.23-7.26 (1H, m), 6.88 (1H, br s), 6.62-6.65 (1H, m), 6.55-6.60 (1H, m), 4.43-4.50 (3H, m), 3.35-3.39 (1H, m), 3.11 (1H, dd, J=7.28, 11.80 Hz), 2.62 (2H, t, J=6.27 Hz), 1.46 (9H, s).

Step 3—Preparation of (S)-tert-butyl (4-benzyl-2-(2-(methoxy(methyl)amino)-2-oxoethyl)-3,4-dihydro-2H-benzo[b][1,4]oxazin-6-yl)carbamate

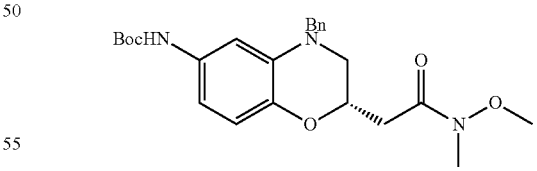

To a solution of (S)-2-(4-benzyl-6-((tert-butoxycarbonyl)amino)-3,4-dihydro-2H-benzo[b][1,4]oxazin-2-yl)acetic acid (2 g, 5.02 mmol) in dichloromethane (20 mL) were added triethylamine (3.50 mL, 25.10 mmol) and HATU (2.290 g, 6.02 mmol), and the resulting mixture was stirred at 20° C. for 30 min, followed by the addition of N,O-dimethylhydroxylamine (1.533 g, 25.10 mmol). The reaction was stirred at 20° C. for 5 minutes, then concentrated under reduced pressure to give the crude product. Flash column chromatography purification (petroleum ether:ethyl acetate=3:1 to 1:1) afforded the title compound as a yellow oil. LCMS (ESI) calculated for $C_{24}H_{32}N_3O_3$ [M+H]$^+$: 442. found: 442. $^1$H NMR (400 MHz, CDCl$_3$) 7.25-7.33 (5H, m), 6.70 (2H, d, J=8.61 Hz), 6.60 (1H, d, J=7.83 Hz), 6.24 (1H, brs), 4.64 (1H, dd, J=1.76, 6.46 Hz), 4.37-4.51 (2H, m), 3.67 (3H, s), 3.41 (1H, dd, J=1.96, 11.74 Hz), 3.21-3.24 (2H, m), 3.01 (3H, s), 2.61 (1H, dd, J=6.46, 15.85 Hz), 1.46 (9H, s), 1.36 (5H, t, J=7.24 Hz).

Step 4—Preparation of (S)-tert-butyl (4-benzyl-2-(2-cyclopropyl-2-oxoethyl)-3,4-dihydro-2H-benzo[b][1,4]oxazin-6-yl)carbamate

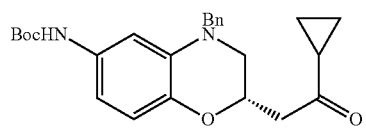 [SMILES: CC(C)(C)OC(=O)Nc1ccc2c(c1)N(Cc1ccccc1)C[C@H](CC(=O)C1CC1)O2]

To a solution of (S)-tert-butyl (4-benzyl-2-(2-(methoxy(methyl)amino)-2-oxoethyl)-3,4-dihydro-2H-benzo[b][1,4]oxazin-6-yl)carbamate (6 g, 13.59 mmol) in THF (30 mL) was added dropwise cyclopropylmagnesium bromide (272 mL, 136 mmol) at 0° C. under N$_2$. The reaction was stirred for 4 h at 0° C., then quenched with sat. NH$_4$Cl aqueous (50 mL). The biphasic mixture was extracted with EtOAc (50 mL×3), dried over Na$_2$SO$_4$ and concentrated to afford the crude title compound as a yellow solid, which was used in next step without further purification. LCMS (ESI) calculated for $C_{25}H_{31}N_2O_4$ [M+H]$^+$: 423. found: 423. $^1$HNMR (400 MHz, CDCl$_3$) δ 7.28-7.34 (5H, m), 6.76 (1H, br s), 6.71 (1H, d, J=8.8 Hz), 6.60 (1H, d, J=6.8 Hz), 6.21 (1H, br s), 4.62 (1H, d, J=0.8 Hz), 4.43 (2H, q, J=8.0 Hz), 3.33-3.36 (1H, m), 3.01-3.13 (2H, m), 2.77-2.79 (1H, m), 1.93-1.96 (1H, m), 1.47 (9H, s), 1.03-1.06 (2H, m), 0.88-0.90 (2H, m).

Step 5—Preparation of tert-butyl ((S)-4-benzyl-2-((S and R)-2-cyano-2-cyclopropylethyl)-3,4-dihydro-2H-benzo[b][1,4]oxazin-6-yl)carbamate

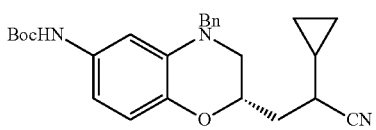 [SMILES: CC(C)(C)OC(=O)Nc1ccc2c(c1)N(Cc1ccccc1)C[C@H](CC(C#N)C1CC1)O2]

To a solution of (S)-tert-butyl (4-benzyl-2-(2-cyclopropyl-2-oxoethyl)-3,4-dihydro-2H-benzo[b][1,4]oxazin-6-yl)carbamate (4.5 g, 10.65 mmol) and 1-((isocyanomethyl)sulfonyl)-4-methylbenzene (4.16 g, 21.30 mmol) in DME (150 mL) and ethanol (5 mL) was added NaOH (1.278 g, 32.0 mmol) in portions under N$_2$ at 0° C. The reaction was stirred at 30° C. for 18 h, then diluted with DCM (100 mL), washed with water (60 mL×2) and brine and dried over Na$_2$SO$_4$. After concentration, the crude product was purified by silica gel column chromatography (petroleum ether:EtOAc=6:1) to afford the title compound as a yellow oil. LCMS (ESI) calculated for $C_{26}H_{32}N_3O_3$ [M+H]$^+$: 434. found: 434. $^1$HNMR (400 MHz, CDCl$_3$) δ 7.29-7.36 (5H, m), 6.81 (1H, d, J=7.2 Hz), 6.72 (1H, d, J=7.2 Hz), 6.60 (1H, d, J=7.2 Hz), 6.23 (1H, br s), 4.42-4.45 (2H, m), 4.33-4.38 (1H, m), 3.24-3.29 (1H, m), 3.08-3.13 (2H, m), 2.55-2.65 (1H, m), 2.41-2.47 (1H, m), 1.85-2.05 (3H, m), 1.47 (9H, s), 0.63-0.66 (2H, m), 0.41-0.45 (2H, m).

Step 6—Preparation of (R and S)-methyl 3-((S)-6-amino-4-benzyl-3,4-dihydro-2H-benzo[b][1,4]oxazin-2-yl)-2-cyclopropylpropanoate

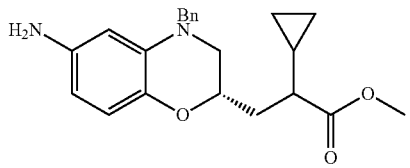 [SMILES: COC(=O)C(C[C@H]1CN(Cc2ccccc2)c2cc(N)ccc2O1)C1CC1]

To MeOH (10 mL) at 0° C. was added slowly sulfurous dichloride (3 mL, 2.076 mmol) and the mixture was stirred at 0° C. for 30 mins. The resulting solution was next added to tert-butyl ((S)-4-benzyl-2-((S and R)-2-cyano-2-cyclopropylethyl)-3,4-dihydro-2H-benzo[b][1,4]oxazin-6-yl)carbamate (900 mg, 2.076 mmol) and the mixture was stirred at 70° C. for 18 h. The reaction was quenched with 5 mL water and the mixture was adjusted to pH=7-8 with saturated NaHCO$_3$. The aqueous layer was extracted with EtOAc (15 mL×3) and the combined organic layers dried over Na$_2$SO$_4$. Purification by flash chromatography (petroleum ether/EtOAc=10:1 to 1:2) afforded the title compound as a black oil. LCMS (ESI) calculated for $C_{22}H_{27}N_2O_3$ [M+H]$^+$: 367. found: 367. $^1$HNMR (400 MHz, CDCl$_3$) δ 7.25-7.36 (5H, m), 6.76-6.78 (1H, m), 6.52-6.58 (2H, m), 4.50-4.59 (2H, m), 3.73 (1H, s), 3.45-3.51 (1H, m), 3.26-3.28 (1H, m), 2.86-3.00 (1H, m), 2.05-2.12 (1H, m), 1.87-1.98 (2H, m), 1.24-1.32 (2H, m), 0.94 (1H, br s), 0.45-0.55 (2H, m).

Step 7—Preparation of (R and S)-methyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-cyclopropylpropanoate

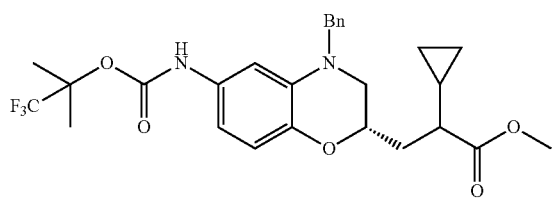 [SMILES: COC(=O)C(C[C@H]1CN(Cc2ccccc2)c2cc(NC(=O)OC(C)(C)C(F)(F)F)ccc2O1)C1CC1]

To a solution of (R and S)-methyl 3-((S)-6-amino-4-benzyl-3,4-dihydro-2H-benzo[b][1,4]oxazin-2-yl)-2-cyclopropylpropanoate (280 mg, 0.797 mmol) in DMSO (8 mL) was added 1-(((1,1,1-trifluoro-2-methylpropan-2-yl)oxy)

carbonyl)-1H-imidazol-3-iumiodide (307 mg, 0.876 mmol) and the mixture was stirred at 20° C. for 1 h. The reaction was extracted with EtOAc and saturated NaHCO$_3$ and the combined organic layer washed with brine, dried over Na$_2$SO$_4$ and purified by pre-TLC (petroleum ether/EtOAc=1:1) to afford the title compound as a red oil. LCMS (ESI) calculated for C$_{27}$H$_{32}$F$_3$N$_2$O$_5$ [M+H]$^+$: 521. found: 521. $^1$HNMR (400 MHz, CDCl$_3$) δ 7.14-7.21 (5H, m), 6.58-6.62 (2H, m), 6.55 (1H, br s), 6.29 (1H, br s), 4.26-4.35 (2H, m), 4.12-4.15 (1H, m), 3.92-3.95 (1H, m), 3.57 (2H, q, J=4.8 Hz), 3.10-3.13 (1H, m), 2.95-3.01 (1H, m), 1.75-1.98 (4H, m), 1.59 (6H, s), 1.13 (1H, s), 0.77 (1H, br s), 0.36-0.43 (2H, m), 0.11-0.27 (2H, m).

Step 8—Preparation of (S)-methyl 2-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoate and (R)-methyl 2-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoate

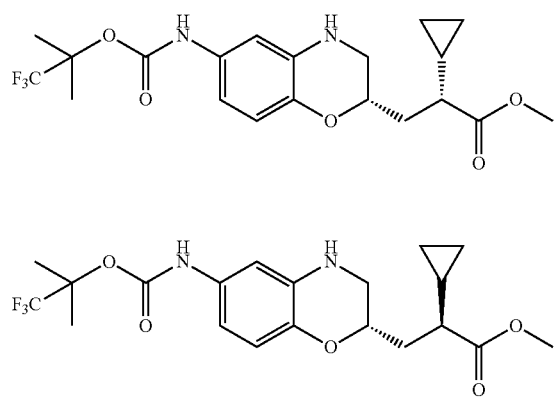

To a solution of (R and S)-methyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-cyclopropylpropanoate (350 mg, 0.672 mmol) in EtOAc (20 mL) was added Pd/C (35 mg, 10%). The reaction mixture was stirred under H$_2$ balloon at 20° C. for 10 hours, then filtered and concentrated to give the title mixture of diastereomers as a light yellow oil. The two isomers were separated by chiral SFC method (SFC-80; Column: Chiralpak AD, 10 μm, Daicel Chemical Industries, Ltd 250×30 mmI.D.; Mobile phase: A: Supercritical CO$_2$, B: EtOH(20%) (contained 80% NH$_3$.H$_2$O); Flow rate: 60 mL/min; Wavelength: 220 nm.

Isomer 1 (faster-eluting peak): LCMS (ESI) calculated for C$_{20}$H$_{26}$F$_3$N$_2$O$_5$ [M+H]$^+$: 431. found: 431. $^1$HNMR (400 MHz, CDCl$_3$) δ 6.67 (1H, br s), 6.50 (2H, q, J=10.0 Hz), 6.27-6.35 (2H, m), 4.10 (1H, br s), 3.86 (1H, br s), 3.56 (3H, s), 3.19 (2H, t, J=10.0 Hz), 2.93-2.98 (1H, m), 1.76-1.98 (3H, m), 1.59 (6H, s), 0.77 (1H, br s), 0.12-0.43 (4H, m). Isomer 2 (slower-eluting peak): LCMS (ESI) calculated for C$_{20}$H$_{26}$F$_3$N$_2$O$_5$ [M+H]$^+$: 431. found: 431. $^1$HNMR (400 MHz, CDCl$_3$) δ 6.55 (1H, br s), 6.36-6.43 (1H, m), 6.14-6.23 (2H, m), 3.98 (1H, br s), 3.44 (3H, s), 3.06-3.13 (2H, m), 2.81-2.86 (2H, m), 1.86 (1H, br s), 1.53-1.67 (2H, m), 1.47 (6H, s), 0.64 (1H, br s), 0.22-0.38 (2H, m), 0.00-0.06 (2H, m).

Step 9—Preparation of (S)-2-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid and (R)-2-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid

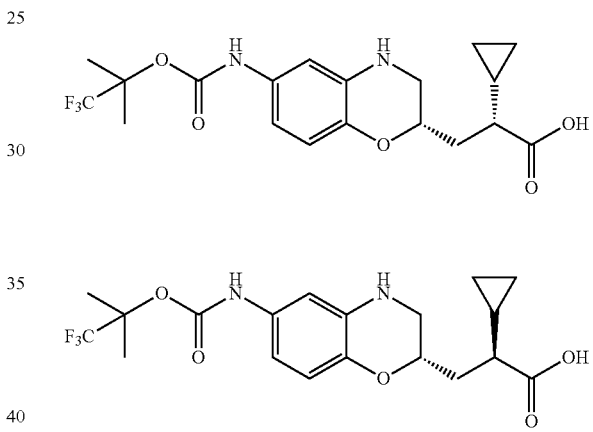

To a mixture of (S or R)-methyl 2-cyclopropyl-3-(S)-6-((((1,1,1-trifluoro-2-methylpropan-2-yl)oxy)carbonyl)amino)-3,4-dihydro-2H-benzo[b][1,4]oxazin-2-yl)propanoate (Isomer 1 in Step 8; 150 mg, 0.348 mmol) in 1,4-dioxane (5 mL) and water (5 mL) was added LiOH (167 mg, 6.97 mmol) and the reaction stirred at 20° C. for 6 h, then acidified to pH=1 with ice cold 1 M HCl solution. The aqueous layer was extracted with ethyl acetate (5 mL×3) and the combined organic layers were washed by brine, dried over sodium sulfate and concentrated under vacuum to afford the crude title compound (S or R)-2-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid (Isomer 1) as red oil, which was directly used in the next step without further purification. LCMS (ESI) calculated for C$_{19}$H$_{24}$F$_3$N$_2$O$_5$ [M+H]$^+$: 417. found: 417.

The other diastereomer (Isomer 2, Step 9) was prepared using a similar procedure starting from Isomer 2, Step 8. LCMS (ESI) calculated for C$_{19}$H$_{24}$F$_3$N$_2$O$_5$ [M+H]$^+$: 417. found: 417.

Step 10—Preparation of (S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-cyclopropylpropanoic acid and (R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-cyclopropylpropanoic acid

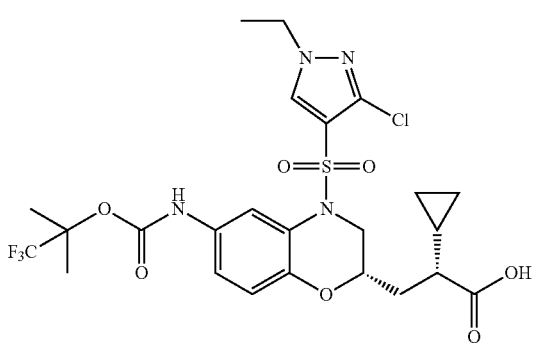

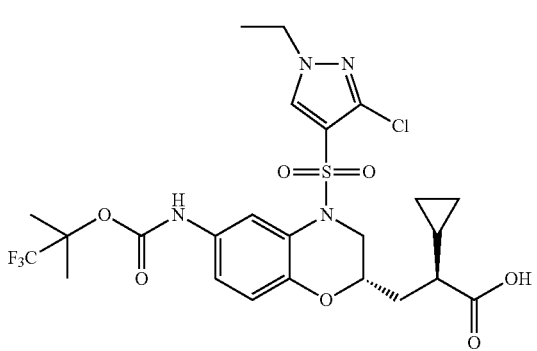

To a solution of (S or R)-2-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid (Isomer 1 in Step 9; 10 mg, 0.024 mmol) in THF (1 mL) were added pyridine (1 mL) and 3-chloro-1-ethyl-1H-pyrazole-4-sulfonyl chloride (33.0 mg, 0.144 mmol) at room temperature under $N_2$. The reaction was stirred at 20° C. for 18 h, then poured into 5 mL of water. The resulting mixture was extracted with ethyl acetate (3 mL×3) and the combined organic layers were washed with brine, dried over sodium sulfate and concentrated. The crude product was purified by prep-HPLC (MeCN/water using TFA buffer) to afford Example No. 9A as a yellow solid. LCMS (ESI) calculated for $C_{24}H_{29}ClF_3N_4O_7S$ [M+H]$^+$: 609. found: 609. $^1$HNMR (400 MHz, CDCl$_3$) δ 8.07 (1H, s), 6.76-6.83 (2H, m), 6.58 (1H, s), 4.37 (1H, d, J=13.6 Hz), 4.10 (2H, q, J=7.2 Hz), 3.97 (1H, br s), 3.35 (1H, t, J=11.2 Hz), 1.91-2.15 (3H, m), 1.76 (6H, s), 1.47 (3H, t, J=7.2 Hz), 0.99 (1H, br s), 0.61 (3H, d, J=4.0 Hz), 0.41-0.45 (1H, m), 0.15-0.22 (1H, m).

The other diastereomer (Example No. 9B) was prepared using a similar procedure starting from Isomer 2 described in Step 9. LCMS (ESI) calculated for $C_{24}H_{29}ClF_3N_4O_7S$ [M+H]$^+$: 609. found: 609. $^1$HNMR (400 MHz, CDCl$_3$) δ 8.07 (1H, s), 6.75-6.84 (2H, m), 6.59 (1H, s), 4.41 (1H, d, J=14.0 Hz), 4.21 (1H, br s), 4.10 (2H, q, J=7.2 Hz), 3.35-3.41 (1H, m), 2.14-2.15 (1H, m), 1.91-1.97 (2H, m), 1.76 (6H, s), 1.47 (3H, t, J=7.2 Hz), 0.85-0.95 (1H, m), 0.58 (2H, d, J=7.6 Hz), 0.41-0.45 (1H, m), 0.21-0.25 (1H, m).

Example 10

Preparation of Additional Propionic Acid Alpha-Substituted Benzoxazines

The compounds in Table 3 were prepared based on the methodology herein and the experimental procedures described in Examples 8 and 9, and can be achieved by one of skill in the art in light of the present disclosure.

TABLE 3

| Ex. No. | Structure | Name | Observed m/z |
|---|---|---|---|
| 10A | 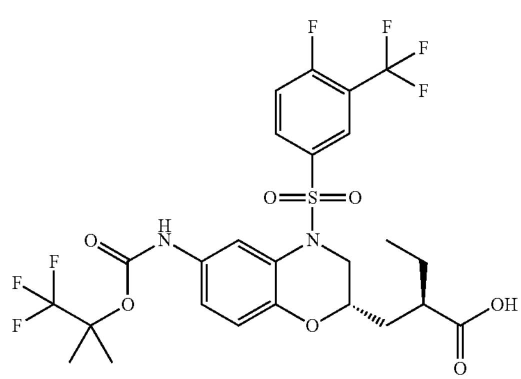 [SMILES: CC[C@H](C[C@H]1CN(S(=O)(=O)c2ccc(F)c(C(F)(F)F)c2)c2cc(NC(=O)OC(C)(C)C(F)(F)F)ccc2O1)C(=O)O] | (R or S)-2-(((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 631 [M + H]+ |

TABLE 3-continued

| Ex. No. | Structure | Name | Observed m/z |
|---|---|---|---|
| 10B | 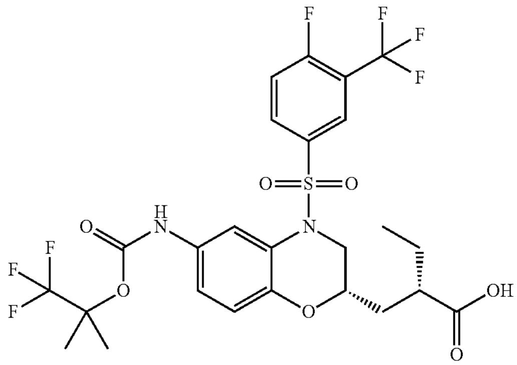 [SMILES: CC[C@@H](C[C@H]1CN(S(=O)(=O)c2ccc(F)c(C(F)(F)F)c2)c2cc(NC(=O)OC(C)(C)C(F)(F)F)ccc2O1)C(=O)O] | (R or S)-2-(((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 631 [M + H]+ |
| 10C | 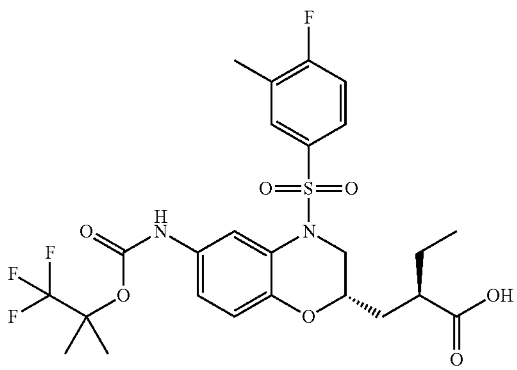 [SMILES: CC[C@H](C[C@H]1CN(S(=O)(=O)c2ccc(F)c(C)c2)c2cc(NC(=O)OC(C)(C)C(F)(F)F)ccc2O1)C(=O)O] | (R or S)-2-(((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 577 [M + H]+ |
| 10D | 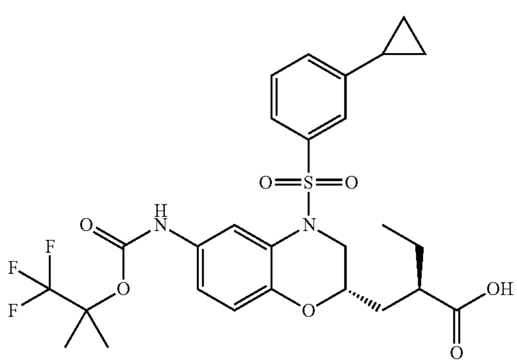 [SMILES: CC[C@H](C[C@H]1CN(S(=O)(=O)c2cccc(C3CC3)c2)c2cc(NC(=O)OC(C)(C)C(F)(F)F)ccc2O1)C(=O)O] | (R or S)-2-(((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 585 [M + H]+ |
| 10E | 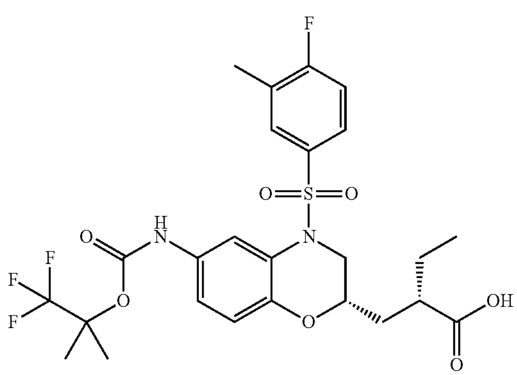 [SMILES: CC[C@@H](C[C@H]1CN(S(=O)(=O)c2ccc(F)c(C)c2)c2cc(NC(=O)OC(C)(C)C(F)(F)F)ccc2O1)C(=O)O] | (R or S)-2-(((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 577 [M + H]+ |

TABLE 3-continued

| Ex. No. | Structure | Name | Observed m/z |
|---|---|---|---|
| 10F | 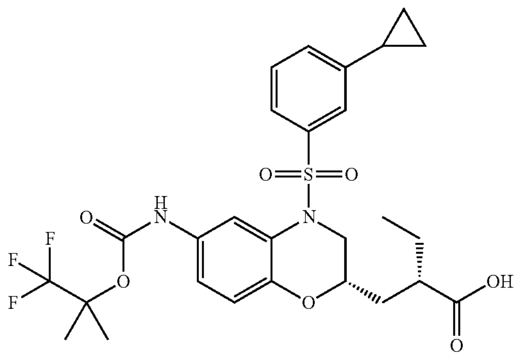 [SMILES: CC[C@@H](C[C@H]1CN(S(=O)(=O)c2cccc(C3CC3)c2)c2cc(NC(=O)OC(C)(C)C(F)(F)F)ccc2O1)C(=O)O] | (R or S)-2-(((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 585 [M + H]+ |
| 10G | 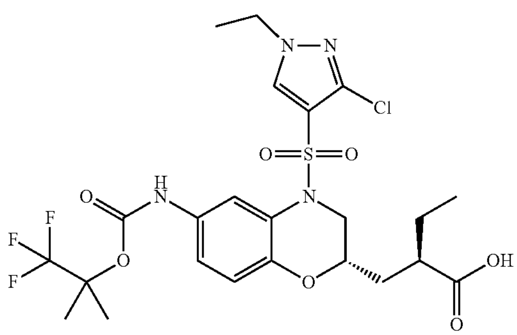 [SMILES: CC[C@H](C[C@H]1CN(S(=O)(=O)c2cn(CC)nc2Cl)c2cc(NC(=O)OC(C)(C)C(F)(F)F)ccc2O1)C(=O)O] | (R or S)-2-(((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 597 [M + H]+ |
| 10H | 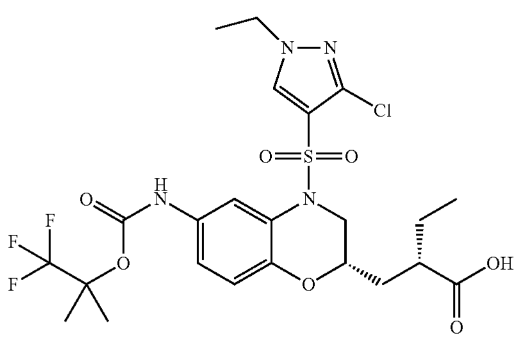 [SMILES: CC[C@@H](C[C@H]1CN(S(=O)(=O)c2cn(CC)nc2Cl)c2cc(NC(=O)OC(C)(C)C(F)(F)F)ccc2O1)C(=O)O] | (R or S)-2-(((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 597 [M + H]+ |
| 10i | 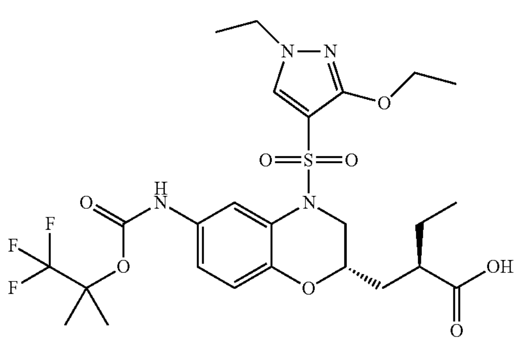 [SMILES: CCOc1nn(CC)cc1S(=O)(=O)N1C[C@H](C[C@@H](CC)C(=O)O)Oc2ccc(NC(=O)OC(C)(C)C(F)(F)F)cc21] | (R or S)-2-(((S)-4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 607 [M + H]+ |

TABLE 3-continued

| Ex. No. | Structure | Name | Observed m/z |
|---|---|---|---|
| 10J | 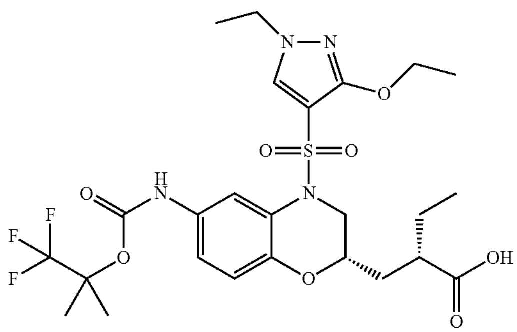 [SMILES: CCOc1nn(CC)cc1S(=O)(=O)N1C[C@H](C[C@H](CC)C(=O)O)Oc2ccc(NC(=O)OC(C)(C)C(F)(F)F)cc21] | (R or S)-2-(((S)-4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 607 [M + H]+ |
| 10K | 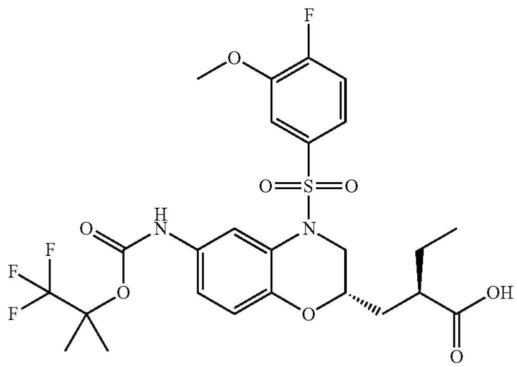 [SMILES: CC[C@H](C[C@H]1CN(S(=O)(=O)c2ccc(F)c(OC)c2)c2cc(NC(=O)OC(C)(C)C(F)(F)F)ccc2O1)C(=O)O] | (R or S)-2-(((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 593 [M + H]+ |
| 10L | 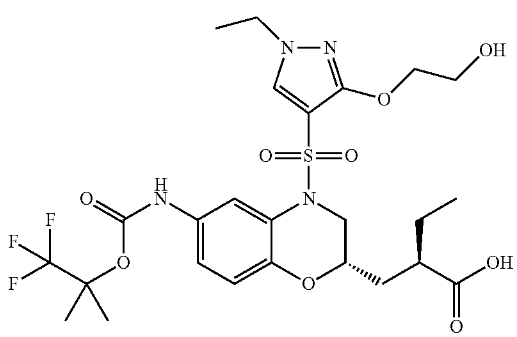 [SMILES: CC[C@H](C[C@H]1CN(S(=O)(=O)c2cn(CC)nc2OCCO)c2cc(NC(=O)OC(C)(C)C(F)(F)F)ccc2O1)C(=O)O] | (R or S)-2-(((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 623 [M + H]+ |
| 10M | 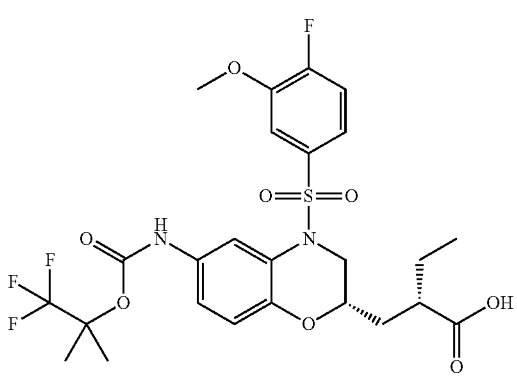 [SMILES: CC[C@@H](C[C@H]1CN(S(=O)(=O)c2ccc(F)c(OC)c2)c2cc(NC(=O)OC(C)(C)C(F)(F)F)ccc2O1)C(=O)O] | (R or S)-2-(((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 593 [M + H]+ |

TABLE 3-continued

| Ex. No. | Structure | Name | Observed m/z |
|---|---|---|---|
| 10N | 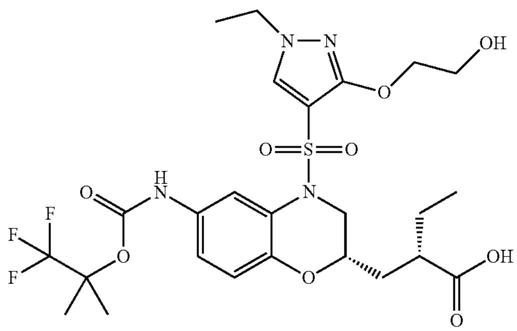 [SMILES: CC[C@@H](C[C@H]1CN(S(=O)(=O)c2cn(CC)nc2OCCO)c2cc(NC(=O)OC(C)(C)C(F)(F)F)ccc2O1)C(=O)O] | (R or S)-2-(((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid | 623 [M + H]+ |
| 10o | 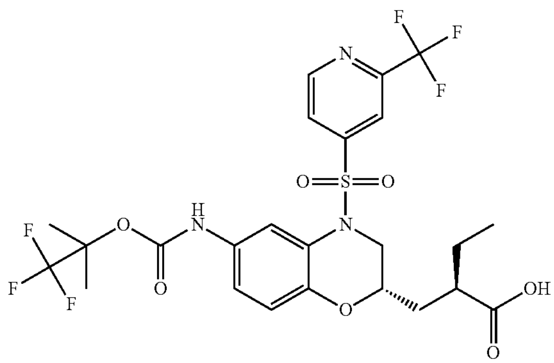 [SMILES: CC[C@H](C[C@H]1CN(S(=O)(=O)c2ccnc(C(F)(F)F)c2)c2cc(NC(=O)OC(C)(C)C(F)(F)F)ccc2O1)C(=O)O] | (R or S)-2-(((S)-6-((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)methyl)butanoic acid | 614 [M + H]+ |
| 10P | 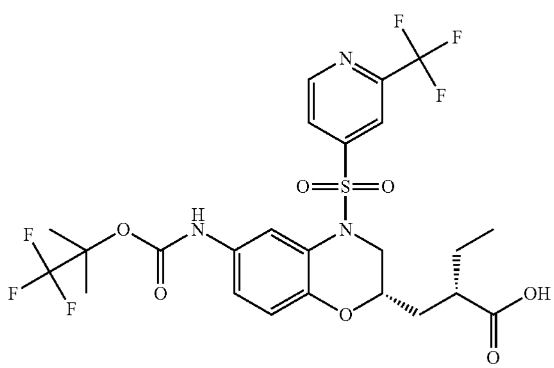 [SMILES: CC[C@@H](C[C@H]1CN(S(=O)(=O)c2ccnc(C(F)(F)F)c2)c2cc(NC(=O)OC(C)(C)C(F)(F)F)ccc2O1)C(=O)O] | (R or S)-2-(((S)-6-((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)methyl)butanoic acid | 614 [M + H]+ |
| 10Q | 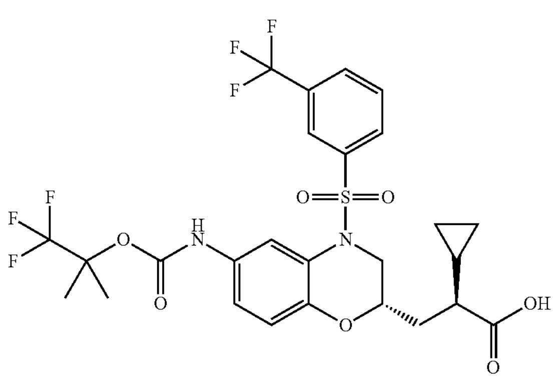 [SMILES: CC(C)(OC(=O)Nc1ccc2c(c1)N(S(=O)(=O)c1cccc(C(F)(F)F)c1)C[C@H](C[C@H](C(=O)O)C1CC1)O2)C(F)(F)F] | (S or R)-2-cyclopropyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 625 [M + H]+ |

TABLE 3-continued

| Ex. No. | Structure | Name | Observed m/z |
|---|---|---|---|
| 10R | 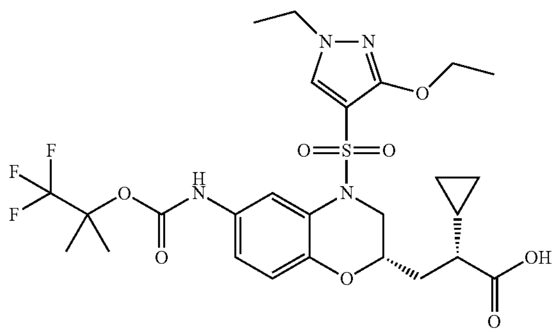 [SMILES: CCOc1nn(CC)cc1S(=O)(=O)N1C[C@H](C[C@@H](C(=O)O)C2CC2)Oc2ccc(NC(=O)OC(C)(C)C(F)(F)F)cc21] | (R or S)-2-cyclopropyl-3-((S)-4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 619 [M + H]+ |
| 10S | 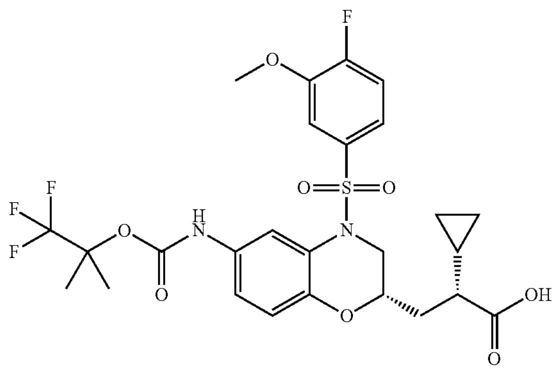 [SMILES: COc1cc(S(=O)(=O)N2C[C@H](C[C@@H](C(=O)O)C3CC3)Oc3ccc(NC(=O)OC(C)(C)C(F)(F)F)cc32)ccc1F] | (R or S)-2-cyclopropyl-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 605 [M + H]+ |
| 10T | 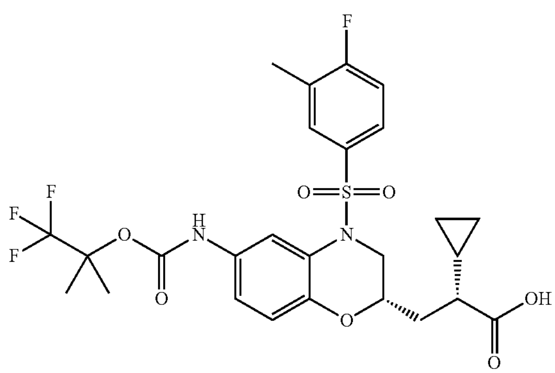 [SMILES: Cc1cc(S(=O)(=O)N2C[C@H](C[C@@H](C(=O)O)C3CC3)Oc3ccc(NC(=O)OC(C)(C)C(F)(F)F)cc32)ccc1F] | (R or S)-2-cyclopropyl-3-((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 589 [M + H]+ |
| 10U | 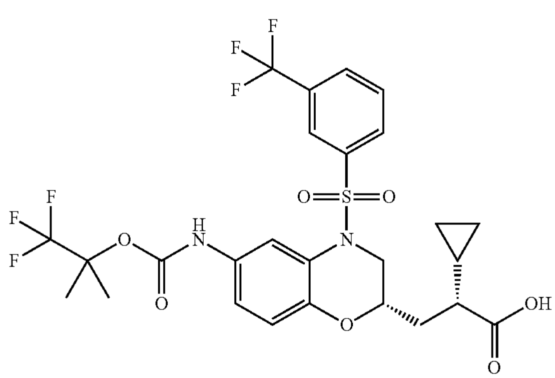 [SMILES: CC(C)(OC(=O)Nc1ccc2c(c1)N(S(=O)(=O)c1cccc(C(F)(F)F)c1)C[C@H](C[C@@H](C(=O)O)C1CC1)O2)C(F)(F)F] | (S or R)-2-cyclopropyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 625 [M + H]+ |

TABLE 3-continued

| Ex. No. | Structure | Name | Observed m/z |
|---|---|---|---|
| 10V | 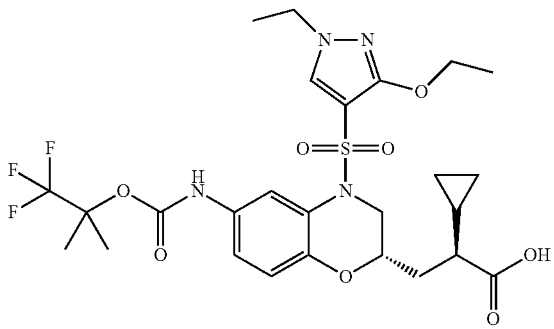 [SMILES: CCOc1nn(CC)cc1S(=O)(=O)N1C[C@H](C[C@H](C(=O)O)C2CC2)Oc2ccc(NC(=O)OC(C)(C)C(F)(F)F)cc21] | (R or S)-2-cyclopropyl-3-((S)-4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 619 [M + H]+ |
| 10W | 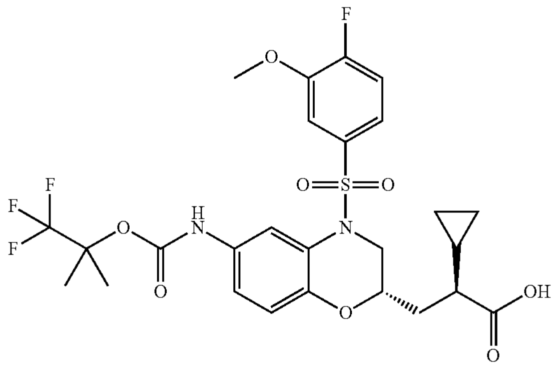 [SMILES: COc1cc(S(=O)(=O)N2C[C@H](C[C@H](C(=O)O)C3CC3)Oc3ccc(NC(=O)OC(C)(C)C(F)(F)F)cc32)ccc1F] | (R or S)-2-cyclopropyl-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 605 [M + H]+ |
| 10X | 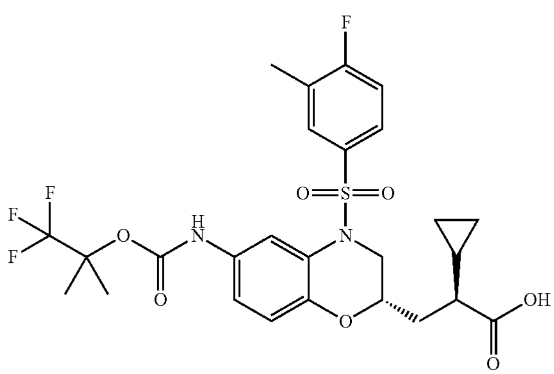 [SMILES: Cc1cc(S(=O)(=O)N2C[C@H](C[C@H](C(=O)O)C3CC3)Oc3ccc(NC(=O)OC(C)(C)C(F)(F)F)cc32)ccc1F] | (R or S)-2-cyclopropyl-3-((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 589 [M + H]+ |
| 10Y | 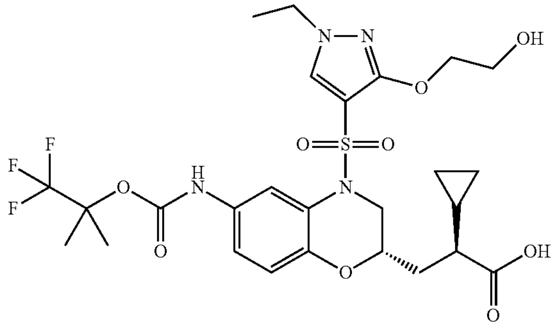 [SMILES: CCn1cc(S(=O)(=O)N2C[C@H](C[C@H](C(=O)O)C3CC3)Oc3ccc(NC(=O)OC(C)(C)C(F)(F)F)cc32)c(OCCO)n1] | (S or R)-2-cyclopropyl-3-((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 635 [M + H]+ |

TABLE 3-continued

| Ex. No. | Structure | Name | Observed m/z |
|---|---|---|---|
| 10Z | 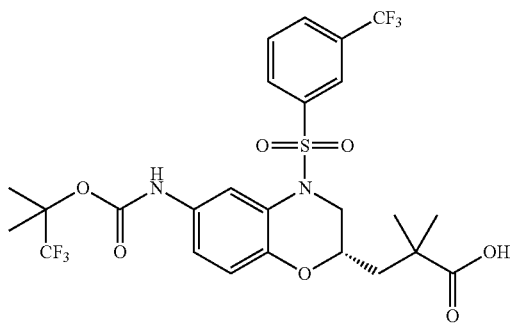 [SMILES: CC(C)(C[C@H]1CN(S(=O)(=O)c2cccc(C(F)(F)F)c2)c2cc(NC(=O)OC(C)(C)C(F)(F)F)ccc2O1)C(=O)O] | (S or R)-2-cyclopropyl-3-((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 635 [M + H]+ |

Example 11

Preparation of (S)-2,2-dimethyl-3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid

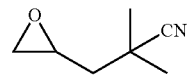

Step 1—Preparation of 2,2-dimethylpent-4-enenitrile

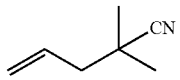

To a solution of isobutyronitrile (40 g, 579 mmol) in THF (250 mL), which was stirred in a 1000 mL of three-neck round bottom flask, was added LDA (637 mL, 637 mmol) dropwise at −78° C. under nitrogen. After stirring for 1 h, 3-bromoprop-1-ene (74.9 g, 619 mmol) was added dropwise to the mixture at −78° C. and stirred at −78° C. for an additional 8 h. Upon completion, the reaction mixture was poured into ice water (800 mL) with stirring and the separated aqueous layer extracted with $CH_2Cl_2$ (3×). The combined organic layers were washed with brine, dried over $Na_2SO_4$ and evaporated at 20° C. to afford 2,2-dimethylpent-4-enenitrile as yellow oil, which was used directly without further purification.

Step 2—Preparation of (S and R)-2,2-dimethyl-3-(oxiran-2-yl)propanenitrile

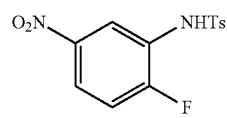

To a solution of 2,2-dimethylpent-4-enenitrile (crude 94 g from step 1, 568 mmol) in DCM (1200 mL), stirred in a 2 L of round bottom flask, was added m-CPBA (118 g, 682 mmol) in portions at 0° C. The reaction mixture was stirred at room temperature (15° C.) for 3 days. The mixture was filtered and the filtrate was diluted with DCM (3000 mL), then washed with 1 N NaOH solution (1200 mL, 3×). The organic layer was dried over $Na_2SO_4$ and evaporated at 25° C. The residue was purified by flash chromatography (petroleum ether:ethyl acetate=50:1 to 10:1) to afford the product mixture of enantiomers (S and R)-2,2-dimethyl-3-(oxiran-2-yl)propanenitrile as a colorless oil.

Step 3—Preparation of N-(2-fluoro-5-nitrophenyl)-4-methylbenzenesulfonamide To a solution of 2-fluoro-5-nitroaniline (96 g, 615 mmol) in pyridine (379 mL, 4686 mmol), which was stirred in a 500 mL round bottom flask, was added Tosyl-Cl (176 g, 922 mmol) in portions at room temperature under nitrogen. The reaction mixture was stirred at 25° C. for 10 hours, filtered and concentrated under reduced pressure. The crude product was rinsed with $CH_2Cl_2$ (100 mL, 2×) and the resulting yellow solid was dried under vacuum to give the crude title compound as yellow solid, which was used directly without further purification.

Step 4—Preparation of (S and R)—N-(4-cyano-2-hydroxy-4-methylpentyl)-N-(2-fluoro-5-nitrophenyl)-4-methylbenzenesulfonamide

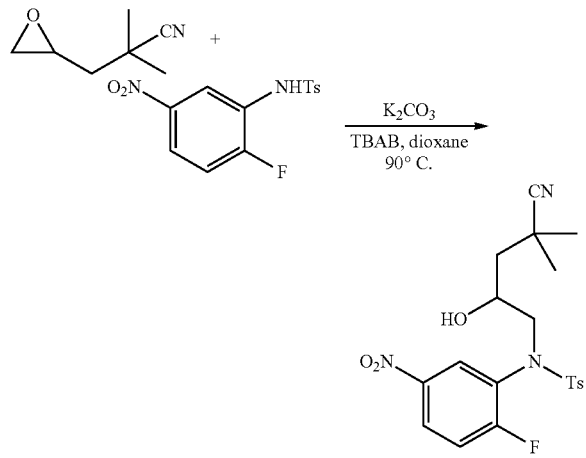

To a mixture of (S and R)-2,2-dimethyl-3-(oxiran-2-yl)propanenitrile (43 g, 344 mmol) and N-(2-fluoro-5-nitrophenyl)-4-methylbenzenesulfonamide (117 g, 378 mmol) in 1,4-Dioxane (400 mL) were added tetrabutylammonium bromide (11.07 g, 34.4 mmol) and $K_2CO_3$ (4.75 g, 34.4 mmol) in one portion at room temperature under nitrogen. The mixture was stirred at 90° C. for 17 h, then concentrated under reduced pressure. The residue was diluted with water (100 mL) and extracted with EtOAc. The combined organic layers were dried over $Na_2SO_4$, filtered and evaporated to dryness. The crude product was purified by flash chromatography (100% dichloromethane) to afford the title compound (S and R)—N-(4-cyano-2-hydroxy-4-methylpentyl)-N-(2-fluoro-5-nitrophenyl)-4-methylbenzenesulfonamide as yellow solid. LCMS (ESI) calculated for $C_{20}H_{23}FN_3O_5S$ (M+H)+: 436.1. found: 436.1.

Step 5—Preparation of (S and R)-2,2-dimethyl-3-(6-nitro-4-tosyl-3,4-dihydro-2H-benzo[b][1,4]oxazin-2-yl)propanenitrile

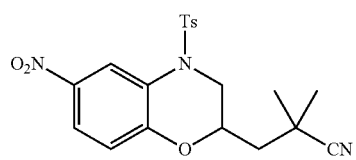 [SMILES: Cc1ccc(S(=O)(=O)N2CC(CC(C)(C)C#N)Oc3ccc([N+](=O)[O-])cc32)cc1]

To a mixture of (S and R)—N-(4-cyano-2-hydroxy-4-methylpentyl)-N-(2-fluoro-5-nitrophenyl)-4-methylbenzenesulfonamide (50 g, 115 mmol) in anhydrous THF (300 mL) were added tetrabutylammonium bromide (3.70 g, 11.5 mmol) and NaOH (18.37 g, 459 mmol) in one portion at room temperature under nitrogen. The reaction mixture was stirred at 80° C. for 1 hour, filtered and the filtrate concentrated under vacuum. The residue was recrystallized from MeOH (100 mL) to afford the title compound as a yellow solid. LCMS (ESI) calculated for $C_{20}H_{22}N_3O_5S$ (M+H)+: 416.1. found: 416.1.

Step 6—Preparation of (R and S)-3-(6-amino-4-tosyl-3,4-dihydro-2H-benzo[b][1,4]oxazin-2-yl)-2,2-dimethylpropanenitrile

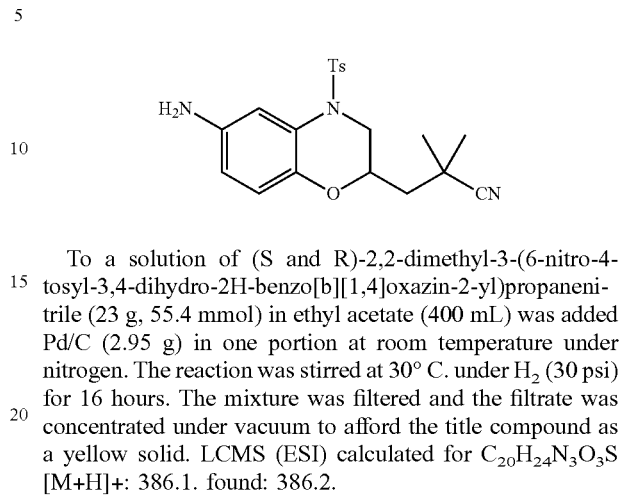

To a solution of (S and R)-2,2-dimethyl-3-(6-nitro-4-tosyl-3,4-dihydro-2H-benzo[b][1,4]oxazin-2-yl)propanenitrile (23 g, 55.4 mmol) in ethyl acetate (400 mL) was added Pd/C (2.95 g) in one portion at room temperature under nitrogen. The reaction was stirred at 30° C. under $H_2$ (30 psi) for 16 hours. The mixture was filtered and the filtrate was concentrated under vacuum to afford the title compound as a yellow solid. LCMS (ESI) calculated for $C_{20}H_{24}N_3O_3S$ [M+H]+: 386.1. found: 386.2.

Step 7—Preparation of (S)-1,1,1-trifluoro-2-methylpropan-2-yl-(2-(2-cyano-2-methylpropyl)-4-tosyl-3,4-dihydro-2H-benzo[b][1,4]oxazin-6-yl)carbamate and (R)-1,1,1-trifluoro-2-methylpropan-2-yl-(2-(2-cyano-2-methylpropyl)-4-tosyl-3,4-dihydro-2H-benzo[b][1,4]oxazin-6-yl)carbamate

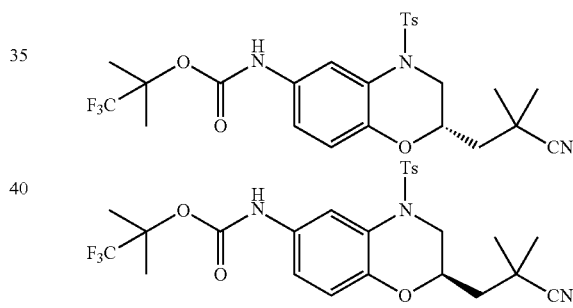

To a solution of (R and S)-3-(6-amino-4-tosyl-3,4-dihydro-2H-benzo[b][1,4]oxazin-2-yl)-2,2-dimethylpropanenitrile (39 g, 101 mmol) in DMSO (300 mL), which was stirred in a 1000 mL of round bottom flask, were added 1,1,1-trifluoro-2-methylpropan-2-yl 1H-imidazole-1-carboxylate (22.48 g, 101 mmol) in one portion and concentrated HCl (4.15 mL) dropwise at room temperature under nitrogen. The mixture was stirred at 80° C. for 5 hours, diluted with water (150 mL) and extracted with EtOAc (250 mL×3). The combined organic layers were washed with brine, dried over $Na_2SO_4$ and evaporated to dryness. The crude product was purified by silica gel chromatography eluted with (petroleum ether:ethyl acetate=10:1 to 3:1) to afford (R and S)-1,1,1-trifluoro-2-methylpropan-2-yl-(2-(2-cyano-2-methylpropyl)-4-tosyl-3,4-dihydro-2H-benzo[b][1,4]oxazin-6-yl)carbamate as a yellow solid.

The mixture of enantiomers was purified by chiral SFC (Column: Chiralpak AD (250×30 mm I.D., 10 um) Mobile phase: Supercritical $CO_2$/MeOH (0.1%) $NH_3 \cdot H_2O$=70/30 at 80 mL/min Column Temp: 38° C. Nozzle Pressure: 100 Bar Wavelength: 220 nm) to give compound Isomer 1 (RT=5.5 min) and Isomer 2 (RT=6.8 min) as yellow solids. LCMS (ESI) calculated for $C_{25}H_{29}F_3N_3O_5S$ [M+H]+: 540.2. found: 540.2.

Step 8—Preparation (S)-1,1,1-trifluoro-2-methyl-propan-2-yl (2-(2,2-dimethyl-3-oxopropyl)-4-tosyl-3,4-dihydro-2H-benzo[b][1,4]oxazin-6-yl)carbamate

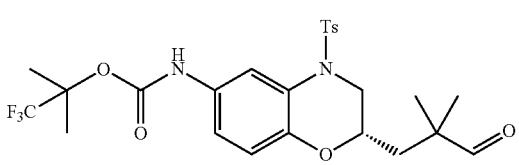 [SMILES: Cc1ccc(S(=O)(=O)N2C[C@H](CC(C)(C)C=O)Oc3ccc(NC(=O)OC(C)(C)C(F)(F)F)cc32)cc1]

To a solution of (S)-1,1,1-trifluoro-2-methylpropan-2-yl (2-(2-cyano-2-methylpropyl)-4-tosyl-3,4-dihydro-2H-benzo[b][1,4]oxazin-6-yl)carbamate (Isomer 2 from Step 7, 10 g, 18.53 mmol) in toluene (600 mL), which was stirred in a 1000 mL of round bottom flask, were added DIBAL-H (74.1 mL, 74.1 mmol) dropwise at −78° C. under nitrogen. The reaction was stirred at −78° C. for 1 h and quenched with MeOH (74 mL), acidified by 1M HCl (244 mL) and stirred at 0° C. for 10 min. The resulting mixture was extracted with EtOAc (500 mL×3). The combined organic layers were washed with brine, dried over $Na_2SO_4$ and evaporated to dryness. The crude product was purified by column chromatography (petroleum ether:ethyl acetate=3:1) to give the title compound as a yellow solid. LCMS (ESI) calculated for $C_{25}H_{30}F_3N_2O_6S$ [M+H]+: 543.2. found: 543.1. Isomer 1 (Step 7) was also taken forward using the above experimental procedure described for Isomer 2.

Step 9—Preparation of (S)-2,2-dimethyl-3-(4-tosyl-6-((((1,1,1-trifluoro-2-methylpropan-2-yl)oxy)carbonyl)amino)-3,4-dihydro-2H-benzo[b][1,4]oxazin-2-yl)propanoic acid

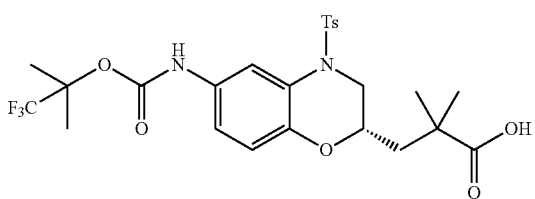 [SMILES: Cc1ccc(S(=O)(=O)N2C[C@H](CC(C)(C)C(=O)O)Oc3ccc(NC(=O)OC(C)(C)C(F)(F)F)cc32)cc1]

To a solution of (S)-1,1,1-trifluoro-2-methylpropan-2-yl (2-(2,2-dimethyl-3-oxopropyl)-4-tosyl-3,4-dihydro-2H-benzo[b][1,4]oxazin-6-yl)carbamate (10.5 g, 19.35 mmol) in THF (400 mL) and water (80 mL) were added sulfamic acid (11.27 g, 116 mmol), potassium dihydrogenphosphate (31.6 g, 232 mmol) and sodium chlorite (2.63 g, 29.0 mmol) at 0° C. The mixture was stirred at 0° C. for 1 h, diluted with water (250 mL) and was extracted with EtOAc (3×500 mL). The combined organic layers were dried over $Na_2SO_4$ and evaporated to dryness. The crude product was purified by column chromatography (petroleum ether:ethyl acetate=10:1 to 1:1) to afford the title compound as a yellow solid. LCMS (ESI) calculated for $C_{25}H_{30}F_3N_2O_7S$ [M+H]+: 559.2. found: 559.2.

Step 10—Preparation of (S)-2,2-dimethyl-3-(6-((((1,1,1-trifluoro-2-methylpropan-2-yl)oxy)carbonyl)amino)-3,4-dihydro-2H-benzo[b][1,4]oxazin-2-yl)propanoic acid

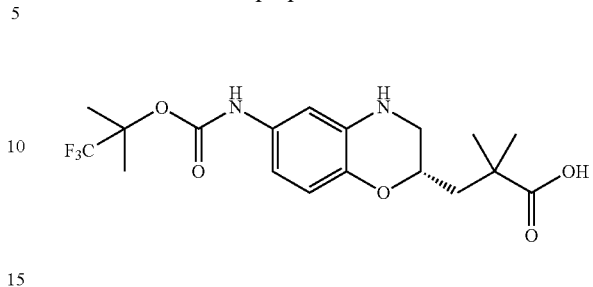

To a solution of (S)-2,2-dimethyl-3-(4-tosyl-6-((((1,1,1-trifluoro-2-methylpropan-2-yl)oxy)carbonyl)amino)-3,4-dihydro-2H-benzo[b][1,4]oxazin-2-yl)propanoic acid (4 g, 7.16 mmol) in MeOH (100 mL), which was stirred in a 250 mL of round bottom flask, was added Mg (3.48 g, 143 mmol) at room temperature under nitrogen. The mixture was stirred at 25° C. for 18 hours, quenched with saturated $NH_4Cl$ (200 mL) and extracted with EtOAc (3×300 mL). The organic layers were combined, dried over $Na_2SO_4$ and the filtrate concentrated under vacuum. The residue was purified by prep-HPLC to afford the title compound as a white solid. LCMS (ESI) calculated for $C_{18}H_{24}F_3N_2O_5$ [M+H]+: 405.2. found: 405.1.

Step 11—Preparation of (S)-2,2-dimethyl-3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid

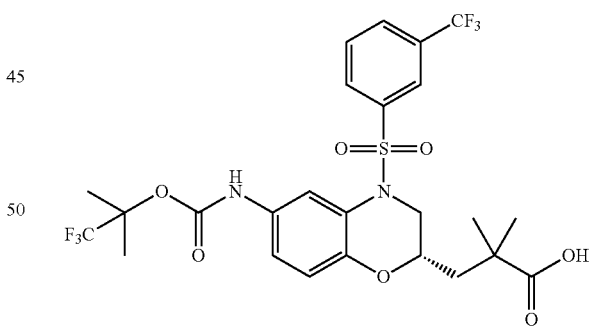

To a mixture of (S)-2,2-dimethyl-3-(6-((((1,1,1-trifluoro-2-methylpropan-2-yl)oxy)carbonyl)amino)-3,4-dihydro-2H-benzo[b][1,4]oxazin-2-yl)propanoic acid (30 mg, 0.074 mmol) in tetrahydrofuran (0.5 mL) were added 3-(trifluoromethyl)benzene-1-sulfonyl chloride (73 mg, 0.30 mmol, 4 equiv) and pyridine (0.5 mL). The reaction mixture was heated to 40° C. for 1 hour, then treated with $H_2O$ (5 mL) and extracted with ethyl acetate (3×4 mL). The organic layers were separated, combined, dried over anhydrous magnesium sulfate and concentrated in vacuo to afford the title compound as a white solid after reverse phase HPLC purification (MeCN/water using TFA buffer). LCMS (ESI): calculated for $C_{25}H_{30}F_6N_3O_7S$ [M+NH$_4$]$^+$: 630. found: 630; $^1$HNMR (400 MHz, CDCl$_3$) δ 8.05 (1H, s), 7.81-7.83 (3H, m), 7.60 (1H, q, J=7.6 Hz), 7.01 (1H, d, J=7.2 Hz), 6.63-6.67 (2H, m), 4.22 (1H, d, J=12.8 Hz), 3.59 (1H, br s), 3.24 (1H, q, J=9.6, 13.6 Hz), 1.93 (1H, q, J=9.6, 13.6 Hz), 1.77 (6H, s), 1.68 (1H, d, J=12.4 Hz), 1.23 (3H, s), 1.16 (3H, s).

Example 12

Preparation of Additional Alpha gem-Dimethyl Propionic Acid-Substituted Benzoxazines The compounds in Table 4 were prepared based on the experimental procedures described in Examples 1, 2, 4 and 11, and can be achieved by one of skill in the art in light of the present disclosure.

TABLE 4

| Ex. No. | Structure | Name | Observed m/z |
|---|---|---|---|
| 12A | 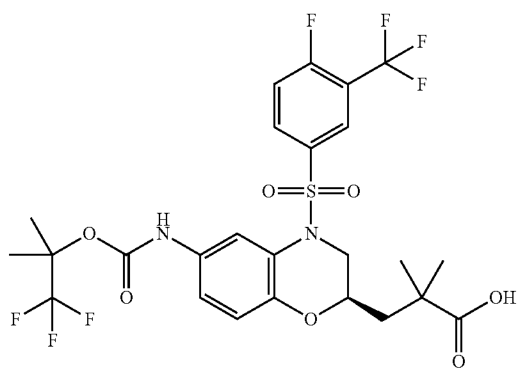 [SMILES: CC(C)(C[C@@H]1CN(S(=O)(=O)c2ccc(F)c(C(F)(F)F)c2)c2cc(NC(=O)OC(C)(C)C(F)(F)F)ccc2O1)C(=O)O] | (R)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 631 [M + H]+ |
| 12B | 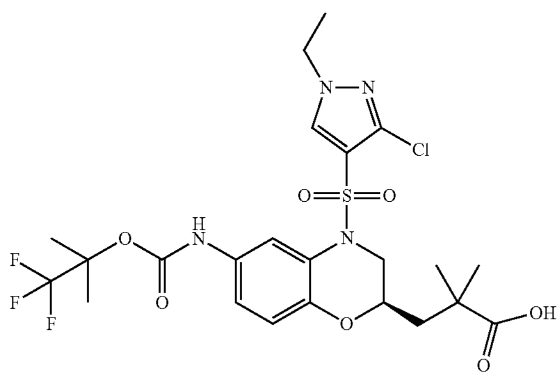 [SMILES: CCn1cc(S(=O)(=O)N2C[C@@H](CC(C)(C)C(=O)O)Oc3ccc(NC(=O)OC(C)(C)C(F)(F)F)cc32)c(Cl)n1] | (R)-3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 598 [M + H]+ |
| 12C | 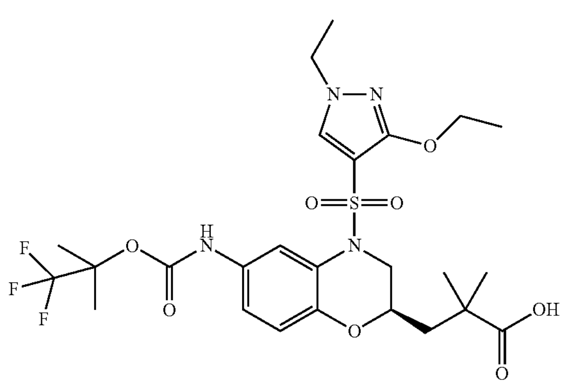 [SMILES: CCOc1nn(CC)cc1S(=O)(=O)N1C[C@@H](CC(C)(C)C(=O)O)Oc2ccc(NC(=O)OC(C)(C)C(F)(F)F)cc21] | (R)-3-(4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 607 [M + H]+ |

TABLE 4-continued

| Ex. No. | Structure | Name | Observed m/z |
|---|---|---|---|
| 12D | 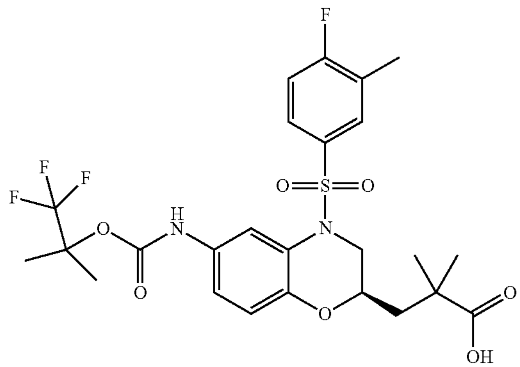 [SMILES: Cc1cc(S(=O)(=O)N2C[C@@H](CC(C)(C)C(=O)O)Oc3ccc(NC(=O)OC(C)(C)C(F)(F)F)cc32)ccc1F] | (R)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 577 [M + H]+ |
| 12E | 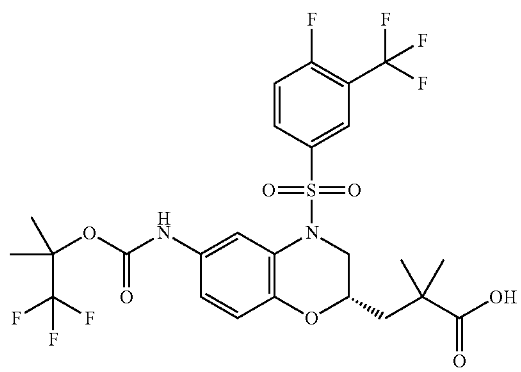 | (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 631 [M + H]+ |
| 12F | 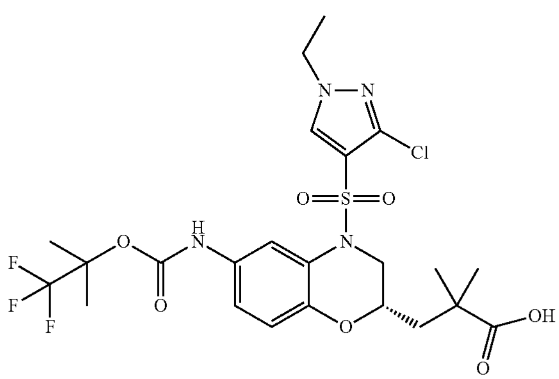 [SMILES: CCn1cc(S(=O)(=O)N2C[C@H](CC(C)(C)C(=O)O)Oc3ccc(NC(=O)OC(C)(C)C(F)(F)F)cc32)c(Cl)n1] | (S)-3-(4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 598 [M + H]+ |
| 12G | 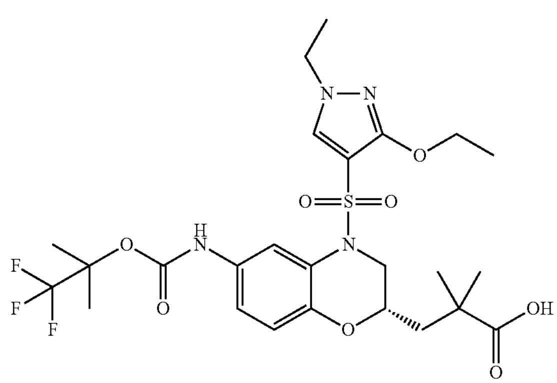 [SMILES: CCOc1nn(CC)cc1S(=O)(=O)N1C[C@H](CC(C)(C)C(=O)O)Oc2ccc(NC(=O)OC(C)(C)C(F)(F)F)cc21] | (S)-3-(4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 607 [M + H]+ |

TABLE 4-continued

| Ex. No. | Structure | Name | Observed m/z |
|---|---|---|---|
| 12H | 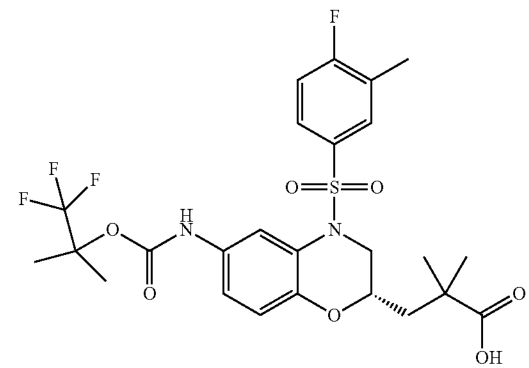 [SMILES: Cc1cc(S(=O)(=O)N2C[C@H](CC(C)(C)C(=O)O)Oc3ccc(NC(=O)OC(C)(C)C(F)(F)F)cc32)ccc1F] | (S)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 577 [M + H]+ |
| 12i | 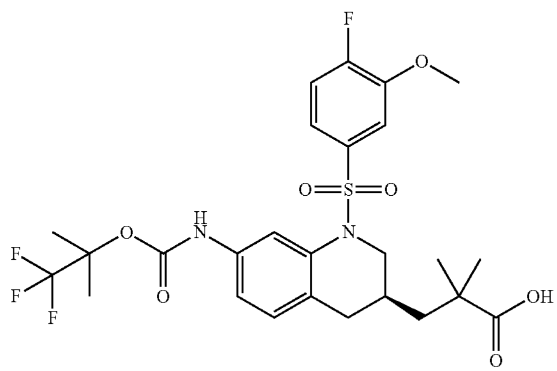 [SMILES: COc1cc(S(=O)(=O)N2C[C@@H](CC(C)(C)C(=O)O)Cc3ccc(NC(=O)OC(C)(C)C(F)(F)F)cc32)ccc1F] | (R)-3-(4-((4-fluoro-3-methoxyphenyl)sulfonyl)-7-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 593 [M + H]+ |
| 12J | 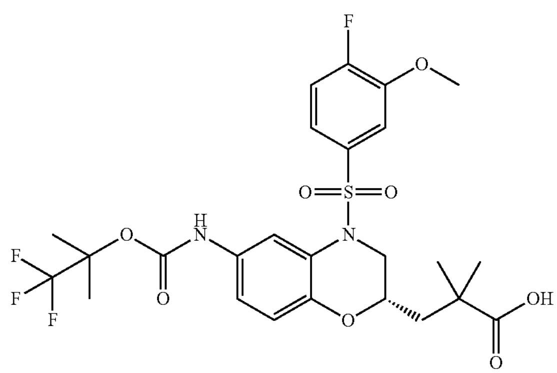 [SMILES: COc1cc(S(=O)(=O)N2C[C@H](CC(C)(C)C(=O)O)Oc3ccc(NC(=O)OC(C)(C)C(F)(F)F)cc32)ccc1F] | (S)-3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid | 593 [M + H]+ |
| 12K | 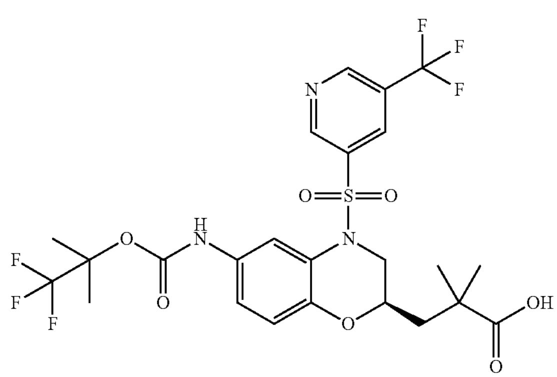 [SMILES: CC(C)(C[C@@H]1CN(S(=O)(=O)c2cncc(C(F)(F)F)c2)c2cc(NC(=O)OC(C)(C)C(F)(F)F)ccc2O1)C(=O)O] | (R)-2,2-dimethyl-3-(6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid | 614 [M + H]+ |

TABLE 4-continued

| Ex. No. | Structure | Name | Observed m/z |
|---|---|---|---|
| 12L | 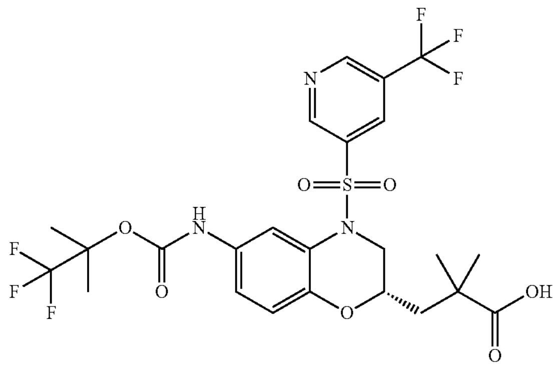 [SMILES: CC(C)(C[C@H]1CN(S(=O)(=O)c2cncc(C(F)(F)F)c2)c2cc(NC(=O)OC(C)(C)C(F)(F)F)ccc2O1)C(=O)O] | (S)-2,2-dimethyl-3-(6-((((1,1,1-trifluoro-2-methylpropan-2-yl)oxy)carbonyl)amion)-4-((5-(trifluoromethyl)pyridin-3-yl)sulfonyl)-3,4-dihydro-2H-benzo[b][1,4]oxazin-2-yl)propanoic acid | 614 [M + H]+ |
| 12M | 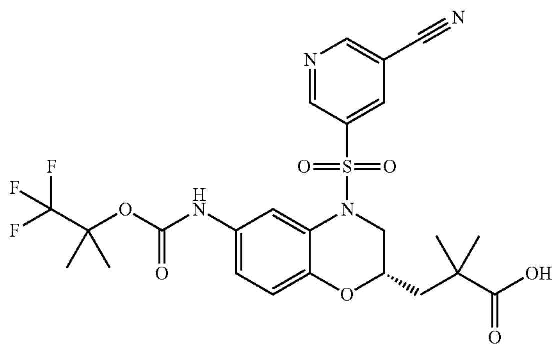 [SMILES: CC(C)(C[C@H]1CN(S(=O)(=O)c2cncc(C#N)c2)c2cc(NC(=O)OC(C)(C)C(F)(F)F)ccc2O1)C(=O)O] | 3-[(2S)-4-[(5-cyanopyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 571 [M + H]+ |
| 12N | 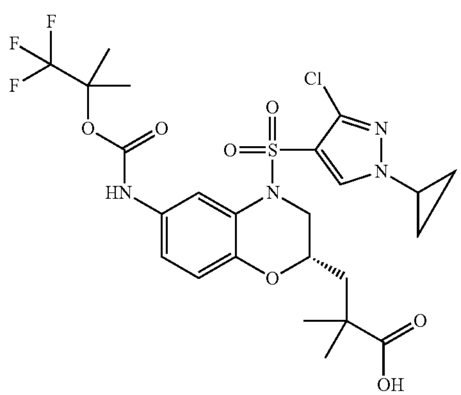 [SMILES: CC(C)(C[C@H]1CN(S(=O)(=O)c2cn(C3CC3)nc2Cl)c2cc(NC(=O)OC(C)(C)C(F)(F)F)ccc2O1)C(=O)O] | 3-[(2S)-4-[(3-chloro-1-cyclopropyl-1H-pyrazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 609 [M + H]+ |
| 12o | 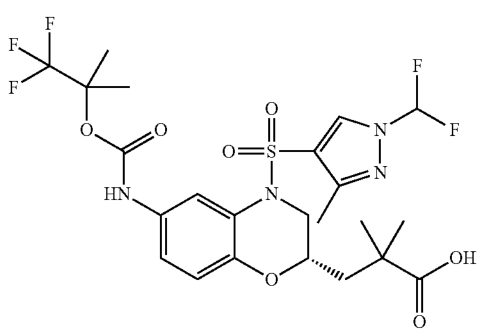 [SMILES: Cc1nn(C(F)F)cc1S(=O)(=O)N1C[C@H](CC(C)(C)C(=O)O)Oc2ccc(NC(=O)OC(C)(C)C(F)(F)F)cc21] | 3-[(2S)-4-{[1-(difluoromethyl)-3-methyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 616 [M + NH4]+ |

TABLE 4-continued

| Ex. No. | Structure | Name | Observed m/z |
|---|---|---|---|
| 12P | 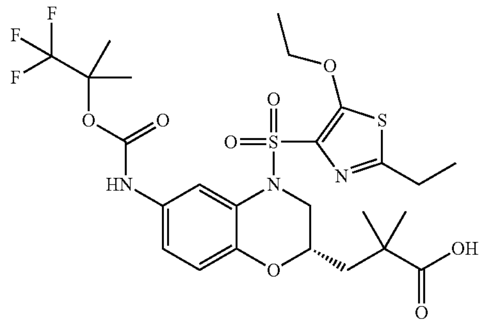 [SMILES: CCOc1sc(CC)nc1S(=O)(=O)N1C[C@H](CC(C)(C)C(=O)O)Oc2ccc(NC(=O)OC(C)(C)C(F)(F)F)cc21] | 3-[(2S)-4-[(5-ethoxy-2-ethyl-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 624 [M + H]+ |
| 12Q | 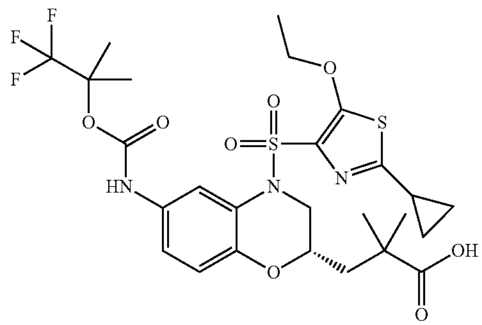 [SMILES: CCOc1sc(C2CC2)nc1S(=O)(=O)N1C[C@H](CC(C)(C)C(=O)O)Oc2ccc(NC(=O)OC(C)(C)C(F)(F)F)cc21] | 3-[(2S)-4-[(2-cyclopropyl-5-ethoxy-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 636 [M + H]+ |
| 12R | 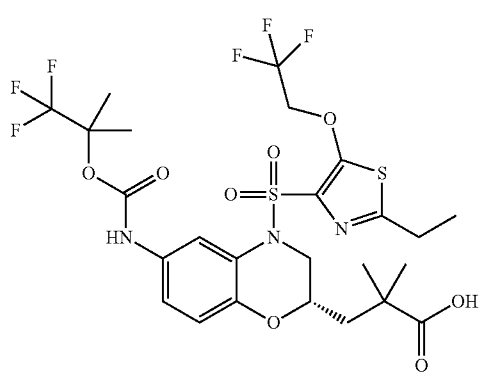 [SMILES: CCc1nc(S(=O)(=O)N2C[C@H](CC(C)(C)C(=O)O)Oc3ccc(NC(=O)OC(C)(C)C(F)(F)F)cc32)c(OCC(F)(F)F)s1] | 3-[(2S)-4-{[2-ethyl-5-(2,2,2-trifluoroethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 678 [M + H]+ |
| 12S | 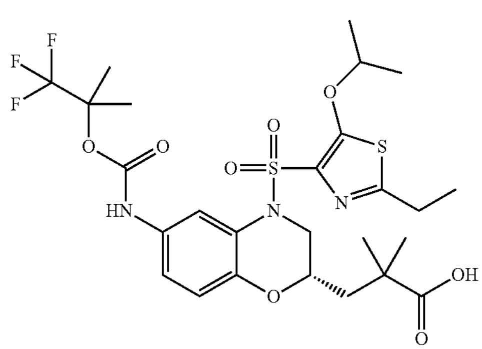 [SMILES: CCc1nc(S(=O)(=O)N2C[C@H](CC(C)(C)C(=O)O)Oc3ccc(NC(=O)OC(C)(C)C(F)(F)F)cc32)c(OC(C)C)s1] | 3-[(2S)-4-{[2-ethyl-5-(1-methylethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 638 [M + H]+ |

TABLE 4-continued

| Ex. No. | Structure | Name | Observed m/z |
|---|---|---|---|
| 12T | 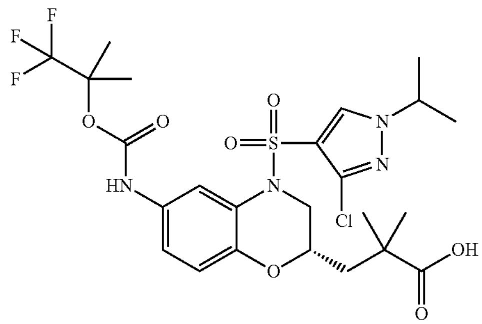 [SMILES: CC(C)n1cc(S(=O)(=O)N2C[C@H](CC(C)(C)C(=O)O)Oc3ccc(NC(=O)OC(C)(C)C(F)(F)F)cc32)c(Cl)n1] | 3-[(2S)-4-{[3-chloro-1-(1-methylethyl)-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 611 [M + H]+ |
| 12U | 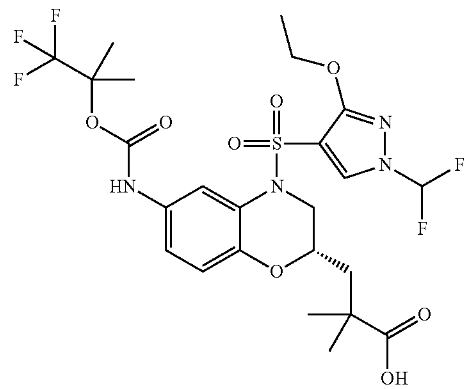 [SMILES: CCOc1nn(C(F)F)cc1S(=O)(=O)N1C[C@H](CC(C)(C)C(=O)O)Oc2ccc(NC(=O)OC(C)(C)C(F)(F)F)cc21] | 3-[(2S)-4-{[1-(difluoromethyl)-3-ethoxy-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 646 [M + NH4]+ |
| 12V | 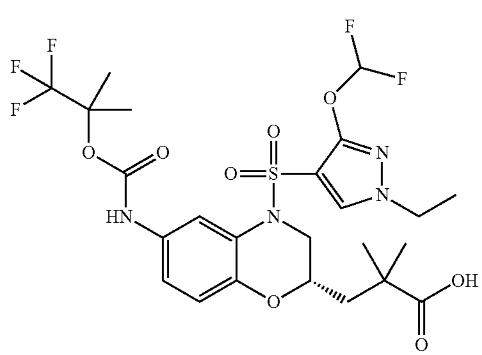 [SMILES: CCn1cc(S(=O)(=O)N2C[C@H](CC(C)(C)C(=O)O)Oc3ccc(NC(=O)OC(C)(C)C(F)(F)F)cc32)c(OC(F)F)n1] | 3-[(2S)-4-{[3-(difluoromethoxy)-1-ethyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 646 [M + NH4]+ |
| 12W | 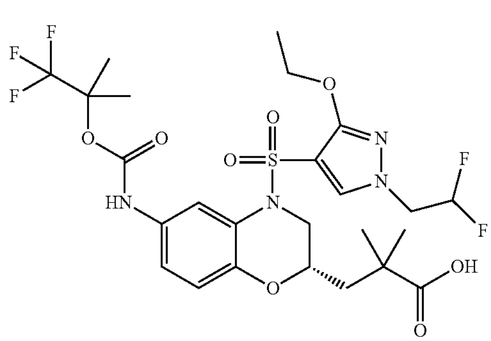 [SMILES: CCOc1nn(CC(F)F)cc1S(=O)(=O)N1C[C@H](CC(C)(C)C(=O)O)Oc2ccc(NC(=O)OC(C)(C)C(F)(F)F)cc21] | 3-[(2S)-4-{[1-(2,2-difluoroethyl)-3-ethoxy-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 660 [M + NH4]+ |

TABLE 4-continued

| Ex. No. | Structure | Name | Observed m/z |
|---|---|---|---|
| 12X | 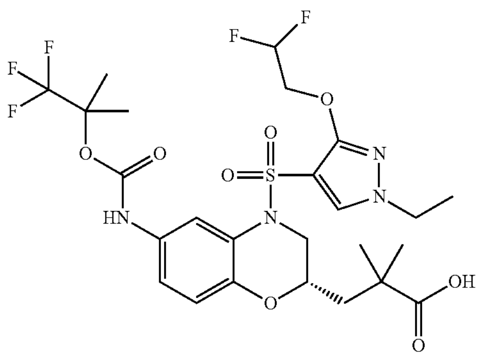 [SMILES: CCn1cc(S(=O)(=O)N2C[C@H](CC(C)(C)C(=O)O)Oc3ccc(NC(=O)OC(C)(C)C(F)(F)F)cc32)c(OCC(F)F)n1] | 3-[(2S)-4-{[3-(2,2-difluoroethoxy)-1-ethyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid | 660 [M + NH4]+ |
| 12Y | 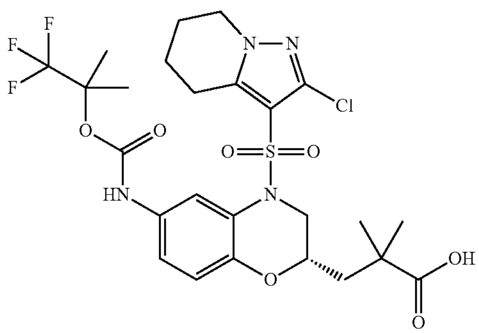 [SMILES: CC(C)(C[C@H]1CN(S(=O)(=O)c2c(Cl)nn3c2CCCC3)c2cc(NC(=O)OC(C)(C)C(F)(F)F)ccc2O1)C(=O)O] | 3-[(2S)-4-[(2-chloro-4,5,6,7-tetrahydropyrazolo[1,5-a]pyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 623 [M + H]+ |
| 12Z | 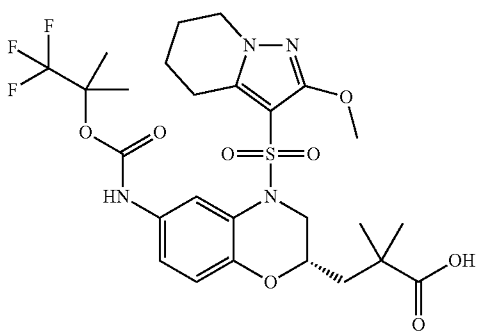 [SMILES: COc1nn2c(c1S(=O)(=O)N1C[C@H](CC(C)(C)C(=O)O)Oc3ccc(NC(=O)OC(C)(C)C(F)(F)F)cc31)CCCC2] | 3-[(2S)-4-[(2-methoxy-4,5,6,7-tetrahydropyrazolo[1,5-a]pyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 619 [M + H]+ |
| 12AA | 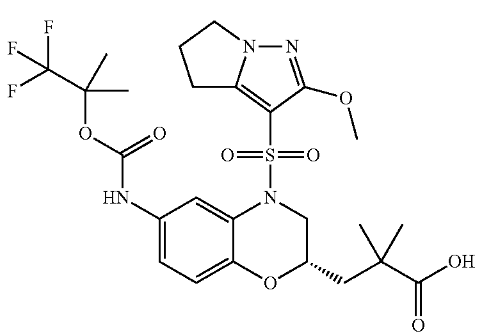 [SMILES: COc1nn2c(c1S(=O)(=O)N1C[C@H](CC(C)(C)C(=O)O)Oc3ccc(NC(=O)OC(C)(C)C(F)(F)F)cc31)CCC2] | 3-[(2S)-4-[(2-methoxy-5,6-dihydro-4H-pyrrolo[1,2-b]pyrazol-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid | 605 [M + H]+ |

Example 13

Preparation of (S)-1-((6-((((1,1,1-trifluoro-2-methyl-propan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid and (R)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid (Example Nos. 13A and 13B)

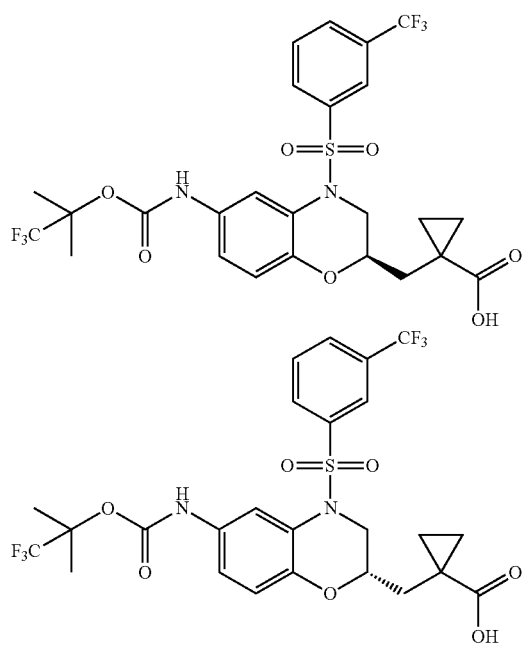

Step 1—Preparation of 1-allylcyclopropanecarbonitrile

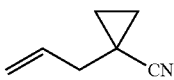

To a solution of cyclopropanecarbonitrile (10 g, 149 mmol) in THF (10 mL), which was stirred in a 250 mL of three-neck round bottom flask, was added LDA (82 mL, 164 mmol) dropwise at 0° C. under nitrogen. After 10 min, the mixture was added dropwise to a solution of 3-bromoprop-1-ene (18.93 g, 157 mmol) in THF (20 mL) at 0° C. The resulting solution was stirred at 0° C. for 1 h, then quenched by saturated NH$_4$Cl solution (20 mL) and diluted with water (200 mL). The organic layer was separated and resulting aqueous layer was extracted with DCM (35 mL×3). The combined organic layers were washed with brine, dried over Na$_2$SO$_4$ and evaporated to dryness at low temperature (<30° C.). The crude product was purified by silica gel chromatography eluting with pure petroleum ether to afford the product 1-allylcyclopropanecarbonitrile as a yellow oil. $^1$H-NMR (CD$_3$OD, 400 MHz) δ 5.83 (1H, tdd, J=6.9, 10.0, 16.8 Hz), 5.11-5.24 (2H, m), 2.20 (2H, br s), 1.18-1.26 (2H, m), 0.79-0.85 (2H, m).

Step 2—Preparation of (R and S)-1-(oxiran-2-ylmethyl)cyclopropanecarbonitrile

To a solution of 1-allylcyclopropanecarbonitrile (8 g, 74.7 mmol) in DCM (80 mL), which was stirred in a 250 mL of round bottom flask, was added m-CPBA (18.19 g, 90 mmol) in portions at 0° C. The reaction was stirred at 25° C. for 30 h, then diluted with DCM (100 mL). The separated organic layer was washed with 1M NaOH solution (60 mL×3) and brine (60 mL×2), dried over Na$_2$SO$_4$ and evaporated to afford the crude title product as a yellow oil, which was used directly without further purification. $^1$H-NMR (CD$_3$OD, 400 MHz) δ 3.11 (1H, d, J=1.9 Hz), 2.82 (1H, t, J=4.1 Hz), 2.56 (1H, dd, J=2.5, 4.1 Hz), 1.89 (1H, dd, J=5.0, 14.4 Hz), 1.42-1.54 (1H, m), 1.20-1.31 (2H, m), 0.90-0.99 (1H, m), 0.82-0.88 (1H, m).

Step 3—Preparation of (S and R)-1-((6-nitro-4-tosyl-3,4-dihydro-2H-benzo[b][1,4]oxazin-2-yl)methyl)cyclopropanecarbonitrile

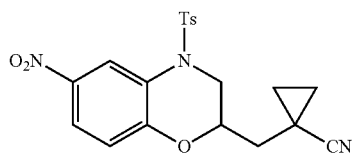

To a solution of N-(2-fluoro-5-nitrophenyl)-4-methylbenzenesulfonamide (1 g, 3.23 mmol) in DMF (10 mL) were added (R and S)-1-(oxiran-2-ylmethyl)cyclopropanecarbonitrile (1 g, 8.13 mmol), N-benzyl-N,N-diethylethanaminium chloride (0.110 g, 0.48 mmol) and potassium carbonate (1.56 g, 11.27 mmol) in one portion at room temperature under nitrogen. The reaction was stirred at 100° C. in a microwave for 2 h. Another two batches were run under the same scale and conditions, and all three crude reaction mixture were combined, diluted with water (400 mL) and extracted with EtOAc (100 mL×4). The combined organic layers were washed with brine, dried over Na$_2$SO$_4$ and evaporated to dryness. The crude product was purified by silica column (petroleum ether:EtOAc=5:1 to 3:1) to afford the title product as a yellow solid. $^1$H-NMR (CDCl$_3$, 400 MHz) δ 8.75 (1H, br s), 7.87-8.00 (1H, m), 7.61 (2H, d, J=8.2 Hz), 7.31 (2H, d, J=7.8 Hz), 6.93 (1H, d, J=9.0 Hz), 4.32 (1H, d, J=14.4 Hz), 3.82 (1H, br s), 3.26 (1H, dd, J=9.3, 14.0 Hz), 2.40 (3H, s), 1.64-1.81 (2H, m), 1.32 (2H, br s), 0.89-0.97 (1H, m), 0.78-0.85 (1H, m).

Step 4—Preparation of (S and R)-1-((6-amino-4-tosyl-3,4-dihydro-2H-benzo[b][1,4]oxazin-2-yl)methyl)cyclopropanecarbonitrile

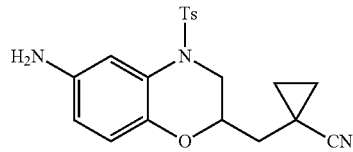 [SMILES: Cc1ccc(S(=O)(=O)N2CC(CC3(C#N)CC3)Oc3ccc([N+](=O)[O-])cc32)cc1]

To a solution of (S and R)-1-((6-nitro-4-tosyl-3,4-dihydro-2H-benzo[b][1,4]oxazin-2-yl)methyl)cyclopropanecarbonitrile (1.5 g, 3.63 mmol) in EtOAc (30 mL) was added Pd/C (0.6 g, 5.64 mmol) in one portion at room temperature. The reaction was stirred at 25° C. under a $H_2$ balloon for 8 h, then filtered and evaporated to dryness. The crude title product was used directly in the next step without further purification. LCMS (ESI) calculated for $C_{20}H_{22}N_3O_3S$ [M+H]$^+$: 384. found: 384. $^1$H-NMR (CDCl$_3$, 400 MHz) δ 7.55 (2H, d, J=8.2 Hz), 7.25 (3H, d, J=7.0 Hz), 6.62 (1H, d, J=8.6 Hz), 6.44 (1H, dd, J=2.5, 8.4 Hz), 4.25 (1H, dd, J=1.7, 14.2 Hz), 3.45-3.56 (1H, m), 3.14 (1H, dd, J=9.5, 14.2 Hz), 2.37 (3H, s), 1.59-1.67 (1H, m), 1.50-1.59 (1H, m), 1.20-1.29 (2H, m), 0.86-0.94 (1H, m), 0.69-0.79 (1H, m).

Step 5—Preparation of (S and R)-1,1,1-trifluoro-2-methylpropan-2-yl (2-((1-cyanocyclopropyl)methyl)-4-tosyl-3,4-dihydro-2H-benzo[b][1,4]oxazin-6-yl)carbamate

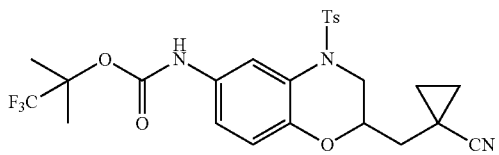 [SMILES: Cc1ccc(S(=O)(=O)N2CC(CC3(C#N)CC3)Oc3ccc(NC(=O)OC(C)(C)C(F)(F)F)cc32)cc1]

To a solution of (S and R)-1-((6-amino-4-tosyl-3,4-dihydro-2H-benzo[b][1,4]oxazin-2-yl)methyl)cyclopropanecarbonitrile (1.3 g, 3.39 mmol) in DMSO (15 mL) was added 1,1,1-trifluoro-2-methylpropan-2-yl 1H-imidazole-1-carboxylate (1.130 g, 5.09 mmol) in one portion at room temperature under $N_2$. The reaction was stirred at 90° C. for 8 h, then diluted with water (50 mL) and extracted with EtOAc (50 mL×3). The combined organic layers were washed with brine, dried over Na$_2$SO$_4$ and evaporated to dryness. The crude product was purified by silica gel column chromatography (petroleum ether:EtOAc=5:1) to afford the title compound as a white solid. LCMS showed the product contains minor (<10%) CF$_3$Boc imidazole. LCMS (ESI) calculated for $C_{25}H_{27}F_3N_3O_5S$ [M+H]$^+$: 538. found: 538. $^1$H-NMR (CDCl$_3$, 400 MHz) δ 7.69 (1H, br s), 7.51 (2H, d, J=8.0 Hz), 7.21 (2H, d, J=8.0 Hz), 6.72 (1H, d, J=9.0 Hz), 6.63 (1H, br s), 4.19 (1H, dd, J=1.7, 14.3 Hz), 3.51 (1H, d, J=4.5 Hz), 3.11 (1H, dd, J=9.5, 14.0 Hz), 2.33 (3H, s), 1.70 (6H, s), 1.58-1.66 (1H, m), 1.48-1.56 (1H, m), 1.17-1.26 (2H, m), 0.81-0.91 (1H, m), 0.67-0.77 (1H, m).

Step 6—Preparation of (S and R)-1,1,1-trifluoro-2-methylpropan-2-yl (2-((1-cyanocyclopropyl)methyl)-3,4-dihydro-2H-benzo[b][1,4]oxazin-6-yl)carbamate

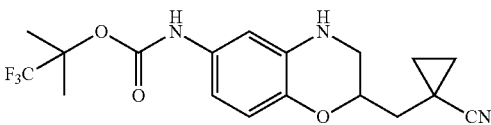 [SMILES: CC(C)(OC(=O)Nc1ccc2c(c1)NCC(CC1(C#N)CC1)O2)C(F)(F)F]

To a solution of (S and R)-1,1,1-trifluoro-2-methylpropan-2-yl (2-((1-cyanocyclopropyl)methyl)-4-tosyl-3,4-dihydro-2H-benzo[b][1,4]oxazin-6-yl)carbamate (1.1 g, 2.046 mmol) in MeOH (10 mL), which was stirred in a 100 mL of round bottom flask, was added magnesium (0.497 g, 20.46 mmol) in one portion at room temperature under $N_2$. The reaction was stirred at 80° C. for 3 h, then diluted with water (100 mL), acidified with 1N HCl (20 mL) and extracted with EtOAc (40 mL×3). The combined organic layers were washed with brine, dried over Na$_2$SO$_4$ and evaporated to dryness. The crude product was purified by silica gel column chromatography (petroleum ether:EtOAc=2:1) to afford the title product as a yellow oil. LCMS (ESI): calculated for $C_{18}H_{21}F_3N_3O_3$ [M+H]$^+$: 384. found: 384. $^1$H NMR (CDCl$_3$, 400 MHz) δ 6.78 (1H, br s), 6.65 (1H, d, J=8.5 Hz), 6.46 (1H, br s), 6.38 (1H, d, J=8.5 Hz), 4.32-4.40 (1H, m), 3.44 (1H, dd, J=2.5, 11.5 Hz), 3.12 (1H, dd, J=6.0, 11.5 Hz), 1.76-1.85 (2H, m), 1.67 (6H, s), 1.21-1.29 (2H, m), 0.88-0.94 (1H, m), 0.79 (1H, d, J=6.0 Hz).

Step 7—Preparation of (S)-1,1,1-trifluoro-2-methylpropan-2-yl (2-((1-cyanocyclopropyl)methyl)-4-((3-(trifluoromethyl)phenyl)sulfonyl)-3,4-dihydro-2H-benzo[b][1,4]oxazin-6-yl)carbamate and (R)-1,1,1-trifluoro-2-methylpropan-2-yl (2-((1-cyanocyclopropyl)methyl)-4-((3-(trifluoromethyl)phenyl)sulfonyl)-3,4-dihydro-2H-benzo[b][1,4]oxazin-6-yl)carbamate

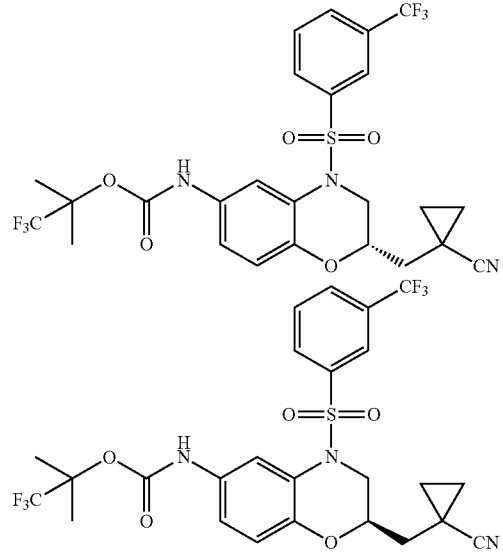

To a solution of (S and R)-1,1,1-trifluoro-2-methylpropan-2-yl (2-((1-cyanocyclopropyl)methyl)-3,4-dihydro-2H-benzo[b][1,4]oxazin-6-yl)carbamate (200 mg, 0.522 mmol) in THF (1 mL) were added pyridine (0.169 mL, 2.087 mmol) and 3-(trifluoromethyl)benzene-1-sulfonyl chloride (254 mg, 1.043 mmol) dropwise at room temperature under $N_2$. The reaction was stirred at 25° C. for 8 h, then concentrated and purified by prep-TLC (petroleum ether:EtOAc=2:1) to afford the title racemate as a yellow oil.

The two enantiomers were separated by chiral SFC method (Chiralpak AD-3 150×4.6 mm I.D., 3 um Mobile phase: ethanol (0.05% DEA) in $CO_2$ from 5% to 40% Flow rate: 2.5 mL/min Wavelength: 220 nm. RT (Isomer 1)=2.656 min, RT (Isomer 2)=3.369 min). Both enantiomers have same analytical data: LCMS (ESI) calculated for $C_{25}H_{24}F_6N_3O_5S$ $[M+H]^+$: 592. found: 592.

Step 8—Preparation of (S)-1,1,1-trifluoro-2-methylpropan-2-yl (2-((1-formylcyclopropyl)methyl)-4-((3-(trifluoromethyl)phenyl)sulfonyl)-3,4-dihydro-2H-benzo[b][1,4]oxazin-6-yl)carbamate and (R)-1,1,1-trifluoro-2-methylpropan-2-yl (2-((1-formylcyclopropyl)methyl)-4-((3-(trifluoromethyl)phenyl)sulfonyl)-3,4-dihydro-2H-benzo[b][1,4]oxazin-6-yl)carbamate

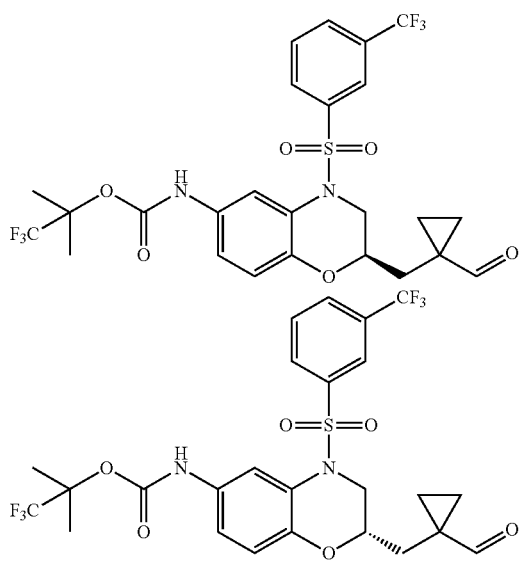

To a solution of (S or R)-1,1,1-trifluoro-2-methylpropan-2-yl (2-((1-cyanocyclopropyl)methyl)-4-((3-(trifluoromethyl)phenyl)sulfonyl)-3,4-dihydro-2H-benzo[b][1,4]oxazin-6-yl)carbamate (64 mg, 0.108 mmol; Isomer 1 in Step 7) in toluene (1 mL) was added DIBAL-H (0.540 mL, 0.540 mmol, 1 M in THF) dropwise at −78° C. under nitrogen. The reaction was stirred at −78° C. for 2 h, then quenched with MeOH (0.5 mL) and acidified with 1M HCl (2 mL). Stirring was continued at 0° C. until the solution became clear. The resulting mixture was extracted with EtOAc (2 mL×3) and the combined organic layers were washed with saturated NaHCO$_3$ and brine, dried over $Na_2SO_4$ and evaporated to dryness to afford the crude title product (60 mg, Isomer 1 in Step 8), which was directly used next step without further purification. The other enantiomer (Isomer 2 in Step 8) was prepared using a similar procedure from Isomer 2 from Step 7.

Step 9—Preparation of (S)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid and (R)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid

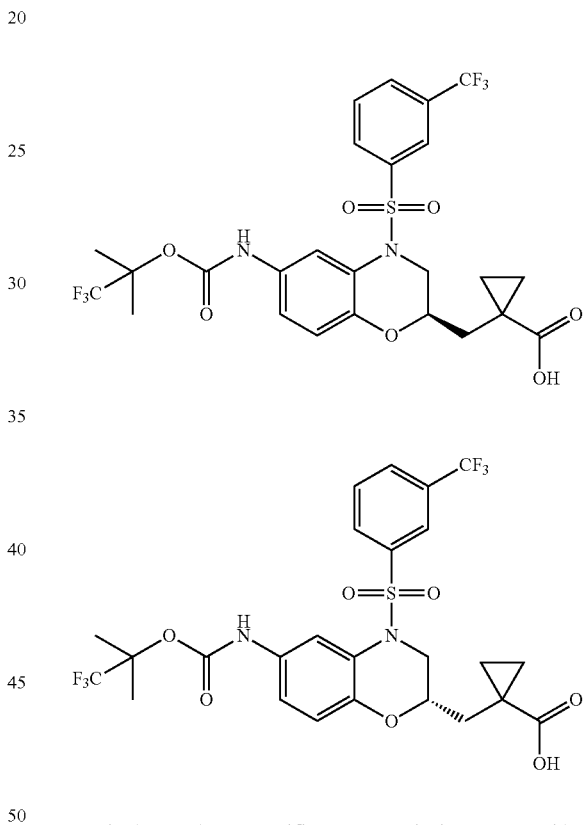

Crude (S or R)-1,1,1-trifluoro-2-methylpropan-2-yl(2-((1-formylcyclopropyl)methyl)-4-((3-(trifluoromethyl)phenyl)sulfonyl)-3,4-dihydro-2H-benzo[b][1,4]oxazin-6-yl)carbamate (crude 60 mg, Isomer 1 in Step 8) was dissolved in THF (2 mL) and treated with $NH_2SO_3H$ (62.9 mg, 0.648 mmol) and $KH_2PO_4$ (176 mg, 1.296 mmol), followed by the addition of a solution of $NaClO_2$ (14.65 mg, 0.162 mmol) in water (0.5 mL) dropwise at 0° C. The reaction was stirred at 0° C. for 1 h, then diluted with water (10 mL) and extracted with EtOAc (3 mL×3). The combined organic layers were evaporated to dryness. The crude product was purified by prep-HPLC (MeCN/water using TFA buffer) to afford Example No. 13A (Isomer 1 in Step 9) as a white solid. The other enantiomer (Example No. 13B, (Isomer 2 in Step 9)

was prepared using a similar procedure from Isomer 2 from Step 8. Both enantiomers have same analytical data: LCMS (ESI): calculated for $C_{25}H_{25}F_6N_2O_7S$ [M+H]$^+$: 611 found: 611. $^1$HNMR (CDCl$_3$, 400 MHz) δ 8.02 (1H, br s), 7.85 (2H, d, J=5.4 Hz), 7.77 (1H, d, J=7.4 Hz), 7.52-7.60 (1H, m), 7.06 (1H, d, J=8.6 Hz), 6.73 (1H, d, J=8.6 Hz), 6.59 (1H, s), 4.33 (1H, d, J=14.0 Hz), 3.82 (1H, brs), 3.21 (1H, dd, J=9.5, 13.8 Hz), 2.08 (1H, dd, J=4.3, 14.8 Hz), 1.75 (6H, s), 1.45 (1H, dd, J=7.6, 14.6 Hz), 1.36 (2H, brs), 0.94-1.02 (1H, m), 0.75-0.82 (1H, m).

Example 14

Preparation of Additional α-Cyclopropanecarboxylic Acid-Substituted Benzoxazines The compounds in Table 5 were prepared based on the experimental procedures described in Example 13, and can be achieved by one of skill in the art in light of the present disclosure.

TABLE 5

| Ex. No. | Structure | Name | Observed m/z |
|---|---|---|---|
| 14A | 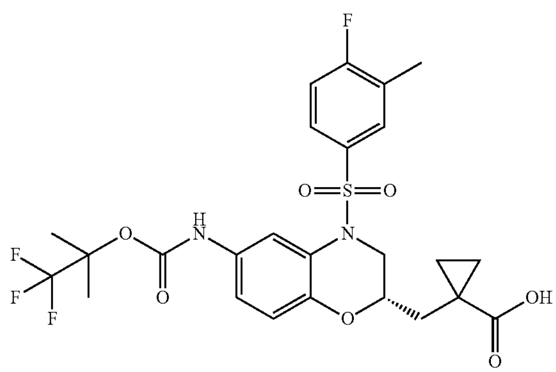 [SMILES: Cc1cc(S(=O)(=O)N2C[C@H](CC3(C(=O)O)CC3)Oc3ccc(NC(=O)OC(C)(C)C(F)(F)F)cc32)ccc1F] | (S)-1-((4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid | 575 [M + H]+ |
| 14B | 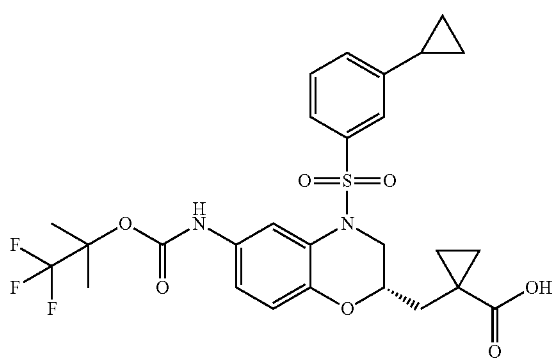 [SMILES: CC(C)(OC(=O)Nc1ccc2c(c1)N(S(=O)(=O)c1cccc(C3CC3)c1)C[C@H](CC1(C(=O)O)CC1)O2)C(F)(F)F] | (S)-1-((4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid | 583 [M + H]+ |
| 14C | 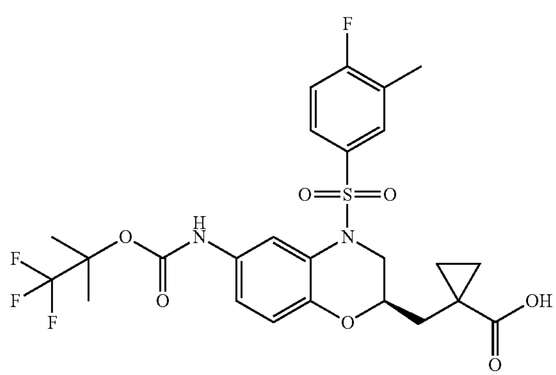 [SMILES: Cc1cc(S(=O)(=O)N2C[C@@H](CC3(C(=O)O)CC3)Oc3ccc(NC(=O)OC(C)(C)C(F)(F)F)cc32)ccc1F] | (R)-1-((4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cylcopropanecarboxylic acid | 575 [M + H]+ |

TABLE 5-continued

| Ex. No. | Structure | Name | Observed m/z |
|---|---|---|---|
| 14D | 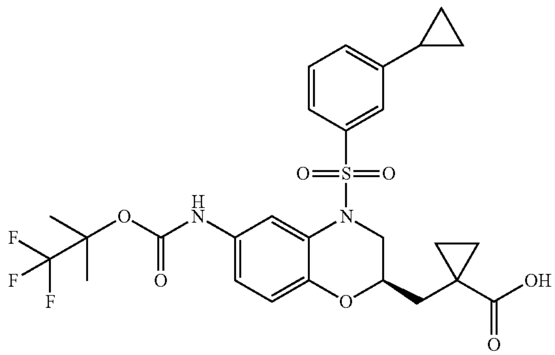 [SMILES: CC(C)(OC(=O)Nc1ccc2c(c1)N(S(=O)(=O)c1cccc(C3CC3)c1)C[C@@H](CC1(C(=O)O)CC1)O2)C(F)(F)F] | (R)-1-((4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)mehtyl)cyclopropanecarboxylic acid | 583 [M + H]+ |
| 14E | 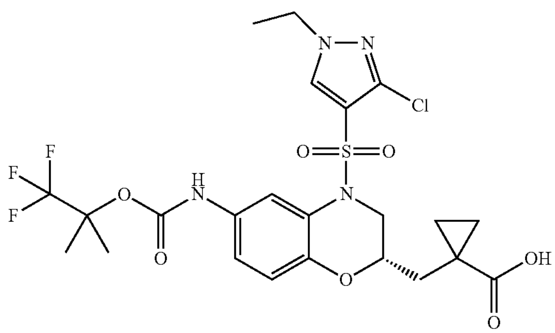 [SMILES: CCn1cc(S(=O)(=O)N2C[C@H](CC3(C(=O)O)CC3)Oc3ccc(NC(=O)OC(C)(C)C(F)(F)F)cc32)c(Cl)n1] | (S)-1-((4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid | 596 [M + H]+ |
| 14F | 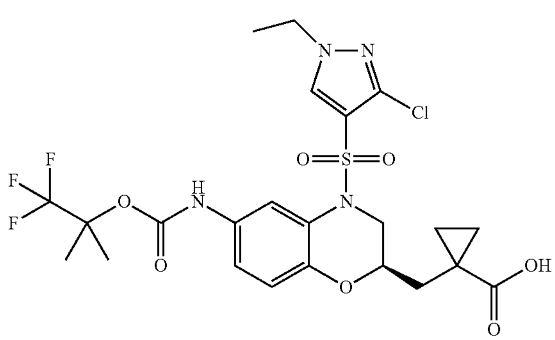 [SMILES: CCn1cc(S(=O)(=O)N2C[C@@H](CC3(C(=O)O)CC3)Oc3ccc(NC(=O)OC(C)(C)C(F)(F)F)cc32)c(Cl)n1] | (R)-1-((4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid | 596 [M + H]+ |
| 14G | 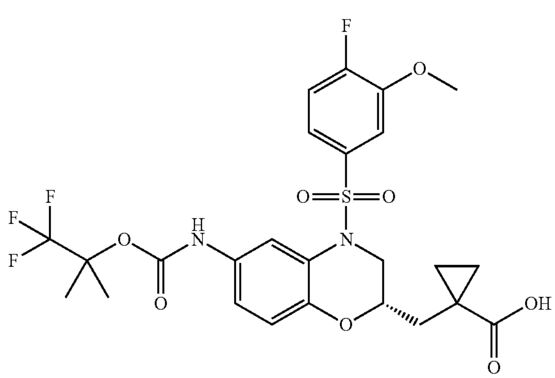 [SMILES: COc1cc(S(=O)(=O)N2C[C@H](CC3(C(=O)O)CC3)Oc3ccc(NC(=O)OC(C)(C)C(F)(F)F)cc32)ccc1F] | (S)-1-((4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid | 591 [M + H]+ |

TABLE 5-continued

| Ex. No. | Structure | Name | Observed m/z |
|---|---|---|---|
| 14H | 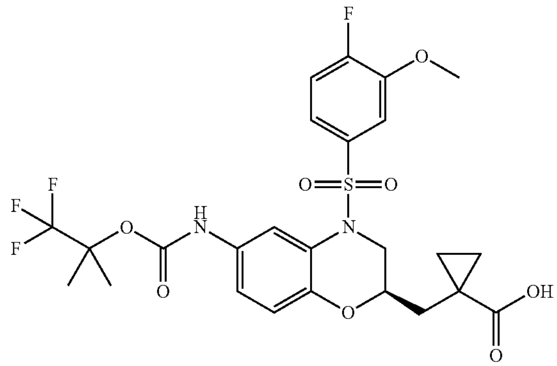 [SMILES: COc1cc(S(=O)(=O)N2C[C@@H](CC3(C(=O)O)CC3)Oc3ccc(NC(=O)OC(C)(C)C(F)(F)F)cc32)ccc1F] | (R)-1-((4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid | 591 [M + H]+ |

Example 15

Preparation of (S and R)-2-hydroxy-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid

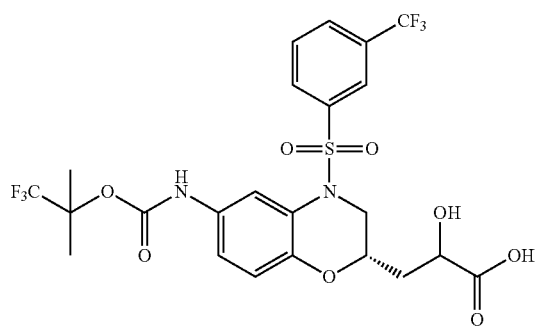 [SMILES: CC(C)(OC(=O)Nc1ccc2c(c1)N(S(=O)(=O)c1cccc(C(F)(F)F)c1)C[C@H](CC(O)C(=O)O)O2)C(F)(F)F]

Step 1—Preparation of (S)-ethyl 3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate

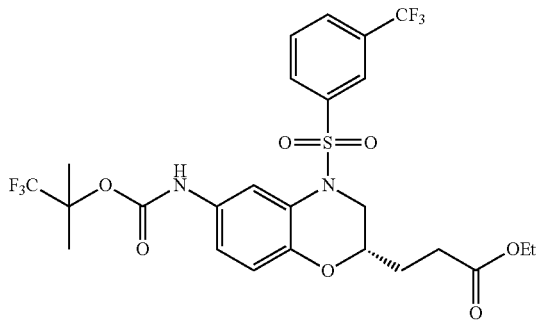 [SMILES: CCOC(=O)CC[C@H]1CN(S(=O)(=O)c2cccc(C(F)(F)F)c2)c2cc(NC(=O)OC(C)(C)C(F)(F)F)ccc2O1]

To a microwave vial loaded with (S)-ethyl 3-(6-((((1,1,1-trifluoro-2-methylpropan-2-yl)oxy)carbonyl)amino)-3,4-dihydro-2H-benzo[b][1,4]oxazin-2-yl)propanoate (1.0 g, 2.50 mmol) and 3-(trifluoromethyl)benzene-1-sulfonyl chloride (0.791 mL, 4.95 mmol) at room temperature was added pyridine (10 mL). The mixture was stirred at 50° C. overnight. The reaction was cooled down to room temperature, diluted with EtOAc, washed with water and brine, then dried over MgSO₄. The crude product was purified by normal phase flash chromatography using EtOAc/hexane (0-25%), to give the title compound as a white solid after lyophilization. MS ESI calculated for $C_{25}H_{27}F_6N_2O_7S$ (M+H)⁺ 613, found 635 (M+Na)⁺.

Step 2—Preparation of (R and S)-ethyl 2-hydroxy-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate

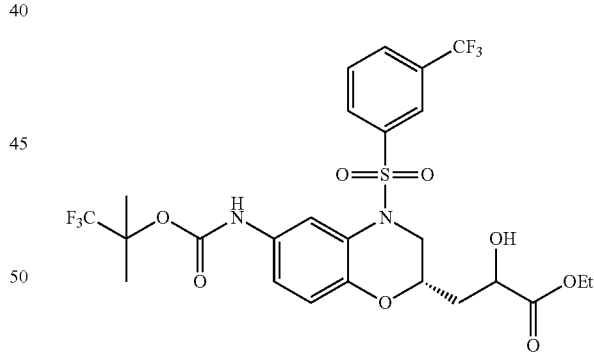

To a solution of (S)-ethyl 3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate (50 mg, 0.082 mmol) in THF (1 mL) at −78° C. under Ar was added potassium bis(trimethylsilyl)amide (0.196 mL, 0.196 mmol; 1.0M in THF) and the mixture was stirred at −78° C. for 30 min. Then a solution of 3-phenyl-2-(phenylsulfonyl)-1,2-oxaziridine (Davis reagent) (64.0 mg, 0.245 mmol) in THF (1 mL) was added and the stirring continued at −78° C. After 30 min, the reaction was warmed up to room temperature and quenched with saturated aqueous NH₄Cl. The reaction was diluted with EtOAc, washed with water and brine, and the combined organics dried over MgSO₄, filtered and concentrated. The crude product was purified by normal phase flash chromatography using EtOAc/hexane (0-50%), to give the title compound as a yellow oil. MS ESI calculated for $C_{25}H_{27}F_6N_2O_8S$ (M+H)⁺ 629, found 646 (M+NH₄)⁺.

Step 3—Preparation of (R and S)-2-hydroxy-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid

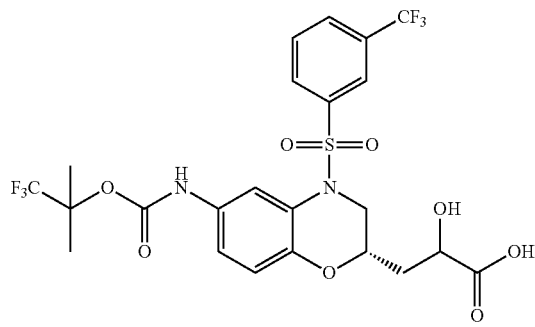 [SMILES: CC(C)(OC(=O)Nc1ccc2c(c1)N(S(=O)(=O)c1cccc(C(F)(F)F)c1)C[C@H](CC(O)C(=O)O)O2)C(F)(F)F]

To a solution of (R and S)-ethyl 2-hydroxy-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate (30 mg, 0.048 mmol) in THF (3 mL)/water (2 mL) was added LiOH (5 mL, 5.00 mmol). The mixture was stirred at room temperature for 1.5 h and then neutralized with 1N HCl and concentrated. The residue was dissolved in DMSO and purified by reverse phase HPLC (MeCN/water using TFA buffer) to afford the title compound as a white solid. MS ESI calculated for $C_{23}H_{23}F_6N_2O_8S$ (M+H)⁺ 601, found 623 (M+Na)⁺. ¹H NMR (600 MHz, d⁶-DMSO) δ 9.72 (s, 1H), 8.03 (dd, J=14.3, 21.8, 4H), 7.79 (dd, J=16.5, 24.4, 1H), 7.03 (t, J=8.1, 1H), 6.79-6.62 (m, 1H), 4.48-4.31 (m, 1H), 4.16-3.99 (m, 1H), 3.77-3.53 (m, 1H), 2.74 (d, J=45.8, 1H), 1.98-1.82 (m, 2H), 1.65 (s, 6H).

Example 16

Preparation of (S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid and (R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid (Example Nos. 16A and 16B)

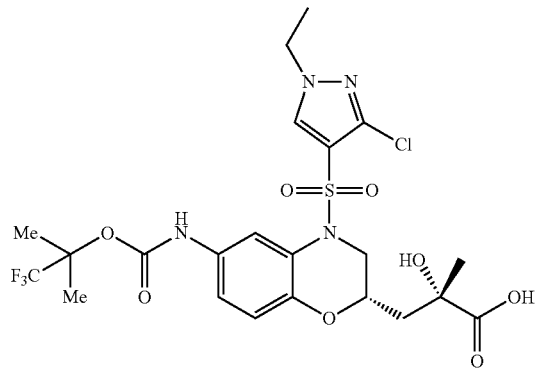

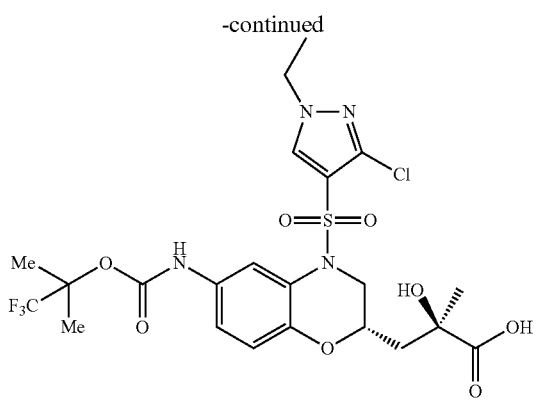

Step 1—Preparation of (S)-tert-butyl(4-benzyl-2-(2-oxopropyl)-3,4-dihydro-2H-benzo[b][1,4]oxazin-6-yl)carbamate

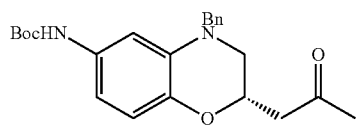 [SMILES: CC(=O)C[C@H]1CN(Cc2ccccc2)c2cc(NC(=O)OC(C)(C)C)ccc2O1]

To a solution of (S)-tert-butyl(4-benzyl-2-(2-(methoxy(methyl)amino)-2-oxoethyl)-3,4-dihydro-2H-benzo[b][1,4]oxazin-6-yl)carbamate (1 g, 2.265 mmol) in tetrahydrofuran (50 mL) was added methylmagnesium bromide (2.7 mL, 8.1 mmol, 3 M in THF) under nitrogen at 0° C., and the reaction was stirred at 0° C. for 2 h. The reaction was quenched with aqueous ammonium chloride and extracted with ethyl acetate (30 mL×3). The combined organic layers were washed with brine, dried over Na₂SO₄ and concentrated under reduced pressure. The crude product was purified by flash column chromatography (petroleum ether:dichloromethane=10:1 to 0:1) to give the title compound as a yellow solid. LCMS (ESI) calculated for $C_{23}H_{29}N_2O_4$ [M+H]⁺: 397. found: 397. ¹HNMR (400 MHz, CDCl₃) δ 7.20-7.38 (5H, m), 6.75-6.85 (1H, m), 6.68-6.72 (1H, m), 6.50-6.65 (1H, m), 6.29 (1H, s), 4.50-4.60 (1H, m), 4.38-4.48 (2H, m), 3.28-3.38 (1H, m), 3.00-3.10 (1H, m), 2.86-2.96 (1H, m), 2.52-2.68 (1H, m), 2.17 (3H, s), 1.44 (9H, s).

Step 2—Preparation of 3-((S)-6-amino-4-benzyl-3,4-dihydro-2H-benzo[b][1,4]oxazin-2-yl)-(2R and 2S)-methyl-2-((trimethylsilyl)oxy)propanenitrile

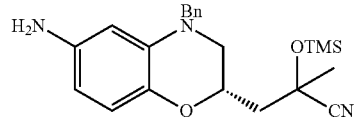

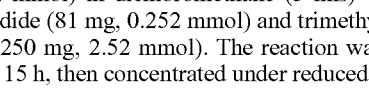

To a solution of (S)-tert-butyl (4-benzyl-2-(2-oxopropyl)-3,4-dihydro-2H-benzo[b][1,4]oxazin-6-yl)carbamate (100 mg, 0.252 mmol) in dichloromethane (5 mL) were added zinc(II) iodide (81 mg, 0.252 mmol) and trimethylsilanecarbonitrile (250 mg, 2.52 mmol). The reaction was stirred at 20° C. for 15 h, then concentrated under reduced pressure to give the crude title compound as orange oil, which was used in next step without further purification. LCMS (ESI) calculated for $C_{22}H_{30}N_3O_2Si$ [M+H]+: 396. found: 396.

Step 3—Preparation of (S)-3-((S)-6-amino-4-benzyl-3,4-dihydro-2H-benzo[b][1,4]oxazin-2-yl)-2-hydroxy-2-methylpropanoic acid and (R)-3-((S)-6-amino-4-benzyl-3,4-dihydro-2H-benzo[b][1,4]oxazin-2-yl)-2-hydroxy-2-methylpropanoic acid

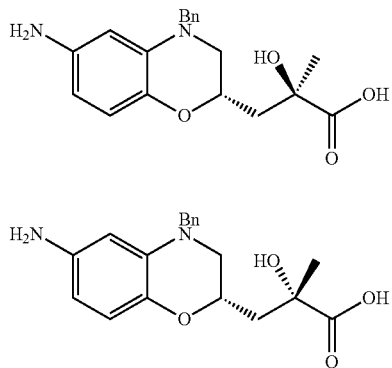

A solution of 3-((S)-6-amino-4-benzyl-3,4-dihydro-2H-benzo[b][1,4]oxazin-2-yl)-2-methyl-2-((trimethylsilyl)oxy)propanenitrile (50 mg, 0.126 mmol) in concentrated HCl (1 mL) and acetic acid (1 mL) was stirred at 100° C. for 1.5 h. Upon completion, the reaction mixture was concentrated under vacuum and purified by pre-HPLC (MeCN/H$_2$O as eluent, 0.05% TFA) to give the titled compounds. Isomer 1 (faster-eluting peak): LCMS (ESI) calculated for $C_{19}H_{23}N_2O_4$ [M+H]+: 343. found: 343. $^1$HNMR (400 MHz, Methanol-d4) δ 7.18-7.40 (5H, m), 6.75-6.87 (1H, m), 6.42-6.56 (2H, m), 4.35-4.62 (3H, m), 3.40-3.52 (1H, m), 3.32-3.27 (1H, m), 2.35-2.22 (1H, m), 1.85-1.92 (1H, m), 1.43 (3H, s). Isomer 2 (slower-eluting peak): LCMS (ESI) calculated for $C_{19}H_{23}N_2O_4$ [M+H]+: 343. found: 343. $^1$HNMR (400 MHz, Methanol-d4) δ 7.21-7.42 (5H, m), 6.76-6.85 (1H, m), 6.45-6.58 (2H, m), 4.36-4.60 (3H, m), 3.42-3.51 (1H, m), 3.26-3.32 (1H, m), 2.08-2.22 (1H, m), 1.96-2.06 (1H, m), 1.48 (3H, s).

Step 4—Preparation of (R)-3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid) and (S)-3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid)

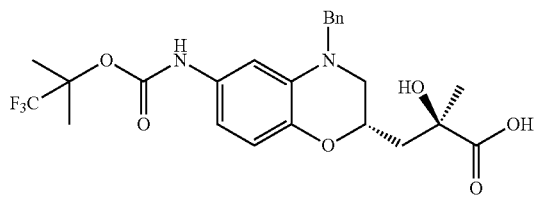
-continued
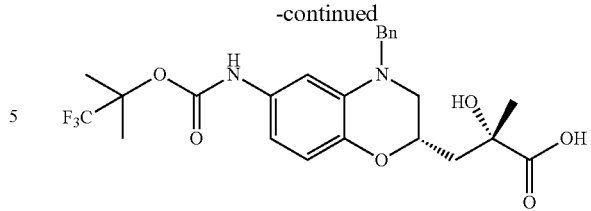

To a solution of (S or R)-3-((S)-6-amino-4-benzyl-3,4-dihydro-2H-benzo[b][1,4]oxazin-2-yl)-2-hydroxy-2-methylpropanoic acid (Isomer 1 from Step 3, 150 mg, 0.44 mmol) in DMSO (5 mL) was added 3-methyl-1-(((1,1,1-trifluoro-2-methylpropan-2-yl)oxy)carbonyl)-1H-imidazol-3-ium iodide (175 mg, 0.48 mmol), and the reaction was stirred at 15° C. for 15 minutes. The reaction mixture was directly purified by pre-HPLC (MeCN/H$_2$O as eluent, 0.05% TFA) to give the titled compound (R or S)-3-(S)-4-benzyl-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid) (Isomer 1 from Step 4) as a white solid. LCMS (ESI) calculated for $C_{24}H_{28}F_3N_2O_6$ [M+H]+: 497. found: 497.

The other isomer (Isomer 2 from Step 4) was prepared using a similar procedure from Isomer 2 from Step 3. LCMS (ESI) calculated for $C_{24}H_{28}F_3N_2O_6$ [M+H]+: 497. found: 497.

Step 5—Preparation of (S)-2-hydroxy-2-methyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid) and (R)-2-hydroxy-2-methyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid)

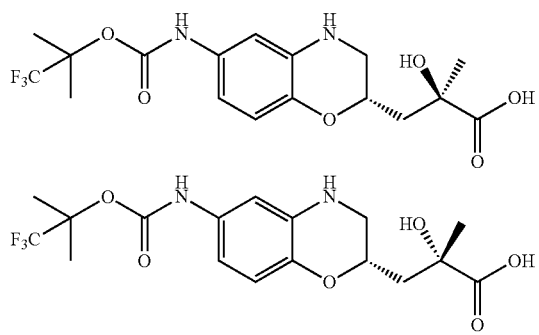

To a solution of (R or S)-3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid (Isomer 1 from Step 4; 20 mg, 0.04 mmol) in methanol (10 mL) was added Pd(OH)$_2$ (15 mg) under argon, and the mixture was stirred at 15° C. under hydrogen balloon for 4 h, then filtered and concentrated under reduced pressure to give the titled compound (S or R)-2-hydroxy-2-methyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid) (Isomer 1 from Step 5) as a dark oil, which was used in next step without purification. LCMS (ESI) calculated for $C_{17}H_{22}F_3N_2O_6$ [M+H]+: 407. found: 407.

The other isomer (Isomer 2 from Step 5) was prepared using a similar procedure from Isomer 2 from Step 4. LCMS (ESI) calculated for $C_{17}H_{22}F_3N_2O_6$ [M+H]$^+$: 407. found: 407.

Step 6—Preparation of (S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid and (R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid

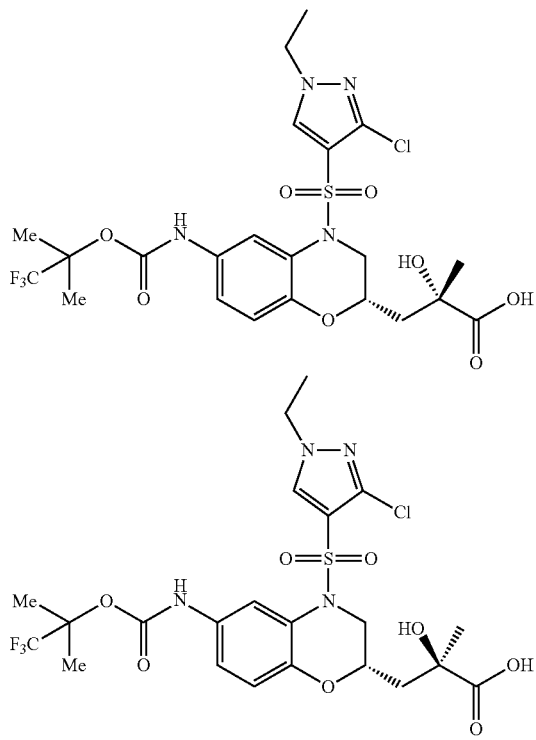

To a solution of (R or S)-2-hydroxy-2-methyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid) (Isomer 1 from Step 5, 15 mg, 0.037 mmol) in tetrahydrofuran (5 mL) were added pyridine (56.7 mg, 0.717 mmol) and 3-chloro-1-ethyl-1H-pyrazole-4-sulfonyl chloride (25.4 mg, 0.11 mmol). The reaction was stirred at 15° C. for 3 h, then concentrated under vacuum. The crude product was purified by pre-HPLC (MeCN/H$_2$O as eluent, 0.05% TFA) to give Example No. 16A (Isomer 1 from Step 6) as a white solid. LCMS (ESI) calculated for $C_{22}H_{27}ClF_3N_4O_8S$ [M+H]$^+$: 599. found: 599. $^1$HNMR (400 MHz, Methanol-d4) δ 8.27 (1H, s), 7.86 (1H, s), 6.96-7.00 (1H, m), 6.72-6.75 (1H, m), 4.38-4.42 (1H, m), 4.12-4.25 (3H, m), 4.00-4.10 (1H, m), 2.00-2.05 (2H, m), 1.74 (6H, s), 1.40-1.43 (6H, m).

The other isomer, Example No. 16B, (Isomer 2 from Step 6) was prepared using a similar procedure from Isomer 2 from Step 5. LCMS (ESI) calculated for $C_{22}H_{27}ClF_3N_4O_8S$ [M+H]$^+$: 599. found: 599. $^1$HNMR (400 MHz, Methanol-d4) δ 8.29 (1H, s), 7.85 (1H, s), 6.90-6.94 (1H, m), 6.70-6.75 (1H, m), 4.40-4.45 (1H, m), 4.00-4.20 (4H, m), 2.20-2.28 (2H, m), 1.73 (6H, s), 1.40-1.48 (6H, m).

Example 17

Preparation of (S)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl) propanoic acid and (R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid (Example Nos. 17A and 17B)

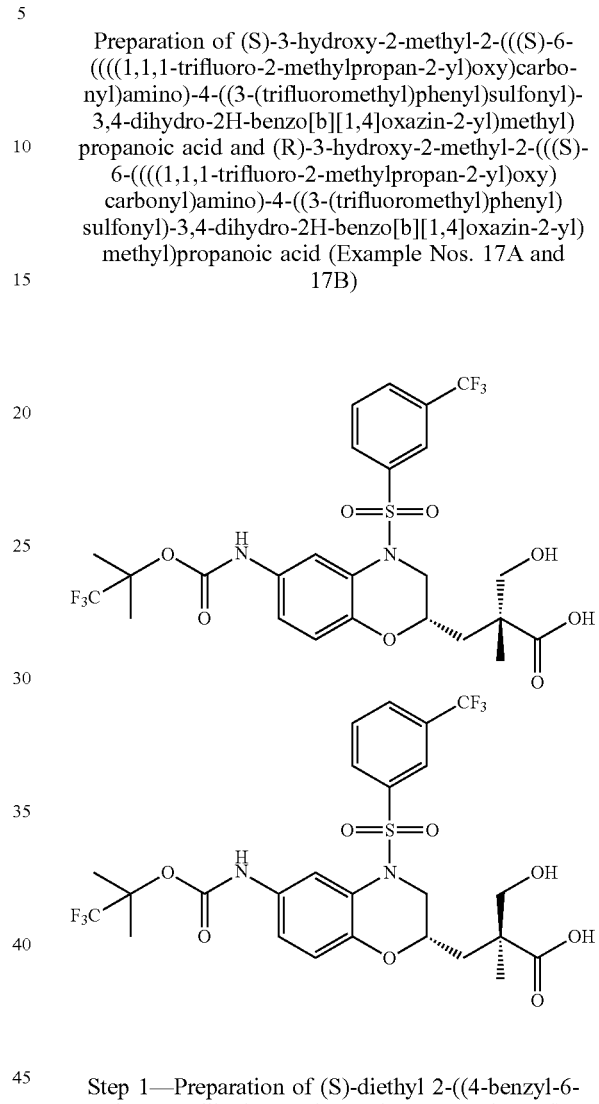

Step 1—Preparation of (S)-diethyl 2-((4-benzyl-6-nitro-3,4-dihydro-2H-benzo[b][1,4]oxazin-2-yl)methyl)-2-methylmalonate

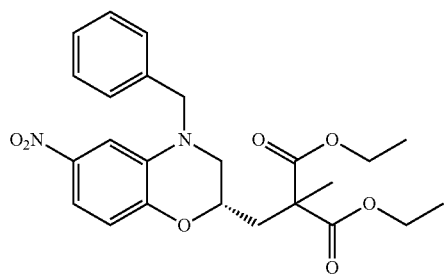 [SMILES: CCOC(=O)C(C)(C[C@H]1CN(Cc2ccccc2)c2cc([N+](=O)[O-])ccc2O1)C(=O)OCC]

To a solution of (S)-diethyl 2-((4-benzyl-6-nitro-3,4-dihydro-2H-benzo[b][1,4]oxazin-2-yl)methyl)malonate (5.00 g, 11.30 mmol) in DMF (60 mL) were added Cs$_2$CO$_3$ (7.36 g, 22.60 mmol) and MeI (1.766 mL, 28.3 mmol). The reaction was stirred at 80° C. for 2 h, then diluted with EtOAc (100 mL) and saturated aqueous NaCl (200 mL). The aqueous layer was extracted with EtOAc (80 mL×3). The combined organic layers was dried over Na$_2$SO$_4$ and concentrated in vacuo to afford the titled compound as an orange oil, which was used directly in the next step without further purification. LCMS (ESI) calculated for C$_{24}$H$_{29}$N$_2$O$_7$ [M+H]$^+$: 457. found: 457.

Step 2—Preparation of (R and S)-ethyl 3-((S)-4-benzyl-6-nitro-3,4-dihydro-2H-benzo[b][1,4]oxazin-2-yl)-2-(hydroxymethyl)-2-methylpropanoate

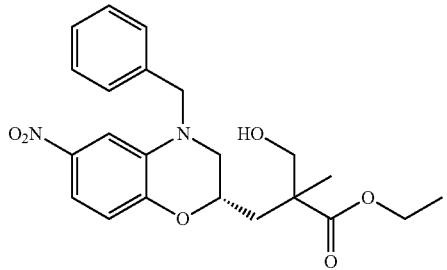

To a solution of (S)-diethyl 2-((4-benzyl-6-nitro-3,4-dihydro-2H-benzo[b][1,4]oxazin-2-yl)methyl)-2-methylmalonate (5.02 g, 11.00 mmol) in xylene (100 mL) was added (t-BuO)$_3$AlH—Li (13.98 g, 55.0 mmol) at 25° C. The mixture was heated to 140° C. for 12 h, then filtered through a pad of CELITE. The filtrate was concentrated to dryness and the crude product purified by column chromatography (SiO$_2$, petroleum ether:EtOAc=10:1 to 3:1) to give the title compound as yellow oil. LCMS (ESI) calculated for C$_{22}$H$_{27}$N$_2$O$_6$ [M+H]$^+$: 415. found: 415.

Step 3—Preparation of (R and S)-ethyl 3-((S)-6-amino-4-benzyl-3,4-dihydro-2H-benzo[b][1,4]oxazin-2-yl)-2-(hydroxymethyl)-2-methylpropanoate

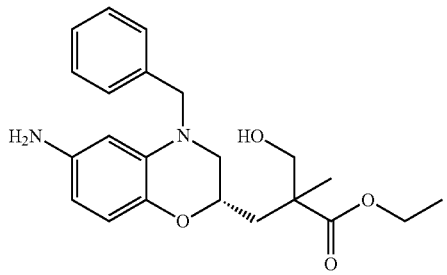 [SMILES: CCOC(=O)C(C)(CO)C[C@H]1CN(Cc2ccccc2)c2cc([N+](=O)[O-])ccc2O1]

To a solution of (R and S)-ethyl 3-((S)-4-benzyl-6-nitro-3,4-dihydro-2H-benzo[b][1,4]oxazin-2-yl)-2-(hydroxymethyl)-2-methylpropanoate (1.40 g, 3.38 mmol) in EtOAc (50 mL) was added Raney Ni (1.0 g, 1.704 mmol). The suspension was degassed under vacuum and purged with H$_2$ several times, then stirred under H$_2$ balloon at 25° C. for 10 mins. The reaction was filtered through a pad of CELITE and the filter cake was washed with EtOAc (30 mL×3). The filtrate were concentrated to dryness to afford the crude title compound as a yellow oil, which was used directly in the next step without further purification. LCMS (ESI) calculated for C$_{22}$H$_{29}$N$_2$O$_4$ [M+H]$^+$: 385. found: 385. $^1$H NMR (400 MHz, CDCl$_3$): δ 7.26-7.32 (2H, m), 7.20-7.24 (3H, m), 6.50-6.58 (1H, m), 6.00-6.05 (1H, m), 5.94-5.98 (1H, m), 4.40-4.48 (2H, m), 4.10-4.26 (3H, m), 3.70-3.85 (2H, m), 3.28-3.15 (2H, m), 1.75-1.95 (2H, m), 1.25-1.32 (6H, m).

Step 4—Preparation of (S and R)-ethyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoate

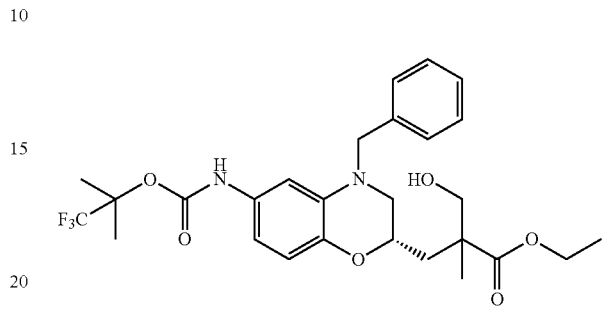

To a mixture of (R and S)-ethyl 3-((S)-6-amino-4-benzyl-3,4-dihydro-2H-benzo[b][1,4]oxazin-2-yl)-2-(hydroxymethyl)-2-methylpropanoate (1.20 g, 3.12 mmol) in DMSO (20 mL) was added 1,1,1-trifluoro-2-methylpropan-2-yl 1H-imidazole-1-carboxylate (0.832 g, 3.75 mmol) and concentrated HCl (0.15 mL, 1.827 mmol). The reaction mixture was stirred at 80° C. for 5 h, then diluted with EtOAc (50 mL) and water (100 mL). The aqueous layer was extracted with EtOAc (30 mL×3). The combined organic layer was dried over Na$_2$SO$_4$ and concentrated in vacuo. The crude product was purified by column chromatography (SiO$_2$, petroleum ether:EtOAc=20:1 to 3:1) to give the title compound as a light yellow oil. LCMS (ESI) calculated for C$_{27}$H$_{34}$F$_3$N$_2$O$_6$ [M+H]$^+$: 539. found: 539. $^1$H NMR (400 MHz, CDCl$_3$): δ 7.26-7.40 (5H, m), 6.70-6.80 (2H, m), 6.60-6.65 (1H, m), 6.45-6.55 (1H, m), 4.45-4.55 (2H, m), 4.28-4.40 (1H, m), 4.08-4.25 (3H, m), 3.72-3.85 (1H, m), 3.15-3.30 (2H, m), 1.80-1.95 (2H, m), 1.73 (6H, s), 1.25-1.38 (6H, m).

Step 5—Preparation of (S)-ethyl 3-hydroxy-2-methyl-2-(((S)-6-(((((1,1,1-trifluoro-2-methylpropan-2-yl)oxy)carbonyl)amino)-3,4-dihydro-2H-benzo[b][1,4]oxazin-2-yl)methyl)propanoate and (R)-ethyl 3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoate

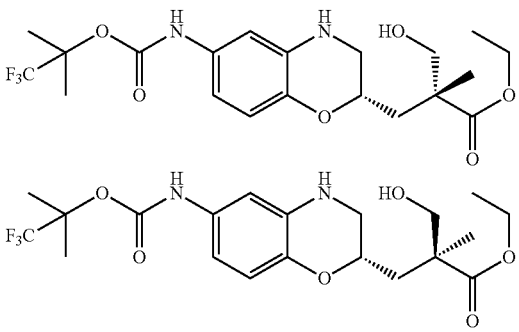

To a solution of (S and R)-ethyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoate (100 mg, 0.186 mmol) in THF (5 mL) was added Pd/C (20 mg). The reaction was degassed under vacuum and purged with H$_2$ several times, then stirred under H$_2$ balloon at 25° C. for 6 h. The reaction mixture was filtered through a pad of CELITE and the filtrate was concentrated to dryness to afford the crude title compound.

The diastereomeric mixture was separated using prep HPLC (MeCN/water with 0.1% TFA) to give two isomers: Isomer 1 (faster-eluting peak): LCMS (ESI) calculated for C$_{20}$H$_{28}$F$_3$N$_2$O$_6$ [M+H]$^+$: 449. found: 449 and Isomer 2 (slower-eluting peak): LCMS (ESI) calculated for C$_{20}$H$_{28}$F$_3$N$_2$O$_6$ [M+H]$^+$: 449. found: 449.

Step 6—Preparation of (S)-3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid and (R)-3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid

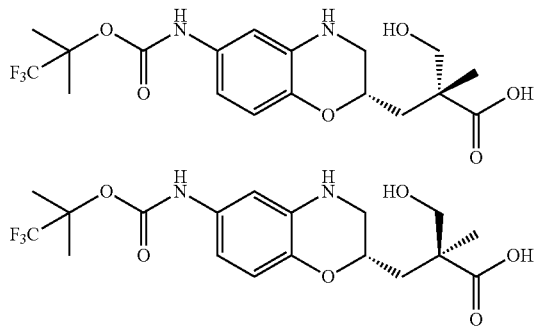

To a solution of (S or R)-ethyl 3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoate (Isomer 1 from Step 5, 120 mg, 0.268 mmol) in 1,4-dioxane (3.0 mL) was added LiOH (32 mg, 1.336 mmol) and water (3.0 mL). The reaction mixture was stirred at 25° C. for 2 h, the treated with 1 N aq. HCl (10 mL) and extracted with EtOAc (15 mL×3). The organic layers were separated, combined, dried over Na$_2$SO$_4$, filtered and concentrated in vacuo to afford the title compound (R or S)-3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid (Isomer 1 from Step 6) as brown oil, which was used in the next step without further purification. LCMS (ESI) calculated for C$_{18}$H$_{24}$F$_3$N$_2$O$_6$ [M+H]$^+$: 421. found: 421.

The other isomer (Isomer 2 from Step 6) was prepared from Isomer 2 from Step 5 using a similar procedure as described above. LCMS (ESI) calculated for C$_{18}$H$_{24}$F$_3$N$_2$O$_6$ [M+H]$^+$: 421. found: 421.

Step 7-Preparation of (S)-3-((tert-butyldimethylsilyl)oxy)-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid and (R)-3-((tert-butyldimethylsilyl)oxy)-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid

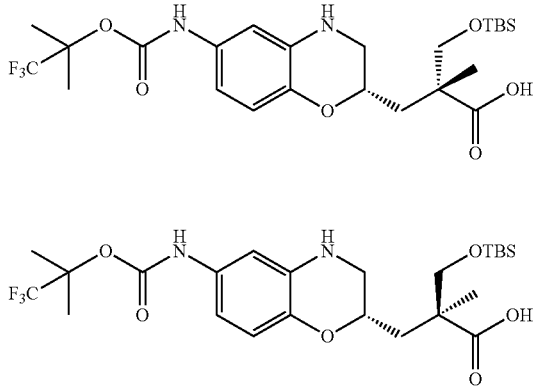 [SMILES: CC(C)(OC(=O)Nc1ccc2c(c1)NC[C@H](C[C@](C)(CO[Si](C)(C)C(C)(C)C)C(=O)O)O2)C(F)(F)F ; CC(C)(OC(=O)Nc1ccc2c(c1)NC[C@H](C[C@@](C)(CO[Si](C)(C)C(C)(C)C)C(=O)O)O2)C(F)(F)F]

To a solution of (R or S)-3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid (Isomer 1 from Step 6; 60 mg, 0.143 mmol) and 1H-imidazole in DMF (2.0 mL) was added tert-butylchlorodimethylsilane (43.0 mg, 0.285 mmol). The reaction mixture was stirred at 25° C. for 6 h, then diluted with water (20 mL) and extracted with ethyl acetate (10 mL×3). The organic layers were separated, combined, dried over Na$_2$SO$_4$, filtered and concentrated in vacuo. The crude product oil was purified by prep-HPLC (MeCN/water using TFA buffer) to afford the title compound (Isomer 1 from Step 7) as a white solid. LCMS (ESI) calculated for C$_{24}$H$_{38}$F$_3$N$_2$O$_6$Si [M+H]$^+$: 535. found: 535. $^1$H NMR (400 MHz, CDCl$_3$): δ 6.75-6.71 (1H, m), 6.55-6.70 (2H, m), 6.40-6.48 (1H, m), 4.15-4.25 (1H, m), 3.90-4.00 (1H, m), 3.60-3.75 (1H, m), 3.30-3.40 (1H, m), 3.05-3.15 (1H, m), 1.85-2.00 (2H, m), 1.73 (6H, s), 1.6 (3H, s), 0.90 (9H, s), 0.87 (6H, s).

The other isomer (Isomer 2 from Step 7) was prepared from (R or S)-3-hydroxy-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid (Isomer 1 from Step 6) using a similar procedure as described above. LCMS (ESI) calculated for C$_{24}$H$_{38}$F$_3$N$_2$O$_6$Si [M+H]$^+$: 535. found: 535. $^1$H NMR (400 MHz, CHCl$_3$-d): δ 6.70-6.75 (1H, m), 6.50-6.60 (1H, m), 6.30-6.38 (2H, m), 4.15-4.20 (1H, m), 3.56-3.75 (2H, m), 3.20-3.25 (1H, m), 2.95-3.10 (2H, m), 1.90-2.00 (1H, m), 1.75-1.85 (1H, m), 1.45-1.65 (8H, m), 0.79 (9H, s), 0.00 (6H, s).

Step 8—Preparation of (R)-3-((tert-butyldimethylsilyl)oxy)-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid and (S)-3-((tert-butyldimethylsilyl)oxy)-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid Step 9—Preparation of (R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid and (S)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid

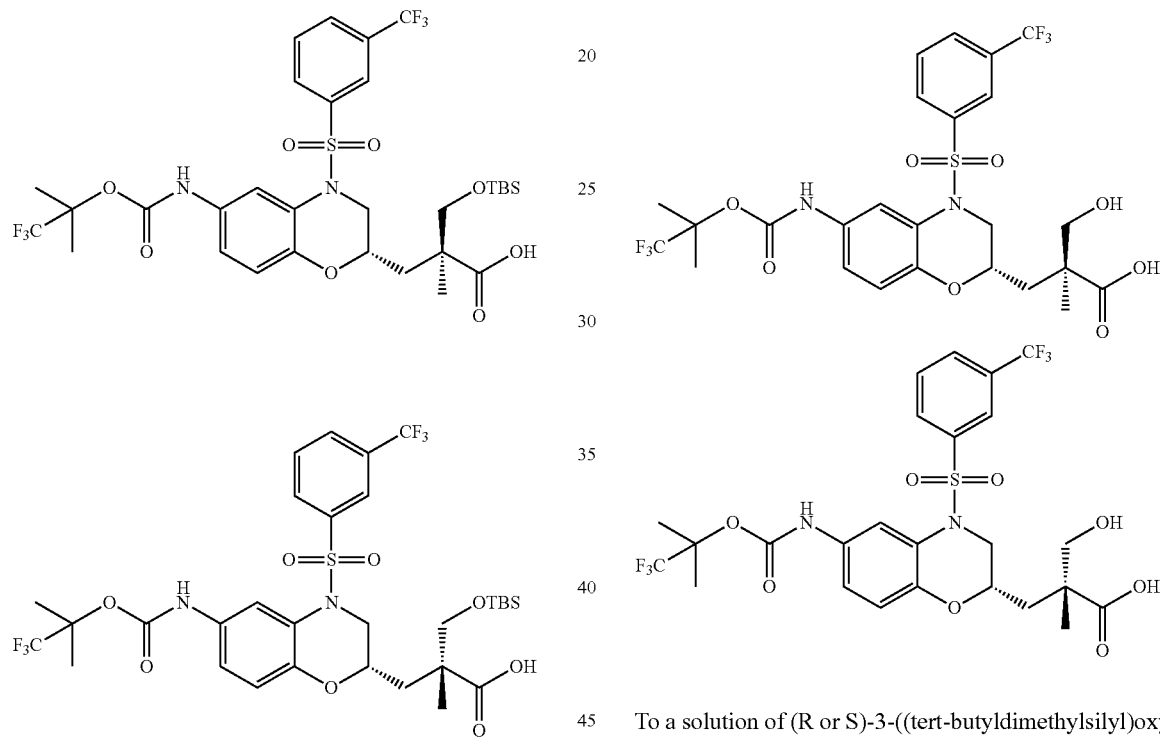

To a solution of (S or R)-3-((tert-butyldimethylsilyl)oxy)-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid (Isomer 1 from Step 7, 22 mg, 0.041 mmol) in THF (1.0 mL) was added 3-(trifluoromethyl)benzene-1-sulfonyl chloride (30 mg, 0.123 mmol) and pyridine (1.0 mL). The reaction mixture was stirred at 15° C. for 24 h, then concentrated in vacuo and the crude product was purified by basic prep-HPLC (MeCN/water using NH4OH buffer) to afford the title compound (Isomer 1 from Step 8) as a white solid. LCMS (ESI) calculated for $C_{31}H_{41}F_6N_2O_8SSi$ [M+H]+: 743. found: 743.

The other isomer (Isomer 2 from Step 8) was prepared from (S or R)-3-((tert-butyldimethylsilyl)oxy)-2-methyl-2-(((S)-6-((((1,1,1-trifluoro-2-methylpropan-2-yl)oxy)carbonyl)amino)-3,4-dihydro-2H-benzo[b][1,4]oxazin-2-yl)methyl)propanoic acid (Isomer 2 from Step 7) using a similar procedure as described above. LCMS (ESI) calculated for $C_{31}H_{41}F_6N_2O_8SSi$ [M+H]+: 743. found: 743.

To a solution of (R or S)-3-((tert-butyldimethylsilyl)oxy)-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid (Isomer 1 from Step 8; 11 mg, 0.015 mmol) in 1,4-dioxane (0.5 mL) was added 4 M HCl/dioxane (0.5 mL). The reaction mixture was stirred at 25° C. for 1 h, then concentrated to dryness. The crude product was purified by prep-HPLC (MeCN/water using TFA buffer) to afford Example No. 17A, (Isomer 1) as a white solid. LCMS(ESI) calculated for $C_{25}H_{25}F_6N_2O_8S$ [M–H]−: 627. found: 627. $^1$H NMR (400 MHz, Methanol-d4): δ 8.00-8.10 (1H, m), 7.96-7.90 (2H, m), 7.70-7.75 (1H, m), 6.90-7.00 (1H, m), 6.60-6.68 (1H, m), 4.30-4.38 (1H, m), 3.55-3.65 (2H, m), 3.40-3.50 (1H, m), 3.20-3.30 (1H, m), 1.90-2.00 (1H, m), 1.75 (6H, s), 1.55-1.65 (1H, m), 1.06 (3H, s).

The other isomer Example No. 17B, (Isomer 2) was prepared from (S or R)-3-((tert-butyldimethylsilyl) oxy)-2-methyl-2-(((S)-6-((((1,1,1-trifluoro-2-methylpropan-2-yl)- oxy)carbonyl)amino)-4-((3-(trifluoromethyl)phenyl)sulfonyl)-3,4-dihydro-2H-benzo[b][1,4]oxazin-2-yl)methyl)propanoic acid (Isomer 2 from Step 8) using a similar procedure as described above. LCMS (ESI) calculated for $C_{25}H_{26}F_6N_2O_8SNa$ [M+Na]$^+$: 651. found: 651. $^1$H NMR (400 MHz, Methanol-d4): δ 8.00-8.15 (2H, m), 7.96-7.90 (1H, m), 7.70-7.80 (1H, m), 7.00-7.05 (1H, m), 6.65-6.75 (1H, m), 4.40-4.48 (1H, m), 3.54 (3H, s), 3.20-3.38 (1H, m), 1.85-1.92 (1H, m), 1.75 (6H, s), 1.55-1.75 (1H, m), 1.09 (3H, s).

Example 18

Preparation of Additional α-Hydroxypropanoic and α-Hydroxymethylpropanoic Acid-Substituted Benzoxazines The compounds in Table 6 were prepared based on the experimental procedures described in Examples 15, 16, and 17, and can be achieved by one of skill in the art in light of the present disclosure.

TABLE 6

| Ex. No. | Structure | Name | Observed m/z |
|---|---|---|---|
| 18A | 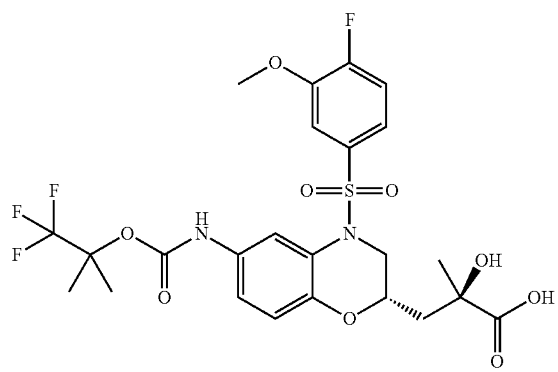 [SMILES: COc1cc(S(=O)(=O)N2C[C@H](C[C@@](C)(O)C(=O)O)Oc3ccc(NC(=O)OC(C)(C)C(F)(F)F)cc32)ccc1F] | (R or S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid | 595 (M + H)+ |
| 18B | 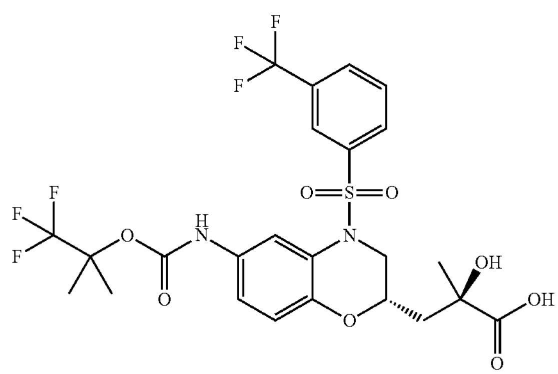 [SMILES: CC(C)(OC(=O)Nc1ccc2c(c1)N(S(=O)(=O)c1cccc(C(F)(F)F)c1)C[C@H](C[C@@](C)(O)C(=O)O)O2)C(F)(F)F] | (R or S)-2-hydroxy-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 615 (M + H)+ |
| 18C | 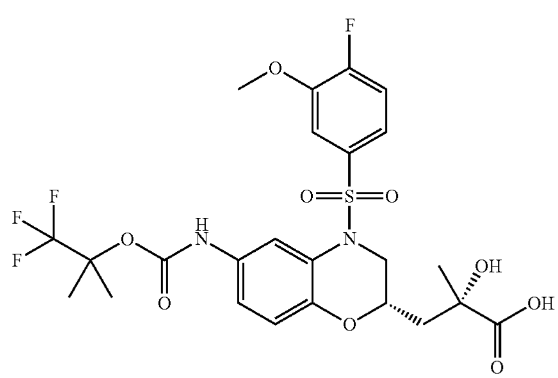 [SMILES: COc1cc(S(=O)(=O)N2C[C@H](C[C@](C)(O)C(=O)O)Oc3ccc(NC(=O)OC(C)(C)C(F)(F)F)cc32)ccc1F] | (R or S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid | 595 (M + H)+ |

TABLE 6-continued

| Ex. No. | Structure | Name | Observed m/z |
|---|---|---|---|
| 18D | 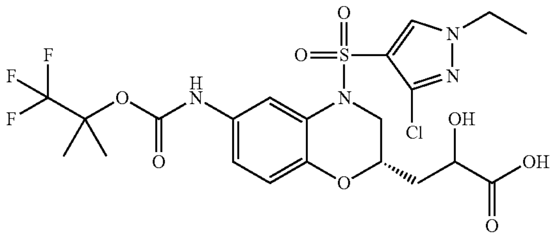 [SMILES: CCn1cc(S(=O)(=O)N2C[C@H](CC(O)C(=O)O)Oc3ccc(NC(=O)OC(C)(C)C(F)(F)F)cc32)c(Cl)n1] | (R and S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid | 585 (M + H)+ |
| 18E | 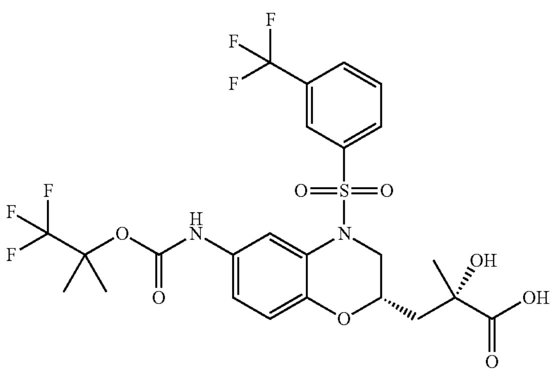 [SMILES: CC(C)(OC(=O)Nc1ccc2c(c1)N(S(=O)(=O)c1cccc(C(F)(F)F)c1)C[C@H](C[C@](C)(O)C(=O)O)O2)C(F)(F)F] | (R or S)-2-hydroxy-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid | 615 (M + H)+ |
| 18F | 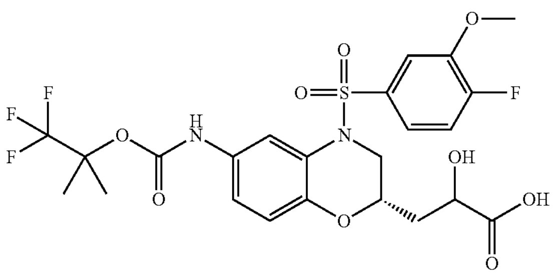 [SMILES: COc1cc(S(=O)(=O)N2C[C@H](CC(O)C(=O)O)Oc3ccc(NC(=O)OC(C)(C)C(F)(F)F)cc32)ccc1F] | (R and S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid | 603 (M + Na)+ |
| 18G | 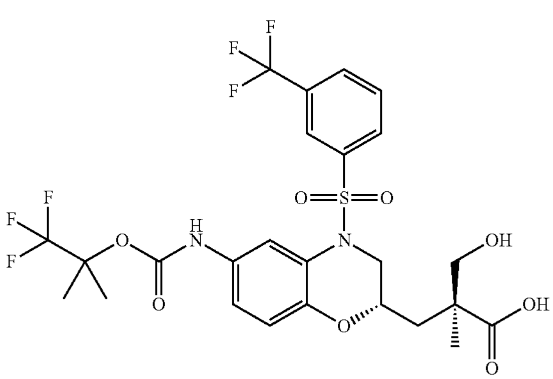 | (S or R)-3-hydroxy-2-methyl-2-((((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid | 629 (M + H)+ |

TABLE 6-continued

| Ex. No. | Structure | Name | Observed m/z |
|---|---|---|---|
| 18H | 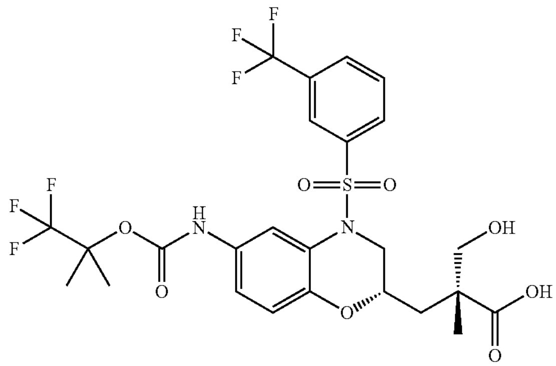 | (S or R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid | 629 (M + H)+ |
| 18i | 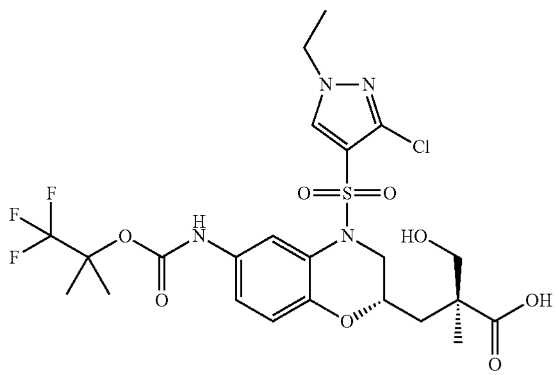 | (S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid | 614 (M + H)+ |
| 18J | 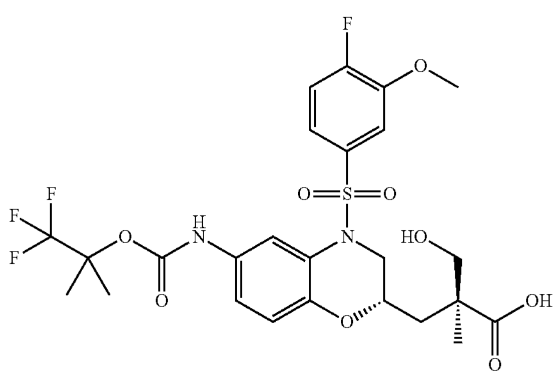 | (S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid | 609 (M + H)+ |
| 18K | 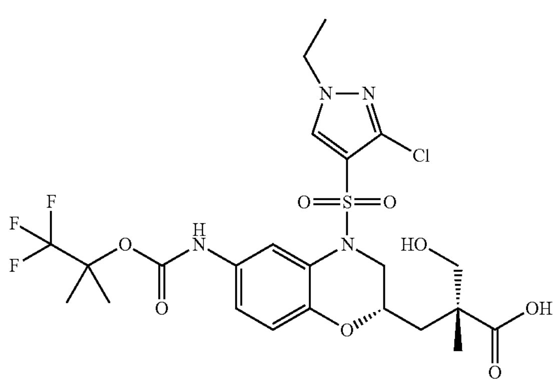 | (S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid | 611 (M − H)− |

TABLE 6-continued

| Ex. No. | Structure | Name | Observed m/z |
|---|---|---|---|
| 18L | 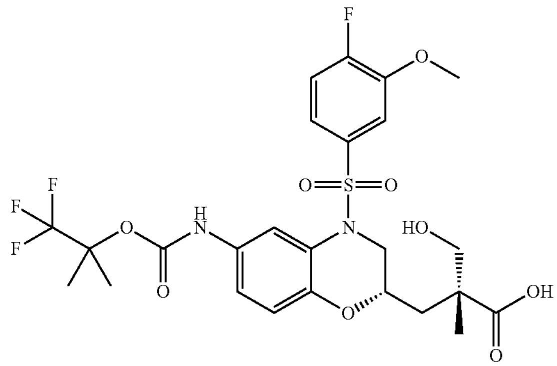 | (S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid | 607 (M − H)− |

Example 19

Preparation of (R)-3-((S)-4-((4-fluoro-3-(trifluoromethyl) phenyl)sulfonyl)-6-((((1,1,1-trifluoro-2-methylpropan-2-yl)oxy)carbonyl)amino)-3,4-dihydro-2H-benzo[b][1,4]oxazin-2-yl)butanoic acid and (S)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)butanoic acid (Example Nos. 19A and 19B)

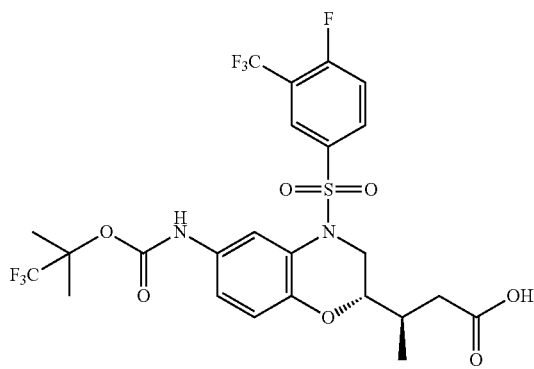

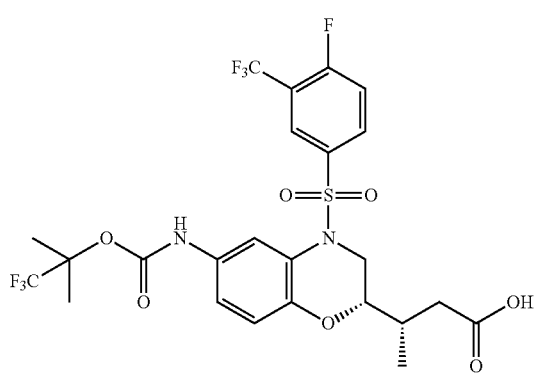

Step 1—Preparation of (R)-1,1,1-trifluoro-2-methylpropan-2-yl (2-acetyl-4-benzyl-3,4-dihydro-2H-benzo[b][1,4]oxazin-6-yl)carbamate A solution of (R)-1,1,1-trifluoro-2-methylpropan-2-yl(4-benzyl-2-(methoxy(methyl)carbamoyl)-3,4-dihydro-2H-benzo[b][1,4]oxazin-6-yl)carbamate (2 g, 4.15 mmol) in anhydrous THF (20 mL) was cooled to −70° C. under $N_2$. Methylmagnesium bromide (6.92 mL, 20.71 mmol, 3.0 M in diethyl ether) was added dropwise at −65° C. and the reaction stirred for 2 h. Upon completion, the reaction was poured into an ice solution of $NH_4Cl$ and the resulting mixture extracted with EtOAc. The combined organic layer was washed with brine, dried over $Na_2SO_4$ and concentrated. The crude product was purified by column chromatography (petroleum ether:EtOAc=10:1) to give the title compound as a light yellow solid. $^1$H NMR (400 MHz, $CDCl_3$) δ 7.31-7.38 (2H, m), 7.29 (1H, d, J=6.65 Hz, 1H), 7.22-7.26 (2H, m), 6.88 (1H, d, J=8.61 Hz), 6.77 (1H, brs), 6.69 (1H, d, J=6.26 Hz), 6.44 (1H, br s), 4.57 (1H, t, J=4.11 Hz), 4.35-4.48 (2H), 3.43 (2H, d, J=4.30 Hz), 2.24-2.29 (3H, m), 1.73 (6H, s).

Step 2—Preparation of (S,E)-methyl 3-(4-benzyl-6-((((1,1,1-trifluoro-2-methylpropan-2-yl)oxy)carbonyl)amino)-3,4-dihydro-2H-benzo[b][1,4]oxazin-2-yl)but-2-enoate To a solution of methyl 2-(dimethoxyphosphoryl)acetate (2.9 g, 16.09 mmol) in THF (26 mL) was added in portions NaH (453 mg, 11.32 mmol, 60% in the mineral oil). After 20 minutes, a solution of (R)-1, 1, 1-trifluoro-2-methylpropan- 2-yl(2-acetyl-4-benzyl-3,4-dihydro-2H-benzo[b][1,4]oxazin-6-yl)carbamate (1.3 g, 2.98 mmol) in THF (26 mL) was slowly added to the above mixture at 0° C. The resulting solution was stirred at room temperature for 2 h, then diluted with water and extracted with EtOAc. The combined organic layer was dried over $Na_2SO_4$ and concentrated. The crude product was purified by column chromatography (petroleum ether:EtOAc=10:1) to afford the title compound as a light yellow solid. $^1H$ NMR (400 MHz, $CDCl_3$) δ 7.14-7.26 (5H, m), 6.67-6.79 (2H, m), 6.56-6.63 (1H, m), 6.38 (1H, br s), 5.97 (1H, s), 5.64-5.74 (1H, m), 4.30-4.49 (3H, m), 3.57-3.63 (3H, m), 3.23-3.30 (1H, m), 2.98-3.15 (1H, m), 2.04 (2H, s), 1.91 (1H, s), 1.64 (6H, s).

Step 3—Preparation of (R)-methyl 3-((S)-6-((((1,1,1-trifluoro-2-methylpropan-2-yl)oxy)carbonyl)amino)-3,4-dihydro-2H-benzo[b][1,4]oxazin-2-yl)butanoate and (S)-methyl 3-((S)-6-((((1,1,1-trifluoro-2-methylpropan-2-yl)oxy)carbonyl)amino)-3,4-dihydro-2H-benzo[b][1,4]oxazin-2-yl)butanoate

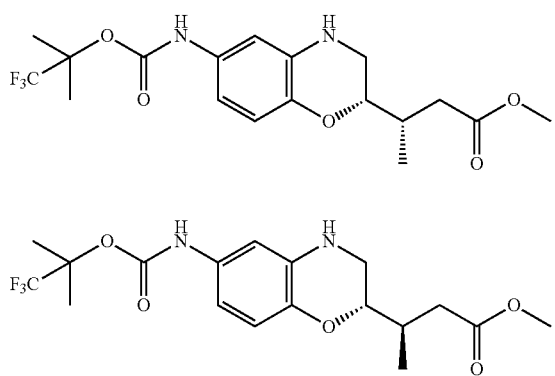

A mixture of (S,E)-methyl 3-(4-benzyl-6-((((1,1,1-trifluoro-2-methylpropan-2-yl)oxy)carbonyl)amino)-3,4-dihydro-2H-benzo[b][1,4]oxazin-2-yl)but-2-enoate (40 mg, 0.08 mmol) and Pd/C (55 mg, 0.46 mmol) in EtOAc (2 mL) was stirred under $H_2$ balloon at room temperature for 3 h. The mixture was filtered and concentrated. The crude product was purified by prep-TLC (petroleum ether:EtOAc=3:1) to afford the title as a light yellow solid.

The two isomers were separated by chiral SFC using Chiralcel OD-H 250×4.6 mm I.D., (Sum) eluted with ethanol (0.05% DEA) in $CO_2$ from 5% to 40% (Flow rate: 2.35 mL/min Wavelength: 220 nm). Isomer 1 (faster-eluting peak): $^1H$ NMR (400 MHz, $CDCl_3$) δ 6.83 (1H, br s), 6.70 (1H, d, J=8.2 Hz), 6.41-6.50 (2H, m), 3.95-4.00 (1H, m), 3.69 (3H, s), 3.28-3.33 (1H, m), 3.18-3.24 (1H, m), 2.60 (1H, dd, J=5.1, 14.9 Hz), 2.27-2.42 (2H, m), 1.74 (6H, s), 1.07 (3H, d, J=6.7 Hz). Isomer 2 (slower-eluting peak): $^1H$ NMR (400 MHz, $CDCl_3$) δ 6.84 (1H, br s), 6.68 (1H, d, J=8.6 Hz), 6.41-6.49 (2H, m), 3.83 (1H, t, J=6.7 Hz), 3.69 (3H, s), 3.42 (1H, d, J=11.4 Hz), 3.16 (1H, dd, J=8.2, 11.4 Hz), 2.77 (1H, d, J=11.0 Hz), 2.24-2.32 (2H, m), 1.74 (6H, s), 1.05 (3H, d, J=6.3 Hz).

Step 4—Preparation of (R)-3-((S)-6-((((1,1,1-trifluoro-2-methylpropan-2-yl)oxy)carbonyl)amino)-3,4-dihydro-2H-benzo[b][1,4]oxazin-2-yl)butanoic acid and (R)-3-((S)-6-((((1,1,1-trifluoro-2-methylpropan-2-yl)oxy)carbonyl)amino)-3,4-dihydro-2H-benzo[b][1,4]oxazin-2-yl)butanoic acid

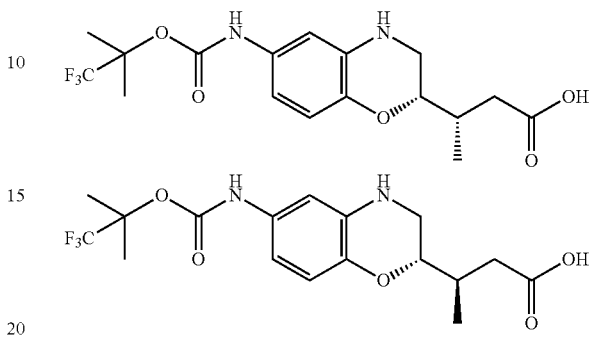

A solution of (R or S)-methyl 3-((S)-6-((((1,1,1-trifluoro-2-methylpropan-2-yl)oxy)carbonyl)amino)-3,4-dihydro-2H-benzo[b][1,4]oxazin-2-yl)butanoate (Isomer 1 from Step 3, 10 mg, 0.025 mmol) and $LiOH \cdot H_2O$ (5 mg, 0.124 mmol) in dioxane/$H_2O$ (1 mL/1 mL) was stirred at 0° C. for 4 h. Upon completion, the reaction was adjusted to pH=~3 with 1N HCl and extracted 3×EtOAc. The combined organic layers were dried over $Na_2SO_4$, filtered and the solvent evaporated under reduced pressure. The crude product was purified by prep-TLC (petroleum ether:EtOAc=1:1) to afford the title compound (Isomer 1 from Step 4) as a light yellow solid. LCMS (ESI) calculated for $C_{17}H_{22}F_3N_2O_5$ [M+H]$^+$: 391. found: 391. $^1H$ NMR (400 MHz, $CDCl_3$) δ 6.86 (1H, br s), 6.72 (1H, d, J=8.6 Hz), 6.46 (2H, br s), 4.02 (1H, br s), 3.37-3.19 (2H, m), 2.67 (1H, d, J=10.6 Hz), 2.44-2.30 (2H, m), 1.74 (6H, s), 1.11 (3H, d, J=6.7 Hz). The other isomer (Isomer 2 from Step 4) was prepared using the similar procedure from Isomer 2 from Step 3. LCMS (ESI) calculated for $C_{17}H_{22}F_3N_2O_5$ [M+H]$^+$: 391. found: 391. $^1H$ NMR (400 MHz, $CDCl_3$) δ 6.85 (1H, br s), 6.69 (1H, d, J=8.6 Hz), 6.39-6.50 (2H, m), 3.86 (1H, br s), 3.44 (1H, d, J=11.3 Hz), 3.18 (1H, dd, J=8.0, 11.2 Hz), 2.82 (1H, d, J=11.3 Hz), 2.29-2.37 (2H, m), 1.74 (6H, s), 1.09 (3H, d, J=5.9 Hz).

Step 5—Preparation of (R)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)butanoic acid and (S)-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)butanoic acid

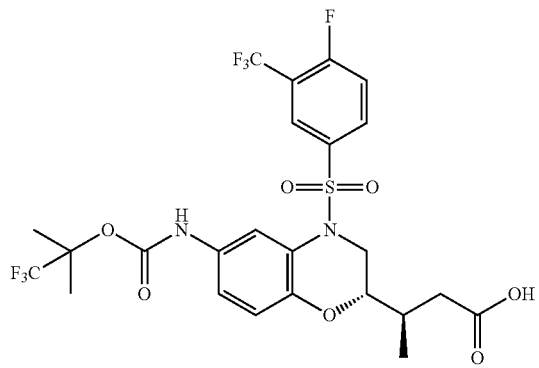

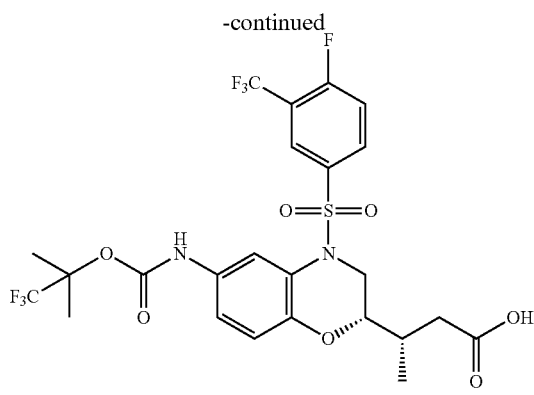

To a solution of (R or S)-3-((S)-6-((((1,1,1-trifluoro-2-methylpropan-2-yl)oxy)carbonyl)amino)-3,4-dihydro-2H-benzo[b][1,4]oxazin-2-yl)butanoic acid (Isomer 1 from Step 4, 7 mg, 0.018 mmol) and pyridine (1 drop) in anhydrous THF (2 mL) was added 4-fluoro-3-(trifluoromethyl)benzene-1-sulfonyl chloride (14 mg, 0.054 mmol). The reaction was stirred at room temperature for 4 h, then quenched with water and extracted with EtOAc. The combined organic layers were dried over $Na_2SO_4$, filtered and the solvent evaporated under reduced pressure. The crude product was purified by prep-HPLC (MeCN/water using TFA buffer) to obtain Example No. 19A (Isomer 1) as a light yellow solid. LCMS (ESI) calculated for $C_{24}H_{23}F_7N_2O_7SNa$ [M+Na]$^+$: 639. found: 639. $^1$H NMR (400 MHz, $CD_3OD$) δ 7.96-8.13 (3H, m), 7.52 (1H, t, J=9.4 Hz), 6.99 (1H, dd, J=2.2, 8.8 Hz), 6.75 (1H, d, J=8.6 Hz), 4.42 (1H, d, J=14.1 Hz), 3.52 (1H, d, J=9.4 Hz), 3.32 (1H, br s, 1H), 2.41-2.52 (1H, m), 2.18-2.28 (2H, m), 1.75 (6H, s), 0.99 (3H, d, J=6.3 Hz). The other isomer, Example No. 19B, (Isomer 2) was prepared using a similar procedure from Isomer 2 from Step 4. LCMS (ESI) calculated for $C_{24}H_{23}F_7N_2O_7SNa$ [M+Na]$^+$: 639. found: 639. $^1$H NMR (400 MHz, $CD_3OD$) δ 7.97-8.15 (3H, m), 7.52 (1H, t, J=9.4 Hz), 6.93-6.99 (1H, m), 6.73 (1H, d, J=9.0 Hz), 4.39 (1H, d, J=12.5 Hz), 3.37 (2H, d, J=19.2 Hz), 2.48-2.58 (1H, m), 2.11-2.24 (2H. m), 1.73 (6H, s), 1.02 (3H, d, J=6.3 Hz).

Example 20

Preparation of (R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-3-cyclopropylpropanoic acid and (S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-3-cyclopropylpropanoic acid (Example Nos. 20A and 20B)

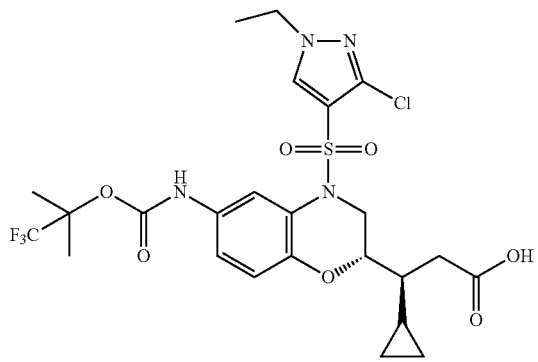

Step 1—Preparation of (R)-1,1,1-trifluoro-2-methylpropan-2-yl(4-benzyl-2-(cyclopropanecarbonyl)-3,4-dihydro-2H-benzo[b][1,4]oxazin-6-yl)carbamate

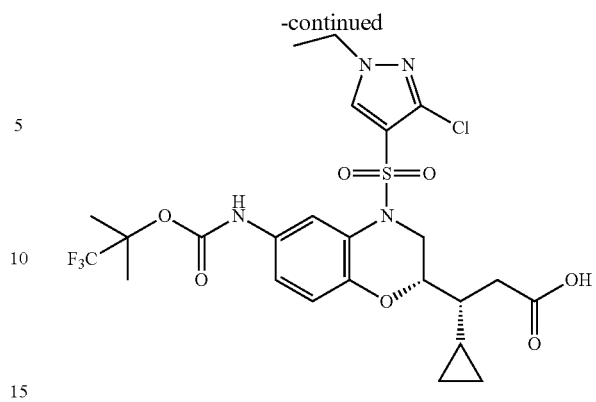

To a solution of (R)-1,1,1-trifluoro-2-methylpropan-2-yl (4-benzyl-2-(methoxy(methyl)carbamoyl)-3,4-dihydro-2H-benzo[b][1,4]oxazin-6-yl)carbamate (5 g, 10.38 mmol) in THF (10 mL) was added cyclopropylmagnesium bromide (20.8 mmol) dropwise at −60° C. and the reaction stirred for 1 h, then poured into ice solution of $NH_4Cl$ (25 mL) and extracted with EtOAc (20 mL×3). The organic layer was concentrated under vacuum and the crude product purified by column chromatography on silica gel (petroleum ether:EtOAc=10:1) to give the title compound as a white solid. $^1$H NMR (400 MHz, $CDCl_3$): 7.17-7.28 (5H, m), 6.82 (1H, d, J=8.6 Hz), 6.65 (2H, d, J=14.9 Hz), 6.39 (1H, br s), 4.63 (1H, t, J=4.3 Hz), 4.25-4.42 (2H, m), 3.39 (2H, d, J=4.3 Hz), 2.31-2.41 (1H, m), 1.64 (7H, s), 1.05 (1H, dd, J=2.0, 4.7 Hz), 0.84-1.00 (3H, m, 3H).

Step 2—Preparation of (S,E)-methyl 3-(4-benzyl-6-((((1,1,1-trifluoro-2-methylpropan-2-yl)oxy)carbonyl)amino)-3,4-dihydro-2H-benzo[b][1,4]oxazin-2-yl)-3-cyclopropylacrylate

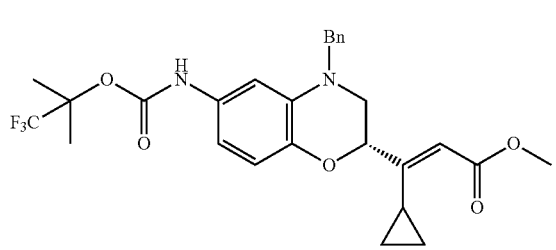 [SMILES: COC(=O)/C=C(\C1CC1)[C@H]1CN(Cc2ccccc2)c2cc(NC(=O)OC(C)(C)C(F)(F)F)ccc2O1]

To a solution of methyl 2-(dimethoxyphosphoryl) acetate (2.1 g, 11.7 mmol) in 15 mL of THF was added sodium hydride (197 mg, 8.22 mmol, 60% in mineral oil) in portions at 0° C. Then the reaction was stirred at 0° C. for 0.5 h, followed by the addition of (R)-1,1,1-trifluoro-2-methylpropan-2-yl(4-benzyl-2-(cyclopropanecarbonyl)-3,4-dihydro-2H-benzo[b][1,4]oxazin-6-yl)carbamate (1 g, 2.16 mmol) in 5 mL of THF slowly at 0° C. The reaction was stirred at 25° C. for 16 h, then quenched with H₂O and extracted with EtOAc. The organic layer was dried and concentrated. The crude product was purified by silica gel column chromatography (petroleum ether:EtOAc=10:1) to give the title compound as a colorless oil. ¹H NMR (400 MHz, CDCl₃): 7.33 (4H, d, J=3.9 Hz), 7.24-7.28 (1H, m), 6.80 (1H, d, J=8.6 Hz), 6.69 (2H, br s), 6.41 (1H, br s), 5.88 (1H, t, J=5.3 Hz), 5.39 (1H, s) 4.36-4.58 (2H, m) 3.63 (3H, s) 3.34 (2H, d, J=5.5 Hz), 1.83-1.91 (1H, m), 1.70 (6H, s), 0.81-0.98 (2H, m), 0.68-0.78 (1H, m), 0.43-0.51 (1H, m).

Step 3—Preparation of (S)-methyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-3-cyclopropylpropanoate and (R)-methyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-3-cyclopropylpropanoate

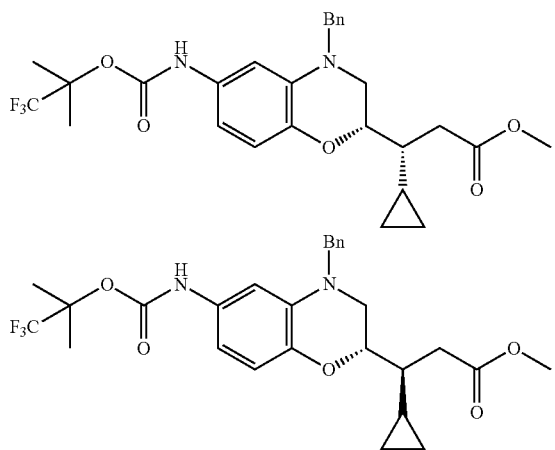

To a solution of (S,E)-methyl 3-(4-benzyl-6-((((1,1,1-trifluoro-2-methylpropan-2-yl)oxy)carbonyl)amino)-3,4-dihydro-2H-benzo[b][1,4]oxazin-2-yl)-3-cyclopropylacrylate (200 mg, 0.386 mmol) in 10 mL of MeOH was added NiCl₂ (56.9 mg, 0.386 mmol) slowly at room temperature (15° C.). The mixture was stirred for 0.5 h, followed by the slow addition of NaBH₄ (14.6 mg, 0.386 mmol). The reaction was stirred for 2 h, then quenched with H₂O and extracted with 3×EtOAc. The organic layer was dried and concentrated. The crude product was purified by silica gel column chromatography (petroleum ether:EtOAc=50:1) to give the title mixture as a colorless oil.

Two isomers were separated by SFC method (Column: OJ 300 mm*50 mm, 10 µm; Mobile phase: 20% IPA, NH₃.H₂O at 200 mL/min). Isomer 1 (faster-eluting peak): ¹HNMR (400 MHz, CDCl₃) δ 7.13-7.21 (5H, m), 6.50-6.56 (3H, m), 6.24 (1H, br s), 4.24-4.38 (2H, m), 3.90-4.00 (1H, m), 3.53 (3H, s), 3.38 (1H, s), 3.05-3.15 (1H, m), 2.56 (1H, dd, J=10.8 Hz, 6.0 Hz), 2.40 (1H, dd, J=10.8 Hz, 6.0 Hz), 1.56 (6H, s), 1.20-1.32 (1H, m), 0.52-0.62 (1H, m), 0.32 (2H, d, J=7.6 Hz), 0.01 (2H, d, J=7.6 Hz). Isomer 2 (slower-eluting peak): ¹HNMR (400 MHz, CDCl₃) δ 7.15-7.36 (5H, m), 6.60-6.70 (3H, m), 6.42 (1H, br s), 4.35-4.50 (2H, m), 4.19 (1H, d, J=8.4 Hz), 3.60 (3H, s), 3.42-3.48 (1H, m), 3.16 (1H, d, J=12.0 Hz), 2.66 (1H, dd, J=11.2 Hz, 7.2 Hz), 2.40 (1H, dd, J=8.8 Hz, 6.4 Hz), 1.65 (6H, s), 1.43-1.50 (1H, m), 0.64-0.68 (1H, m), 0.35-0.50 (2H, m), 0.00-0.015 (2H, m).

Step 4—Preparation of (S)-methyl 3-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoate and (R)-methyl 3-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoate

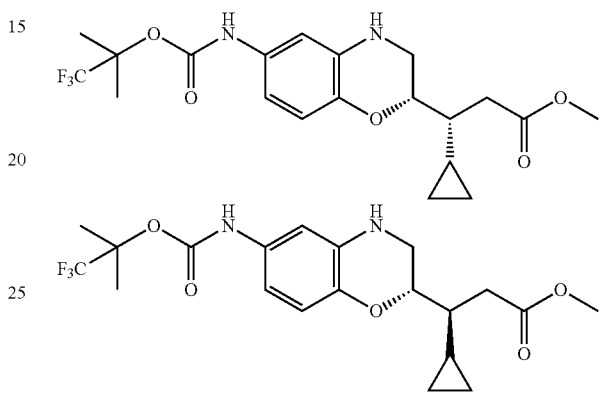

To a solution of (S or R)-methyl 3-((S)-4-benzyl-6-((((1,1,1-trifluoro-2-methylpropan-2-yl)oxy)carbonyl)amino)-3,4-dihydro-2H-benzo[b][1,4]oxazin-2-yl)-3-cyclopropylpropanoate (Isomer 1 from Step 3, 500 mg, 0.961 mmol) in EtOAc (30 mL) was added Pd/C (15 mg, 0.141 mmol). The reaction mixture was stirred under 1 atm of H₂ at 25° C. for 12 h, then filtered through a pad of CELITE and concentrated. The crude product was purified by flash column chromatography on silica gel (petroleum ether:ethyl acetate=3:1) to give the title compound (S or R)-methyl 3-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoate (Isomer 1 from Step 4) as a yellow solid. LCMS (ESI) calculated for C₂₀H₂₆F₃N₂O₅ [M+H]⁺: 431. found: 431.

The other isomer (Isomer 2 from Step 4) was prepared using a similar procedure from Isomer 2 from Step 3. LCMS (ESI) calculated for C₂₀H₂₆F₃N₂O₅ [M+H]⁺: 431. found: 431.

Step 5—Preparation of (S)-3-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid) and (R)-3-cyclopropyl-3-((S)-6-((((1,1,1-trifluoro-2-methylpropan-2-yl)oxy)carbonyl)amino)-3,4-dihydro-2H-benzo[b][1,4]oxazin-2-yl)propanoic acid)

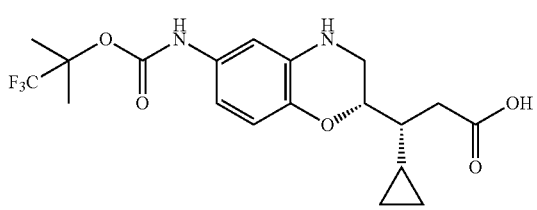

223

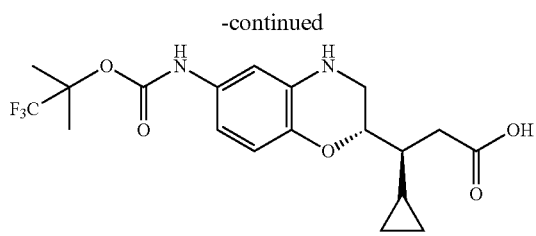

To a solution of (S or R)-methyl 3-cyclopropyl-3-((S)-6-(((((1,1,1-trifluoro-2-methylpropan-2-yl)oxy)carbonyl)amino)-3,4-dihydro-2H-benzo[b][1,4]oxazin-2-yl)propanoate (Isomer 1 from Step 4, 36 mg, 0.084 mmol) in 1,4-dioxane (0.5 mL) was added LiOH (10 mg, 0.418 mmol) in water (0.5 mL) and the reaction mixture was stirred at 25° C. for 2 h. Hydrochloric acid (1M, 5 mL) was added to the reaction mixture and the solution was extracted with ethyl acetate (5 mL×3). The organic layers were separated, combined, dried over anhydrous magnesium sulfate, filtered and concentrated in vacuo to afford the title compound (S or R)-3-cyclopropyl-3-((S)-6-(((((1,1,1-trifluoro-2-methylpropan-2-yl)oxy)carbonyl)amino)-3,4-dihydro-2H-benzo[b][1,4]oxazin-2-yl)propanoic acid) (Isomer 1 from Step 5) as brown oil, which was used directly in the next step without further purification. LCMS (ESI) calculated for $C_{19}H_{24}F_3N_2O_5$ [M+H]$^+$: 417. found: 417.

The other isomer (Isomer 2 from Step 5) was prepared using a similar procedure from Isomer 2 from Step 4. LCMS (ESI) calculated for $C_{19}H_{24}F_3N_2O_5$ [M+H]$^+$: 417. found: 417.

Step 6—Preparation of (R)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-3-cyclopropylpropanoic acid and (S)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-3-cyclopropylpropanoic acid

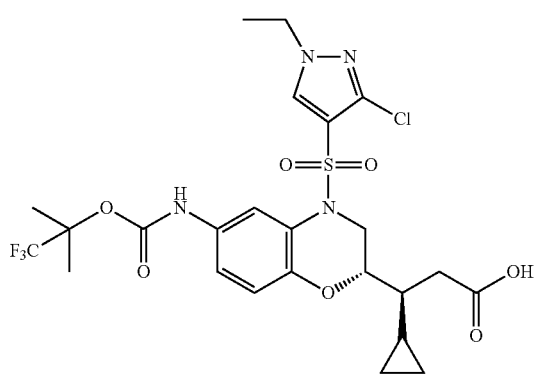

224

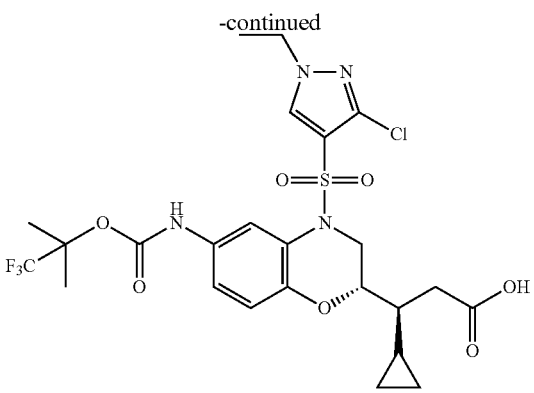

To a solution of (S or R)-3-cyclopropyl-3-((S)-6-(((((1,1,1-trifluoro-2-methylpropan-2-yl)oxy)carbonyl)amino)-3,4-dihydro-2H-benzo[b][1,4]oxazin-2-yl)propanoic acid) (Isomer 1 from Step 5, 26 mg, 0.062 mmol) in tetrahydrofuran (0.5 mL) and pyridine (0.5 mL) was added 3-chloro-1-ethyl-1H-pyrazole-4-sulfonyl chloride (36 mg, 0.157 mmol). The reaction was stirred at 25° C. for 2 h, then diluted with water (3 mL) and extracted with ethyl acetate (2 mL×3). The organic layers combined, dried over anhydrous magnesium sulfate, filtered and concentrated in vacuo. The crude product was purified by prep-HPLC (MeCN/water using TFA buffer) to afford Example No. 20A (R or S)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-3-cyclopropylpropanoic acid (Isomer 1 from Step 6) as a white solid. LCMS (ESI) calculated for $C_{24}H_{29}ClF_3N_4O_7S$ [M+H]$^+$: 609. found: 609. $^1$HNMR (400 MHz, CDCl$_3$) δ 8.91 (1H, d, J=4.4 Hz), 8.09 (1H, br), 7.80-7.92 (2H, m), 6.72-6.85 (2H, m), 6.63 (1H, s), 4.77 (1H, d, J=13.2 Hz), 4.09 (2H, q, J=7.2 Hz), 3.28-3.37 (1H, m), 2.56-2.75 (2H, m), 1.76 (6H, s), 1.46 (4H, t, J=7.2 Hz), 0.81-0.92 (1H, m), 0.64-0.71 (1H, m), 0.54-0.62 (1H, m), 0.24-0.40 (2H, m).

The other isomer, Example No. 20B, (Isomer 2 from Step 6) was prepared using a similar procedure from Isomer 2 from Step 5. LCMS (ESI) calculated for $C_{24}H_{29}ClF_3N_4O_7S$ [M+H]$^+$: 609. found: 609. $^1$HNMR (400 MHz, CDCl$_3$) δ 8.07 (1H, s), 7.88 (1H, br), 6.77-6.90 (2H, m), 6.63 (1H, s), 4.49 (1H, d, J=13.2 Hz), 4.03-4.14 (3H, m), 3.57-3.68 (1H, m), 2.73-2.82 (1H, m), 2.54-2.63 (1H, m), 1.76 (6H, s), 1.51-1.60 (1H, m), 1.46 (3H, t, J=7.2 Hz), 0.79-0.90 (1H, m), 0.51-0.63 (2H, m), 0.18-0.31 (2H, m).

Example 21

Preparation of Additional β-Substituted Propanoic Acids

The compounds in Table 7 were prepared based on the experimental procedures described in Example 20, and can be achieved by one of skill in the art in light of the present disclosure.

TABLE 7

| Ex. No. | Structure | Name | Observed m/z |
|---|---|---|---|
| 21A | 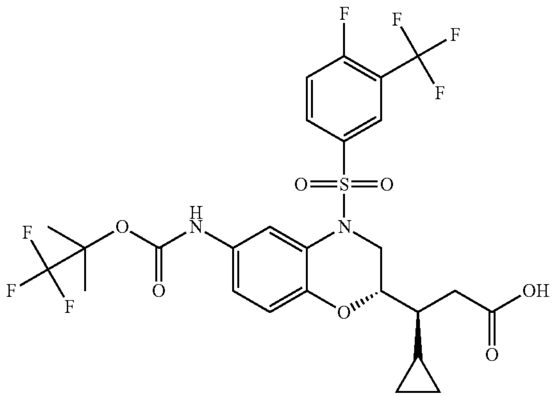 [SMILES: CC(C)(OC(=O)Nc1ccc2c(c1)N(S(=O)(=O)c1ccc(F)c(C(F)(F)F)c1)C[C@H]([C@@H](CC(=O)O)C1CC1)O2)C(F)(F)F] | (S or R)-3-cyclopropyl-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 643 (M + H)+ |
| 21B | 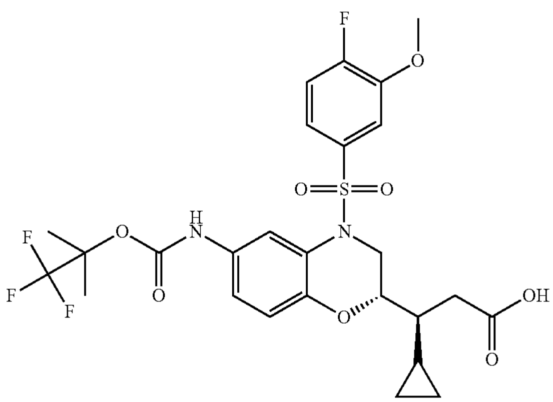 [SMILES: COc1cc(S(=O)(=O)N2C[C@H]([C@@H](CC(=O)O)C3CC3)Oc3ccc(NC(=O)OC(C)(C)C(F)(F)F)cc32)ccc1F] | (S or R)-3-cyclopropyl-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 605 (M + H)+ |
| 21C | 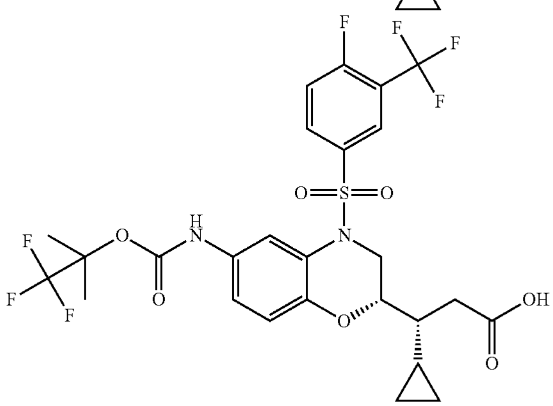 | (S or R)-3-cyclopropyl-3-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 643 (M + H)+ |
| 21D | 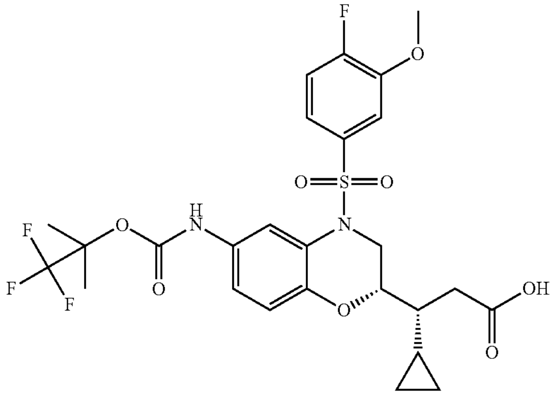 [SMILES: COc1cc(S(=O)(=O)N2C[C@H]([C@H](CC(=O)O)C3CC3)Oc3ccc(NC(=O)OC(C)(C)C(F)(F)F)cc32)ccc1F] | (S or R)-3-cyclopropyl-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid | 605 (M + H)+ |

Example 22

Preparation of (1R,2S)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid, (1S,2R)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid, (1R,2R)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid and (1S,2S)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid (Example Nos. 22A, 22B, 22C, and 22D)

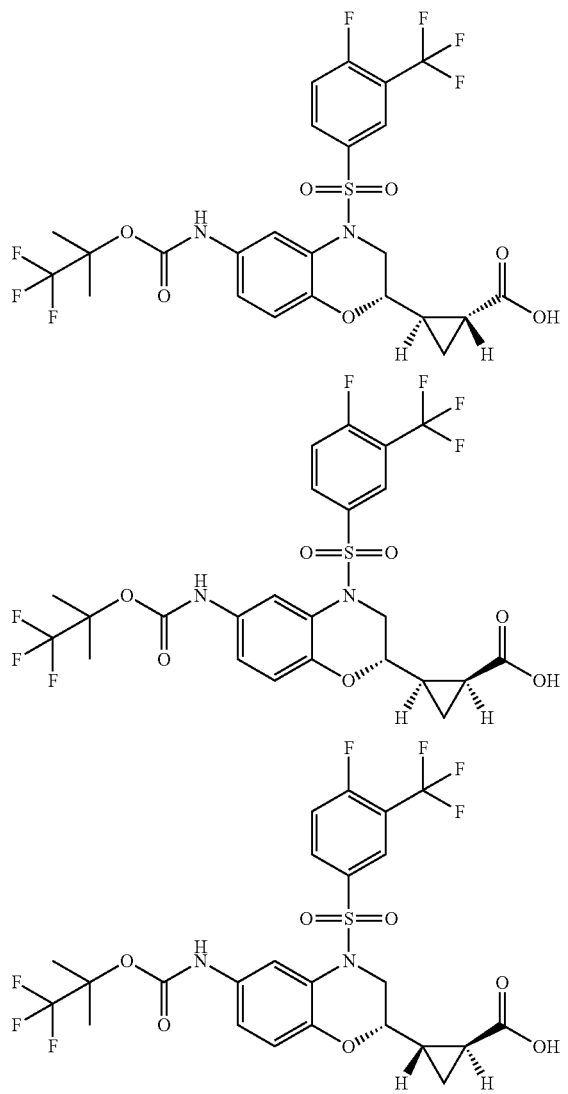

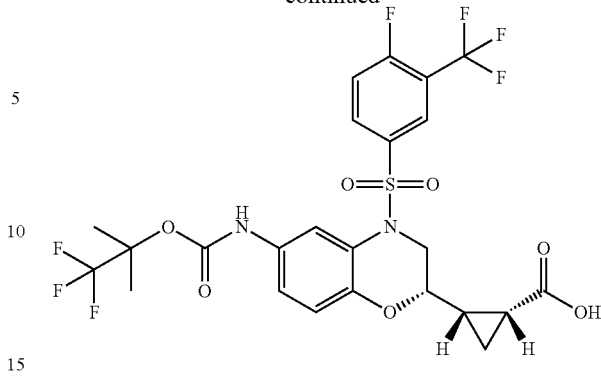

Step 1—Preparation of ethyl 2-(oxiran-2-yl)cyclopropanecarboxylate

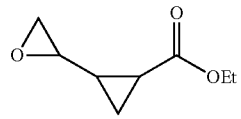 [SMILES: CCOC(=O)C1CC1C1CO1]

Sodium hydride (169 mg, 4.22 mmol, 60% in mineral oil) was added to the solution of trimethylsulfonium iodide (861 mg, 4.22 mmol) in THF (10 mL) and DMSO (10 mL) at 0° C., and the resulting mixture stirred at 0° C. for 10 mins, followed by the addition of ethyl 2-formylcyclopropanecarboxylate (500 mg, 3.52 mmol). The reaction was stirred for another 1 h, quenched with aqueous NH$_4$Cl and extracted with petroleum ether (30 mL×2). The combined organic layers were washed with brine, dried and concentrated to afford the title crude compound as colorless oil, which was used in the next step without further purification. LCMS (ESI) calculated for C$_8$H$_{13}$O$_3$ [M+H]$^+$: 157. found: 157, $^1$H NMR (400 MHz, CDCl$_3$) δ 4.11 (2H, d, J=7.0 Hz,), 2.99-2.78 (1H, m), 2.78-2.70 (1H, m), 2.58-2.47 (1H, m), 1.69-1.59 (2H, m), 1.30-1.17 (3H, m), 1.11-1.04 (1H, m), 0.85 (2H, s).

Step 2—Preparation of ethyl 2-(6-nitro-4-tosyl-3,4-dihydro-2H-benzo[b][1,4]oxazin-2-yl)cyclopropanecarboxylate as a mixture of diastereomers

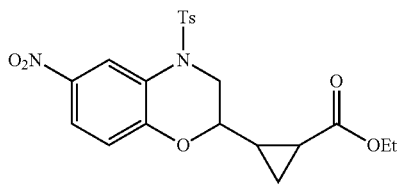

Benzyltriethylammonium chloride (102 mg, 0.448 mmol) and N-(2-fluoro-5-nitrophenyl)-4-methylbenzenesulfonamide (1391 mg, 4.48 mmol) were added to a solution of potassium carbonate (743 mg, 5.38 mmol) and ethyl 2-(oxiran-2-yl) cyclopropanecarboxylate (700 mg, 4.48 mmol) in dioxane (0.2 mL). The reaction was stirred at 90° C. for 16 h, then cooled to room temperature and dissolved in EtOAc (20 mL). The organic layer was washed with water and brine, dried and concentrated and the crude product purified by chromatography on silica gel eluting with 30% EtOAc in petroleum ether to afford the title compound as a yellow solid. LCMS (ESI) calculated for $C_{21}H_{23}N_2O_7S$ [M+H]$^+$: 448. found: 448, $^1$H NMR (400 MHz, DMSO-d$_6$) δ 8.51-8.56 (1H, m), 7.92-8.04 (1H, m), 7.70-7.78 (2H, m), 7.41-7.50 (2H, m), 7.11-7.18 (1H, m), 4.35-4.44 (1H, m), 4.04-4.19 (2H, m), 3.54-3.66 (1H, m), 2.40 (3H, s), 1.82-1.92 (1H, m), 1.64-1.72 (1H, m), 1.24 (3H, s), 0.99-1.15 (2H, m).

Step 3—Preparation of 2-(6-amino-4-tosyl-3,4-dihydro-2H-benzo[b][1,4]oxazin-2-yl) cyclopropanecarboxylate as a mixture of diastereomers

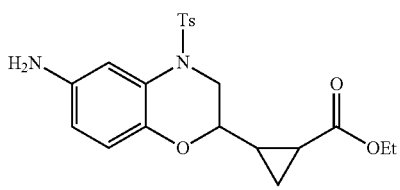 [SMILES: CCOC(=O)C1CC1C1CN(S(=O)(=O)c2ccc(C)cc2)c2cc([N+](=O)[O-])ccc2O1]

To a solution of ethyl 2-(6-nitro-4-tosyl-3,4-dihydro-2H-benzo[b][1,4]oxazin-2-yl) cyclopropanecarboxylate (700 mg, 1.57 mmol) in EtOH (10 mL) and water (1 mL) was added iron powder (876 mg, 15.7 mmol) and ammonium chloride (839 mg, 15.7 mmol). The reaction mixture was stirred at 80° C. for 1 h, then filtered through CELITE and extracted with ethyl acetate. The organic layer was washed with water and brine, dried and concentrated to afford the crude title compound as a gray solid, which was used in the next step without further purification. LCMS (ESI) calculated for $C_{21}H_{25}N_2O_5S$ [M+H]$^+$: 417. found: 417, $^1$H NMR (400 MHz, DMSO-d$_6$) δ 7.63-7.75 (2H, m), 7.45 (2H, br s), 6.99-7.08 (1H, m), 6.53-6.64 (1H, m), 6.29-6.42 (1H, m), 4.83-5.09 (1H, m), 4.18-4.30 (1H, m), 4.05-4.17 (2H, m), 3.47-3.57 (1H, m), 2.76-3.17 (1H, m), 2.42 (3H, s), 1.49-1.82 (2H, m), 1.24 (3H, s), 1.06-1.16 (2H, m), 0.92-1.03 (1H, m).

Step 4—Preparation of ethyl 2-(6-amino-4-tosyl-3,4-dihydro-2H-benzo[b][1,4]oxazin-2-yl)cyclopropanecarboxylate as a mixture of diastereomers

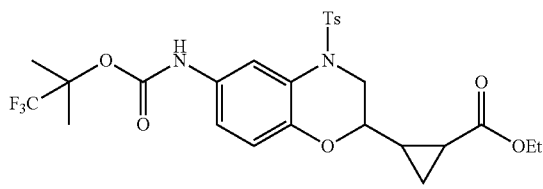 [SMILES: CCOC(=O)C1CC1C1CN(S(=O)(=O)c2ccc(C)cc2)c2cc(NC(=O)OC(C)(C)C(F)(F)F)ccc2O1]

To a solution of ethyl 2-(6-amino-4-tosyl-3,4-dihydro-2H-benzo[b][1,4]oxazin-2-yl)cyclopropanecarboxylate (600 mg, 1.44 mmol) in DMSO (5 mL) was added 3-methyl-1-((((1,1,1-trifluoro-2-methylpropan-2-yl)oxy)carbonyl)-1H-imidazol-3-ium iodide (577 mg, 1.58 mmol) and the reaction mixture stirred at 23° C. for 1 h. Water was then added and the reaction extracted with EtOAc (30 mL×2). The combined organic layer was washed with brine, dried and concentrated to afford the crude title compound as a white solid, which was directly used in the next step without further purification. LCMS (ESI) calculated for $C_{26}H_{30}F_3N_2O_7S$ [M+H]$^+$: 571. found: 571, $^1$H NMR (400 MHz, CDCl$_3$) δ 7.62-7.74 (1H, m), 7.44-7.57 (2H, m), 7.15-7.29 (3H, m), 6.74 (2H, s), 4.21-4.34 (1H, m), 4.04-4.12 (2H, m), 3.08-3.23 (1H, m), 2.62-2.97 (1H, m), 2.32-2.41 (3H, m), 1.74 (6H, m), 1.40-1.60 (2H, m), 1.21-1.26 (3H, m), 1.17 (1H, m), 0.73-0.91 (1H, m).

Step 5—Preparation of ethyl 2-(6-((((1,1,1-trifluoro-2-methylpropan-2-yl)oxy) carbonyl)amino)-3,4-dihydro-2H-benzo[b][1,4]oxazin-2-yl)cyclopropanecarboxylate as a mixture of diastereomers

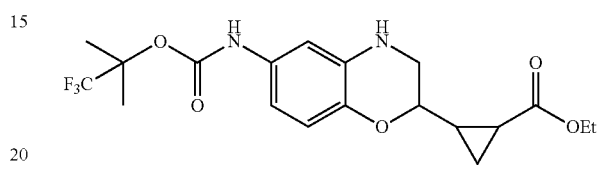

To a solution of ethyl 2-(4-tosyl-6-((((1,1,1-trifluoro-2-methylpropan-2-yl)oxy) carbonyl)amino)-3,4-dihydro-2H-benzo[b][1,4]oxazin-2-yl)cyclopropanecarboxylate (680 mg, 1.19 mmol) in MeOH (10 mL) was added magnesium dust (290 mg, 11.9 mmol) and the reaction was stirred at 80° C. for 1 h, then filtered through CELITE. The solvent was removed in vacuo, and the crude product was purified by chromatography on silica gel, eluting with 25% EtOAc in petroleum ether to afford the title compound as a white solid. LCMS (ESI) calculated for $C_{19}H_{24}F_3N_2O_5$[M+H]$^+$: 417. found: 417, $^1$H NMR (400 MHz, CDCl$_3$) δ 6.73-6.89 (1H, m), 6.63-6.71 (1H, m), 6.36-6.55 (2H, m), 3.74-3.85 (1H, m), 3.64-3.72 (4H, m), 3.53-3.62 (1H, m), 3.35-3.45 (1H, m), 3.17-3.27 (1H, m), 1.79-1.87 (1H, m), 1.72-1.78 (1H, m), 1.71 (7H, s), 0.94-1.17 (1H, m).

Step 6—Preparation of ethyl 2-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl) cyclopropanecarboxylate as a mixture of diastereomers

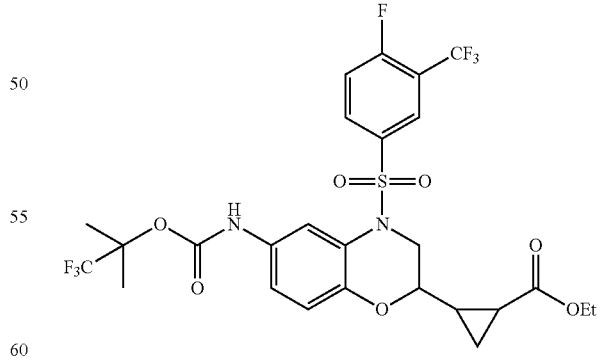

To a solution of methyl 2-(6-((((1,1,1-trifluoro-2-methylpropan-2-yl)oxy) carbonyl)amino)-3,4-dihydro-2H-benzo[b][1,4]oxazin-2-yl)cyclopropanecarboxylate (280 mg, 0.696 mmol) in THF (15 mL) and pyridine (15 mL) was added 4-fluoro-3-(trifluoromethyl) benzene-1-sulfonyl chloride (183 mg, 0.696 mmol) and the reaction stirred at 70° C.

overnight. The solvent was removed in vacuo, and the crude product was purified by chromatography on silica gel, eluting with 30% EtOAc in petroleum ether to afford the title compound as a white solid. LCMS (ESI) calculated for $C_{26}H_{26}F_7N_2O_7S$ [M+H]$^+$: 643. found: 643.

Step 7—Preparation of (1R,2S)-2-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid, (1S,2R)-2-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid, (1R,2R)-2-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid and (1S,2S)-2-((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid

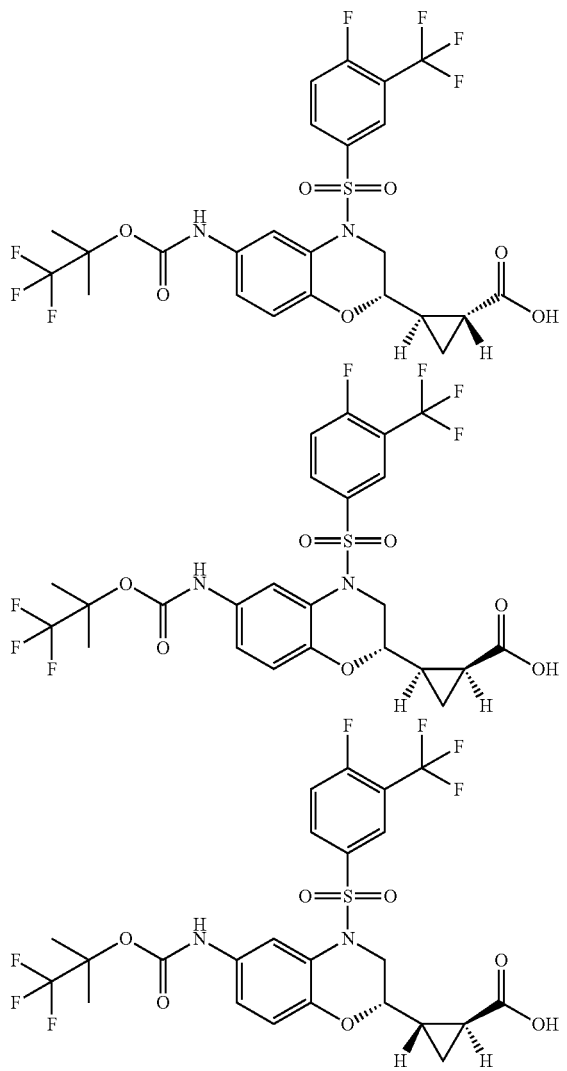

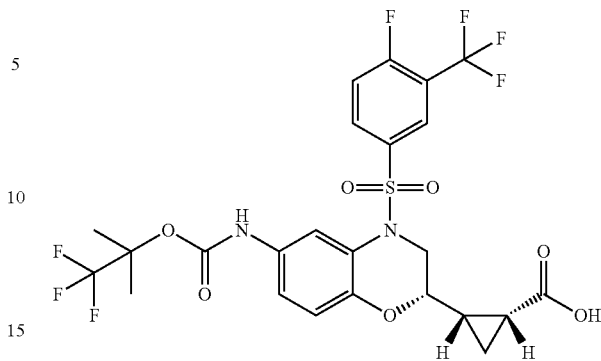

To a solution of methyl 2-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylate (25 mg, 0.040 mmol) in THF (0.5 mL) and water (1 mL) was added lithium hydroxide (15 mg, 0.63 mmol) and the reaction stirred at room temperature for 24 h. The reaction mixture was directly purified by prep-HPLC to afford the title compound (mixture) as a white solid. LCMS (ESI) calculated for $C_{24}H_{22}F_7N_2O_7S$ [M+H]$^+$: 615. found: 615.

The mixture was separated by chiral SFC (Chiralcel OD-3 150×4.6 mm I.D., 3 um; Mobile phase: methanol (0.05% DEA) in $CO_2$ from 5% to 40%) to only afford 4 pure diastereomers. Example No. 22A, Isomer 1: $^1$H NMR (400 MHz, CDCl$_3$) δ 8.03-8.16 (1H, m), 7.88-7.98 (1H, m), 7.77-7.86 (1H, m), 7.27-7.37 (1H, m), 6.93-7.02 (1H, m), 6.77 (1H, d, J=9.0 Hz), 6.55-6.65 (1H, m), 4.29-4.43 (1H, m), 3.24-3.38 (1H, m), 3.11-3.22 (1H, m), 1.68-1.78 (7H, m), 1.55-1.65 (1H, m), 1.27-1.36 (1H, m), 0.96-1.07 (1H, m). Example No. 22B, Isomer 2: $^1$H NMR (400 MHz, CDCl$_3$) δ 8.06-8.15 (1H, m), 7.90-7.99 (1H, m), 7.79-7.88 (1H, m), 7.32 (1H, s), 6.92-7.00 (1H, m), 6.77 (1H, s), 6.58 (1H, s), 4.33-4.44 (1H, m), 3.37-3.47 (1H, m), 3.23-3.34 (1H, m), 1.74 (7H, s), 1.62-1.70 (1H, m), 1.26-1.34 (1H, m), 1.04-1.12 (1H, m). Example No. 22C, Isomer 3: $^1$HNMR (400 MHz, CDCl$_3$) δ 8.05-8.15 (1H, m), 7.86-7.98 (1H, m), 7.77-7.86 (1H, m), 7.27-7.36 (1H, m), 6.93-7.01 (1H, m), 6.79 (1H, s), 6.54-6.62 (1H, m), 4.31-4.42 (1H, m), 3.25-3.38 (1H, m), 3.12-3.23 (1H, m), 1.68-1.79 (7H, m), 1.55-1.65 (1H, m), 1.26-1.36 (1H, m), 0.97-1.07 (1H, m). Example No. 22D, Isomer 4: $^1$H NMR (400 MHz, CDCl$_3$) δ 8.11 (1H, br s), 7.90-8.01 (1H, m), 7.84 (1H, br s), 7.32 (1H, t, J=9.0 Hz), 6.96 (1H, dd, J=8.8 Hz, 2.2 Hz), 6.76 (1H, d, J=9.0 Hz), 6.57 (1H, s), 4.37 (1H, d, J=13.3 Hz), 3.41 (1H, d, J=6.3 Hz), 3.23-3.34 (1H, m), 1.74 (7H, s), 1.61-1.69 (1H, m), 1.25-1.34 (1H, m), 1.03-1.13 (1H, m).

The compounds in Table 8 were prepared based on the experimental procedures described above in Example 22, and can be achieved by one of skill in the art in light of the present disclosure.

TABLE 8

| Ex. No. | Structure | Name | Observed m/z |
|---|---|---|---|
| 22E | 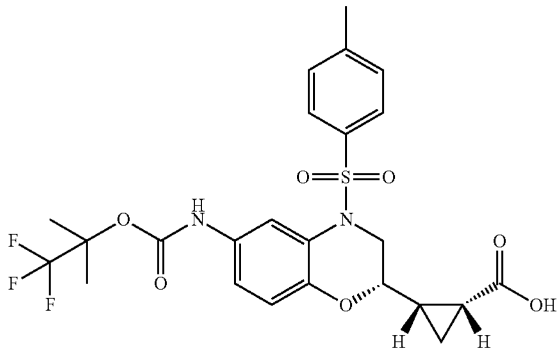 [SMILES: Cc1ccc(S(=O)(=O)N2C[C@H]([C@H]3C[C@H]3C(=O)O)Oc3ccc(NC(=O)OC(C)(C)C(F)(F)F)cc32)cc1] | (1S,2S or 1R,2R or 1S,2R or 1R,2S)-2-((S)-4-tosyl-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid | 543 (M + H)+ |
| 22F | 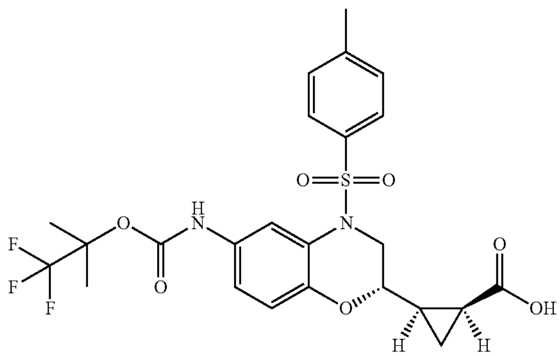 [SMILES: Cc1ccc(S(=O)(=O)N2C[C@H]([C@@H]3C[C@@H]3C(=O)O)Oc3ccc(NC(=O)OC(C)(C)C(F)(F)F)cc32)cc1] | (1S,2S or 1R,2R or 1S,2R or 1R,2S)-2-((S)-4-tosyl-6-((((1,1,1-trifluoro-2-methylpropan-2-yl)oxy)carbonyl)amino)-3,4-dihydro-2H-benzo[b][1,4]oxazin-2-yl)cylcopropanecarboxylic acid | 543 (M + H)+ |
| 22G | 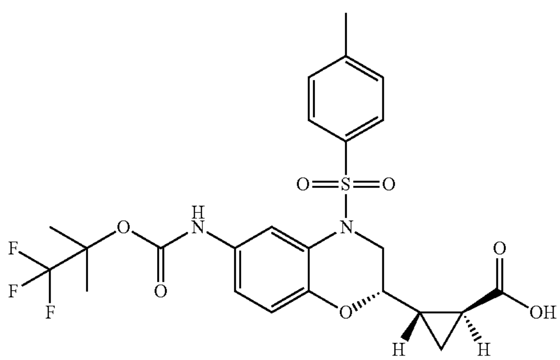 | (1S,2S or 1R,2R or 1S,2R or 1R,2S)-2-((S)-4-tosyl-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid | 543 (M + H)+ |
| 22H | 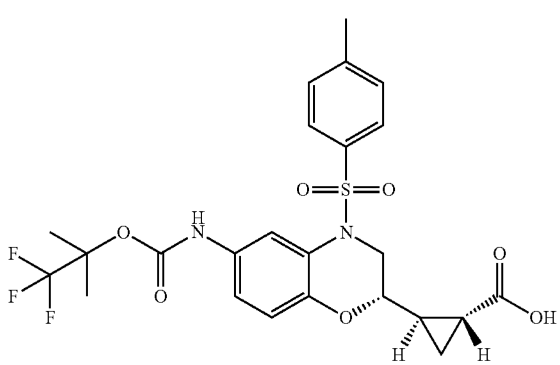 [SMILES: Cc1ccc(S(=O)(=O)N2C[C@H]([C@@H]3C[C@H]3C(=O)O)Oc3ccc(NC(=O)OC(C)(C)C(F)(F)F)cc32)cc1] | (1S,2S or 1R,2R or 1S,2R or 1R,2S)-2-((S)-4-tosyl-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid | 543 (M + H)+ |

TABLE 8-continued

| Ex. No. | Structure | Name | Observed m/z |
|---|---|---|---|
| 22i | 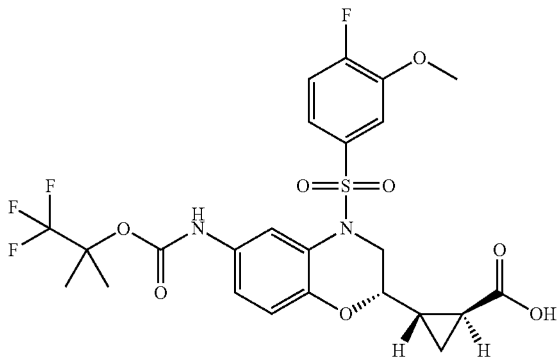 [SMILES: COc1cc(S(=O)(=O)N2C[C@H]([C@H]3C[C@@H]3C(=O)O)Oc3ccc(NC(=O)OC(C)(C)C(F)(F)F)cc32)ccc1F] | (1R,2S or 1R,2R or 1S,2S or 1S,2R)-2-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)cylcopropanecarboxylic acid | 577 (M + H)+ |
| 22J | 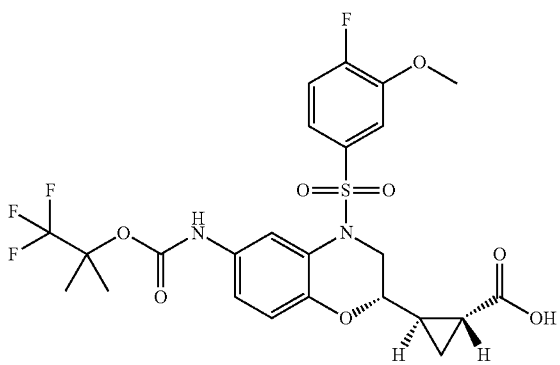 [SMILES: COc1cc(S(=O)(=O)N2C[C@H]([C@@H]3C[C@H]3C(=O)O)Oc3ccc(NC(=O)OC(C)(C)C(F)(F)F)cc32)ccc1F] | (1R,2S or 1R,2R or 1S,2S or 1S,2R)-2-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid | 577 (M + H)+ |
| 22K | 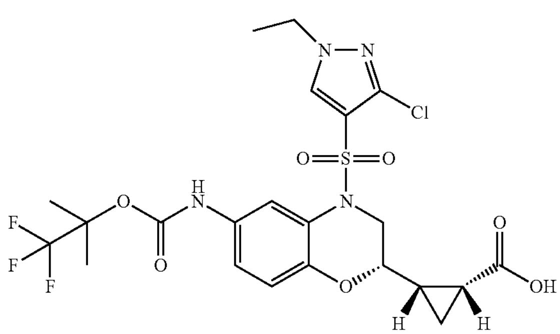 [SMILES: CCn1cc(S(=O)(=O)N2C[C@H]([C@H]3C[C@H]3C(=O)O)Oc3ccc(NC(=O)OC(C)(C)C(F)(F)F)cc32)c(Cl)n1] | (1R,2S or 1R,2R or 1S,2S or 1S,2R)-2-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid | 582 (M + H)+ |
| 22L | 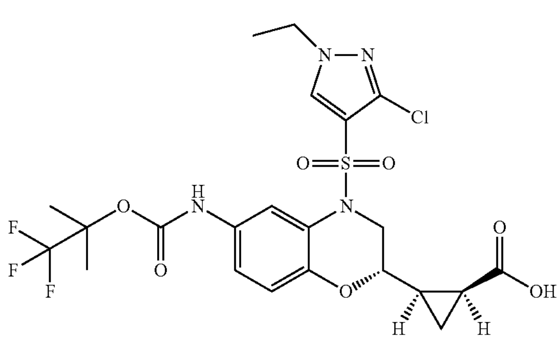 [SMILES: CCn1cc(S(=O)(=O)N2C[C@H]([C@@H]3C[C@@H]3C(=O)O)Oc3ccc(NC(=O)OC(C)(C)C(F)(F)F)cc32)c(Cl)n1] | (1R,2S or 1R,2R or 1S,2S or 1S,2R)-2-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)cyclopropanecarboxylic acid | 582 (M + H)+ |

TABLE 8-continued

| Ex. No. | Structure | Name | Observed m/z |
|---|---|---|---|
| 22M | 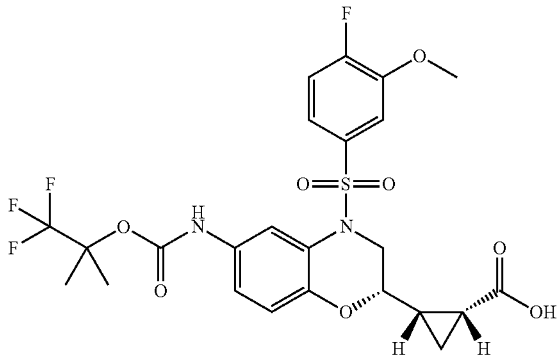 [SMILES: COc1cc(S(=O)(=O)N2C[C@H]([C@H]3C[C@H]3C(=O)O)Oc3ccc(NC(=O)OC(C)(C)C(F)(F)F)cc32)ccc1F] | (1R,2S or 1R,2R or 1S,2S or 1S,2R)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid | 577 (M + H)+ |
| 22N | 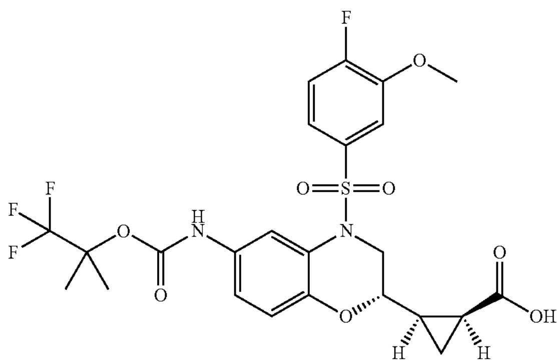 [SMILES: COc1cc(S(=O)(=O)N2C[C@H]([C@@H]3C[C@@H]3C(=O)O)Oc3ccc(NC(=O)OC(C)(C)C(F)(F)F)cc32)ccc1F] | (1R,2S or 1R,2R or 1S,2S or 1S,2R)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid | 577 (M + H)+ |
| 22o | 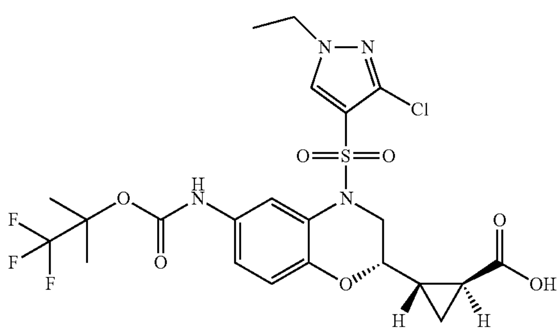 [SMILES: CCn1cc(S(=O)(=O)N2C[C@H]([C@H]3C[C@@H]3C(=O)O)Oc3ccc(NC(=O)OC(C)(C)C(F)(F)F)cc32)c(Cl)n1] | (1R,2S or 1R,2R or 1S,2S or 1S,2R)-2-((S)-4-((3-chloro-1-ehtyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid | 582 (M + H)+ |
| 22P | 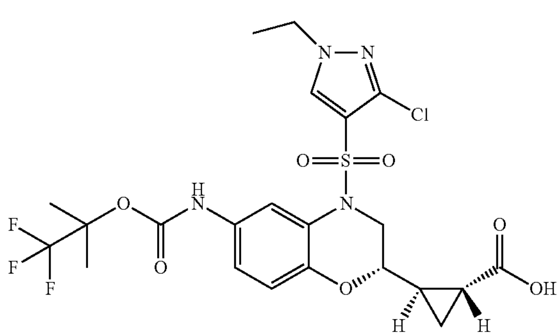 [SMILES: CCn1cc(S(=O)(=O)N2C[C@H]([C@@H]3C[C@H]3C(=O)O)Oc3ccc(NC(=O)OC(C)(C)C(F)(F)F)cc32)c(Cl)n1] | (1R,2S or 1R,2R or 1S,2S or 1S,2R)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid | 582 (M + H)+ |

Example 23

Preparation of 3-((S)-4-((4-fluoro-3-methoxyphenyl)sulfonyl)-6-(((((S)-1,1,1-trifluoro-3,3-dimethylbutan-2-yl)oxy)carbonyl)amino)-3,4-dihydro-2H-benzo[b][1,4]oxazin-2-yl)propanoic acid and 3-((S)-4-((4-fluoro-3-methoxyphenyl)sulfonyl)-6-(((((R)-1,1,1-trifluoro-3,3-dimethylbutan-2-yl)oxy)carbonyl)amino)-3,4-dihydro-2H-benzo[b][1,4]oxazin-2-yl)propanoic acid (Example Nos. 23A and 23B)

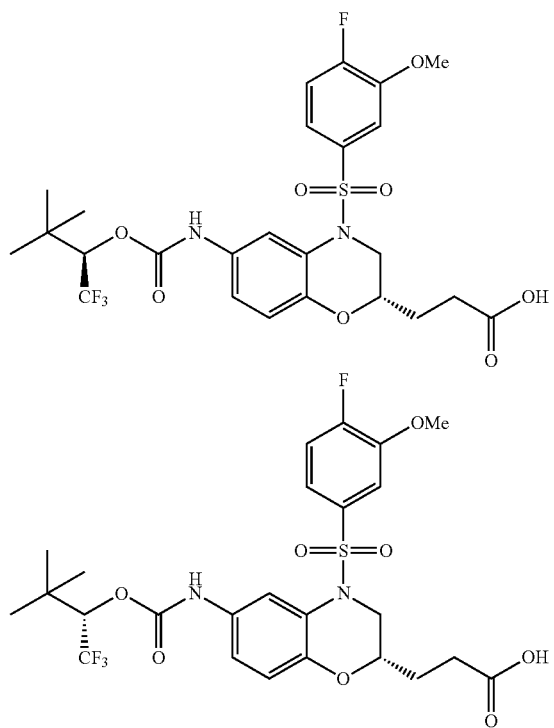

Step 1—Preparation of (S)-ethyl 3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate

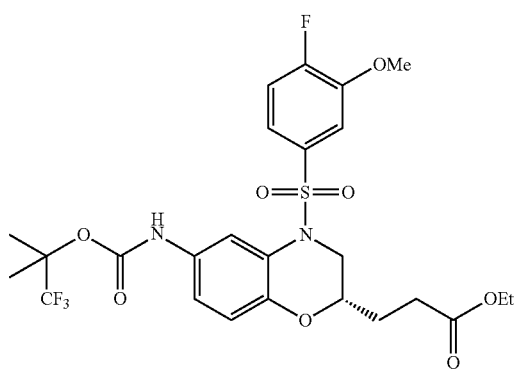 [SMILES: CCOC(=O)CC[C@H]1CN(S(=O)(=O)c2ccc(F)c(OC)c2)c2cc(NC(=O)OC(C)(C)C(F)(F)F)ccc2O1]

To a microwave vial loaded with (S)-ethyl 3-(6-((((1,1,1-trifluoro-2-methylpropan-2-yl)oxy)carbonyl)amino)-3,4-dihydro-2H-benzo[b][1,4]oxazin-2-yl)propanoate (1.0 g, 2.47 mmol) and 4-fluoro-3-methoxybenzene-1-sulfonyl chloride (1.1 g, 4.95 mmol) at room temperature was added pyridine (10 mL). The mixture was stirred at 50° C. for 12 h and then at 80° C. with an additional sulfonyl chloride (1 equiv.) for 2 h. The reaction was cooled down to room temperature, diluted with EtOAc and washed with water and brine. The combined organic layers were dried over MgSO4, filtered and concentrated. The crude product was purified by normal phase flash chromatography eluting with EtOAc/hexane (0-25%) to afford the title compound as a yellow oil. MS ESI calculated for $C_{25}H_{29}F_4N_2O_8S$ $[M+H]^+$ 593, found 610 $(M+NH_4)^+$.

Step 2—Preparation of (S)-3-(6-amino-4-((4-fluoro-3-methoxyphenyl)sulfonyl)-3,4-dihydro-2H-benzo[b][1,4]oxazin-2-yl)propanoic acid

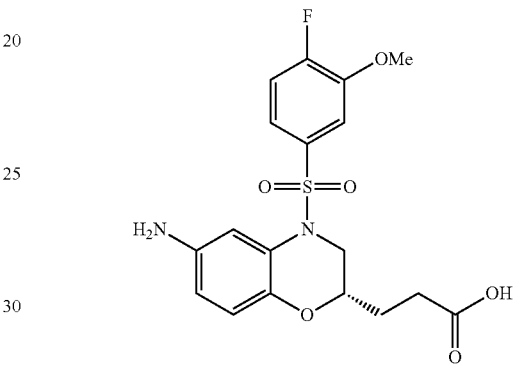

To a solution of (S)-ethyl 3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate (1100 mg, 1.86 mmol) in THF (25 mL)/water (5 mL) was added LiOH (445 mg, 18.6 mmol). The reaction mixture was stirred at room temperature for 72 h, diluted with water and acidified with 1N HCl to pH 1-2. The aqueous layer was extracted 3 times with EtOAc and the combined organic layer was washed with brine, dried over MgSO4, filtered and concentrated to afford the crude title compound as an orange solid, which was used in the next step without further purification. MS ESI calculated for $C_{18}H_{20}FN_2O_6S$ $(M+H)^+$ 411, found 411 $(M+H)^+$.

Step 3—Preparation of (S)-methyl 3-(6-amino-4-((4-fluoro-3-methoxyphenyl)sulfonyl)-3,4-dihydro-2H-benzo[b][1,4]oxazin-2-yl)propanoate

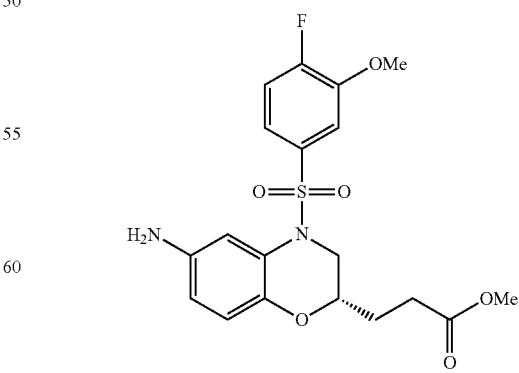

To a solution of (S)-3-(6-amino-4-((4-fluoro-3-methoxyphenyl)sulfonyl)-3,4-dihydro-2H-benzo[b][1,4]oxazin-2-yl)

propanoic acid (700 mg, 1.71 mmol) in MeOH (10 mL) at room temperature was added thionyl chloride (0.622 mL, 8.53 mmol) and the mixture was stirred at reflux for 3 h. Upon completion, the solvent was removed in vacuo and the residue was diluted with EtOAc. The organic layer was washed with NaHCO$_3$ and brine, dried over MgSO4, and filtered and concentrated. The resulting crude product was used in the next step without further purification. MS ESI calculated for C$_{19}$H$_{22}$FN$_2$O$_6$S (M+H)$^+$ 425, found 425 (M+H)$^+$.

Step 4—Preparation of methyl 3-((S)-4-((4-fluoro-3-methoxyphenyl)sulfonyl)-6-(((((R and S)-1,1,1-trifluoro-3,3-dimethylbutan-2-yl)oxy)carbonyl)amino)-3,4-dihydro-2H-benzo[b][1,4]oxazin-2-yl)propanoate

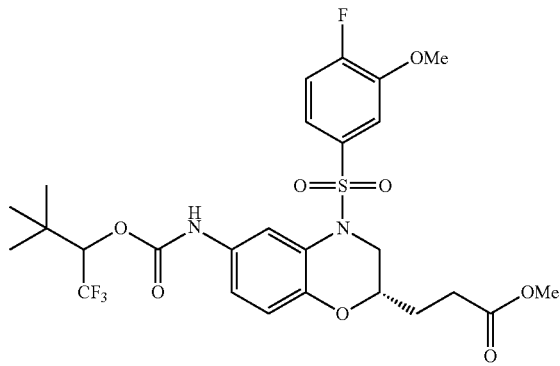 [SMILES: COC(=O)CC[C@H]1CN(S(=O)(=O)c2ccc(F)c(OC)c2)c2cc(NC(=O)OC(C(C)(C)C)C(F)(F)F)ccc2O1]

To a microwave vial loaded with (S)-methyl 3-(6-amino-4-((4-fluoro-3-methoxyphenyl)sulfonyl)-3,4-dihydro-2H-benzo[b][1,4]oxazin-2-yl)propanoate (40 mg, 0.094 mmol), CDI (61.1 mg, 0.377 mmol) and DMAP (23 mg, 0.188 mmol) was added acetonitrile (1 mL) and the vial was sealed and stirred at 80° C. for 12 h. Then 1,1,1-trifluoro-3,3-dimethylbutan-2-ol (147 mg, 0.942 mmol) was added and the mixture was stirred at 110° C. for an additional 5 h. Upon completion, the reaction mixture was cooled down to room temperature, and used in the next step without removal of the solvent. MS ESI calculated for C$_{26}$H$_{31}$F$_4$N$_2$O$_8$S (M+H)$^+$ 607, found 624 (M+NH$_4$)$^+$.

Step 5—Preparation of methyl 3-((S)-4-((4-fluoro-3-methoxyphenyl)sulfonyl)-6-(((((R)-1,1,1-trifluoro-3,3-dimethylbutan-2-yl)oxy)carbonyl)amino)-3,4-dihydro-2H-benzo[b][1,4]oxazin-2-yl)propanoate and methyl 3-((S)-4-((4-fluoro-3-methoxyphenyl)sulfonyl)-6-(((((S)-1,1,1-trifluoro-3,3-dimethylbutan-2-yl)oxy)carbonyl)amino)-3,4-dihydro-2H-benzo[b][1,4]oxazin-2-yl)propanoate

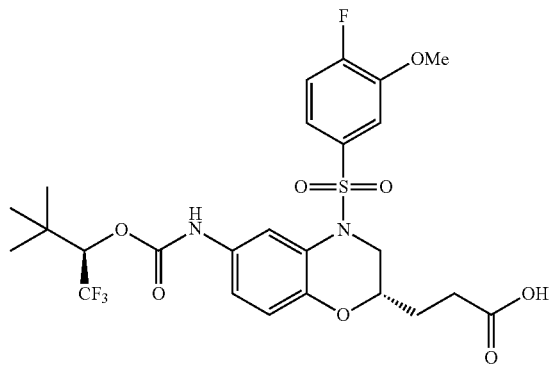

-continued

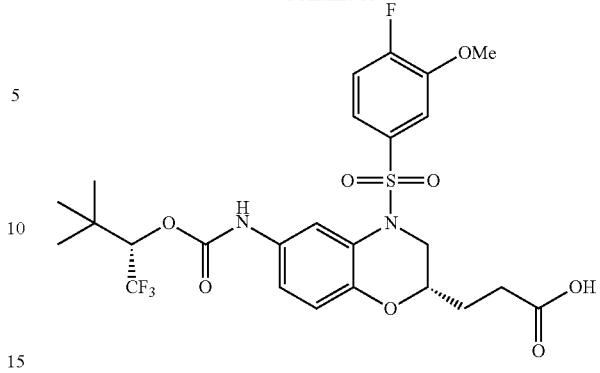

To a solution of methyl 3-((S)-4-((4-fluoro-3-methoxyphenyl)sulfonyl)-6-(((((R and S)-1,1,1-trifluoro-3,3-dimethylbutan-2-yl)oxy)carbonyl)amino)-3,4-dihydro-2H-benzo[b][1,4]oxazin-2-yl)propanoate (55 mg, 0.091 mmol) in THF (3 mL) and water (2 mL) was added LiOH (5.4 mg, 0.227 mmol). The reaction was stirred at room temperature for 3 h, filtered and the filtrate directly purified by reverse phase HPLC (MeCN/water using TFA buffer) to afford the racemic product mixture. Chiral SFC purification afforded the two title compounds as white solids: Column & Dimensions: Chiralcel OJ-H, 21×250 (mm); Outlet Pressure (bar): 100; UV wavelength (nm): 220; Flow rate (mL/min): 70; Modifier: Methanol+0.25% Dimethyl Ethyl Amine; % modifier in CO$_2$: 15; Sample amount (mg): 30; Diluent: Methanol/CAN; Diluent volume (mL): 2; Injection volume (mL): 0.25; Instrument: Thar 80.

Example No. 23A

Isomer 1 (rT=2.99 min): MS ESI calculated for C$_{25}$H$_{29}$F$_4$N$_2$O$_8$S (M+H)$^+$ 593, found 593 (M+H)$^+$, $^1$H NMR (600 MHz, d6-DMSO) δ 10.02 (s, 1H), 8.02 (s, 1H), 7.37 (dd, J=21.3, 32.2 Hz, 3H), 7.10 (d, J=8.2 Hz, 1H), 6.76 (d, J=8.8 Hz, 1H), 5.06 (d, J=8.0 Hz, 1H), 4.27 (d, J=13.7 Hz, 1H), 3.76 (s, 3H), 3.48 (s, 1H), 3.31-3.17 (m, 2H), 1.86-1.59 (m, 2H), 1.02 (s, 9H).

Example No. 23B

Isomer 2 (rT=3.58 min): MS ESI calculated for C$_{25}$H$_{29}$F$_4$N$_2$O$_8$S (M+H)$^+$ 593, found 593 (M+H)$^+$ and 610 (M+NH$_4$)$^+$, $^1$H NMR (600 MHz, d6-DMSO) δ 10.02 (s, 1H), 8.03 (s, 1H), 7.36 (d, J=53.6 Hz, 3H), 7.10 (s, 1H), 6.75 (d, J=8.3 Hz, 1H), 5.07 (s, 1H), 4.27 (d, J=13.9 Hz, 1H), 3.76 (s, 3H), 3.47 (s, 2H), 3.25 (s, 3H), 1.73 (d, J=67.4 Hz, 2H), 1.19 (s, 1H), 1.03 (s, 9H).

Example 24

Preparation of Additional 6-Benzoxazine Carbamates

The compounds in Table 9 were prepared based on the experimental procedures described in Example 23, and can be achieved by one of skill in the art in light of the present disclosure.

TABLE 9

| Ex. No. | Structure | Name | Observed m/z |
|---|---|---|---|
| 24A | 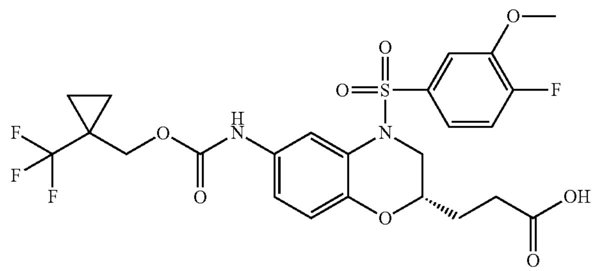 [SMILES: COc1cc(S(=O)(=O)N2C[C@H](CCC(=O)O)Oc3ccc(NC(=O)OCC4(C(F)(F)F)CC4)cc32)ccc1F] | 3-{(2S)-4-[(4-fluoro-3-methoxyphenyl)sulfonyl]-6-[({[1-(trifluoromethyl)cyclopropyl]methoxy}carbonyl)amino]-3,4-dihydro-2H-1,4-benzoxazin-2-yl}propanoic acid | 577 (M + H)+ |
| 24B | 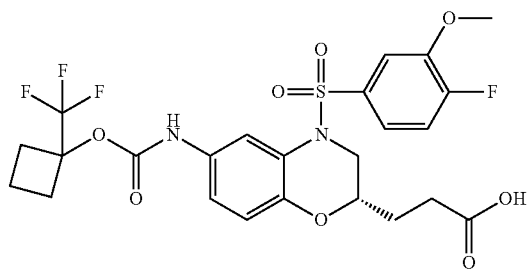 [SMILES: COc1cc(S(=O)(=O)N2C[C@H](CCC(=O)O)Oc3ccc(NC(=O)OC4(C(F)(F)F)CCC4)cc32)ccc1F] | 3-{(2S)-4-[(4-fluoro-3-methoxyphenyl)sulfonyl]-6-[({[1-(trifluoromethyl)cyclobutyl]oxy}carbonyl)amino]-3,4-dihydro-2H-1,4-benzoxazin-2-yl}propanoic acid | 594 (M + NH4)+ |
| 24C | 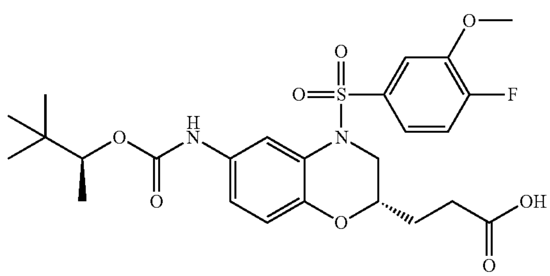 [SMILES: COc1cc(S(=O)(=O)N2C[C@H](CCC(=O)O)Oc3ccc(NC(=O)O[C@@H](C)C(C)(C)C)cc32)ccc1F] | 3-{(2S)-4-[(4-fluoro-3-methoxyphenyl)sulfonyl]-6-[({[(1S or 1R)-1,2,2-trimethylpropyl]oxy}carbonyl)amino]-3,4-dihydro-2H-1,4-benzoxazin-2-yl}propanoic acid | 561 (M + Na)+ |
| 24D | 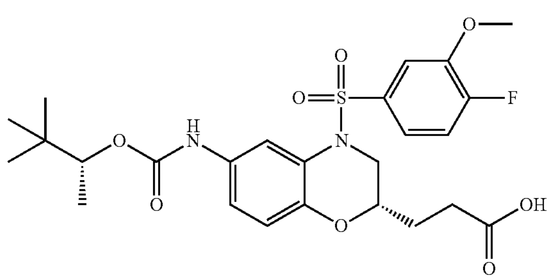 [SMILES: COc1cc(S(=O)(=O)N2C[C@H](CCC(=O)O)Oc3ccc(NC(=O)O[C@H](C)C(C)(C)C)cc32)ccc1F] | 3-{(2S)-4-[(4-fluoro-3-methoxyphenyl)sulfonyl]-6-[({[(1S or 1R)-1,2,2-trimethylpropyl]oxy}cxarbonyl)amino]-3,4-dihydro-2H-1,4-benzoxazin-2-yl}propanoic acid | 561 (M + Na)+ |
| 24E | 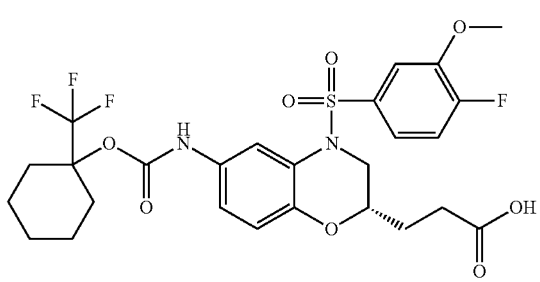 [SMILES: COc1cc(S(=O)(=O)N2C[C@H](CCC(=O)O)Oc3ccc(NC(=O)OC4(C(F)(F)F)CCCCC4)cc32)ccc1F] | 3-{(2S)-4-[(4-fluoro-3-methoxyphenyl)sulfonyl]-6-[({[1-(trifluoromethyl)cyclohexyl]oxy}carbonyl)amino]-3,4-dihydro-2H-1,4-benzoxazin-2-yl}propanoic acid | 605 (M + H)+ |

TABLE 9-continued

| Ex. No. | Structure | Name | Observed m/z |
|---|---|---|---|
| 24F | 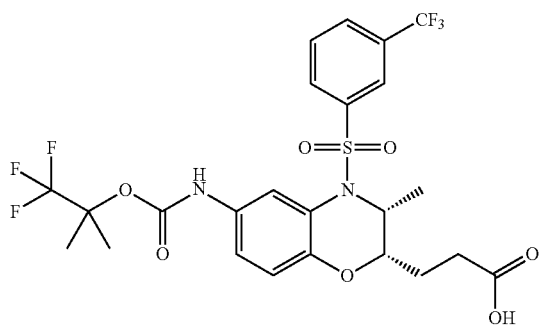 [SMILES: C[C@@H]1[C@H](CCC(=O)O)Oc2ccc(NC(=O)OC(C)(C)C(F)(F)F)cc2N1S(=O)(=O)c1cccc(C(F)(F)F)c1] | 3-((S)-4-((4-fluoro-3-methoxyphenyl)sulfonyl)-6-(((((R and S)-1,1,1-trifluoro-2-methylbutan-2-yl)oxy)carbonyl)amino)-3,4-dihydro-2H-benzo[b][1,4]oxazin-2-yl)propanoic acid | 601 (M + Na)+ |

Example 25

Preparation of 3-((2S,3R)-3-methyl-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid

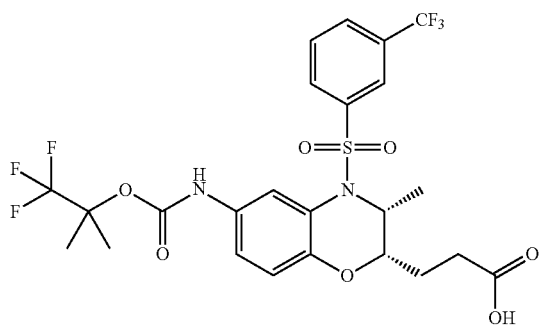 [SMILES: C[C@@H]1[C@H](CCC(=O)O)Oc2ccc(NC(=O)OC(C)(C)C(F)(F)F)cc2N1S(=O)(=O)c1cccc(C(F)(F)F)c1]

Step 1—Preparation of (S)—N-allyl-5-oxotetrahydrofuran-2-carboxamide

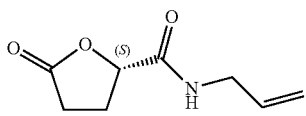

To (2S)-5-oxotetrahydrofuran-2-carboxylic acid (10 g, 76.9 mmol) in dichloromethane (200 mL) at 0° C. was added oxalyl chloride (25 g, 197 mmol) followed by the dropwise addition of anhydrous N,N-dimethylformamide (0.4 mL). The reaction was stirred at 0° C. for 20 minutes, then allowed to warm to ambient temperature overnight. The reaction was next concentrated in vacuo and azeotroped with toluene 3x. The resulting oil was redissolved in dichloromethane (150 mL) and kept at temperature between −30° and −40° C., followed by the dropwise addition of a mixture of allylamine (5.8 mL, 76.9 mmol) and triethylamine (21 mL, 154 mmol). The resulting solution was stirred at −40° C. for 15 minutes, then at ambient temperature for 2 hours. Water (100 mL) was added to the reaction, then acidified with 1M hydrogen chloride. The aqueous layer was extracted with dichloromethane (3x) and the combined organic layers washed with brine, dried with sodium sulfate, filtered and concentrated in vacuo. The crude product was purified by column chromatography eluting with a gradient of 20-100% ethyl acetate in hexanes to yield the title compound. $^1$H-NMR (400 MHz, DMSO-$d_6$) δ 8.34 (m, 1H), 5.76 (m, 1H), 5.12-5.02 (m, 2H), 4.84 (m, 1H), 3.69 (m, 2H), 2.41 (m, 1H), 2.06 (m, 1H).

Step 2—Preparation of (S)-1-allyl-3-hydroxypiperidine-2,6-dione

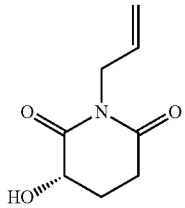

To a solution of (S)—N-allyl-5-oxotetrahydrofuran-2-carboxamide (8.7 g, 51.4 mmol) in anhydrous tetrahydrofuran (40 mL) under nitrogen at −78° C. was added 1M potassium tert-butoxide (25.7 mL, 25.7 mmol) in tetrahydrofuran. The reaction was stirred for 1 hour, allowed to warm to −40° C., then quenched with saturated aqueous ammonium chloride solution. The aqueous layer was extracted with ethyl acetate and the combined extracts washed with brine, dried with sodium sulfate, filtered and concentrated in vacuo to yield the title compound. $^1$H-NMR (400 MHz, DMSO-$d_6$) δ 5.79 (d, 1H, J=4.5 Hz), 5.75-5.65 (m, 1H), 5.02 (m, 2H), 4.25-4.17 (m, 3H), 2.66 (m, 2H), 2.0 (m, 1H), 1.8 (m, 1H).

Step 3—Preparation of (S)-1-allyl-3-((tert-butyldimethylsilyl)oxy)piperidine-2,6-dione

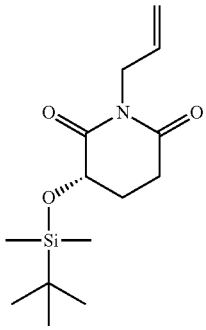 [SMILES: C=CCN1C(=O)CC[C@H](O[Si](C)(C)C(C)(C)C)C1=O]

To a solution of (S)-1-allyl-3-hydroxypiperidine-2,6-dione (7.73 g, 45.7 mmol) in dichloromethane (100 mL) was added imidazole (6.2 g, 91.4 mmol) and 4-dimethylaminopyridine (1.1 g, 9.1 mmol), followed by t-butyldimethylchlorosilane (8.3 g, 54.8 mmol). The reaction was stirred at ambient temperature overnight, then washed with 10% citric acid, the layers separated and extracted once with dichloromethane. The combined organic extracts were washed with brine, dried with sodium sulfate, filtered and concentrated onto silica. The crude product was purified by column chromatography eluting with a gradient of 2-40% ethyl acetate in hexanes to yield the title compound. $^1$H-NMR (400 MHz, DMSO-d$_6$) δ 5.75 (m, 1H), 5.08 (m, 2H), 4.55 (m, 1H), 4.24 (m, 2H), 2.78 (m, 2H), 2.07 (m, 1H), 1.97 (m, 1H), 0.92 (s, 9H), 0.14 (s, 6H).

Step 4—Preparation of (5S,6R)-1-allyl-5-((tert-butyldimethylsilyl)oxy)-6-methylpiperidin-2-one

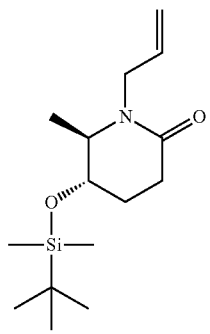 [SMILES: C=CCN1C(=O)CC[C@H](O[Si](C)(C)C(C)(C)C)[C@H]1C]

To a solution of (S)-1-allyl-3-((tert-butyldimethylsilyl)oxy)piperidine-2,6-dione (11.38 g, 40.2 mmol) in anhydrous tetrahydrofuran (100 mL) under nitrogen at 0° C. was added 3M methylmagnesium bromide in diethyl ether (40 mL, 120 mmol) slowly. The reaction was stirred at 0° C. for 3 hours, then carefully quenched with saturated ammonium chloride. The aqueous layer was extracted with ethyl acetate and the combined extracts washed with brine, dried with sodium sulfate, filtered and concentrated in vacuo (11.7 g). To the resulting oil (11.7 g, 39.1 mmol) in anhydrous dichloromethane (100 mL) under nitrogen at −78° C. was added triethylsilane (31.2 mL, 195 mmol) dropwise followed by boron trifluoride diethyl etherate (7.2 mL, 58.6 mmol) dropwise. The reaction was stirred at −78° C. for 3 hours, then at ambient temperature for 2 hours. The reaction was quenched with saturated sodium bicarbonate and stirred for 30 minutes. The layers were separated and the aqueous layer extracted with dichloromethane (2×). The combined organic layers were dried with sodium sulfate, filtered and concentrated. The crude product was purified by column chromatography eluting with a gradient of 20-80% ethyl acetate in hexanes to yield the title compound. $^1$H-NMR (400 MHz, DMSO-d$_6$) δ 5.59 (m, 1H), 5.14 (m, 1H), 5.00 (m, 1H), 4.35 (m, 1H), 3.83 (m, 1H), 3.33-3.20 (m, 2H), 2.28 (m, 1H), 2.10 (m, 1H), 1.95 (m, 1H), 1.59 (m, 1H), 1.07 (d, 3H, J=6.6 Hz), 0.82 (s, 9H), 0.00 (m, 6H).

Step 5—Preparation of (5S,6R)-1-allyl-5-hydroxy-6-methylpiperidin-2-one

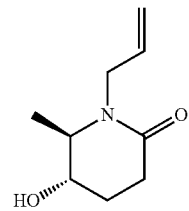

To (5S,6R)-1-allyl-5-((tert-butyldimethylsilyl)oxy)-6-methylpiperidin-2-one (0.67 g, 2.4 mmol) in anhydrous tetrahydrofuran (10 mL) under nitrogen at ambient temperature was added 1M tetrabutylammonium fluoride in tetrahydrofuran (3.5 mL, 3.5 mmol). The reaction was stirred for 2 hours, then concentrated onto silica. The crude product was purified by column chromatography eluting with a gradient of methanol in dichloromethane to yield the title compound. $^1$H-NMR (400 MHz, DMSO-d$_6$) δ 5.64 (m, 1H), 5.16 (dd, 1H, J=17.4, 1.7 Hz), 5.03 (dd, 1H, J=10.1, 1.1 Hz), 4.98 (d, 1H, J=3.3 Hz), 4.2 (m, 1H), 3.63 (m, 1H), 3.50 (dd, 1H, J=15.7, 6.1 Hz), 3.25 (m, 1H), 2.30 (m, 1H), 2.08 (m, 1H), 1.89 (m, 1H), 1.64 (m, 1H), 1.07 (d, 3H, J=6.6 Hz).

Step 6—Preparation of (5S,6R)-1-allyl-5-(2-bromo-4-nitrophenoxy)-6-methylpiperidin-2-one

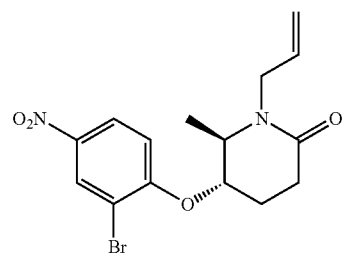 [SMILES: C=CCN1C(=O)CC[C@H](Oc2ccc([N+](=O)[O-])cc2Br)[C@H]1C]

To a solution of (5S,6R)-1-allyl-5-hydroxy-6-methylpiperidin-2-one in anhydrous N,N-dimethylformamide (10 mL) under nitrogen at 0° C. was added 1-bromo-2-fluoro-5-nitrobenzene (0.7 g, 3.2 mmol) followed by the addition of sodium hydride (60% in mineral oil, 0.15 g, 3.8 mmol). The reaction was stirred at 0° C. for 10 minutes until gas evolution subsided, then rinsed the flask sidewalls with anhydrous N,N-dimethylformamide (5 mL). The cooling bath was removed and the reaction stirred at ambient temperature for 2 hours, then quenched with water and extracted with ethyl acetate. The organic layer was washed with saturated sodium bicarbonate solution, brine, dried with sodium sulfate, filtered and concentrated in vacuo. The crude product was purified by column chromatography eluting with a gradient of 0-10% methanol in dichloromethane to yield the title compound. MS (ESI): calculated for $C_{15}H_{18}BrN_2O_4$ (M+H)$^+$: 369, 371. found: 368.98, 370.98 (Br pattern).

Step 7—Preparation of (5S,6R)-5-(2-bromo-4-nitrophenoxy)-6-methylpiperidin-2-one

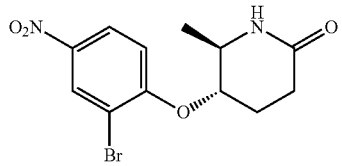 [SMILES: C[C@H]1NC(=O)CC[C@@H]1Oc1ccc([N+](=O)[O-])cc1Br]

A suspension of (5S,6R)-1-allyl-5-(2-bromo-4-nitrophenoxy)-6-methylpiperidin-2-one (2.6 g, 6 mmol) and rhodium (III) chloride hydrate (47 mg, 0.3 mmol) in 2-propanol (15 mL) was refluxed overnight. The hot reaction mixture was filtered through CELITE and washed with methanol. The filtrates were concentrated in vacuo and the resulting material was partitioned between ethyl acetate and 10% citric acid. The layers were separated and the combined organic layer washed with water, brine, dried with sodium sulfate, filtered and concentrated in the presence of silica. The crude product was purified by column chromatography eluting with a gradient of 0-10% methanol in dichloromethane to yield the title compound. $^1$H-NMR (400 MHz, DMSO-$d_6$) δ 8.42 (d, 1H, J=2.7 Hz), 8.21 (dd, 1H, J=9.0, 2.8 Hz), 7.55 (s, 1H), 7.44 (d, 1H, J=9.4 Hz), 4.74 (m, 1H), 3.56 (m, 1H), 2.26 (m, 2H), 2.10 (m, 1H), 1.95 (m, 1H), 1.18 (d, 3H, J=6.7 Hz).

Step 8—Preparation of (5S,6R)-5-(2-bromo-4-nitrophenoxy)-6-methyl-1-((3-(trifluoromethyl)phenyl)sulfonyl)piperidin-2-one

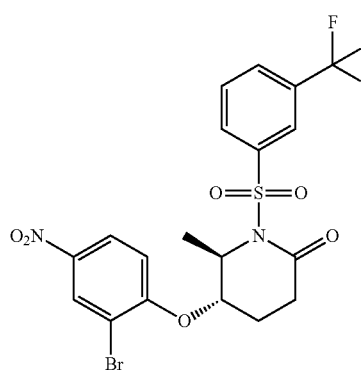

To (5S,6R)-5-(2-bromo-4-nitrophenoxy)-6-methylpiperidin-2-one (0.31 g, 0.94 mmol) in anhydrous tetrahydrofuran (5 mL) at −78° C. under $N_2$ was added 1M lithium bis(trimethylsilyl)amide in tetrahydrofuran (1.0 mL, 1.0 mmol) dropwise. The reaction was stirred for 5 minutes at −78° C., then treated with 3-(trifluoromethyl)benzenesulfonyl chloride (0.18 mL, 1.1 mmol). The cooling bath was removed and the reaction allowed to warm to ambient temperature, then stirred for an additional 1 hour. The reaction was quenched with saturated ammonium chloride and extracted with ethyl acetate. The combined organic layer was washed with brine, dried with sodium sulfate, filtered and concentrated in vacuo. The crude product was purified by column chromatography eluting with a gradient of ethyl acetate in hexanes to yield the title compound. MS (ESI): calculated for $C_{19}H_{16}BrF_3N_2O_6SNa$ (M+Na)$^+$: 559, 561. found: 568.9, 560.9 (Br pattern).

Step 9—Preparation of ethyl (4S,5R)-4-((2-bromo-4-nitrophenoxy)-5-((3-(trifluoromethyl)phenyl)sulfonamido)hexanoate

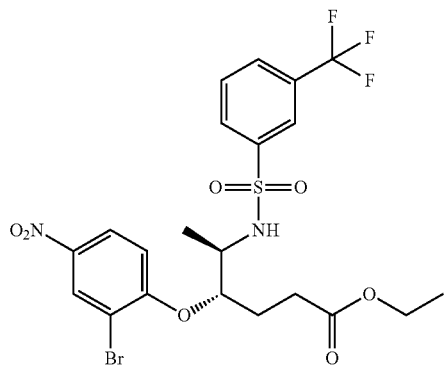 [SMILES: CCOC(=O)CC[C@H](Oc1ccc([N+](=O)[O-])cc1Br)[C@@H](C)NS(=O)(=O)c1cccc(C(F)(F)F)c1]

To a solution of (5S,6R)-5-(2-bromo-4-nitrophenoxy)-6-methyl-1-((3-(trifluoromethyl)phenyl)sulfonyl)piperidin-2-one (0.15 g, 0.28 mmol) in ethanol (2 mL) was added a 21 wt. % sodium ethoxide in ethanol solution (0.13 mL, 0.34 mmol) and the reaction stirred at ambient temperature for 1 hour. Upon completion, the solution was acidified with 1M hydrogen chloride, then partitioned between ethyl acetate and brine. The organic layer was dried with sodium sulfate, filtered and concentrated in vacuo to yield the title compound. MS (ESI): calculated for $C_{21}H_{22}BrF_3N_2O_7SNa$ (M+Na)$^+$: 605, 607. found: 604.96, 606.91 (Br pattern).

Step 10—Preparation of ethyl 3-((2S,3R)-3-methyl-6-nitro-4-((3-(trifluoromethyl)phenyl)sulfonyl)-3,4-dihydro-2H-benzo[b][1,4]oxazin-2-yl)propanoate

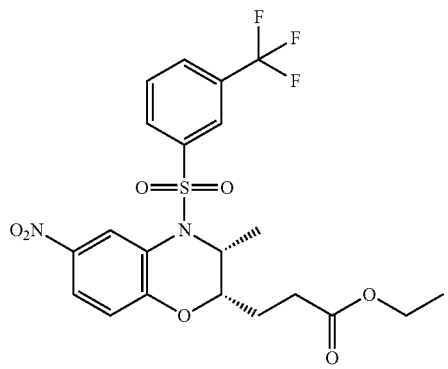 [SMILES: CCOC(=O)CC[C@@H]1Oc2ccc([N+](=O)[O-])cc2N(S(=O)(=O)c2cccc(C(F)(F)F)c2)[C@@H]1C]

To ethyl (4S,5R)-4-((2-bromo-4-nitrophenoxy)-5-((3-(trifluoromethyl)phenyl)sulfonamido)hexanoate (155 mg, 0.27 mmol) dissolved in warm toluene (3 mL) under nitrogen was added potassium phosphate tribasic (0.11 g, 0.53 mmol), copper(I) iodide (8 mg, 0.04 mmol), and N,N'-dimethylethylenediamine (14 μl, 0.13 mmol). The resulting mixture was refluxed overnight, then cooled and partitioned between ethyl acetate and saturated ammonium chloride. The layers were separated and the organic layer washed with saturated Step 11—Preparation of ethyl 3-((2S,3R)-6-amino-3-methyl-4-((3-(trifluoromethyl)phenyl)sulfonyl)-3,4-dihydro-2H-benzo[b][1,4]oxazin-2-yl)propanoate

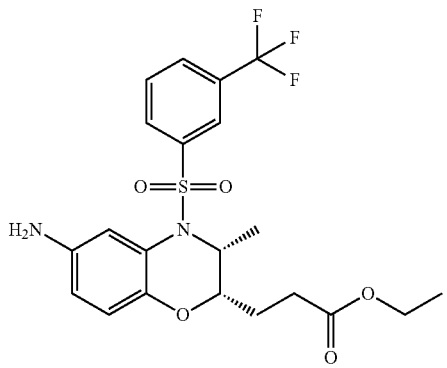 [SMILES: CCOC(=O)CC[C@@H]1Oc2ccc(N)cc2N(S(=O)(=O)c2cccc(C(F)(F)F)c2)[C@@H]1C]

A suspension of ethyl 3-((2S,3R)-3-methyl-6-nitro-4-((3-(trifluoromethyl)phenyl)sulfonyl)-3,4-dihydro-2H-benzo[b][1,4]oxazin-2-yl)propanoate (0.1 g, 0.2 mmol) and ammonium formate (0.13 g, 2 mmol) in methanol (3 mL) was degassed under vacuum, while refilling with nitrogen three times. 10% palladium on carbon (25 mg) was next added and the reaction refluxed for 1 hour, then cooled to ambient temperature and filtered through CELITE. The filtrate was concentrated in vacuo and the resulting solution partitioned between ethyl acetate and water. The organic layer was washed with brine, dried with sodium sulfate, filtered and concentrated in vacuo to yield the title compound. MS (ESI): calculated for $C_{21}H_{24}F_3N_2O_5S$ (M+H)$^+$: 473. found: 473.07.

Step 12—Preparation of ethyl 3-((2S,3R)-3-methyl-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate

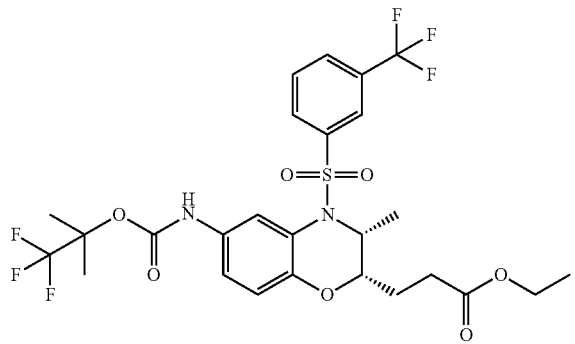 [SMILES: CCOC(=O)CC[C@@H]1Oc2ccc(NC(=O)OC(C)(C)C(F)(F)F)cc2N(S(=O)(=O)c2cccc(C(F)(F)F)c2)[C@@H]1C]

To ethyl 3-((2S,3R)-6-amino-3-methyl-44(3-(trifluoromethyl)phenyl)sulfonyl)-3,4-dihydro-2H-benzo[b][1,4]oxazin-2-yl)propanoate (0.08 g, 0.17 mmol) in anhydrous N,N-dimethylformamide (1 mL) under nitrogen was added (2,2,2-trifluoro-1,1-dimethyl-ethyl) imidazole-1-carboxylate (64 mg, 0.29 mmol) and catalytic tosic acid monohydrate (3 mg, 0.02 mmol) and the reaction heated to 100° C. for 1 hour. Once cooled, the reaction was diluted with ethyl acetate, washed with water, 0.1M hydrogen chloride and brine. The organic layer was next dried with sodium sulfate, filtered and concentrated in vacuo to yield the title compound as a crude mixture which was carried on without further purification. MS (ESI): calculated for $C_{26}H_{28}F_6N_2O_7SNa$ (M+Na)$^+$: 649. found: 649.09.

Step 13—Preparation of 3-((2S,3R)-3-methyl-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid

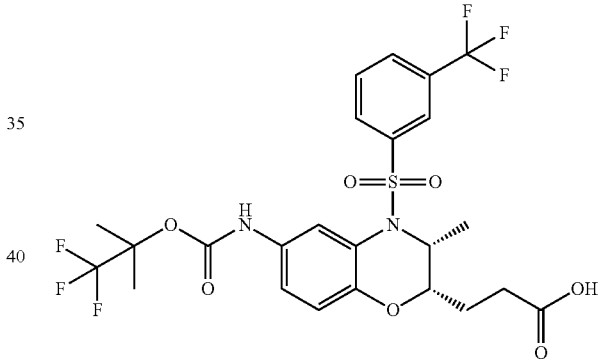

To ethyl 3-((2S,3R)-3-methyl-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoate (0.11 g, 0.17 mmol) in 1,4-dioxane (2 mL) and was added lithium hydroxide (40 mg, 1.7 mmol) in water (1 mL). The reaction was stirred at ambient temperature for 45 minutes, then acidified with 1M hydrogen chloride. The layers were partitioned between ethyl acetate and brine, separated, and the organics concentrated in vacuo. The crude product was purified by preparatory HPLC to yield the title compound. MS (ESI): calculated for $C_{24}H_{24}F_6N_2O_7SNa$ (M+Na)$^+$: 621. found: 621.11. $^1$H-NMR (400 MHz, DMSO-d$_6$) δ 9.72 (s, 1H), 8.05-8.00 (m, 4H), 7.81 (t, 1H, J=8.0 Hz), 7.04 (dd, 1H, J=9.0, 2.3 Hz), 6.74 (d, 1H, J=9.0 Hz), 4.58 (m, 1H), 3.25 (m, 2H), 2.30-2.19 (m, 2H), 1.77 (m, 1H), 1.68 (s, 6H), 1.64 (m, 1H), 0.97 (d, 3H, J=6.8 Hz).

Example 26

Preparation of 3-((2S,3S)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid, 3-((2S,3R)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid, 3-((2R,3R)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid and 3-((2R,3S)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid (Example Nos. 26A, 26B, 26C, and 26D)

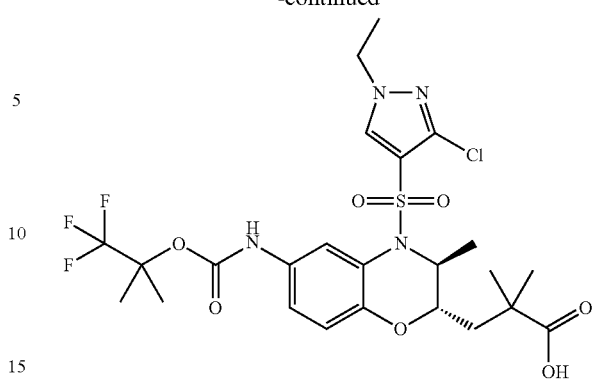

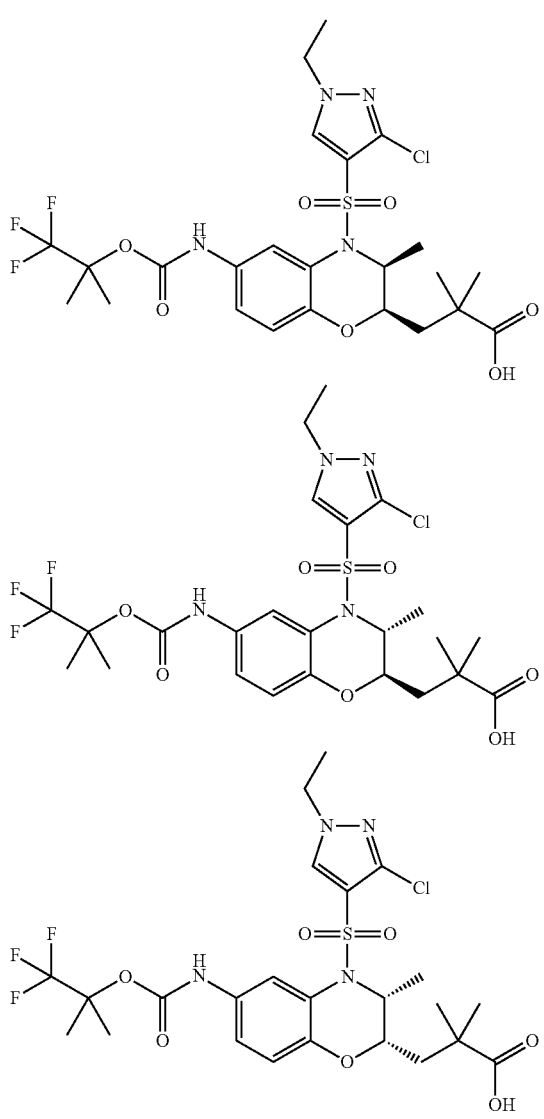

Step 1—Preparation of (E)-2,2-dimethylhex-4-enenitrile

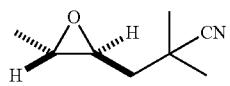

To a solution of isobutyronitrile (4 g, 57.9 mmol) in THF (20 mL), which was stirred in a 100 mL three-neck round bottom flask, was added LDA (31.8 mL, 63.7 mmol) dropwise at −78° C. under nitrogen. After stirring for 1 h, the reaction was treated dropwise with (E)-1-bromobut-2-ene (8.21 g, 60.8 mmol) at −78° C. The resulting solution was stirred at −78° C. for 8 h, then poured into ice water (60 mL). The separated aqueous layer was extracted with EtOAc (30 mL×2) and the combined organic layers were washed with brine (20 mL×2), dried over anhydrous $Na_2SO_4$ and evaporated to afford the title compound as a yellow oil. $^1$HNMR (400 MHz, $CDCl_3$) δ 5.46-5.62 (2H, m), 2.19 (2H, d, J=7.2 Hz), 1.71 (3H, d, J=6.0 Hz), 1.30 (6H, s).

Step 2—Preparation of 2,2-dimethyl-3-((2S,3S and 2R,3R)-3-methyloxiran-2-yl)propanenitrile To a solution of (E)-2,2-dimethylhex-4-enenitrile (19 g, 154 mmol) in DCM (500 mL), which was stirred in a 1 L of round bottom flask, was added 3-chlorobenzoperoxoic acid (31.9 g, 185 mmol) in portions at 0° C. The reaction was stirred at 15° C. for 3 days, then diluted with DCM (300 mL). The organic layer was washed with 1 N NaOH solution (200 mL×4), dried over $Na_2SO_4$ and evaporated at 25° C. The crude product was purified by column chromatography on silica gel (petroleum ether:ethyl acetate=10:1) to afford the title compound as a colorless oil. $^1$HNMR (400 MHz, $CDCl_3$) δ 2.77-2.83 (2H, m), 1.79-1.84 (1H, m), 1.64-1.67 (1H, m), 1.43 (3H, s), 1.39 (3H, s), 1.32 (3H, d, J=4.8 Hz).

Step 3—Preparation of (4S,5R and 4R,5S)-4-bromo-5-hydroxy-2,2-dimethylhexanenitrile

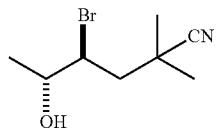

To a solution of 2,2-dimethyl-3-((2S,3S and 2R,3R)-3-methyloxiran-2-yl)propanenitrile (1.5 g, 10.78 mmol) in DCM (50 mL) were added saturated HBr aqueous solution (5 mL, 44.2 mmol) and AcOH (5 mL, 87 mmol) at 0° C. and the reaction was stirred at 0° C. for 1 h. The reaction mixture was adjusted to pH=8 with saturated NaHCO$_3$ and the separated organic layer was washed with brine (10 mL×3), dried over anhydrous Na$_2$SO$_4$ and evaporated under vacuum. The crude product was purified by column chromatography on silica gel (EtOAc:petroleum ether=0-20%) to afford the title compound as a colorless oil. $^1$HNMR (400 MHz, CDCl$_3$) δ 4.19-4.22 (1H, m), 3.88-3.91 (1H, m), 2.20-2.25 (1H, m), 2.04-2.12 (2H, m), 1.50 (3H, s), 1.42 (3H, s), 1.31 (3H, d, J=6.0 Hz).

Step 4—Preparation of 4-bromo-2,2-dimethyl-5-oxohexanenitrile

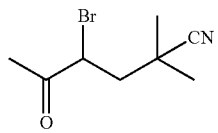

At −78° C., to a solution of (COCl)$_2$ (0.636 mL, 7.27 mmol) in DCM (30 mL) was added (methylsulfinyl)methane (1136 mg, 14.54 mmol) and the reaction was stirred at −78° C. for 30 minutes, followed by the addition of (4S,5R and 4R,5S)-4-bromo-5-hydroxy-2,2-dimethylhexanenitrile (800 mg, 3.63 mmol). The mixture was stirred at −78° C. for 1 h, then treated with Et$_3$N (4.05 mL, 29.1 mmol) and stirred at −78° C. for an additional 1 h. The reaction was next diluted with 30 mL of DCM and washed with brine (20 mL×3). The separated organic layer was dried over anhydrous Na$_2$SO$_4$ and evaporated under vacuum. The crude product was purified by column chromatography on silica gel (EtOAc: petroleum ether=0 to 30%) to afford the title compound as a colorless oil. $^1$HNMR (400 MHz, CDCl$_3$) δ 4.38-4.46 (1H, m), 3.10-3.17 (2H, m), 2.52-2.61 (2H, m), 2.42 (3H, s), 1.27 (3H, s), 1.24 (3H, s).

Step 5—Preparation of (S and R)-2,2-dimethyl-3-(3-methyl-6-nitro-2H-benzo[b][1,4]oxazin-2-yl)propanenitrile

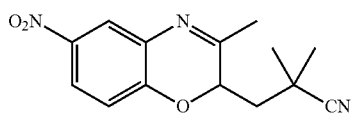 [SMILES: CC1=Nc2cc([N+](=O)[O-])ccc2OC1CC(C)(C)C#N]

To a solution of 4-bromo-2,2-dimethyl-5-oxohexanenitrile in acetone (10 mL) were added 2-amino-4-nitrophenol (495 mg, 3.21 mmol) and K$_2$CO$_3$ (887 mg, 6.42 mmol). The reaction was heated to 60° C. and for 16 h, then poured into water, and extracted with EtOAc (20 mL×3). The combined organic layers were washed with brine (20 mL×3), dried over anhydrous Na$_2$SO$_4$ and evaporated under vacuum. The crude product was purified by column chromatography on silica gel (petroleum ether:EtOAc=30%) to afford the title compound as a yellow solid. LCMS (ESI) calculated for C$_{14}$H$_{16}$N$_3$O$_3$ [M+H]$^+$: 274. found: 274. $^1$HNMR (400 MHz, CDCl$_3$) δ 8.18 (1H, s), 8.07 (1H, d, J=8.4 Hz), 7.04 (1H, d, J=8.8 Hz), 5.01 (1H, d, J=11.2 Hz), 2.25 (3H, s), 2.02 (1H, t, J=11.6 Hz), 1.67 (1H, d, J=11.6 Hz), 1.47-1.49 (6H, m).

Step 6—Preparation of 2,2-dimethyl-3-((2R,3S,2R, 3R,2S,3R and 2S,3S)-3-methyl-6-nitro-3,4-dihydro-2H-benzo[b][1,4]oxazin-2-yl)propanenitrile

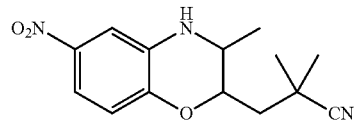

To a solution of (S and R)-2,2-dimethyl-3-(3-methyl-6-nitro-2H-benzo[b][1,4]oxazin-2-yl)propanenitrile (500 mg, 1.830 mmol) in MeOH (5 mL) was added NaBH$_4$ (138 mg, 3.66 mmol) in portions at 0° C. and the reaction was stirred at 15° C. for 1 h, then poured into water and extracted with DCM (10 mL×3). The combined organic layers were washed with brine (10 mL×3), dried over anhydrous Na$_2$SO$_4$ and concentrated under reduced pressure. The crude product was purified by prep-TLC (petroleum ether:EtOAc=1:1) to afford the title compound as a yellow solid. LCMS (ESI) calculated for C$_{14}$H$_{18}$N$_3$O$_3$ [M+H]$^+$: 276. found: 276. $^1$HNMR (400 MHz, CDCl$_3$) δ 7.58-7.61 (1H, m), 7.48 (1H, d, J=2.8 Hz), 6.86 (1H, d, J=9.2 Hz), 4.49 (1H, d, J=9.2 Hz), 3.59-3.60 (1H, m), 3.19-3.30 (1H, m), 2.38-2.49 (1H, m), 1.72-1.86 (3H, m), 1.46-1.57 (8H, m).

Step 7—Preparation of 3-((2R,3S, 2R,3R, 2S,3R and 2S,3S)-6-amino-3-methyl-3,4-dihydro-2H-benzo[b][1,4]oxazin-2-yl)-2,2-dimethylpropanenitrile

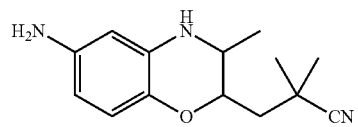 [SMILES: CC1Nc2cc([N+](=O)[O-])ccc2OC1CC(C)(C)C#N]

Pd—C(120 mg, 10% w/w) was added to a solution of the 2,2-dimethyl-3-((2R,3S, 2R,3R, 2S,3R and 2S,3S)-3-methyl-6-nitro-3,4-dihydro-2H-benzo[b][1,4]oxazin-2-yl) propanenitrile (600 mg, 2.179 mmol) in MeOH (10 mL). The reaction was stirred under H$_2$ atmosphere (50 psi) at 10° C. for 16 h, then filtered. The filtrate was concentrated under vacuum and the crude product was purified by column chromatography on silica gel (EtOAc:petroleum ether=0 to 30%) to afford the title compound as a yellow solid. LCMS (ESI) calculated for C$_{14}$H$_{20}$N$_3$O [M+H]$^+$: 246. found: 246. $^1$HNMR (400 MHz, CDCl$_3$) δ 6.59-6.63 (1H, m), 6.02-6.06

(1H, m), 5.97-5.98 (1H, m), 4.29 (1H, d, J=8.8 Hz), 3.52 (1H, d, J=2.0 Hz), 1.65-1.81 (3H, m), 1.47 (3H, s), 1.42 (3H, s), 1.16 (1H, d, J=6.8 Hz).

Step 8—Preparation of (2R, 3R)-2-(2-cyano-2-methylpropyl)-3-methyl-3,4-dihydro-2H-benzo[b][1,4]oxazin-6-yl)carbamate, (2S, 3S)-2-(2-cyano-2-methylpropyl)-3-methyl-3,4-dihydro-2H-benzo[b][1,4]oxazin-6-yl)carbamate, (2R, 3S)-2-(2-cyano-2-methylpropyl)-3-methyl-3,4-dihydro-2H-benzo[b][1,4]oxazin-6-yl)carbamate and (2S, 3R)-2-(2-cyano-2-methylpropyl)-3-methyl-3,4-dihydro-2H-benzo[b][1,4]oxazin-6-yl)carbamate

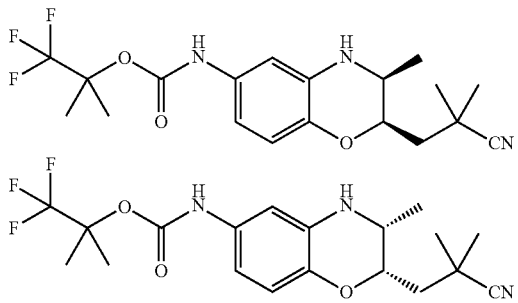

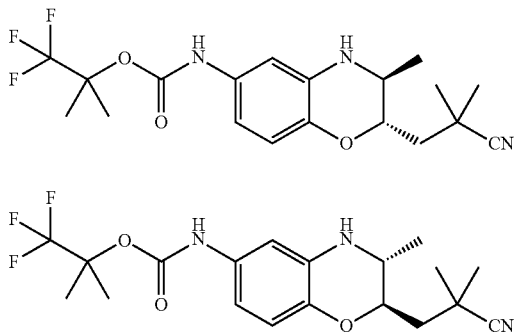

A solution of 3-((2R,3S, 2R, 3R, 2S, 3R and 2S,3S)-6-amino-3-methyl-3,4-dihydro-2H-benzo[b][1,4]oxazin-2-yl)-2,2-dimethylpropanenitrile (300 mg, 1.223 mmol) and 1,1,1-trifluoro-2-methylpropan-2-yl 1H-imidazole-1-carboxylate (299 mg, 1.345 mmol) in DMSO (5 mL) was added concentrated hydrochloric acid (60.3 mg, 0.611 mmol) and stirred at 80° C. for 5 h, then diluted with water (20 mL). The biphasic mixture was extracted with EtOAc (20 mL×3) and the combined organic layers washed with brine (20 mL×3), dried over $Na_2SO_4$ and concentrated in vacuo. The crude product was purified by column chromatography (petroleum ether:EtOAc=30:1 to 3:1) to give the title mixture as a yellow solid.

The above mixture of 4 diastereomers was separated by SFC method (Instrument: Thar SFC 350; Column: AD 250 mm*30 mm, 5 μm; Mobile phase: A: Supercritical $CO_2$, B: MeOH (0.1% $NH_3.H_2O$), A:B=80:20 at 60 mL/min; Column Temp: 38° C.; Wavelength:

220 nm) to afford four isomers: Isomer 1-trans: LCMS (ESI) calculated for $C_{19}H_{25}F_3N_3O_3$ [M+H]$^+$: 400. found: 400. Isomer 2-cis: LCMS (ESI) calculated for $C_{19}H_{25}F_3N_3O_3$ [M+H]$^+$: 400. found: 400. Isomer 3-trans: LCMS (ESI) calculated for $C_{19}H_{25}F_3N_3O_3$ [M+H]$^+$: 400. found: 400. Isomer 4-cis: LCMS (ESI) calculated for $C_{19}H_{25}F_3N_3O_3$ [M+H]$^+$: 400. found: 400.

Step 9. Preparation of 1,1,1-trifluoro-2-methylpropan-2-yl ((2S,3R)-4-((3-chloro-1-ethyl-1H-pyrazol-4-yl)sulfonyl)-2-(2-cyano-2-methylpropyl)-3-methyl-3,4-dihydro-2H-benzo[b][1,4]oxazin-6-yl)carbamate, 1,1,1-trifluoro-2-methylpropan-2-yl ((2S, 3S)-4-((3-chloro-1-ethyl-1H-pyrazol-4-yl)sulfonyl)-2-(2-cyano-2-methylpropyl)-3-methyl-3,4-dihydro-2H-benzo[b][1,4]oxazin-6-yl)carbamate, 1,1,1-trifluoro-2-methylpropan-2-yl ((2R,3R)-4-((3-chloro-1-ethyl-1H-pyrazol-4-yl)sulfonyl)-2-(2-cyano-2-methylpropyl)-3-methyl-3,4-dihydro-2H-benzo[b][1,4]oxazin-6-yl)carbamate and 1,1,1-trifluoro-2-methylpropan-2-yl ((2R,3S)-4-((3-chloro-1-ethyl-1H-pyrazol-4-yl)sulfonyl)-2-(2-cyano-2-methylpropyl)-3-methyl-3,4-dihydro-2H-benzo[b][1,4]oxazin-6-yl)carbamate

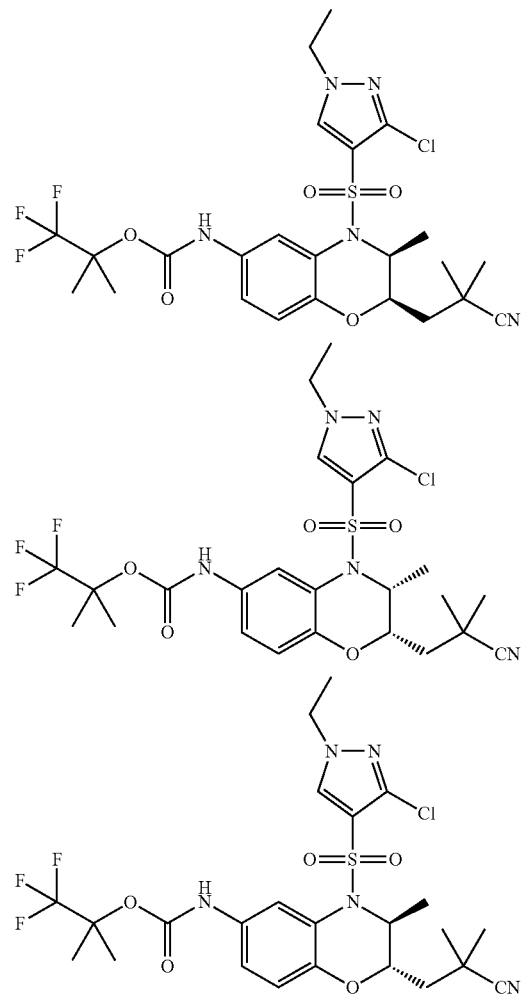

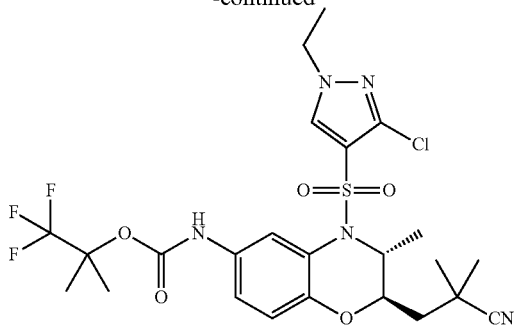

To a solution of (2R, 3S or 2S, 3R; cis)-2-(2-cyano-2-methylpropyl)-3-methyl-3,4-dihydro-2H-benzo[b][1,4]oxazin-6-yl)carbamate (Isomer 2-cis from Step 8) (100 mg, 0.250 mmol) in pyridine (2 mL) and THF (2 mL) was added 3-chloro-1-ethyl-1H-pyrazole-4-sulfonyl chloride (57.4 mg, 0.250 mmol). The reaction was stirred at 60° C. for 3 h, then treated with 1M HCl aqueous solution to pH=4. The aqueous layer was extracted with EtOAc (10 mL×3), dried over anhydrous $Na_2SO_4$, and concentrated. The title compound (Isomer 2-cis from Step 9) was obtained by prep-TLC (petroleum ether:EtOAc=2:1) as a yellow solid. LCMS (ESI) calculated for $C_{24}H_{30}ClF_3N_5O_5S$ $[M+H]^+$: 592. found: 592.

The other three isomers were respectively obtained from the corresponding intermediates (Isomer 1, 3 and 4 from Step 8) using a similar procedure.

Step 10—Preparation of 1,1,1-trifluoro-2-methylpropan-2-yl((2S,3S)-4-((3-chloro-1-ethyl-1H-pyrazol-4-yl)sulfonyl)-2-(2,2-dimethyl-3-oxopropyl)-3-methyl-3,4-dihydro-2H-benzo[b][1,4]oxazin-6-yl)carbamate, 1,1,1-trifluoro-2-methylpropan-2-yl ((2S, 3R)-4-((3-chloro-1-ethyl-1H-pyrazol-4-yl)sulfonyl)-2-(2,2-dimethyl-3-oxopropyl)-3-methyl-3,4-dihydro-2H-benzo[b][1,4]oxazin-6-yl)carbamate, 1,1,1-trifluoro-2-methylpropan-2-yl ((2R,3S)-4-((3-chloro-1-ethyl-1H-pyrazol-4-yl)sulfonyl)-2-(2,2-dimethyl-3-oxopropyl)-3-methyl-3,4-dihydro-2H-benzo[b][1,4]oxazin-6-yl)carbamate and 1,1,1-trifluoro-2-methylpropan-2-yl ((2R,3R)-4-((3-chloro-1-ethyl-1H-pyrazol-4-yl)sulfonyl)-2-(2,2-dimethyl-3-oxopropyl)-3-methyl-3,4-dihydro-2H-benzo[b][1,4]oxazin-6-yl)carbamate

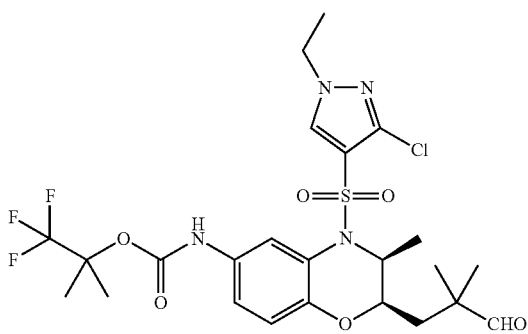

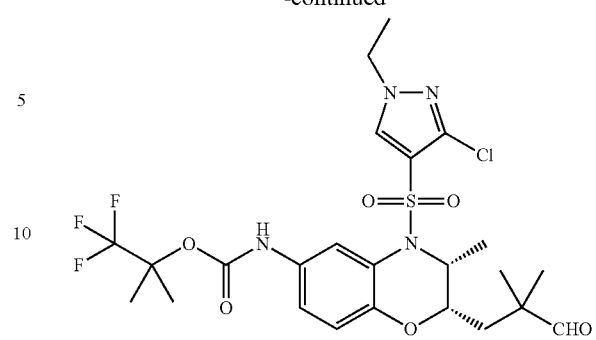

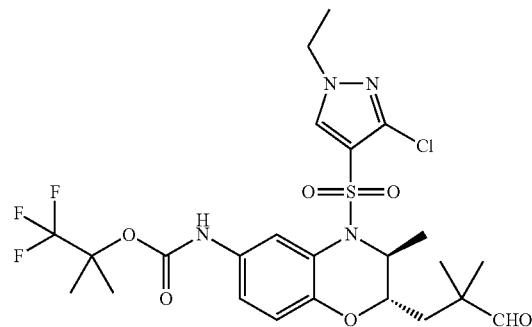

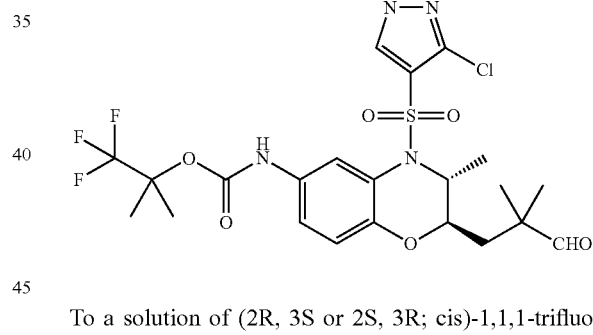

To a solution of (2R, 3S or 2S, 3R; cis)-1,1,1-trifluoro-2-methylpropan-2-yl (4-((3-chloro-1-ethyl-1H-pyrazol-4-yl)sulfonyl)-2-(2-cyano-2-methylpropyl)-3-methyl-3,4-dihydro-2H-benzo[b][1,4]oxazin-6-yl)carbamate (Isomer 2-cis from Step 9) (40 mg, 0.068 mmol) in toluene (10 mL) was added DIBAL-H (0.270 mL, 0.270 mmol) dropwise at −78° C. under nitrogen. The reaction was stirred at −78° C. for 1 h, then quenched by MeOH (0.3 mL) and acidified with 1M HCl (1 mL). After stirring at 0° C. for 10 min, the resulting mixture was extracted with EtOAc (10 mL×3) and the combined organic layers washed with brine (10 mL×3), dried over anhydrous $Na_2SO_4$ and evaporated. The crude product was purified by prep-TLC (petroleum ether:EtOAc=3:1) to give the title compound (Isomer 2-cis from Step 10) as a light yellow solid. LCMS (ESI) calculated for $C_{24}H_{31}ClF_3N_4O_6S$ $[M+H]^+$: 595. found: 595.

The other three isomers were respectively obtained from the corresponding intermediates (Isomer 1, 3 and 4 from Step 9) using a similar procedure as described above.

Step 11. Preparation of 3-((2S,3S)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid, 3-((2S,3R)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid, 3-((2R,3S)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid and 3-((2R,3R)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid

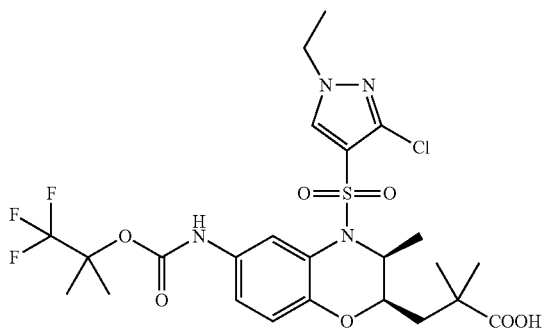

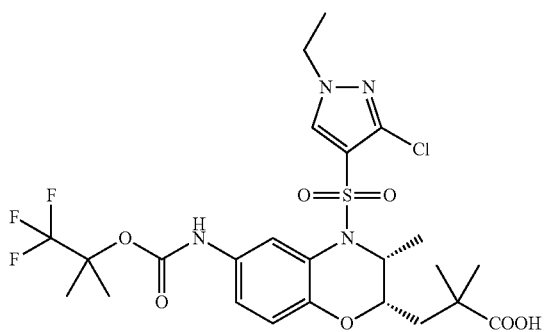

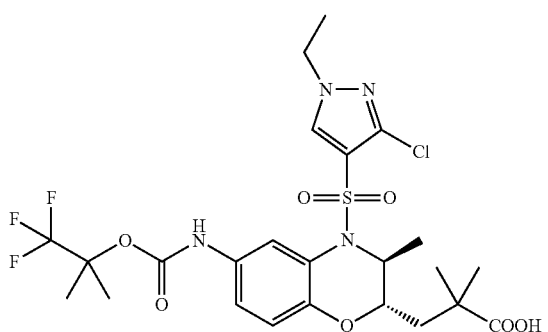

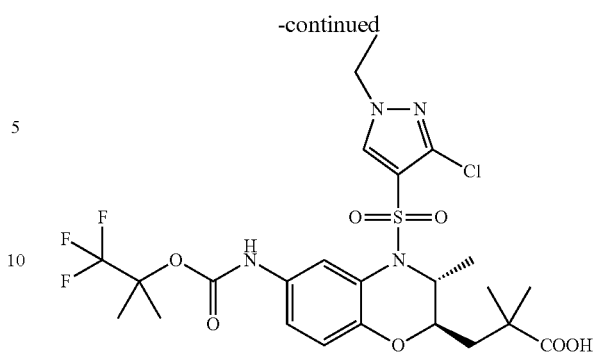

To a solution of (2R, 3S or 2S, 3R; cis)-1,1,1-trifluoro-2-methylpropan-2-yl(4-((3-chloro-1-ethyl-1H-pyrazol-4-yl)sulfonyl)-2-(2,2-dimethyl-3-oxopropyl)-3-methyl-3,4-dihydro-2H-benzo[b][1,4]oxazin-6-yl)carbamate (Isomer 2-cis from Step 10, 40 mg, 0.067 mmol) in tetrahydrofuran (10 mL) and water (2 mL) were added sulfamic acid (39.2 mg, 0.403 mmol), potassium dihydrogenphosphate (110 mg, 0.807 mmol) and sodium chlorite (9.12 mg, 0.101 mmol) in one portion at 0° C. The reaction was stirred at 0° C. for 1 h, then diluted with water (10 mL). The biphasic mixture was extracted with EtOAc (20 mL×3) and the combined organic layers dried over anhydrous $Na_2SO_4$ and evaporated to dryness. The crude product was purified by prep-HPLC (MeCN/water using TFA buffer) to afford Example No. 26A (Isomer 2-cis) as a white solid. LCMS (ESI) calculated for $C_{24}H_{29}ClF_3N_4O_7S$ [M−H]−: 609. found: 609. $^1$HNMR (400 MHz, DMSO) δ 8.23 (1H, s), 7.90 (1H, s), 7.00 (1H, dd, J=2.0, 8.8 Hz), 6.74 (1H, d, J=8.8 Hz), 4.46 (1H, d, J=7.2 Hz), 4.12 (2H, q, J=7.2 Hz), 3.77 (1H, d, J=8.0 Hz), 1.81-1.87 (2H, m), 1.76 (6H, s), 1.41 (3H, t, J=7.2 Hz), 1.22 (3H, s), 1.18 (3H,$), 1.11 (3H, d, J=6.4 Hz)

The other three isomers were respectively obtained from the corresponding intermediates (Isomer 1, 3 and 4 from Step 10) using a similar procedure as described above. Example No. 26B: Isomer 1-trans: LCMS (ESI) calculated for $C_{24}H_{29}ClF_3N_4O_7S$ [M−H]−: 609. found: 609. $^1$HNMR (400 MHz, CDCl$_3$) δ 8.36 (1H, s), 8.02 (1H, s), 6.67-6.72 (2H, m), 6.58 (1H, d, J=7.6 Hz), 4.57 (1H, d, J=2.0 Hz), 4.11-4.27 (3H, m), 1.98 (1H, t, J=7.2 Hz), 1.74 (6H, s), 1.68 (1H, d, J=14.4 Hz), 1.51 (3H, t, J=7.2 Hz), 1.11-1.28 (9H, m). Example No. 26C: Isomer 3-trans: LCMS (ESI) calculated for $C_{24}H_{29}ClF_3N_4O_7S$ [M−H]−: 609. found: 609. $^1$HNMR (400 MHz, CDCl$_3$) δ 8.35 (1H, s), 8.01 (1H, s), 6.68-6.71 (2H, m), 6.58 (1H, d, J=8.0 Hz), 4.57 (1H, d, J=6.4 Hz), 4.26 (1H, d, J=8.4 Hz), 4.12 (2H, q, J=7.2 Hz), 1.97-2.00 (1H, m), 1.74 (6H, s), 1.68 (1H, d, J=14.4 Hz), 1.51 (3H, t, J=7.2 Hz), 1.15-1.28 (9H, m). Example No. 26D: Isomer 4-cis: LCMS (ESI) calculated for $C_{24}H_{29}ClF_3N_4O_7S$ [M−H]−: 609. found: 609. $^1$HNMR (400 MHz, CDCl$_3$) δ 8.01 (1H, s), 7.84 (1H, s), 6.79 (1H, d, J=7.6 Hz), 6.70 (1H, d, J=8.8 Hz), 6.63 (1H, br s), 4.51 (1H, d, J=6.4 Hz), 4.07 (2H, q, J=7.2 Hz), 3.86 (1H, d, J=8.8 Hz), 1.99-2.02 (1H, m), 1.74 (6H, d, J=7.2 Hz), 1.44 (3H, t, J=7.2 Hz), 1.30 (3H, s), 1.25 (3H, s), 1.17 (3H, d, J=7.2 Hz).

Example 27

Preparation of Additional 3-Methyl Benzoxazine Propanoic Acids

The compounds in Table 10 were prepared based on the experimental procedures described in Example 26, and can be achieved by one of skill in the art in light of the present disclosure.

TABLE 10

| Ex. No. | Structure | Name | Observed m/z |
|---|---|---|---|
| 27A | 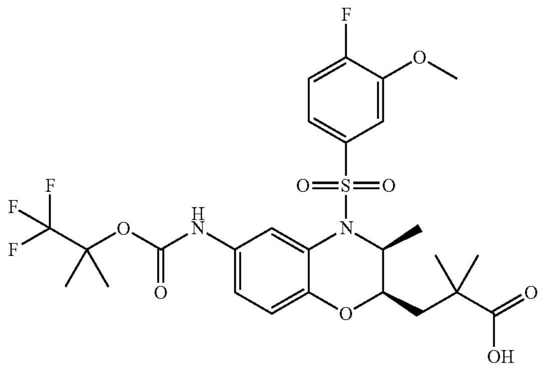 [SMILES: COc1cc(S(=O)(=O)N2c3cc(NC(=O)OC(C)(C)C(F)(F)F)ccc3O[C@H](CC(C)(C)C(=O)O)[C@@H]2C)ccc1F] | 3-[(2R,3S)-4-[(4-fluoro-3-methoxyphenyl)sulfonyl]-3-methyl-6-{[(2,2,2-trifluoro-1,1-dimethylethoxy)carbonyl]amino}-3,4-dihydro-2H-1,4-benzoxazin-2-yl]-2,2-dimethylpropanoic acid | 607 (M + H)+ |
| 27B | 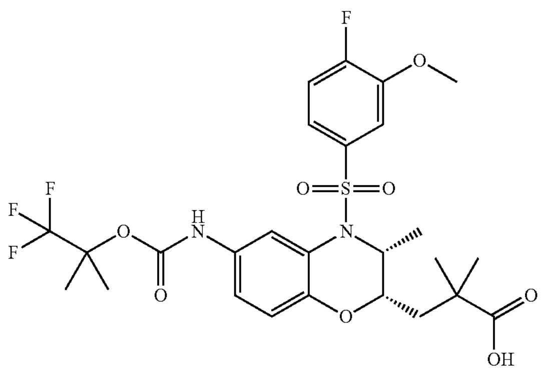 [SMILES: COc1cc(S(=O)(=O)N2c3cc(NC(=O)OC(C)(C)C(F)(F)F)ccc3O[C@@H](CC(C)(C)C(=O)O)[C@H]2C)ccc1F] | 3-[(2S,3R)-4-[(4-fluoro-3-methoxyphenyl)sulfonyl]-3-methyl-6-{[(2,2,2-trifluoro-1,1-dimethylethoxy)carbonyl]amino}-3,4-dihydro-2H-1,4-benzoxazin-2-yl]-2,2-dimethylpropanoic acid | 607 (M + H)+ |

Example 28

(S)-3-(8-fluoro-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid

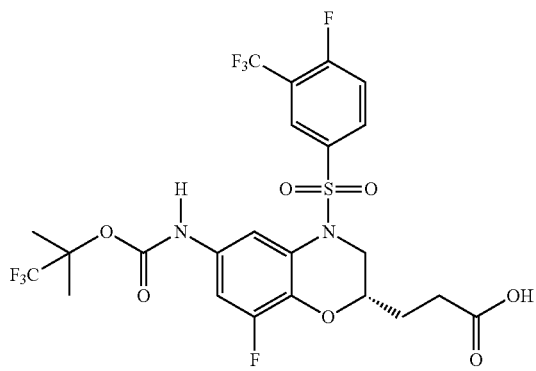 [SMILES: CC(C)(OC(=O)Nc1cc(F)c2c(c1)N(S(=O)(=O)c1ccc(F)c(C(F)(F)F)c1)C[C@H](CCC(=O)O)O2)C(F)(F)F]

Step 1—Preparation of 2-(benzylamino)-6-fluoro-4-nitrophenol

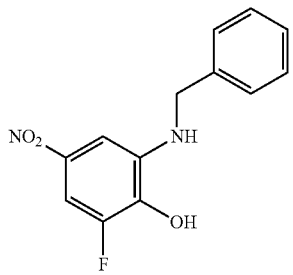 [SMILES: O=[N+]([O-])c1cc(F)c(O)c(NCc2ccccc2)c1]

To a solution of 2-amino-6-fluoro-4-nitrophenol (4.2 g, 24.4 mmol) in 84 mL of MeOH was added benzaldehyde (3.36 g, 68.38 mmol) and stirred for 1 h. The reaction mixture was then treated with NaBH$_4$ (924 mg, 24.4 mmol) at 0° C. After 1 h, the reaction mixture was concentrated to remove the MeOH solvent and the residue was poured into 50 mL of water, and then extracted with EtOAc (20 mL×3). The combined organic layer was washed with brine (30 mL×2) and dried over Na$_2$SO$_4$. After concentrated in vacuo, the crude product was purified by column chromatography on silica gel (petroleum ether:EtOAc=10:1) to give the title compound as a red oil. LCMS (ESI) calculated for C$_{13}$H$_{12}$FN$_2$O$_3$ [M+H]$^+$: 263. found: 263. $^1$H-NMR (400 MHz, CDCl$_3$) δ 7.29-7.35 (5H, m), 7.21 (1H, t, J=6.4 Hz), 6.99 (1H, s), 4.40 (2H, s).

Step 2—Preparation of (R)-(4-benzyl-8-fluoro-6-nitro-3,4-dihydro-2H-benzo[b][1,4]oxazin-2-yl)methanol

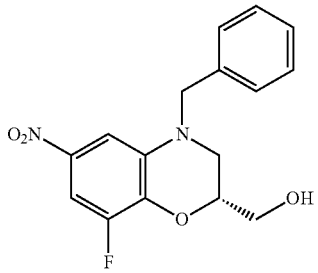 [SMILES: O=[N+]([O-])c1cc(F)c2c(c1)N(Cc1ccccc1)C[C@H](CO)O2]

To a mixture of 2-(benzylamino)-6-fluoro-4-nitrophenol (9.5 g, 36.3 mmol) and LiClO$_4$ (4.89 g, 45.99 mmol) in 150 mL of toluene was added (S)-2-(chloromethyl)oxirane (3.17 g, 34.5 mmol) at 50° C. The result mixture was further stirred at 50° C. for 10 hours. Then NaOMe (2.35 g, 43.5 mmol) in 20 mL of MeOH was added slowly. The mixture was stirred at 50° C. for an additional 3 hours. Once cooled to 0° C., the reaction was quenched with 100 mL of H$_2$O and extracted with EtOAc (50 mL×3). The organic layer was dried over Na$_2$SO$_4$ and concentrated. The crude product was purified by silica column chromatography (petroleum ether:EtOAc=5:1 to 3:1) to afford the title compound as a red oil. LCMS (ESI) calculated for C$_{16}$H$_{16}$FN$_2$O$_4$ [M+H]$^+$: 319. found: 319. $^1$H-NMR (400 MHz, CDCl$_3$) δ 7.18-7.38 (7H, m), 4.47 (2H, s), 4.27-4.30 (1H, m), 3.76-3.87 (2H, m), 3.32-3.35 (2H, m).

Step 3—Preparation of (R)-4-benzyl-2-(bromomethyl)-8-fluoro-6-nitro-3,4-dihydro-2H-benzo[b][1,4]oxazine

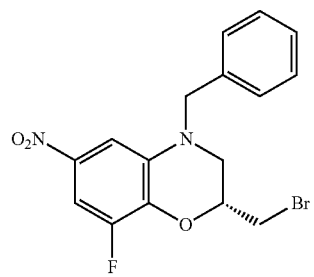 [SMILES: O=[N+]([O-])c1cc(F)c2c(c1)N(Cc1ccccc1)C[C@H](CBr)O2]

To a solution of (R)-(4-benzyl-8-fluoro-6-nitro-3,4-dihydro-2H-benzo[b][1,4]oxazin-2-yl)methanol (1.8 g, 5.66 mmol) and CBr$_4$ (2.82 g, 8.49 mmol) in THF (90 mL) was added PPh$_3$ (3.72 g, 14.15 mmol) portionwise. The reaction mixture was stirred at 60° C. for 1 h, then concentrated in vacuo. The residue was poured into 50 mL of water and extracted with EtOAc (30 mL×3). The combined organic layer was washed with brine (30 mL×3) and dried over Na$_2$SO$_4$. After concentrated in vacuo, the crude product was purified by silica gel column chromatography (petroleum ether:EtOAc=10:1) to give the title compound as a yellow solid. LCMS (ESI) calculated for C$_{16}$H$_{15}$BrFN$_2$O$_3$ [M+H]$^+$: 381. found: 381. $^1$H-NMR (400 MHz, Methanol-d4) δ 7.28-7.45 (7H, m), 4.55-4.62 (3H, m), 3.67 (2H, d, J=6.0 Hz), 3.63 (1H, dd, J=12.0 Hz), 3.76-3.87 (2H, m), 3.46-3.50 (1H, m).

Step 4—Preparation of (S)-methyl 3-(4-benzyl-8-fluoro-6-nitro-3,4-dihydro-2H-benzo[b][1,4]oxazin-2-yl)propanoate

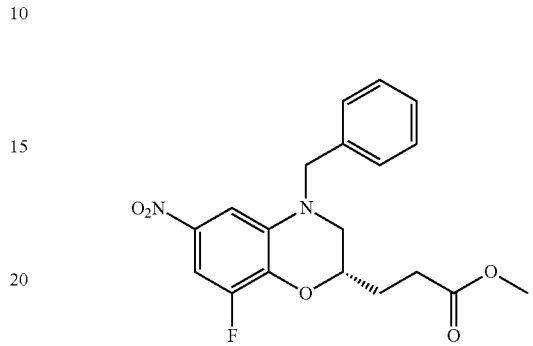

A mixture of (R)-4-benzyl-2-(bromomethyl)-8-fluoro-6-nitro-3,4-dihydro-2H-benzo[b][1,4]oxazine (500 mg, 1.3 mmol), dimethyl malonate (1.7 g, 13.1 mmol) and NaHCO$_3$ (99 mg, 1.1 mmol) in 10 mL of DMF was stirred at 100° C. for 20 h. The mixture was cooled to room temperature, poured into water (50 mL) and extracted with ethyl acetate (30 mL×3). The combined organic fractions were washed with saturated aqueous ammonium chloride (50 mL), dried over Na$_2$SO$_4$, filtered and evaporated under reduced pressure. The crude product was purified by silica gel column chromatography (petroleum ether:EtOAc=20:1 to 10:1) to afford the title compound as a yellow solid. LCMS (ESI) calculated for C$_{19}$H$_{20}$FN$_2$O$_5$ [M+H]$^+$: 375. found: 375. $^1$H NMR (CDCl$_3$, 400 MHz) δ 7.25-7.49 (6H, m), 7.18-7.23 (1H, m), 4.44-4.56 (2H, m), 4.27 (1H, brs), 3.68 (3H, s), 3.36 (1H, dd, J=2.1, 12.3 Hz), 3.19 (1H, dd, J=7.6, 12.3 Hz), 2.58 (2H, t, J=7.0 Hz), 1.91-2.05 (2H, m).

Step 5—Preparation of (S)-methyl 3-(6-amino-4-benzyl-8-fluoro-3,4-dihydro-2H-benzo[b][1,4]oxazin-2-yl)propanoate

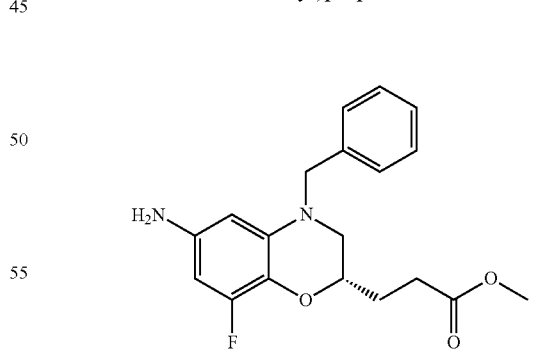

A mixture of (S)-methyl 3-(4-benzyl-8-fluoro-6-nitro-3,4-dihydro-2H-benzo[b][1,4]oxazin-2-yl)propanoate (1.5 g, 4.0 mmol) and 100 mg of Pd/C (5%) in ethyl acetate (80 mL) were stirred under H$_2$ at 50 psi at 25° C. for 8 h. The reaction mixture was the filtrated and concentrated to obtain the title compound as black oil, which was taken forward without further purification. LCMS (ESI) calculated for C$_{19}$H$_{22}$FN$_2$O$_3$ [M+H]$^+$: 345. found: 345. $^1$H NMR (CDCl$_3$, 400 MHz) δ 7.19-7.34 (3H, m), 7.16 (2H, brs), 5.69-5.87 (2H, m), 4.25-4.44 (2H, m), 3.98-4.09 (1H, m), 3.61 (3H, s), 3.06-3.26 (2H, m), 2.44-2.60 (2H, m), 1.83-1.98 (2H, m).

Step 6—Preparation of (S)-methyl 3-(4-benzyl-8-fluoro-6-((((1,1,1-trifluoro-2-methylpropan-2-yl)oxy)carbonyl)amino)-3,4-dihydro-2H-benzo[b][1,4]oxazin-2-yl)propanoate

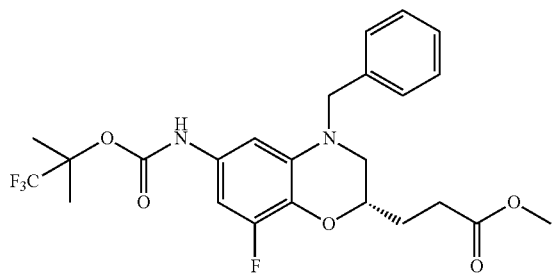 [SMILES: COC(=O)CC[C@H]1CN(Cc2ccccc2)c2cc(NC(=O)OC(C)(C)C(F)(F)F)cc(F)c2O1]

A solution of (S)-methyl 3-(6-amino-4-benzyl-8-fluoro-3,4-dihydro-2H-benzo[b][1,4]oxazin-2-yl)propanoate (1.38 g, 4.01 mmol) and 3-methyl-1-(((1,1,1-trifluoro-2-methylpropan-2-yl)oxy)carbonyl)-1H-imidazol-3-ium iodide (1.6 g, 4.4 mmol) in DMSO (20 mL) was stirred at 30° C. for 10 h. The mixture was cooled to room temperature, then poured into water (100 mL) and extracted with ethyl acetate (40 mL×3). The combined organic layer was washed with brine (30 mL×2), dried over $Na_2SO_4$, filtered and evaporated under reduced pressure. The crude product was purified by column chromatography on silica gel (petroleum ether:EtOAc=20:1 to 3:1) to give the title compound as a colorless oil. LCMS (ESI) calculated for $C_{24}H_{27}F_4N_2O_5$ [M+H]$^+$: 499. found: 499. $^1$HNMR (CDCl$_3$, 400 MHz) δ 7.20-7.35 (3H, m), 7.13-7.19 (2H, m), 6.60 (1H, d, J=9.7 Hz), 6.25-6.44 (2H, m), 4.28-4.44 (2H, m), 3.99-4.08 (1H, m), 3.61 (3H, s), 3.04-3.28 (2H, m), 2.44-2.58 (2H, m), 1.81-1.94 (2H, m), 1.64 (6H, s).

Step 7—Preparation of (S)-methyl 3-(8-fluoro-6-((((1,1,1-trifluoro-2-methylpropan-2-yl)oxy)carbonyl)amino)-3,4-dihydro-2H-benzo[b][1,4]oxazin-2-yl)propanoate

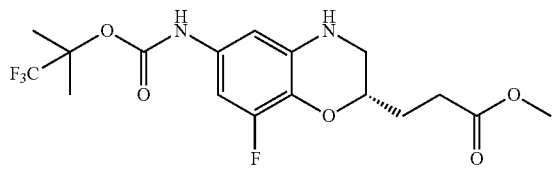 [SMILES: COC(=O)CC[C@H]1CNc2cc(NC(=O)OC(C)(C)C(F)(F)F)cc(F)c2O1]

A mixture of (S)-methyl 3-(4-benzyl-8-fluoro-6-((((1,1,1-trifluoro-2-methylpropan-2-yl)oxy)carbonyl)amino)-3,4-dihydro-2H-benzo[b][1,4]oxazin-2-yl)propanoate (1.2 g, 2.4 mmol) and dihydroxypalladium (100 mg) in EtOH (60 mL) was stirred under H$_2$ at 1 atm 50° C. for 6 h. The reaction mixture was then filtrated and concentrated. The crude product was purified by silica gel column chromatography (petroleum ether:EtOAc=4:1) to obtain the title compound as a black oil. LCMS (ESI) calculated for $C_{17}H_{21}F_4N_2O_5$ [M+H]$^+$: 409. found: 409. $^1$H NMR (CDCl$_3$, 400 MHz) δ 6.33-6.53 (2H, m), 4.02-4.10 (1H, m), 3.57-3.72 (3H, m), 3.35 (1H, d, J=11.7 Hz), 3.10 (1H, dd, J=7.6, 11.5 Hz), 2.44-2.64 (2H, m), 1.87-1.98 (2H, m), 1.66 (6H, s).

Step 8—Preparation of (S)-methyl 3-(8-fluoro-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoate

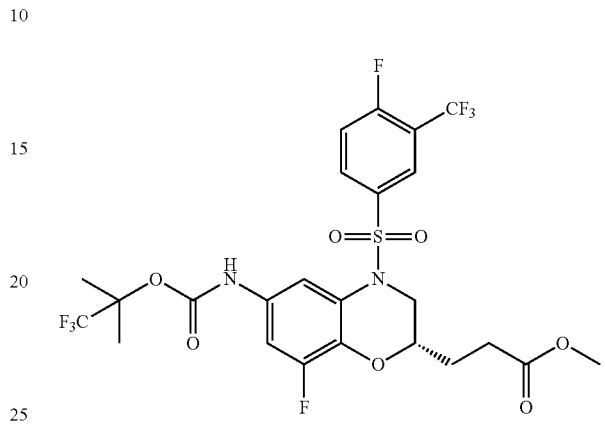

To a solution of (S)-methyl 3-(8-fluoro-6-((((1,1,1-trifluoro-2-methylpropan-2-yl)oxy)carbonyl)amino)-3,4-dihydro-2H-benzo[b][1,4]oxazin-2-yl)propanoate (60 mg, 0.1 mmol) and pyridine (69.7 mg, 0.8 mmol) in THF (1 mL) was added 4-fluoro-3-(trifluoromethyl)benzene-1-sulfonyl chloride (55 mg, 0.2 mmol) and the reaction was stirred at 20° C. for 20 h, then poured into water (2 mL) and extracted with ethyl acetate (1 mL×3). The combined organic layer was washed with brine (1 mL×2), dried over Na$_2$SO$_4$ and filtered. The solvent was evaporated under reduced pressure and the crude product purified by prep-TLC, eluting with (petroleum ether:EtOAc=3:1), to give the title compound as a colorless solid. LCMS (ESI) calculated for $C_{24}H_{23}F_8N_2O_7S$ [M+H]$^+$: 635. found: 635.

Step 9—Preparation of (S)-3-(8-fluoro-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid

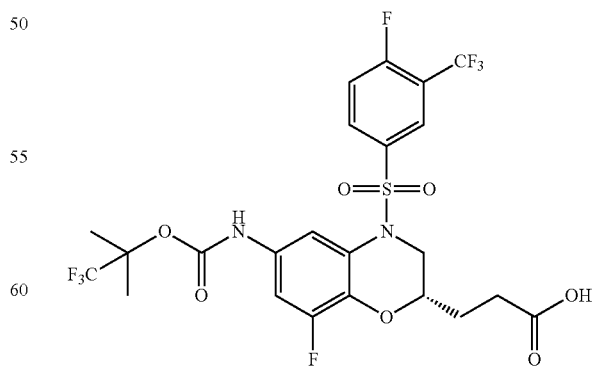

(S)-methyl 3-(8-fluoro-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin- 2-yl)propanoate (40 mg, 0.06 mmol) and lithium hydroxide hydrate (42.8 mg, 1.0 mmol) were stirred at 0° C. for 2 h in 1,4-Dioxane (1 mL)/Water (0.5 mL), then treated with hydrochloric acid (1M, 10 mL). The biphasic mixture was extracted with ethyl acetate (10 mL) and the combined organic layers were washed with aqueous ammonium chloride (5 mL), dried ($Na_2SO_4$), filtered and concentrated under reduced pressure. The crude product was purified by prep-HPLC (MeCN/water using TFA buffer) to give the title compound as a white solid. LCMS (ESI) calculated for $C_{23}H_{21}F_8N_2O_7S$ [M+H]$^+$: 621. found: 621. $^1$H NMR (CDCl$_3$, 400 MHz) δ 8.11 (d, J=4.0 Hz, 1H), 7.93 (br s, 1H), 7.61 (br s, 1H), 7.34 (t, J=9.2 Hz, 1H), 6.99-7.10 (m, 1H), 6.62 (s, 1H), 4.35 (d, J=14.0 Hz, 1H), 3.74 (br s, 1H), 3.29 (dd, J=9.5, 14.0 Hz, 1H), 2.57-2.64 (m, 2H), 1.86-2.01 (m, 2H), 1.77 (s, 6H).

Example 29

Preparation of Additional 8-Fluoro Benzoxazine Propanoic Acids

The compounds in Table 11 were prepared based on the experimental procedures described in Example 28, and can be achieved by one of skill in the art in light of the present disclosure.

TABLE 11

| Ex. No. | Structure | Name | Observed m/z |
|---|---|---|---|
| 29A | 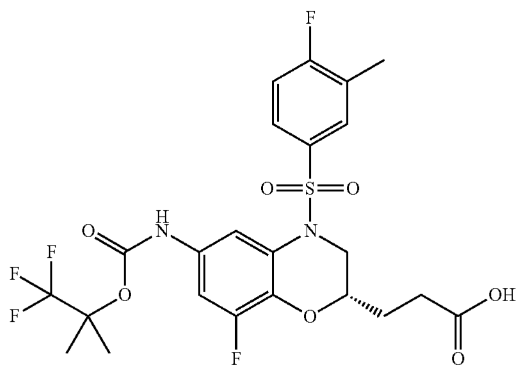 [SMILES: Cc1cc(S(=O)(=O)N2C[C@H](CCC(=O)O)Oc3c(F)cc(NC(=O)OC(C)(C)C(F)(F)F)cc32)ccc1F] | 3-[(2S)-8-fluoro-4-[(4-fluoro-3-methylphenyl)sulfonyl]-6-{[(2,2,2-trifluoro-1,1-dimethylethoxy)carbonyl]amino}-3,4-dihydro-2H-1,4-benzoxazin-2-yl]propanoic acid | 567 [M + H]+ |
| 29B | 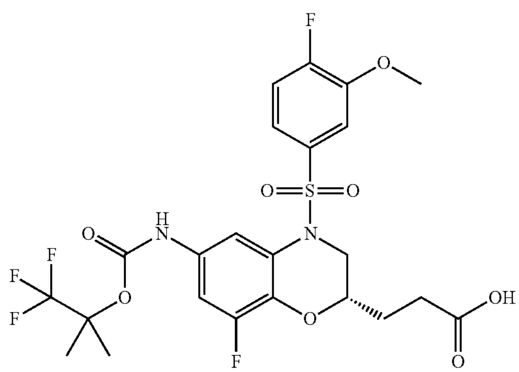 [SMILES: COc1cc(S(=O)(=O)N2C[C@H](CCC(=O)O)Oc3c(F)cc(NC(=O)OC(C)(C)C(F)(F)F)cc32)ccc1F] | 3-[(2S)-8-fluoro-4-[(4-fluoro-3-methoxyphenyl)sulfonyl]-6-{[(2,2,2-trifluoro-1,1-dimethylethoxy)carbonyl]amino}-3,4-dihydro-2H-1,4-benzoxazin-2-yl]propanoic acid | 583 [M + H]+ |
| 29C | 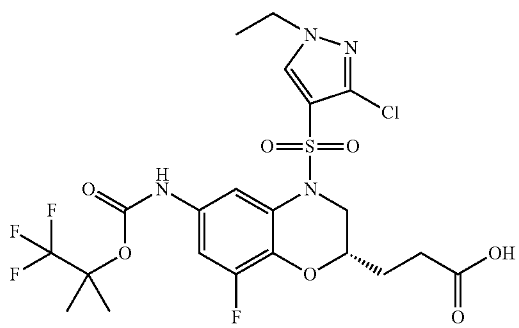 [SMILES: CCn1cc(S(=O)(=O)N2C[C@H](CCC(=O)O)Oc3c(F)cc(NC(=O)OC(C)(C)C(F)(F)F)cc32)c(Cl)n1] | 3-[(2S)-4-[(3-chloro-1-ethyl-1H-pyrazol-4-yl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid | 587 [M + H]+ |

TABLE 11-continued

| Ex. No. | Structure | Name | Observed m/z |
|---|---|---|---|
| 29D | 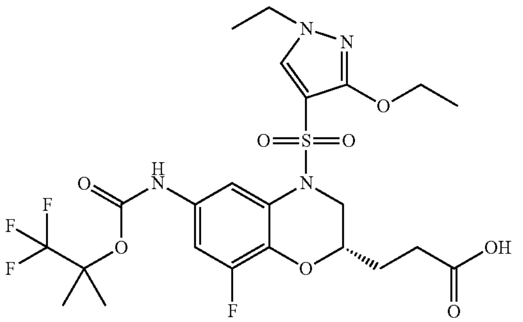 [SMILES: CCOc1nn(CC)cc1S(=O)(=O)N1C[C@H](CCC(=O)O)Oc2c(F)cc(NC(=O)OC(C)(C)C(F)(F)F)cc21] | 3-[(2S)-4-[(3-ethoxy-1-ethyl-1H-pyrazol-4-yl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid | 597 [M + H]+ |
| 29E | 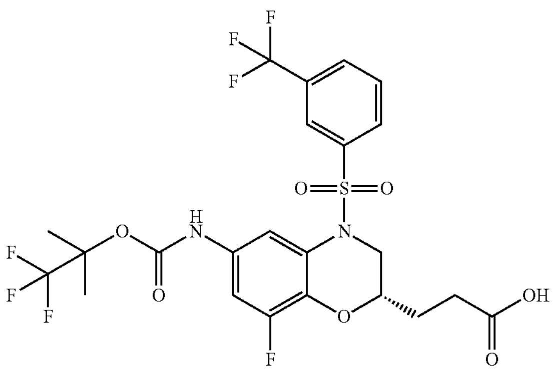 [SMILES: CC(C)(OC(=O)Nc1cc(F)c2c(c1)N(S(=O)(=O)c1cccc(C(F)(F)F)c1)C[C@H](CCC(=O)O)O2)C(F)(F)F] | 3-[(2S)-8-fluoro-6-{[(2,2,2-trifluoro-1,1-dimethylethoxy)carbonyl]amino}-4-{[3-(trifluoromethyl)phenyl]sulfonyl}-3,4-dihydro-2H-1,4-benzoxazin-2-yl]propanoic acid | 603 [M + H]+ |
| 29F | 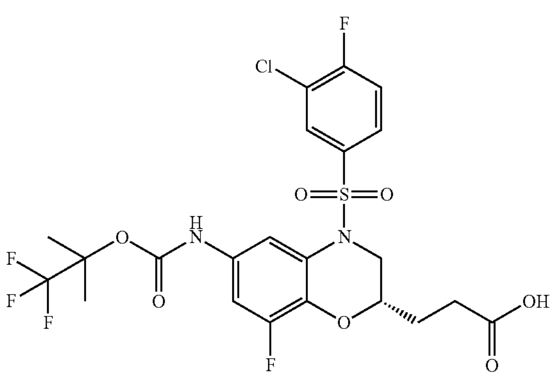 [SMILES: CC(C)(OC(=O)Nc1cc(F)c2c(c1)N(S(=O)(=O)c1ccc(F)c(Cl)c1)C[C@H](CCC(=O)O)O2)C(F)(F)F] | 3-[(2S)-4-[(3-chloro-4-fluorophenyl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid | 587 [M + H]+ |
| 29G | 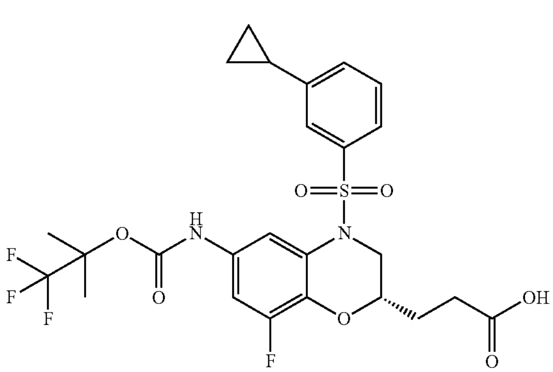 [SMILES: CC(C)(OC(=O)Nc1cc(F)c2c(c1)N(S(=O)(=O)c1cccc(C3CC3)c1)C[C@H](CCC(=O)O)O2)C(F)(F)F] | 3-[(2S)-4-[(3-cyclopropylphenyl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid | 575 [M + H]+ |

TABLE 11-continued

| Ex. No. | Structure | Name | Observed m/z |
|---|---|---|---|
| 29H | 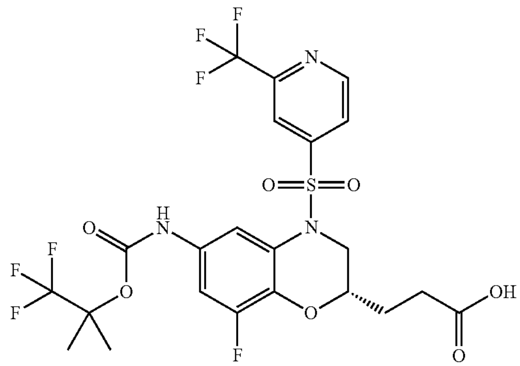 [SMILES: CC(C)(OC(=O)Nc1cc(F)c2c(c1)N(S(=O)(=O)c1ccnc(C(F)(F)F)c1)C[C@H](CCC(=O)O)O2)C(F)(F)F] | 3-[(2S)-8-fluoro-6-{[(2,2,2-trifluoro-1,1-dimethylethoxy)carbonyl]amino}-4-{[2-(trifluoromethyl)pyridin-4-yl]sulfonyl}-3,4-dihydro-2H-1,4-benzoxazin-2-yl]propanoic acid | 604 [M + H]+ |
| 29i | 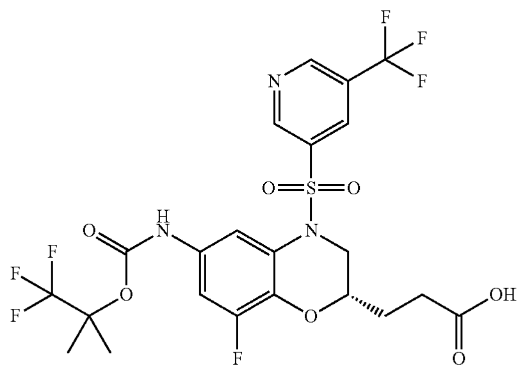 [SMILES: CC(C)(OC(=O)Nc1cc(F)c2c(c1)N(S(=O)(=O)c1cncc(C(F)(F)F)c1)C[C@H](CCC(=O)O)O2)C(F)(F)F] | 3-[(2S)-8-fluoro-6-{[(2,2,2-trifluoro-1,1-dimethylethoxy)carbonyl]amino}-4-{[5-(trifluoromethyl)pyridin-3-yl]sulfonyl}-3,4-dihydro-2H-1,4-benzoxazin-2-yl]propanoic acid | 604 [M + H]+ |

Example 30

Preparation of (R)-3-(4-((3-chloro-1-ethyl-1H-pyrazol-4-yl)sulfonyl)-5-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid and (S)-3-(4-((3-chloro-1-ethyl-1H-pyrazol-4-yl)sulfonyl)-5-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid (Example Nos. 30A and 30B)

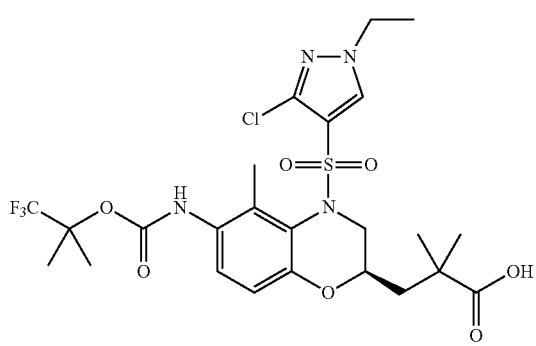

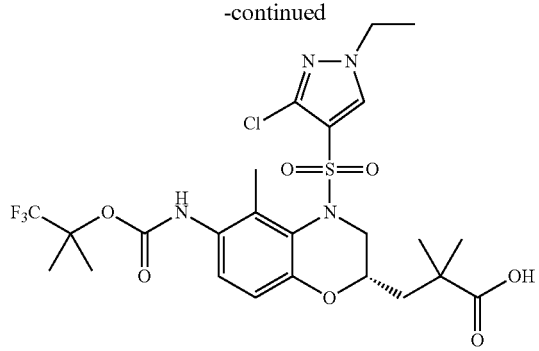

Step 1—Preparation of N-(2-fluoro-6-methylphenyl)-4-methylbenzenesulfonamide

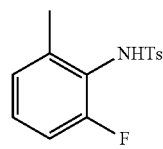

To a solution of 2-fluoro-6-methylaniline (5 g, 40.0 mmol) in pyridine (24.6 mL, 304 mmol), was added tosyl chloride (11.43 g, 59.9 mmol) in portions at 0° C. under nitrogen. The reaction was stirred at 25° C. for 8 hours, then diluted with water (30 mL) and acidified with 1M HCl solution (pH=2). The yellow precipitate was collected and washed with CH$_2$Cl$_2$ (100 mL×2) to afford the title compound as yellow solid, which was used directly without further purification. $^1$H-NMR (400 MHz, CDCl$_3$) δ 7.57 (2H, d, J=8.4 Hz), 7.22 (2H, d, J=8.4 Hz), 7.08-7.11 (1H, m), 6.73 (1H, t, J=8.8 Hz), 6.06 (1H, s), 2.42 (3H, s), 2.40 (3H, s).

Step 2—Preparation of (R and S)—N-(4-cyano-2-hydroxy-4-methylpentyl)-N-(2-fluoro-6-methylphenyl)-4-methylbenzenesulfonamide

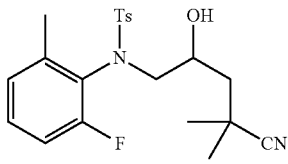 [SMILES: Cc1ccc(S(=O)(=O)N(CC(O)CC(C)(C)C#N)c2c(C)cccc2F)cc1]

To a mixture of N-(2-fluoro-6-methylphenyl)-4-methylbenzenesulfonamide (12 g, 43.0 mmol) and (R and S)-2,2-dimethyl-3-(oxiran-2-yl)propanenitrile (6.45 g, 51.6 mmol) in 1,4-Dioxane (100 mL) was added tetrabutylammonium bromide (2.77 g, 8.59 mmol) and potassium carbonate (17.81 g, 129 mmol) in one portion at room temperature under nitrogen. The reaction was stirred at 90° C. for 17 hours, then concentrated, diluted with water (80 mL) and extracted with EtOAc (150 mL×4). The combined organic layers were dried over Na$_2$SO$_4$, filtered and evaporated to dryness. The crude product was purified by silica gel column chromatography (100% EtOAc) to give the title compound as colorless oil. LCMS (ESI) calculated for C$_{21}$H$_{26}$FN$_2$O$_3$S [M+H]$^+$: 405.2. found: 405.1; $^1$H-NMR (400 MHz, CDCl$_3$) δ 7.60-7.63 (2H, m), 7.22-7.31 (3H, m), 7.08-7.11 (1H, m), 6.76-6.87 (1H, m), 3.90-4.04 (1H, m), 3.53-3.59 (1H, m), 3.33-3.45 (1H, m), 2.39-2.46 (6H, m), 1.62-1.67 (2H, m), 1.43-1.51 (1H, m), 1.34-1.37 (3H, m), 1.17-1.30 (3H, m).

Step 3—Preparation of (R and S)-2,2-dimethyl-3-(5-methyl-4-tosyl-3,4-dihydro-2H-benzo[b][1,4]oxazin-2-yl)propanenitrile

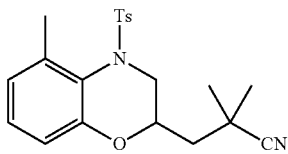 [SMILES: Cc1ccc(S(=O)(=O)N2CC(CC(C)(C)C#N)Oc3cccc(C)c32)cc1]

To a mixture of (R and S)—N-(4-cyano-2-hydroxy-4-methylpentyl)-N-(2-fluoro-6-methylphenyl)-4-methylbenzenesulfonamide (7.3 g, 18.05 mmol) in anhydrous THF (100 mL) was added tetrabutylammonium bromide (1.164 g, 3.61 mmol) and sodium hydroxide (2.89 g, 72.2 mmol) in one portion at 20° C. under nitrogen. The reaction was stirred at 80° C. for 1 hour, then filtered and the filtrate concentrated in vacuo. The crude product was purified by column chromatography (petroleum ether:ethyl acetate=4:1) to afford the title compound as colorless oil. LCMS (ESI) calculated for C$_{21}$H$_{25}$N$_2$O$_3$S [M+H]$^+$: 385.2. found: 385.1;

$^1$H-NMR (400 MHz, CDCl$_3$) δ 7.57 (2H, d, J=8 Hz), 7.30 (2H, d, J=9.2 Hz), 7.07-7.11 (1H, m), 6.89 (1H, d, J=7.2 Hz), 6.68 (1H, d, J=8 Hz), 4.10-4.15 (1H, m), 3.97-4.00 (1H, m), 2.97-3.06 (1H, m), 2.51 (3H, s), 2.44 (3H, s), 1.63-1.69 (2H, m), 1.53-1.58 (1H, m), 1.35 (3H, s), 1.30 (3H, s).

Step 4—Preparation of (R and S)-2,2-dimethyl-3-(5-methyl-6-nitro-4-tosyl-3,4-dihydro-2H-benzo[b][1,4]oxazin-2-yl)propanenitrile

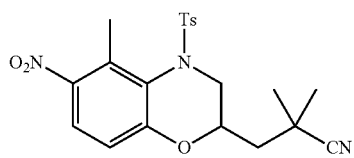 [SMILES: Cc1ccc(S(=O)(=O)N2CC(CC(C)(C)C#N)Oc3ccc([N+](=O)[O-])c(C)c32)cc1]

A solution of (R and S)-2,2-dimethyl-3-(5-methyl-4-tosyl-3,4-dihydro-2H-benzo[b][1,4]oxazin-2-yl)propanenitrile (4.05 g, 10.53 mmol) in dry CH$_2$Cl$_2$ (50 mL) was cooled at −20° C., followed by the addition of nitronium tetrafluoroborate (1.539 g, 11.59 mmol) in portions. The reaction was stirred at −20° C. for 4 h, then diluted with DCM (20 mL) and quenched with water (20 mL). The organic layer was separated, washed with brine, dried over Na$_2$SO$_4$ and concentrated in vacuo. The crude product was purified by column chromatography (petroleum ether:ethyl acetate=3:1) to afford the title compound as a yellow oil. LCMS (ESI) calculated for C$_{21}$H$_{23}$N$_3$O$_5$SNa [M+Na]$^+$: 452.1. found: 452.1; $^1$H-NMR (400 MHz, CDCl$_3$) δ 7.92 (1H, d, J=9.2 Hz), 7.59 (2H, d, J=7.6 Hz), 7.29-7.34 (2H, m), 6.76-6.82 (1H, m), 4.17-4.23 (1H, m), 2.92-2.99 (1H, m), 2.66 (3H, s), 2.54 (1H, s), 2.44 (3H, s), 1.68-1.84 (2H, m), 1.62-1.63 (1H, m), 1.37 (3H, s), 1.31 (3H, s).

Step 5—Preparation of (R and S)-3-(6-amino-5-methyl-4-tosyl-3,4-dihydro-2H-benzo[b][1,4]oxazin-2-yl)-2,2-dimethylpropanenitrile

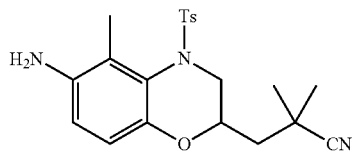

To a solution of (R and S)-2,2-dimethyl-3-(5-methyl-6-nitro-4-tosyl-3,4-dihydro-2H-benzo[b][1,4]oxazin-2-yl)propanenitrile (3 g, 6.99 mmol) in EtOAc (50 mL) was added Pd/C (0.372 g, 3.49 mmol) in one portion at 25° C. under nitrogen. The reaction was stirred at 25° C. under H$_2$ (30 psi) for 16 hours, then filtered and evaporated to dryness. The crude product was purified by silica gel chromatography (petroleum ether:ethyl acetate=1:1) to afford the title compound as yellow oil. LCMS (ESI) calculated for C$_{21}$H$_{26}$N$_3$O$_3$S [M+H]$^+$: 400.2. found: 400.1.

Step 6—Preparation of (R)-1,1,1-trifluoro-2-methyl-propan-2-yl(2-(2-cyano-2-methylpropyl)-5-methyl-4-tosyl-3,4-dihydro-2H-benzo[b][1,4]oxazin-6-yl)carbamate and (S)-1,1,1-trifluoro-2-methylpropan-2-yl(2-(2-cyano-2-methylpropyl)-5-methyl-4-tosyl-3,4-dihydro-2H-benzo[b][1,4]oxazin-6-yl)carbamate

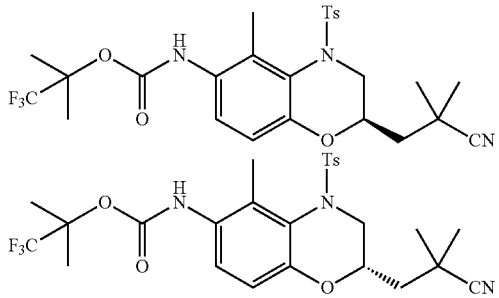

To a solution of (R and S)-3-(6-amino-5-methyl-4-tosyl-3,4-dihydro-2H-benzo[b][1,4]oxazin-2-yl)-2,2-dimethyl-propanenitrile (1.97 g, 4.93 mmol) in DMSO (20 mL) was added 1,1,1-trifluoro-2-methylpropan-2-yl 1H-imidazole-1-carboxylate (1.096 g, 4.93 mmol) in one portion, followed by concentrated HCl (0.202 mL, 2.466 mmol) at 20° C. under nitrogen. The reaction was stirred at 80° C. for 5 hours under nitrogen, then diluted with EtOAc (100 mL) and washed with brine (30 mL×3). The organic layer was dried over Na$_2$SO$_4$ and evaporated to dryness. The crude product was purified by silica gel chromatography eluted with petroleum ether:ethyl acetate=4:1 to afford the title racemic mixture as yellow oil.

The racemate was resolved by chiral SFC (Column: OJ (300 mm*50 mm, 10 um; Mobile phase: 20% IPA, NH$_3$H$_2$O; 180 mL/min; Column Temp: 38° C.; Nozzle Pressure: 100 Bar; Wavelength: 220 nm) to afford two enantiomers (faster eluent, Isomer 1 and slower eluent, Isomer 2) as yellow solids, which have the same analytical data: LCMS (ESI) calculated for C$_{26}$H$_{31}$F$_3$N$_3$O$_5$S [M+H]$^+$: 554.2. found: 554.1.

Step 7—Preparation of (R)-1,1,1-trifluoro-2-methyl-propan-2-yl(2-(2-cyano-2-methylpropyl)-5-methyl-3,4-dihydro-2H-benzo[b][1,4]oxazin-6-yl)carbamate and (S)-1,1,1-trifluoro-2-methylpropan-2-yl(2-(2-cyano-2-methylpropyl)-5-methyl-3,4-dihydro-2H-benzo[b][1,4]oxazin-6-yl)carbamate

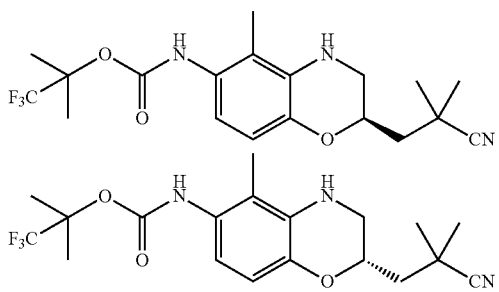

To a solution of 1,1,1-trifluoro-2-methylpropan-2-yl (R or S)-(2-(2-cyano-2-methylpropyl)-5-methyl-4-tosyl-3,4-dihydro-2H-benzo[b][1,4]oxazin-6-yl)carbamate (Isomer 1 from Step 6, 500 mg, 0.873 mmol) in MeOH (20 mL) was added Mg (424 mg, 17.46 mmol) in one portion at room temperature under nitrogen. The reaction was stirred at 25° C. for 18 hours, then quenched with saturated NH$_4$Cl solution (15 mL) and extracted with EtOAc (3×30 mL). The organic layers were combined, dried over Na$_2$SO$_4$, filtered and the filtrate was concentrated under vacuum to afford the title compound (Isomer 1 from Step 7) as white solid.

The other enantiomer (Isomer 2 from Step 7) was prepared using a similar procedure as above from Isomer 2 from Step 6. Both enantiomers have the same analytical data: LCMS (ESI) calculated for C$_{19}$H$_{25}$F$_3$N$_3$O$_3$ [M+H]$^+$: 400.2. found: 400.1.

Step 8—Preparation of (R)-1,1,1-trifluoro-2-methyl-propan-2-yl(4-((3-chloro-1-ethyl-1H-pyrazol-4-yl)sulfonyl)-2-(2-cyano-2-methylpropyl)-5-methyl-3,4-dihydro-2H-benzo[b][1,4]oxazin-6-yl)carbamate and (S)-1,1,1-trifluoro-2-methylpropan-2-yl (4(3-chloro-1-ethyl-1H-pyrazol-4-yl)sulfonyl)-2-(2-cyano-2-methylpropyl)-5-methyl-3,4-dihydro-2H-benzo[b][1,4]oxazin-6-yl)carbamate

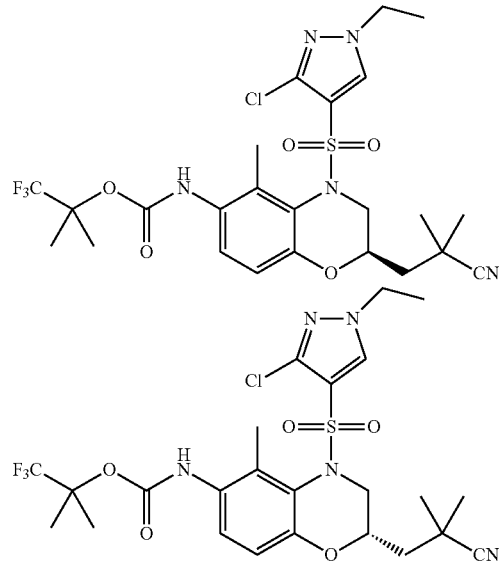

To a mixture of (R or S)-1,1,1-trifluoro-2-methylpropan-2-yl(2-(2-cyano-2-methylpropyl)-5-methyl-3,4-dihydro-2H-benzo[b][1,4]oxazin-6-yl)carbamate (Isomer 1 from Step 7, 100 mg, 0.250 mmol) in THF (1 mL) was added 3-chloro-1-ethyl-1H-pyrazole-4-sulfonyl chloride (115 mg, 0.501 mmol) and pyridine (1 mL). The reaction was stirred at 20° C. for 6 hours, then diluted with water (3 mL) and extracted with ethyl acetate (3×5 mL). The organic layers were combined, dried over anhydrous magnesium sulfate, filtered and concentrated under vacuum. The residual oil was purified by prep-HPLC (MeCN/water using TFA buffer) to afford the title compound (Isomer 1 from Step 8) as white solid.

The other enantiomer (Isomer 2 from Step 8) was prepared using a similar procedure as above from Isomer 2 from Step 7. Both enantiomers have the same analytical data: LCMS (ESI) calculated for $C_{24}H_{30}ClF_3N_5O_5S$ [M+H]$^+$: 592.2. found: 592.1; $^1$H-NMR (400 MHz, CDCl$_3$) δ 7.45-7.66 (1H, m), 6.72 (1H, d, J=8.8 Hz), 6.36 (1H, s), 4.48 (1H, s), 4.33 (1H, d, J=12 Hz), 4.09 (2H, d, J=7.2 Hz), 3.00-3.07 (1H, m), 2.34 (3H, s), 2.11 (2H, s), 1.75 (6H, d, J=6.8 Hz), 1.39-1.46 (9H, m).

Step 9—Preparation of (R)-1,1,1-trifluoro-2-methyl-propan-2-yl(4-((3-chloro-1-ethyl-1H-pyrazol-4-yl)sulfonyl)-2-(2,2-dimethyl-3-oxopropyl)-5-methyl-3,4-dihydro-2H-benzo[b][1,4]oxazin-6-yl)carbamate and (S)-1,1,1-trifluoro-2-methylpropan-2-yl (4-((3-chloro-1-ethyl-1H-pyrazol-4-yl)sulfonyl)-2-(2,2-dimethyl-3-oxopropyl)-5-methyl-3,4-dihydro-2H-benzo[b][1,4]oxazin-6-yl)carbamate

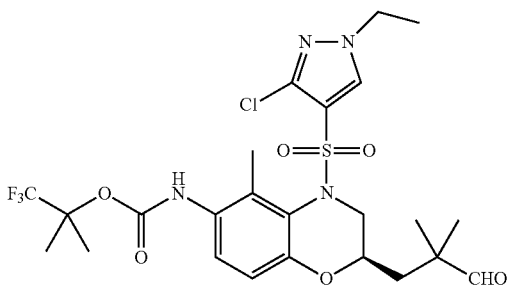

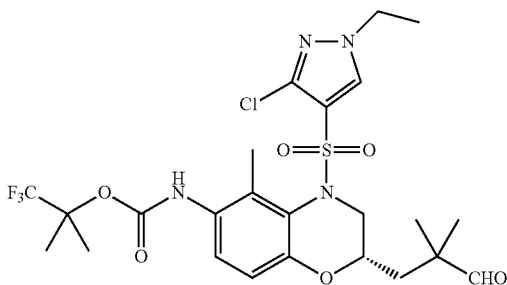

To a solution of (R or 5)-1,1,1-trifluoro-2-methylpropan-2-yl(4-((3-chloro-1-ethyl-1H-pyrazol-4-yl)sulfonyl)-2-(2-cyano-2-methylpropyl)-5-methyl-3,4-dihydro-2H-benzo[b][1,4]oxazin-6-yl)carbamate (Isomer 1 from Step 8, 50 mg, 0.084 mmol) in toluene (6 mL) was added DIBAL-H (0.338 mL, 0.338 mmol) dropwise at −78° C. under nitrogen. The reaction was stirred at −78° C. for 1 h, then quenched with MeOH (0.5 mL), acidified with 1M HCl (1 mL) and stirred at 0° C. for 10 min. The resulting biphasic mixture was extracted with EtOAc (10 mL×3) and the combined organic layers washed with brine (4 mL), dried over Na$_2$SO$_4$ and concentrated under reduced pressure to afford the title compound (Isomer 1 from Step 9) as light yellow solid.

The other enantiomer (Isomer 2 from Step 9) was prepared using a similar procedure as above from Isomer 2 from Step 8. Both enantiomers have the same analytical data: LCMS (ESI) calculated for $C_{24}H_{31}ClF_3N_4O_6S$ [M+H]$^+$: 595.2. found: 595.2.

Step 10—Preparation of (R)-3-(4-((3-chloro-1-ethyl-1H-pyrazol-4-yl)sulfonyl)-5-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid and (S)-3-(4-((3-chloro-1-ethyl-1H-pyrazol-4-yl)sulfonyl)-5-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid

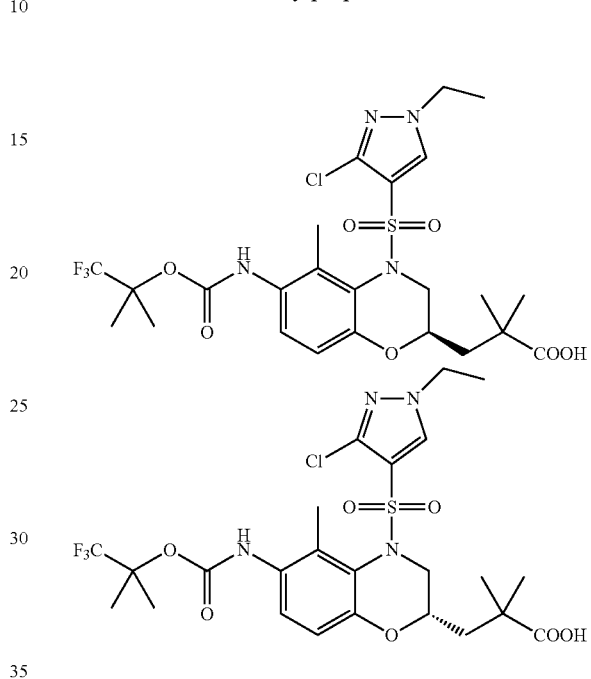

To a solution of (R or 5)-1,1,1-trifluoro-2-methylpropan-2-yl (4-((3-chloro-1-ethyl-1H-pyrazol-4-yl)sulfonyl)-2-(2,2-dimethyl-3-oxopropyl)-5-methyl-3,4-dihydro-2H-benzo[b][1,4]oxazin-6-yl)carbamate (Isomer 1 from Step 9, 43 mg, 0.072 mmol) in THF (3 mL) and water (0.5 mL), was added sulfamic acid (42.1 mg, 0.434 mmol), potassium dihydrogenphosphate (118 mg, 0.867 mmol) and sodium chlorite (9.80 mg, 0.108 mmol) in one portion at 0° C. The reaction was stirred at 0° C. for 1 h, then diluted with water (5 mL). The biphasic mixture was extracted with EtOAc (3×8 mL) and the combined organic layers were dried over Na$_2$SO$_4$ and evaporated to dryness. The crude product was purified by prep-HPLC (MeCN/water using TFA buffer) to afford Example No. 30A (Isomer 1 from Step 10) as white solid.

The other enantiomer, Example No. 30B, (Isomer 2 from Step 10) was prepared using a similar procedure as above from Isomer 2 from Step 9. Both enantiomers have the same analytical data: LCMS (ESI) calculated for $C_{24}H_{31}ClF_3N_4O_7S$ [M+H]$^+$: 611.2. found: 611.1; $^1$H-NMR (400 MHz, CDCl$_3$) δ 7.33-7.44 (1H, m), 6.56 (1H, d, J=8.8 Hz), 6.40 (1H, s), 4.25-4.29 (2H, m), 4.05 (2H, d, J=6.8 Hz), 2.83-3.06 (1H, m), 2.30 (3H, s), 1.86-1.89 (1H, m), 1.74 (6H, d, J=4 Hz), 1.61-1.66 (1H, m), 1.39-1.43 (3H, m), 1.23-1.28 (6H, d, J=14.8 Hz).

Biological Assays

The compounds of the invention inhibit RORgammaT activity. Activation of RORgammaT activity can be measured using, e.g., a biochemical TR-FRET assay. In such an assay, interaction of cofactor-derived peptides with human RORgammaT-Ligand Binding Domain (LBD) can be measured. The TR-FRET technique is a sensitive biochemical proximity assay that will give information concerning the interaction of a ligand with the LBD, in the presence of cofactor-derived peptides (Zhou et al., Methods 25:54-61, 2001).

To identify novel antagonists of RORgammaT, an assay was developed which employs the interaction of RORgammaT with its co-activator peptide SRC1_2. This peptide mimics the recruitment of co-activators to RORgammaT through its interaction with the LXXLL (SEQ ID NO:1) (e.g., NR box) motifs (Xie et al., J. Immunol. 175: 3800-09, 2005; Kurebayashi et al., Biochem. Biophys. Res. Commun. 315: 919-27, 2004; Jin et al., Mol. Endocrinology 24:923-29, 2010). The RORγ-Ligand Binding Domain TR-FRET Assay was run according to the following protocol.

HIS-tagged RORγ-LBD protein was recombinantly expressed in *Escherichia coli*. The RORγ-LBD protein was purified by $Ni^{2+}$-affinity resin. Purified protein was then diluted in assay buffer (50 mM Tris pH 7.0, 50 mM KCl, 1 mM EDTA, 0.1 mM DTT, 100 µg/mL bovine serum albumin, delipidated) to obtain a RORγ-LBD final concentration of 3 nM. Europium tagged anti-HIS antibody was also added to this solution (1.25 nM). Separately, SF9 cells not expressing any recombinant protein were lysed (32,000 cells per µl in 25 mM Tris, 50 mM NaCl) and the previously frozen lysate was added to the diluted RORγ-LBD solution at a ratio of 0.75 µl SF9 lysate per 15 µl of diluted RORγ-LBD.

Compounds to be tested were injected to the 384-well assay plate using Acoustic Droplet Ejection technology by Echo 550 liquid handler (Labcyte, CA).

A stock of biotinylated-LXXLL peptide from coactivator SRC1 (Biotin-SPSSHSSLTERHKILHRLLQEGSP) (SEQ ID NO:2) and APC-conjugated streptavidin (final concentrations 100 nM and 8 nM respectively) were also added to each well.

The final assay mixture was incubated overnight at 4° C., warmed to room temperature and the fluorescence signal was measured on an Envision plate reader: (Excitation filter=340 nm; APC emission=665 nm; Europium emission=615 nm; dichroic mirror=D400/D630; delay time=100 µs, integration time=200 µs). $IC_{50}$ values for test compounds were calculated from the quotient of the fluorescence signal at 665 nm divided by the fluorescence signal at 615 nm.

The $IC_{50}$ values for representative compounds of the invention are set forth below.

| Ex. No. | $IC_{50}$ (nM) |
| --- | --- |
| 1A | 11 |
| 1B | 11 |
| 2A | 7 |
| 2B | 6 |
| 3A | 11 |
| 3B | 3 |
| 3C | 13 |
| 3D | 30 |
| 3E | 6 |
| 3F | 7 |
| 3G | 8 |
| 3H | 8 |
| 3i | 7 |
| 3J | 5 |
| 3K | 12 |
| 3L | 6 |
| 4 | 6 |
| 5A | 7 |
| 5B | 8 |
| 6A | 11 |
| 6B | 5 |
| 6C | 6 |
| 6D | 20 |
| 6E | 6 |
| 6F | 23 |
| 6G | 39 |
| 6H | 5 |
| 6i | 17 |
| 6J | 9 |
| 6K | 15 |
| 6L | 11 |
| 6M | 34 |
| 6N | 14 |
| 6o | 4 |
| 6P | 4 |
| 6Q | 23 |
| 6R | 12 |
| 6S | 6 |
| 6T | 4 |
| 6U | 8 |
| 6V | 8 |
| 6W | 7 |
| 6X | 15 |
| 6Y | 4 |
| 6Z | 4 |
| 6AA | 6 |
| 6AB | 9 |
| 6AC | 8 |
| 6AD | 9 |
| 6AE | 12.45 |
| 6AF | 6.204 |
| 6AG | 42.26 |
| 6AH | 8.835 |
| 6Ai | 25.53 |
| 6AJ | 13.96 |
| 6AK | 11.12 |
| 6AL | 15.03 |
| 6AM | 59.75 |
| 6AN | 14.13 |
| 6Ao | 11.84 |
| 6AP | 5.645 |
| 6AQ | 17.14 |
| 6AR | 4.857 |
| 6AS | 12.47 |
| 6AT | 9.932 |
| 6AU | 33.91 |
| 6AV | 24.06 |
| 6AW | 7.713 |
| 6AX | 9.923 |
| 6AY | 5.765 |
| 6AZ | 13.11 |
| 6BA | 7.312 |
| 6BC | 11.91 |
| 6BD | 14.82 |
| 6BE | 280.2 |
| 6BF | 58.25 |
| 6BG | 13.29 |
| 6BH | 23.9 |
| 6Bi | 18.04 |
| 6BJ | 15.11 |
| 6BK | 62.39 |
| 6BL | 57.83 |
| 6BM | 16.84 |
| 6BN | 27.99 |
| 6Bo | 11.94 |
| 6BP | 26.63 |
| 6BQ | 17.63 |
| 6BR | 12.34 |
| 6BS | 520.4 |
| 6BT | 63.16 |
| 6BU | 10.95 |
| 6BV | 8.843 |
| 6BW | 171.2 |
| 6BX | 32.38 |
| 6BY | 27.05 |
| 6BZ | 7.114 |
| 6CA | 11.37 |
| 6CB | 6.962 |
| 6CC | 12.4 |
| 6CD | 14.37 |
| 6CE | 67.46 |
| 6CF | 20.04 |
| 6CG | 22.95 |
| 6CH | 18.05 |
| 6Ci | 12.93 |

| Ex. No. | IC$_{50}$ (nM) |
|---|---|
| 6CJ | 11.96 |
| 6CK | 14.49 |
| 6CL | 16.88 |
| 6CM | 5.252 |
| 6CN | 6.078 |
| 6Co | 8.376 |
| 6CP | 11.59 |
| 6CQ | 10.25 |
| 6CR | 12.94 |
| 6CS | 5.439 |
| 6CT | 7.961 |
| 6CU | 17.77 |
| 6CV | 12.93 |
| 6CW | 10.16 |
| 6CX | 7.347 |
| 6CY | 8.353 |
| 6CZ | 15.28 |
| 6DA | 14.91 |
| 6DB | 11.46 |
| 6DC | 16.23 |
| 6DD | 23.58 |
| 6DE | 40.27 |
| 8A | 14.2 |
| 8B | 24.58 |
| 9A | 19.68 |
| 9B | 67.58 |
| 10A | 22.61 |
| 10B | 15.66 |
| 10C | 16.99 |
| 10D | 12.78 |
| 10E | 10.44 |
| 10F | 13.31 |
| 10G | 11.11 |
| 10H | 10.91 |
| 10i | 24.26 |
| 10J | 28.29 |
| 10K | 21.51 |
| 10L | 49.53 |
| 10M | 8.039 |
| 10N | 67.24 |
| 10o | 15.43 |
| 10P | 13.29 |
| 10Q | 60.33 |
| 10R | 54.02 |
| 10S | 12.94 |
| 10T | 16.05 |
| 10U | 22.33 |
| 10V | 41.61 |
| 10W | 38.21 |
| 10X | 32.79 |
| 10Y | 131.7 |
| 10Z | 101 |
| 11 | 25.5 |
| 12A | 57.18 |
| 12B | 44.04 |
| 12C | 130.7 |
| 12D | 64.38 |
| 12E | 30.86 |
| 12F | 9.961 |
| 12G | 17.19 |
| 12H | 42.84 |
| 12i | 148.9 |
| 12J | 13.35 |
| 12K | 53.85 |
| 12L | 24.99 |
| 12M | 61.81 |
| 12N | 73.09 |
| 12o | 14.87 |
| 12P | 9.223 |
| 12Q | 18.64 |
| 12R | 12.56 |
| 12S | 16.42 |
| 12T | 331.5 |
| 12U | 17.89 |
| 12V | 13.76 |
| 12W | 15.21 |
| 12X | 60.19 |
| 12Y | 14.36 |
| 12Z | 12.24 |
| 12AA | 17.36 |
| 13A | 13.75 |
| 13B | 28.22 |
| 14A | 11.56 |
| 14B | 17.47 |
| 14C | 29.08 |
| 14D | 36.67 |
| 14E | 17.52 |
| 14F | 33.21 |
| 14G | 11.44 |
| 14H | 108.2 |
| 15 | 18.1 |
| 16A | 45.92 |
| 16B | 14.63 |
| 17A | 16.64 |
| 17B | 23.94 |
| 18A | 12.94 |
| 18B | 38.24 |
| 18C | 24.99 |
| 18D | 14.15 |
| 18E | 28.65 |
| 18F | 9.391 |
| 18G | 16.64 |
| 18H | 23.94 |
| 18i | 12.73 |
| 18J | 9.133 |
| 18K | 11.39 |
| 18L | 10.39 |
| 19A | 13.7 |
| 19B | 31.74 |
| 20A | 12.68 |
| 20B | 16.21 |
| 21A | 28.03 |
| 21B | 19.45 |
| 21C | 30.39 |
| 21D | 15.23 |
| 22A | 22.35 |
| 22B | 13.53 |
| 22C | 8.713 |
| 22D | 5.872 |
| 22E | 47.13 |
| 22F | 75.68 |
| 22G | 34.25 |
| 22H | 140.7 |
| 22i | 22.35 |
| 22J | 13.53 |
| 22K | 4.634 |
| 22L | 7.101 |
| 22M | 8.713 |
| 22N | 5.872 |
| 22o | 24.91 |
| 22P | 25.86 |
| 23A | 3.044 |
| 23B | 4.358 |
| 24A | 17.73 |
| 24B | 11.98 |
| 24C | 3.8 |
| 24D | 3.734 |
| 24E | 4.714 |
| 24F | 4.692 |
| 25 | 10.08 |
| 26A | 23.51 |
| 26B | 9586 |
| 26C | 8401 |
| 26D | 332.6 |
| 27A | 8204 |
| 27B | 17.54 |
| 28 | 10.16 |
| 29A | 5.711 |
| 29B | 3.895 |
| 29C | 9.681 |
| 29D | 7.915 |
| 29E | 10.19 |
| 29F | 5.701 |
| 29G | 23.31 |

-continued

| Ex. No. | IC$_{50}$ (nM) |
|---|---|
| 29H | 10.06 |
| 29i | 9.01 |
| 30A | 16.42 |
| 30B | 616.9 |

While the present invention has been described in conjunction with the specific embodiments set forth above, many alternatives, modifications and other variations thereof will be apparent to those of ordinary skill in the art in light of the present disclosure. All such alternatives, modifications, and variations are intended to fall within the spirit and scope of the present invention.

What is claimed is:

1. A compound of the Formula (I)

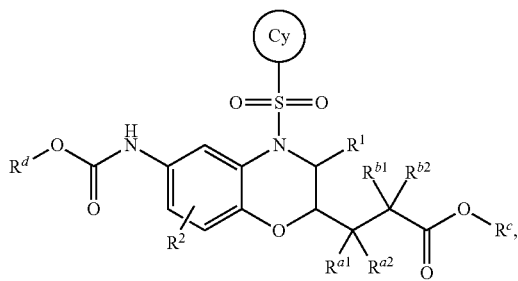

(I)

or a pharmaceutically acceptable salt thereof, wherein:
$R^1$ is H or $C_1$-$C_3$ alkyl,
$R^2$ is H, $C_1$-$C_3$ alkyl, or halo;
$R^{a1}$ and $R^{a2}$ are independently H, $C_1$-$C_3$ alkyl, trifluoromethyl, or cyclopropyl;
$R^{b1}$ and $R^{b2}$ are independently H, $C_1$-$C_3$ alkyl, trifluoromethyl, hydroxyl, hydroxymethyl, or cyclopropyl;
alternatively:
(a.) $R^{a1}$ and $R^{b1}$ together with the carbon atoms to which they are attached form a $C_3$-$C_6$ cycloalkyl ring;
(b.) $R^{a1}$ and $R^{b1}$ together form a second bond; or
(c.) $R^{b1}$ and $R^{b2}$ together with the carbon atom to which they are attached form a $C_3$-$C_6$ cycloalkyl ring;

$R^c$ is
(a.) H or
(b.) $C_1$-$C_6$ alkyl;
$R^d$ is
(a.) $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl;
(b.) $C_2$-$C_8$ alkenyl, wherein said $C_2$-$C_8$ alkenyl of $R^d$ is unsubstituted or independently substituted by 1 to 6 fluoro or cyano; or
(c.) a group of the formula -M-$R^{CH}$; wherein
M is
(i.) a bond; or
(ii.) $C_1$-$C_6$ alkylene, wherein said $C_1$-$C_6$ alkylene of M is unsubstituted or substituted by 1 to 6 fluoro;
$R^{CH}$ is a ring selected from the group consisting of
(i.) $C_3$-$C_9$ mono- or bicycloalkyl;
(ii.) phenyl; and (iii.) a 3- to 6-membered heterocyclyl, wherein said heterocyclyl of $R^{CH}$ contains 1 to 2 heteroatoms independently selected from the group consisting of N, O, and S;
wherein $R^{CH}$ is unsubstituted or independently substituted by 1 to 4 halo, $C_1$-$C_3$ alkyl, $C_1$-$C_3$ trifluoroalkyl, cyano, $C_1$-$C_4$ alkylcarbonylamino, or oxo;

Cy is
(a.) phenyl;
(b.) a 5- to 7-membered, monocyclic heterocyclyl containing 1 to 3 heteroatoms independently selected from the group consisting of N, O, and S; or
(c.) $C_3$-$C_6$ cycloalkyl;
wherein Cy is unsubstituted or independently substituted by 1 to 4 $R^k$ moieties selected from the group consisting of:
(i.) $C_1$-$C_6$ alkyl, wherein said $C_1$-$C_6$ alkyl is unsubstituted or independently substituted by 1 to 3 hydroxy or fluoro;
(ii.) $C_1$-$C_6$ alkoxy, wherein said $C_1$-$C_6$ alkoxy is unsubstituted or independently substituted by 1 to 3 fluoro, hydroxy, methoxy, or phenyl;
(iii.) —N($R^e$)$_2$;
(iv.) —O(CH$_2$)$_{n1}$C(O)N($R^e$)$_2$;
(v.) —O(CH$_2$)$_{n2}$CO$_2$R$^f$;
(vi.) hydroxyl;
(vii.) oxo;
(viii.) halo;
(ix.) $C_1$-$C_3$ alkylsulfonyl;
(x.) cyano;
(xi.) oxetanyl;
(xii.) cyclopropyl; and
(xiii.) —SF$_5$;
or alternatively, two $R^k$ moieties, when substituted on adjacent ring atoms of Cy, form a second ring, wherein said second ring is a 5- to 7-membered saturated, partially saturated, or aromatic ring system that contains 0, 1, or 2 heteroatoms independently selected from the group consisting of N, O, and S; wherein said second ring is unsubstituted or substituted by 1 to 3 $R^k$ moieties independently selected from (i)-(xii);
each $R^e$ is independently H or $C_1$-$C_3$ alkyl,
$R^f$ is H or $C_1$-$C_3$ alkyl;
the subscript n1 is 1, 2, or 3; and
the subscript n2 is 1, 2, or 3.

2. The compound of claim 1 or a pharmaceutically acceptable salt thereof, wherein $R^{a1}$ and $R^{a2}$ are H.

3. The compound of claim 2 or a pharmaceutically acceptable salt thereof, wherein $R^{b1}$ is H.

4. The compound of claim 1 or a pharmaceutically acceptable salt thereof, wherein $R^1$ is H.

5. The compound of claim 1 or a pharmaceutically acceptable salt thereof, wherein $R^d$ is $C_1$-$C_8$ alkyl, wherein said $C_1$-$C_8$ alkyl of $R^d$ is unsubstituted or independently substituted by 1 to 6 halo, $C_1$-$C_3$ alkoxy, hydroxy, cyano, trimethylsilyl, or methylsulfonyl.

6. The compound of claim 5 or a pharmaceutically acceptable salt thereof, wherein $R^d$ is

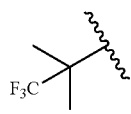

7. The compound of claim 1 or a pharmaceutically acceptable salt thereof, wherein Cy is a group of the formula

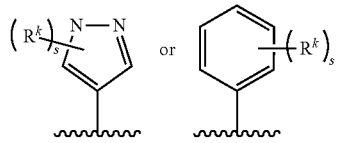

wherein the subscript s is 0, 1, 2, or 3.

8. The compound of claim 1, having the Formula (TB)

(IB)

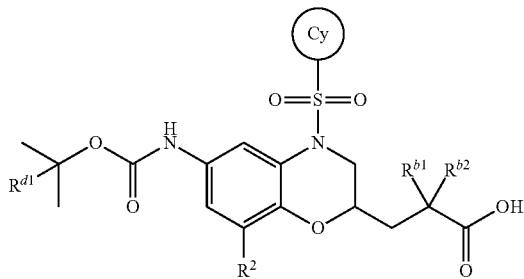

wherein
Cy is

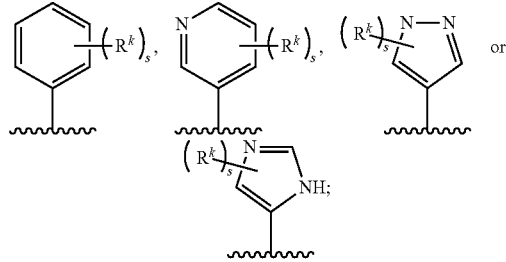

$R^2$ is H or F;
the subscript s is 0, 1, 2, or 3;
$R^{b1}$ and $R^{b2}$ are independently H or CH$_3$; and
$R^{d1}$ is CH$_3$, CHF$_2$, CH$_2$F, or CF$_3$;
or a pharmaceutically acceptable salt thereof.

9. The compound of claim 8 or a pharmaceutically acceptable salt thereof, wherein each $R^k$ is independently:
(i.) $C_1$-$C_6$ alkyl, wherein said $C_1$-$C_6$ alkyl is unsubstituted or independently substituted by 1 to 3 hydroxy or fluoro;
(ii.) $C_1$-$C_6$ alkoxy, wherein said $C_1$-$C_6$ alkoxy is unsubstituted or independently substituted by 1 to 3 fluoro, hydroxy, methoxy, or phenyl;
(iii.) a halo selected from fluoro or chloro;
(iv.) cyano; or
alternatively, two $R^k$ moieties, when substituted on adjacent ring atoms of Cy, form a second ring, wherein said second ring is a 5- to 6-membered partially saturated or aromatic ring system that contains 0 or 1 N atom; wherein said second ring is unsubstituted or substituted by 1 to 2 $R^k$ moieties independently selected from (i)-(iv).

10. The compound of claim 8 or a pharmaceutically acceptable salt thereof, wherein Cy is:

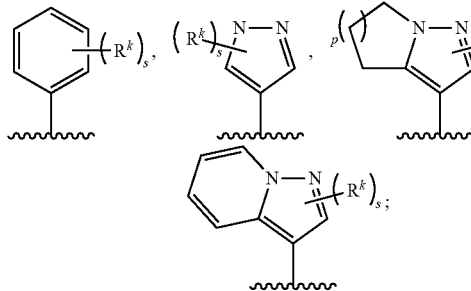

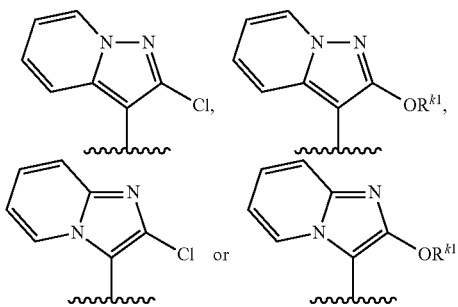

wherein
$R^{k1}$ is $C_1$-$C_6$ alkyl or $CH_2CH_2OH$.

15. The compound of claim 8 or a pharmaceutically acceptable salt thereof, wherein $R^{d1}$ is $CF_3$.

16. A pharmaceutical composition comprising a therapeutically effective amount of a compound of claim 1 or a pharmaceutically acceptable salt thereof and a pharmaceutically acceptable carrier.

17. A method of treating a disease or condition mediated by RORgammaT comprising administering a therapeutically effective amount of a compound of claim 1 or a pharmaceutically acceptable salt thereof to a patient in need of such treatment, wherein the disease or condition is multiple sclerosis, inflammatory bowel disease, Crohn's disease, ankylosing spondylitis, psoriasis, rheumatoid arthritis, asthma, osteoarthritis, Kawasaki disease, Hashimoto's thyroiditis, or mucosal leishmaniasis.

18. The method of claim 17, wherein the disease or condition is multiple sclerosis, inflammatory bowel disease, Crohn's disease, ankylosing spondylitis, psoriasis, rheumatoid arthritis, or asthma.

19. The method of claim 17, wherein the disease or condition is ankylosing spondylitis or psoriasis.

20. The method of claim 19, wherein the compound is a compound of claim 8.

21. A compound selected from the following, or a pharmaceutically acceptable salt thereof:

(S)-ethyl 3-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoate;

(S)-ethyl 3-(6-((tert-butoxycarbonyl)amino)-4-((4-fluoro-3-(trifluoromethyl)phenyl)sulfonyl)-3,4-dihydro-2H-benzo[b][1,4]oxazin-2-yl)propanoate;

(S)-3-((S)-4-((3-chloro-4-fluorophenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(R)-3-((S)-4-((3-chloro-4-fluorophenyl) sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-ethyl 3-(6-((tert-butoxycarbonyl)amino)-4-((4-fluoro-3-(trifluoromethyl)phenyl) sulfonyl)-3,4-dihydro-2H-benzo[b][1,4]oxazin-2-yl)propanoate;

(R)-ethyl 3-((S)-4-((3-methoxy-1,5-dimethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoate;

(S)-ethyl 3-((S)-4-((3-methoxy-1,5-dimethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2-methylpropanoate;

wherein
the subscript p is 1 or 2; and
s is 0, 1, or 2.

11. The compound of claim 8 or a pharmaceutically acceptable salt thereof, wherein Cy is

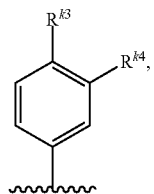

wherein $R^{k3}$ and $R^{k4}$ are independently F, Cl, $CF_3$, methyl, methoxy, cyclopropyl, or cyano.

12. The compound of claim 8 or a pharmaceutically acceptable salt thereof, wherein Cy is

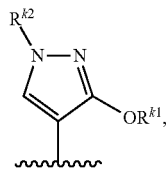

wherein
$R^{k1}$ is $C_1$-$C_6$ alkyl or $CH_2CH_2OH$; and
$R^{k2}$ is $C_1$-$C_3$ alkyl or $CHF_2$.

13. The compound of claim 8 or a pharmaceutically acceptable salt thereof, wherein Cy is

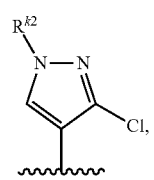

wherein $R^{k2}$ is $C_1$-$C_3$ alkyl or $CHF_2$.

14. The compound of claim 8 or a pharmaceutically acceptable salt thereof, wherein Cy is (S)-ethyl 3-((S)-4-((3-chloro-1-ethyl-1H-pyrazol-4-yl) sulfonyl)-6-((((1,1,1-trifluoro-2-methylpropan-2-yl) oxy)carbonyl)amino)-3,4-dihydro-2H-benzo[b][1,4] oxazin-2-yl)-2-methylpropanoate;

(R)-ethyl 3-((S)-4-((3-chloro-1-ethyl-1H-pyrazol-4-yl) sulfonyl)-6-((((1,1,1-trifluoro-2-methylpropan-2-yl) oxy)carbonyl)amino)-3,4-dihydro-2H-benzo[b][1,4] oxazin-2-yl)-2-methylpropanoate;

(S)-ethyl 3-((S)-4-((4-fluoro-3-(trifluoromethyl)phenyl) sulfonyl)-6-((((1,1,1-trifluoro-2-methylpropan-2-yl) oxy)carbonyl)amino)-3,4-dihydro-2H-benzo[b][1,4] oxazin-2-yl)-2-methylpropanoate;

(R)-ethyl 3-((S)-4-((4-fluoro-3-(trifluoromethyl)phenyl) sulfonyl)-6-((((1,1,1-trifluoro-2-methylpropan-2-yl) oxy)carbonyl)amino)-3,4-dihydro-2H-benzo[b][1,4] oxazin-2-yl)-2-methylpropanoate;

(S)-ethyl 3-(4-((3-chloro-4-fluorophenyl) sulfonyl)-6-((((1,1,1-trifluoro-2-methylpropan-2-yl)oxy)carbonyl) amino)-3,4-dihydro-2H-benzo[b][1,4]oxazin-2-yl)propanoate;

(S)-ethyl 3-(6-((((1,1,1-trifluoro-2-methylpropan-2-yl) oxy)carbonyl)amino)-4-((3-(trifluoromethyl)phenyl) sulfonyl)-3,4-dihydro-2H-benzo[b][1,4]oxazin-2-yl) propanoate;

(S)-ethyl 3-(4-((3-methoxy-1,5-dimethyl-1H-pyrazol-4-yl) sulfonyl)-6-((((1,1,1-trifluoro-2-methylpropan-2-yl)oxy)carbonyl)amino)-3,4-dihydro-2H-benzo[b][1,4] oxazin-2-yl)propanoate;

(S)-ethyl 3-(4-((3-chloro-1-ethyl-1H-pyrazol-4-yl) sulfonyl)-6-((((1,1,1-trifluoro-2-methylpropan-2-yl)oxy) carbonyl)amino)-3,4-dihydro-2H-benzo[b][1,4]oxazin-2-yl)propanoate (S)-3-(4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl) propanoic acid;

(S)-3-((S)-4-((3-chloro-4-fluorophenyl)sulfonyl)-6-((((1,1,1-trifluoro-2-methylpropan-2-yl)oxy)carbonyl) amino)-3,4-dihydro-2H-benzo[b][1,4]oxazin-2-yl)-2-methylpropanoic acid;

(R)-3-((S)-4-((3-chloro-4-fluorophenyl)sulfonyl)-6-((((1,1,1-trifluoro-2-methylpropan-2-yl)oxy)carbonyl) amino)-3,4-dihydro-2H-benzo[b][1,4]oxazin-2-yl)-2-methylpropanoic acid;

(S)-3-(4-((3-chloro-4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(S)-3-(4-((3-methoxy-1,5-dimethyl-1H-pyrazol-4-yl)sulfonyl)-6-((((1,1,1-trifluoro-2-methylpropan-2-yl)oxy) carbonyl)amino)-3,4-dihydro-2H-benzo[b][1,4]oxazin-2-yl)propanoic acid;

(S)-3-(4-((3-chloro-1-ethyl-1H-pyrazol-4-yl)sulfonyl)-6-((((1,1,1-trifluoro-2-methylpropan-2-yl)oxy)carbonyl) amino)-3,4-dihydro-2H-benzo[b][1,4]oxazin-2-yl)propanoic acid;

(R)-3-((S)-4-((3-methoxy-1,5-dimethyl-1H-pyrazol-4-yl) sulfonyl)-6-((((1,1,1-trifluoro-2-methylpropan-2-yl) oxy)carbonyl)amino)-3,4-dihydro-2H-benzo[b][1,4] oxazin-2-yl)-2-methylpropanoic acid;

(S)-3-((S)-4-((3-methoxy-1,5-dimethyl-1H-pyrazol-4-yl) sulfonyl)-6-((((1,1,1-trifluoro-2-methylpropan-2-yl) oxy)carbonyl)amino)-3,4-dihydro-2H-benzo[b][1,4] oxazin-2-yl)-2-methylpropanoic acid;

(R)-3-((S)-4-((3-chloro-1-ethyl-1H-pyrazol-4-yl)sulfonyl)-6-((((1,1,1-trifluoro-2-methylpropan-2-yl)oxy) carbonyl)amino)-3,4-dihydro-2H-benzo[b][1,4]oxazin-2-yl)-2-methylpropanoic acid;

(S)-3-((S)-4-((3-chloro-1-ethyl-1H-pyrazol-4-yl)sulfonyl)-6-((((1,1,1-trifluoro-2-methylpropan-2-yl)oxy) carbonyl)amino)-3,4-dihydro-2H-benzo[b][1,4]oxazin-2-yl)-2-methylpropanoic acid;

(R)-3-((S)-4-((4-fluoro-3-(trifluoromethyl)phenyl) sulfonyl)-6-((((1,1,1-trifluoro-2-methylpropan-2-yl)oxy) carbonyl)amino)-3,4-dihydro-2H-benzo[b][1,4]oxazin-2-yl)-2-methylpropanoic acid;

(S)-3-((S)-4-((4-fluoro-3-(trifluoromethyl)phenyl)sulfonyl)-6-((((1,1,1-trifluoro-2-methylpropan-2-yl)oxy) carbonyl)amino)-3,4-dihydro-2H-benzo[b][1,4]oxazin-2-yl)-2-methylpropanoic acid;

(S)-3-(4-((3-cyanophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3,4-difluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-methoxy-5,6-dihydro-4H-pyrrolo[1,2-b] pyrazol-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(6-((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid;

(S)-3-(4-((3-(difluoromethoxy)phenyl)sulfonyl)-6-((((1,1,1-trifluoro-2-methylpropan-2-yl)oxy)carbonyl) amino)-3,4-dihydro-2H-benzo[b][1,4]oxazin-2-yl)propanoic acid;

(S)-3-(4-((3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-(methylsulfonyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(6-((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

(S)-3-(4-((2-methoxy-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-bromophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((1-(difluoromethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-chlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2,3-dihydrobenzofuran-5-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-5-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-6-chloroimidazo[2,1-b]thiazole;

(S)-3-(4-((2-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3,4-dichlorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-chloro-2-fluorophenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chloro-4-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chloro-5-fluoro-2-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-2-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-5-chloropyridine;

(S)-3-(4-((4-chloro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((5-chloro-2-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-chloro-5-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-methoxy-5-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-methoxy-4-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-1-(2,2-difluoroethyl)-3-ethoxy-1H-pyrazole;

(S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-3-(2,2-difluoroethoxy)-1-ethyl-1H-pyrazole;

(S)-3-(4-((3-fluoro-5-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3,5-bis(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-2-methoxypyridine;

(S)-3-(4-((2,4-difluoro-5-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-4-((2-(2-carboxyethyl)-6-((((1,1,1-trifluoro-2-methylpropan-2-yl)oxy)carbonyl)amino)-2H-benzo[b][1,4]oxazin-4(3H)-yl)sulfonyl)-1-(difluoromethyl)-3-methyl-1H-pyrazole;

(S)-3-(4-((2-chloro-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((4-fluoro-3,5-dimethylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((2-chloro-4-fluoro-5-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-(difluoromethoxy)-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

3-[(2S)-4-{[3-(pentafluoro-lambda~6~-sulfanyl)phenyl]sulfonyl}-6-{[(2,2,2-trifluoro-1,1-dimethylethoxy)carbonyl]amino}-3,4-dihydro-2H-1,4-benzoxazin-2-yl]propanoic acid;

(R or S)-3-((S)-4-((3-chloro-1-isopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-chloro-1-cyclopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((1-(difluoromethyl)-3-methyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((1-(difluoromethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-(difluoromethoxy)-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((1-(2,2-difluoroethyl)-3-ethoxy-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-(2,2-difluoroethoxy)-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-methoxy-5,6-dihydro-4H-pyrrolo[1,2-b]pyrazol-3-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-methoxy-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-chloro-4,5,6,7-tetrahydropyrazolo[1,5-a]pyridin-3-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((5-ethoxy-2-ethylthiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-cyclopropyl-5-ethoxythiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-ethyl-5-isopropoxythiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-ethyl-5-(2,2,2-trifluoroethoxy)thiazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S)-3-(4-((3-chloro-1-isopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S)-3-(4-((3-chloro-1-cyclopropyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

3-[(2S)-4-[(5-bromopyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid;

3-[(2S)-4-[(5-cyclopropylpyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid;

3-[(2S)-6-{[(2,2,2-trifluoro-1,1-dimethylethoxy)carbonyl]amino}-4-{[6-(trifluoromethyl)pyridin-2-yl]sulfonyl}-3,4-dihydro-2H-1,4-benzoxazin-2-yl]propanoic acid;

3-[(2S)-4-[(5-methylpyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid;

3-[(2S)-4-[(5-methoxypyridin-3-yl)sulfonyl]-6-{[(2,2,2-trifluoro-1,1-dimethylethoxy)carbonyl]amino}-3,4-dihydro-2H-1,4-benzoxazin-2-yl]propanoic acid;

3-[(2S)-4-[(3-cyclopropyl-4-fluorophenyl)sulfonyl]-6-{[(2,2,2-trifluoro-1,1-dimethylethoxy)carbonyl]amino}-3,4-dihydro-2H-1,4-benzoxazin-2-yl]propanoic acid;

3-(4-{[1-ethyl-3-(2-hydroxyethoxy)-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl)propanoic acid;

3-(4-[(3-ethoxy-1-ethyl-1H-pyrazol-4-yl)sulfonyl]-6-{[(2,2,2-trifluoro-1,1-dimethylethoxy)carbonyl]amino}-3,4-dihydro-2H-1,4-benzoxazin-2-yl)propanoic acid;

3-[(2S)-4-[(5-ethoxy-2-ethyl-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]propanoic acid;

3-[(2S)-4-[(2-cyclopropyl-5-ethoxy-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]propanoic acid;

3-[(2S)-4-{[5-ethoxy-2-(trifluoromethyl)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]propanoic acid;

3-[(2S)-4-{[2-ethyl-5-(1-methylethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]propanoic acid;

3-[(2S)-4-{[2-ethyl-5-(2,2,2-trifluoroethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]propanoic acid;

3-[(2S)-4-[(5-cyclopropyl-2-fluorophenyl)sulfonyl]-6-{[(2,2,2-trifluoro-1,1-dimethylethoxy)carbonyl]amino}-3,4-dihydro-2H-1,4-benzoxazin-2-yl]propanoic acid;

(S or R)-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(S or R)-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(S or R)-2-methyl-3-((S)-4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-3-((S)-4-((3-(difluoromethoxy)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-3-((S)-4-((3-(difluoromethoxy)phenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-2-methyl-3-((S)-4-(m-tolylsulfonyl)-6-((((1,1,1-trifluoro-2-methylpropan-2-yl)oxy)carbonyl)amino)-3,4-dihydro-2H-benzo[b][1,4]oxazin-2-yl)propanoic acid;

(R or S)-2-methyl-3-((S)-6-((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid;

(S or R)-2-methyl-3-((S)-6-(((((1,1,1-trifluoro-2-methylpropan-2-yl)oxy)carbonyl)amino)-4-((3-(trifluoromethoxy)phenyl)sulfonyl)-3,4-dihydro-2H-benzo[b][1,4]oxazin-2-yl)propanoic acid;

(R or S)-3-((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-3-((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-3-((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-2-methyl-3-((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R or S)-3-((S)-4-((3-cyclopropylphenyl) sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(S or R)-2-methyl-3-((S)-6-(((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

(S or R)-2-methyl-3-((S)-6-(((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

(R or S)-2-methyl-3-((S)-6-(((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)propanoic acid;

(R or S)-2-methyl-3-((S)-6-(((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)propanoic acid;

(R or S)-3-((S)-4-((2-cyclopropylpyridin-4-yl) sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((2-cyclopropylpyridin-4-yl) sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-chloro-1-(difluoromethyl)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R or S)-3-((S)-4-((3-chloro-1-(difluoromethyl)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-methylpropanoic acid;

(R)-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid;

(S)-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)butanoic acid;

(S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-cyclopropylpropanoic acid;

(R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-cyclopropylpropanoic acid;

(R or S)-2-(((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((3-ethoxy-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-4-((1-ethyl-3-(2-hydroxyethoxy)-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)butanoic acid;

(R or S)-2-(((S)-6-((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)methyl)butanoic acid;

(R or S)-2-(((S)-6-(((((1,1,1-trifluoro-2-methylpropan-2-yl)oxy)carbonyl)amino)-4-((2-(trifluoromethyl)pyridin-4-yl)sulfonyl)-3,4-dihydro-2H-benzo[b][1,4]oxazin-2-yl)methyl)butanoic acid;

(S or R)-2-cyclopropyl-3-((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R or S)-2-cyclopropyl-3-((S)-4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(R or S)-2-cyclopropyl-3-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(R or S)-2-cyclopropyl-3-((S)-4-((4-fluoro-3-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S or R)-2-cyclopropyl-3-((S)-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R or S)-2-cyclopropyl-3-((S)-4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(R or S)-2-cyclopropyl-3-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(R or S)-2-cyclopropyl-3-((S)-4-((4-fluoro-3-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S or R)-2-cyclopropyl-3-((S)-4-((1-ethyl-3-(2-hydroxyethoxy)-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S or R)-2-cyclopropyl-3-((S)-4-((1-ethyl-3-(2-hydroxyethoxy)-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S)-2,2-dimethyl-3-(6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

(R)-3-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((4-fluoro-3-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((3-ethoxy-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((4-fluoro-3-methylphenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-3-(4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(S)-3-(4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

(R)-2,2-dimethyl-3-(6-(((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

(S)-2,2-dimethyl-3-(6-(((((1,1,1-trifluoro-2-methylpropan-2-yl)oxy)carbonyl)amino)-4-((5-(trifluoromethyl)pyridin-3-yl)sulfonyl)-3,4-dihydro-2H-benzo[b][1,4]oxazin-2-yl)propanoic acid;

3-[(2S)-4-[(5-cyanopyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(3-chloro-1-cyclopropyl-1H-pyrazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[1-(difluoromethyl)-3-methyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(5-ethoxy-2-ethyl-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-[(2-cyclopropyl-5-ethoxy-1,3-thiazol-4-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[2-ethyl-5-(2,2,2-trifluoroethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[2-ethyl-5-(1-methylethoxy)-1,3-thiazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[3-chloro-1-(1-methylethyl)-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[1-(difluoromethyl)-3-ethoxy-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;

3-[(2S)-4-{[3-(difluoromethoxy)-1-ethyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S)-4-{[1-(2,2-difluoroethyl)-3-ethoxy-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S)-4-{[3-(2,2-difluoroethoxy)-1-ethyl-1H-pyrazol-4-yl]sulfonyl}-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S)-4-[(2-chloro-4,5,6,7-tetrahydropyrazolo[1,5-a]pyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S)-4-[(2-methoxy-4,5,6,7-tetrahydropyrazolo[1,5-a]pyridin-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S)-4-[(2-methoxy-5,6-dihydro-4H-pyrrolo[1,2-b]pyrazol-3-yl)sulfonyl]-6-{[(2,2,2-trifluoro-1,1-dimethylethoxy)carbonyl]amino}-3,4-dihydro-2H-1,4-benzoxazin-2-yl]-2,2-dimethylpropanoic acid; (S)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid;
(R)-1-((6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)cyclopropanecarboxylic acid;
(S)-1-((4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(S)-1-((4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(R)-1-((4-((4-fluoro-3-methylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(R)-1-((4-((3-cyclopropylphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(S)-1-((4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(R)-1-((4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(S)-1-((4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(R)-1-((4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)methyl)cyclopropanecarboxylic acid;
(S and R)-2-hydroxy-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;
(S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;
(R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;
(S)-3-hydroxy-2-methyl-2-(S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;
(R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;
(R or S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;
(R or S)-2-hydroxy-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;
(R or S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxy-2-methylpropanoic acid;
(R and S)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid;
(R or S)-2-hydroxy-2-methyl-3-((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;
(R and S)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-hydroxypropanoic acid;
(S or R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;
(S or R)-3-hydroxy-2-methyl-2-(((S)-6-((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)methyl)propanoic acid;
(S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;
(S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;
(S or R)-3-((S)-4-((3-chloro-1-ethyl-1H-pyrazol-4-yl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;
(S or R)-3-((S)-4-((4-fluoro-3-methoxyphenyl)sulfonyl)-6-((((1,1,1-trifluoro-2-methylpropan-2-yl)oxy)carbonyl)amino)-3,4-dihydro-2H-benzo[b][1,4]oxazin-2-yl)-2-(hydroxymethyl)-2-methylpropanoic acid;

(R)-3-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)butanoic acid;

(S)-3-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)butanoic acid;

(R)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-3-cyclopropylpropanoic acid;

(S)-3-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)-3-cyclopropylpropanoic acid;

(S or R)-3-cyclopropyl-3-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S or R)-3-cyclopropyl-3-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S or R)-3-cyclopropyl-3-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(S or R)-3-cyclopropyl-3-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)propanoic acid;

(1R,2S)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2R)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2R)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2S)-2-((S)-4-((4-fluoro-3-(trifluoromethyl)phenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2S)-2-((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2R)-2-((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2R)-2-((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2S)-2-((S)-4-tosyl-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2S)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2R)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2S)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1R,2R)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2S)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2R)-2-((S)-4-((4-fluoro-3-methoxyphenyl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1 S,2S)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

(1S,2R)-2-((S)-4-((3-chloro-1-ethyl-1H-pyrazol-4-yl)sulfonyl)-6-(((((1,1,1-trifluoro-2-methylpropan-2-yl)oxy)carbonyl)amino)-3,4-dihydro-2H-benzo[b][1,4]oxazin-2-yl)cyclopropanecarboxylic acid;

3-((S)-4-((4-fluoro-3-methoxyphenyl) sulfonyl)-6-(((((S)-1,1,1-trifluoro-3,3-dimethylbutan-2-yl)oxy)carbonyl)amino)-3,4-dihydro-2H-benzo[b][1,4]oxazin-2-yl)propanoic acid;

3-((S)-4-((4-fluoro-3-methoxyphenyl) sulfonyl)-6-(((((R)-1,1,1-trifluoro-3,3-dimethylbutan-2-yl)oxy)carbonyl)amino)-3,4-dihydro-2H-benzo[b][1,4]oxazin-2-yl)propanoic acid;

3-{(2S)-4-[(4-fluoro-3-methoxyphenyl) sulfonyl]-6-[(({[1-(trifluoromethyl)cyclopropyl]methoxy}carbonyl)amino]-3,4-dihydro-2H-1,4-benzoxazin-2-yl}propanoic acid;

3-{(2S)-4-[(4-fluoro-3-methoxyphenyl) sulfonyl]-6-[(({[1-(trifluoromethyl)cyclobutyl]oxy}carbonyl)amino]-3,4-dihydro-2H-1,4-benzoxazin-2-yl}propanoic acid;

3-{(2S)-4-[(4-fluoro-3-methoxyphenyl)sulfonyl]-6-[(({[(1S or 1R)-1,2,2-trimethylpropyl]oxy}carbonyl)amino]-3,4-dihydro-2H-1,4-benzoxazin-2-yl}propanoic acid;

3-{(2S)-4-[(4-fluoro-3-methoxyphenyl)sulfonyl]-6-[(({[(1S or 1R)-1,2,2-trimethylpropyl]oxy}carbonyl)amino]-3,4-dihydro-2H-1,4-benzoxazin-2-yl}propanoic acid;

3-{(2S)-4-[(4-fluoro-3-methoxyphenyl) sulfonyl]-6-[(({[1-(trifluoromethyl)cyclohexyl]oxy}carbonyl)amino]-3,4-dihydro-2H-1,4-benzoxazin-2-yl}propanoic acid;

3-((S)-4-((4-fluoro-3-methoxyphenyl) sulfonyl)-6-(((((R and S)-1,1,1-trifluoro-2-methylbutan-2-yl)oxy)carbonyl)amino)-3,4-dihydro-2H-benzo[b][1,4]oxazin-2-yl)propanoic acid;

3-((2S,3R)-3-methyl-6-(((((1,1,1-trifluoro-2-methylpropan-2-yl)oxy)carbonyl)amino)-4-((3-(trifluoromethyl)phenyl)sulfonyl)-3,4-dihydro-2H-benzo[b][1,4]oxazin-2-yl)propanoic acid;

3-((2S,3S)-4-((3-chloro-1-ethyl-1H-pyrazol-4-yl)sulfonyl)-3-methyl-6-(((((1,1,1-trifluoro-2-methylpropan-2-yl)oxy)carbonyl)amino)-3,4-dihydro-2H-benzo[b][1,4]oxazin-2-yl)-2,2-dimethylpropanoic acid;

3-((2S,3R)-4-((3-chloro-1-ethyl-1H-pyrazol-4-yl)sulfonyl)-3-methyl-6-(((((1,1,1-trifluoro-2-methylpropan-2- yl)oxy)carbonyl)amino)-3,4-dihydro-2H-benzo[b][1,4]
oxazin-2-yl)-2,2-dimethylpropanoic acid;
3-((2R,3R)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]
oxazin-2-yl)-2,2-dimethylpropanoic acid;
3-((2R,3S)-4-((3-chloro-1-ethyl-1H-pyrazol-4-yl)sulfonyl)-3-methyl-6-((((1,1,1-trifluoro-2-methylpropan-2-yl)oxy)carbonyl)amino)-3,4-dihydro-2H-benzo[b][1,4]
oxazin-2-yl)-2,2-dimethylpropanoic acid;
3-[(2R,3S)-4-[(4-fluoro-3-methoxyphenyl) sulfonyl]-3-methyl-6-{[(2,2,2-trifluoro-1,1-dimethylethoxy)carbonyl]amino}-3,4-dihydro-2H-1,4-benzoxazin-2-yl]-2,2-dimethylpropanoic acid;
3-[(2S,3R)-4-[(4-fluoro-3-methoxyphenyl) sulfonyl]-3-methyl-6-{[(2,2,2-trifluoro-1,1-dimethylethoxy)carbonyl]amino}-3,4-dihydro-2H-1,4-benzoxazin-2-yl]-2,2-dimethylpropanoic acid;
(S)-3-(8-fluoro-4-((4-fluoro-3-(trifluoromethyl)phenyl)sulfonyl)-6-((((1,1,1-trifluoro-2-methylpropan-2-yl)oxy)carbonyl)amino)-3,4-dihydro-2H-benzo[b][1,4]
oxazin-2-yl)propanoic acid;
3-[(2S)-8-fluoro-4-[(4-fluoro-3-methylphenyl)sulfonyl]-6-{[(2,2,2-trifluoro-1,1-dimethylethoxy)carbonyl]amino}-3,4-dihydro-2H-1,4-benzoxazin-2-yl]propanoic acid;
3-[(2S)-8-fluoro-4-[(4-fluoro-3-methoxyphenyl)sulfonyl]-6-{[(2,2,2-trifluoro-1,1-dimethylethoxy)carbonyl]amino}-3,4-dihydro-2H-1,4-benzoxazin-2-yl]propanoic acid;
3-[(2S)-4-[(3-chloro-1-ethyl-1H-pyrazol-4-yl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-4-[(3-ethoxy-1-ethyl-1H-pyrazol-4-yl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-8-fluoro-6-{[(2,2,2-trifluoro-1,1-dimethylethoxy)carbonyl]amino}-4-1 [3-(trifluoromethyl)phenyl]sulfonyl}-3,4-dihydro-2H-1,4-benzoxazin-2-yl]propanoic acid;
3-[(2S)-4-[(3-chloro-4-fluorophenyl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-4-[(3-cyclopropylphenyl)sulfonyl]-8-fluoro-6-{[(2,2,2-trifluoro-1,1-dimethylethoxy)carbonyl]amino}-3,4-dihydro-2H-1,4-benzoxazin-2-yl]propanoic acid;
3-[(2S)-8-fluoro-6-{[(2,2,2-trifluoro-1,1-dimethylethoxy)carbonyl]amino}-4-{[2-(trifluoromethyl)pyridin-4-yl]sulfonyl}-3,4-dihydro-2H-1,4-benzoxazin-2-yl]propanoic acid;
3-[(2S)-8-fluoro-6-{[(2,2,2-trifluoro-1,1-dimethylethoxy)carbonyl]amino}-4-{[5-(trifluoromethyl)pyridin-3-yl]sulfonyl}-3,4-dihydro-2H-1,4-benzoxazin-2-yl]propanoic acid;
(R)-3-(4-((3-chloro-1-ethyl-1H-pyrazol-4-yl)sulfonyl)-5-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid; and
(S)-3-(4-((3-chloro-1-ethyl-1H-pyrazol-4-yl)sulfonyl)-5-methyl-6-((((1,1,1-trifluoro-2-methylpropan-2-yl)oxy)carbonyl)amino)-3,4-dihydro-2H-benzo[b][1,4]oxazin-2-yl)-2,2-dimethylpropanoic acid.

\* \* \* \* \*

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: SRC1_2 peptide
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 1

Leu Xaa Xaa Leu Leu
1               5

<210> SEQ ID NO 2
<211> LENGTH: 24
<212> TYPE: PRT
<213> ORGANISM: Artificial Sequence
<220> FEATURE:
<223> OTHER INFORMATION: SRC1_2 peptide

<400> SEQUENCE: 2

Ser Pro Ser Ser His Ser Ser Leu Thr Glu Arg His Lys Ile Leu His
1               5                   10                  15

Arg Leu Leu Gln Glu Gly Ser Pro
            20
```